(12) United States Patent
Gao et al.

(10) Patent No.: US 11,608,332 B2
(45) Date of Patent: Mar. 21, 2023

(54) FGFR4 INHIBITOR AND PREPARATION METHOD AND USE THEREOF

(71) Applicants: Jiangsu Hansoh Pharmaceutical Group Co., Ltd., Jiangsu (CN); Shanghai Hansoh Biomedical Co., Ltd., Shanghai (CN)

(72) Inventors: Peng Gao, Jiangsu (CN); Guangjun Sun, Jiangsu (CN); Songliang Tan, Jiangsu (CN); Lei Liu, Jiangsu (CN); Rudi Bao, Jiangsu (CN)

(73) Assignees: Jiangsu Hansoh Pharmaceutical Group Co., Ltd., Jiangsu (CN); Shanghai Hansoh Biomedical Co., Ltd., Shanghai (CN)

( * ) Notice: Subject to any disclaimer, the term of this patent is extended or adjusted under 35 U.S.C. 154(b) by 1006 days.

(21) Appl. No.: 16/322,738

(22) PCT Filed: Aug. 11, 2017

(86) PCT No.: PCT/CN2017/097044
§ 371 (c)(1),
(2) Date: Feb. 1, 2019

(87) PCT Pub. No.: WO2018/028664
PCT Pub. Date: Feb. 15, 2018

(65) Prior Publication Data
US 2022/0024913 A1 Jan. 27, 2022

(30) Foreign Application Priority Data

Aug. 12, 2016 (CN) .......................... 201610668101.5
Dec. 20, 2016 (CN) .......................... 201611187674.2

(51) Int. Cl.
*C07D 471/04* (2006.01)
*C07D 519/00* (2006.01)

(52) U.S. Cl.
CPC .......... *C07D 471/04* (2013.01); *C07D 519/00* (2013.01)

(58) Field of Classification Search
CPC .................................................. C07D 471/04
See application file for complete search history.

(56) References Cited

U.S. PATENT DOCUMENTS

| 11,352,353 B2 * | 6/2022 | Zhang | ................... C07D 519/00 |
| 2019/0276451 A1 * | 9/2019 | Gao | ..................... A61K 31/553 |

FOREIGN PATENT DOCUMENTS

| CN | 104011051 A | 8/2014 | | |
| CN | 105683188 A | 6/2016 | | |
| WO | 2010119284 A1 | 10/2010 | | |
| WO | WO-2015059668 A1 * | 4/2015 | ......... | A61K 31/4375 |
| WO | WO-2017202390 A1 * | 11/2017 | ......... | A61K 31/4375 |

OTHER PUBLICATIONS

PubChem CID 91754685, National Center for Biotechnology Information. PubChem Compound Summary for CID 91754685. https://pubchem.ncbi.nlm.nih.gov/compound/91754685. Accessed Dec. 2, 2021, create date May 11, 2015. (Year: 2015).*
Int'l Search Report dated Nov. 24, 2017 in Int'l Application No. PCT/CN2017/097044.
Zhou et al, "A Structure-Guided Approach to Creating Covalent FGFR Inhibitors," Chemistry & Biology, vol. 17, pp. 285-295 (Mar. 26, 2010).

* cited by examiner

*Primary Examiner* — Laura L Stockton
(74) *Attorney, Agent, or Firm* — Ice Miller LLP

(57) ABSTRACT

Provided are an FGFR4 inhibitor with the structure of formula (I) and a preparation method and use thereof. The series of compounds of formula (I) have a very strong inhibitory effect on the FGFR4 kinase activity, and have a very high selectivity; and the same can be widely used to prepare drugs for treating cancers, in particular, liver cancer, stomach cancer, prostate cancer, skin cancer, ovarian cancer, lung cancer, breast cancer or colon cancer, and it is expected that the same can be developed into a new generation of FGFR4 inhibitor drugs.

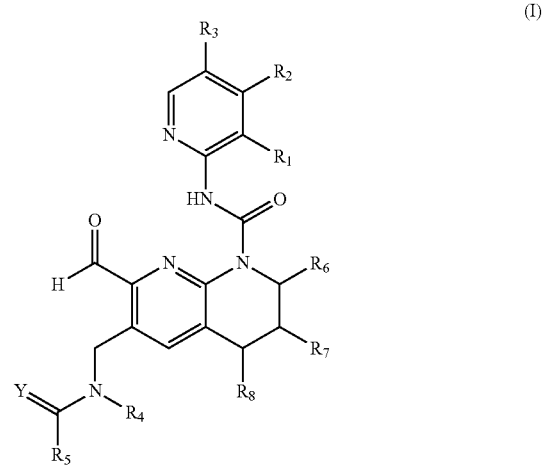

4 Claims, No Drawings

FGFR4 INHIBITOR AND PREPARATION METHOD AND USE THEREOF

CROSS-REFERENCE TO RELATED APPLICATION

This application is a Section 371 of International Application No. PCT/CN2017/097044, filed Aug. 11, 2017, which was published in the Chinese language on Feb. 15, 2018, under International Publication No. WO 2018/028664 A1, which claims priority under 35 U.S.C. § 119(b) to Chinese Application No. 201610668101.5, filed Aug. 12, 2016, and Chinese Application No. 201611187674.2, filed Dec. 20, 2016, the disclosures of which are incorporated herein by reference in their entirety.

FIELD OF THE INVENTION

The present invention belongs to the field of pharmaceutical synthesis, and specifically relates to an FGFR4 inhibitor, preparation method and use thereof.

BACKGROUND OF THE INVENTION

Fibroblast growth factor receptor (FGFR) belongs to transmembrane receptor of receptor tyrosine kinase, and includes four receptor subtypes, namely FGFR1, FGFR2, FGFR3 and FGFR4. FGFR regulates various functions such as cell proliferation, survival, differentiation and migration, and plays an important role in human development and adult body functions. Expression of FGFR is abnormal in a variety of human tumors, including gene amplication, mutation, and overexpression, therefore FGFR is a vital target for tumor-targeted therapeutic research.

FGFR4 is a member of FGFR receptor family and can form dimers on the cell membrane by binding to its ligand, fibroblast growth factor 19 (FGF19). The formation of these dimers can cause phosphorylation of key tyrosine residues in FGFR4's own cells, thereby activating multiple downstream signaling pathways in cells. These intracellular signaling pathways play an important role in cell proliferation, survival and anti-apoptosis. FGFR4 is overexpressed in many cancers and thus is a predictor of malignant tumor invasion. Decreasing and reducing FGFR4 expression can reduce cell proliferation and promote cell apoptosis. Recently, more and more studies have shown that the signaling pathway of FGF19/FGFR4 is continuously activated in about one-third of liver cancer patients, which is the main carcinogenic factor leading to liver cancer in this type of patients. Meanwhile, expression or high expression of FGFR4 is also closely related to many other tumors, such as gastric cancer, prostate cancer, skin cancer, ovarian cancer, lung cancer, breast cancer, colon cancer, etc.

The incidence of liver cancer in China is the highest in the world, and the number of new patients and dead patients each year is about half of the total number of liver cancer in the world. At present, the incidence of liver cancer in China is about 28.7 per 100 thousand people, and 394770 new cases were found in 2012, therefore liver cancer becomes the third malignant tumor after gastric cancer and lung cancer. The onset of primary liver cancer with the features of high invasiveness and poor prognosis is a multi-factor, multi-step complex process. Surgical treatment such as liver resection and liver transplantation can improve the survival rate of some patients, but only limited patients can undergo surgical treatment and most patients have a poor prognosis due to recurrence and metastasis after surgery. Sorafenib is the only drug approved on the market for the treatment of liver cancer, but the clinically overall survival can only be extended for about 3 months, and the treatment effect is not satisfying. Therefore, it is urgent to develop a liver cancer systematic treatment drug with new molecules. Since FGFR4 is a major carcinogenic factor of a considerable part of liver cancer, the development of small molecule inhibitors of FGFR4 has significant potentiality in clinical application.

At present, some FGFR inhibitors as anti-tumor drugs have entered into the clinical research phase, but these drugs are mainly inhibitors of FGFR1, 2 and 3, of which the inhibition of FGFR4 activity is weak, and the inhibition of FGFR1-3 has target-related side effects such as hyperphosphatemia. Highly selective inhibitors of FGFR4 can be effective in the treatment of cancer diseases caused by abnormal FGFR4 signaling pathway, and can avoid the side effects such as hyperphosphatemia caused by the inhibition of FGFR1-3. Therefore, highly selective small molecule inhibitors against FGFR4 have great application prospects in the field of tumor targeted therapy.

SUMMARY OF THE INVENTION

During the course of research, the inventors found a FGFR4 inhibitor having the structure of formula (I), which has a strong inhibitory effect on FGFR4 kinase activity and has a very high selectivity, and can be used as a medicant to treat cancer, specially liver cancer, gastric cancer, prostate cancer, skin cancer, ovarian cancer, lung cancer, breast cancer or colon cancer and is expected to be developed into a new generation of FGFR4 inhibitor drugs.

In the first aspect, the present invention provides a compound of formula (I), a stereoisomer or a pharmaceutically acceptable salt thereof:

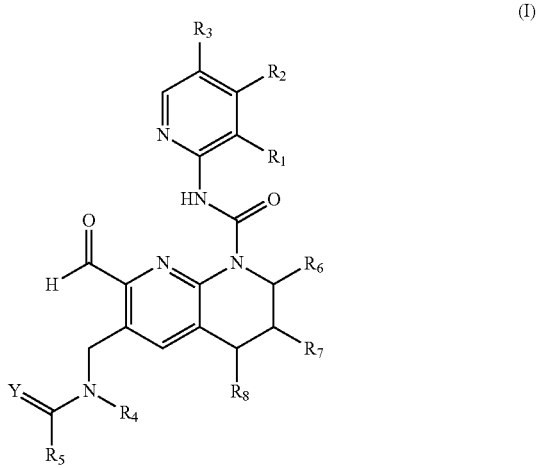

wherein:

$R_1$ is selected from the group consisting of hydrogen, deuterium, halogen, hydroxy, thiol, cyano, nitro, azido, $C_{1-8}$ alkyl, halo$C_{1-8}$ alkyl $C_{3-8}$ cycloalkyl, 3 to 8 membered heterocyclyl, 3 to 8 membered heterocyclyloxy, 3 to 8 membered heterocyclylthio, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-N(R_{12})-C(O)R_{11}$, and $-N(R_{12})-C(O)OR_{10}$;

$R_2$ is selected from the group consisting of hydrogen, deuterium, halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3 to 8 membered heterocyclyl, 3 to 8 membered heterocyclyloxy, 3 to 8 membered heterocyclylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$, and —N(R$_{12}$)—C(O)OR$_{10}$, optionally substituted by one or more groups selected from the group consisting of halogen, hydroxy, alkyl, haloC$_{1-8}$ alkyl, C$_{3-8}$ cycloalkyl, 3 to 8 membered heterocyclyl, 3 to 8 membered heterocyclyloxy, 3 to 8 membered heterocyclylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$;

or, $R_1$ and $R_2$ together with the carbon atom to which they are directly attached form a 5 to 7 membered cycloalkyl or 5 to 7 membered heterocyclyl, optionally substituted by one or more groups selected from the group consisting of halogen, thiol, cyano, nitro, azido, C$_{1-8}$ alkyl, C$_{2-8}$ alkenyl, C$_{2-8}$ alkynyl, haloC$_{1-8}$ alkyl, C$_{3-8}$ cycloalkyl, 3 to 8 membered heterocyclyl, 3 to 8 membered heterocyclyloxy, 3 to 8 membered heterocyclylthio, C$_{5-10}$ aryl, C$_{5-10}$ aryloxy, C$_{5-10}$ arylthio, 5 to 10 membered heteroaryl, 5 to 10 membered heteroaryloxy, 5 to 10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$, and —N(R$_{12}$)—C(O)OR$_{10}$;

$R_3$ is selected from the group consisting of hydrogen, deuterium, halogen, hydroxy, thiol, cyano, thiocyano, nitro, azido, C$_{1-8}$ alkyl, C$_{2-8}$ alkenyl, C$_{2-8}$ alkynyl, C$_{3-8}$ cycloalkyl, 3 to 8 membered heterocyclyl, C$_{1-8}$ alkyloxy, C$_{3-8}$ cycloalkoxy and 3 to 8 membered heterocyclyloxy, optionally substituted by one or more groups selected from the group consisting of halogen, hydroxy, thiol, cyano, nitro, azido, C$_{1-8}$ alkyl, C$_{2-8}$ alkenyl, C$_{2-8}$ alkynyl, haloC$_{1-8}$ alkyl, C$_{3-8}$ cycloalkyl, 3 to 8 membered heterocyclyl, 3 to 8 membered heterocyclyloxy, 3 to 8 membered heterocyclylthio, C$_{5-10}$ aryl, C$_{5-10}$ aryloxy, C$_{5-10}$ arylthio, 5 to 10 membered heteroaryl, 5 to 10 membered heteroaryloxy, 5 to 10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$;

$R_4$ is selected from the group consisting of hydrogen, deuterium, C$_{1-8}$ alkyl, C$_{2-8}$ alkenyl, C$_{2-8}$ alkynyl, —$C_{0-8}$—C(O)R$_{11}$, C$_{3-8}$ cycloalkyl, 3 to 8 membered heterocyclyl, optionally substituted by one or more groups selected from the group consisting of halogen, hydroxy, thiol, cyano, nitro, azido, C$_{1-8}$ alkyl, C$_{2-8}$ alkenyl, C$_{2-8}$ alkynyl, haloC$_{1-8}$ alkyl, C$_{3-8}$ cycloalkyl, 3 to 8 membered heterocyclyl, 3 to 8 membered heterocyclyloxy, 3 to 8 membered heterocyclylthio, C$_{5-10}$ aryl, C$_{5-10}$ aryloxy, C$_{5-10}$ arylthio, 5 to 10 membered heteroaryl, 5 to 10 membered heteroaryloxy, 5 to 10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$, and —N(R$_{12}$)—C(O)OR$_{10}$;

$R_5$ is selected from the group consisting of hydrogen, C$_{1-8}$ alkyl and 3 to 8 membered heterocyclyl, optionally substituted by one or more groups selected from the group consisting of halogen, hydroxy, thiol, cyano, nitro, azido, C$_{1-8}$ alkyl, C$_{2-8}$ alkenyl, C$_{2-8}$ alkynyl, haloC$_{1-8}$ alkyl, C$_{3-8}$ cycloalkyl, 3 to 8 membered heterocyclyl, 3 to 8 membered heterocyclyloxy, 3 to 8 membered heterocyclylthio, C$_{5-10}$ aryl, C$_{5-10}$ aryloxy, C$_{5-10}$ arylthio, 5 to 10 membered heteroaryl, 5 to 10 membered heteroaryloxy, 5 to 10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_1$, and —N(R$_{12}$)—C(O)OR$_{10}$;

or, $R_4$ and $R_5$ together with the amido group to which they are directly attached form a 5 to 7 membered heterocyclyl containing lactam, optionally substituted by one or more substituents selected from the group consisting of halogen, thiol, cyano, nitro, azido, C$_{1-8}$ alkyl, C$_{2-8}$ alkenyl, C$_{2-8}$ alkynyl, haloC$_{1-8}$ alkyl, C$_{3-8}$ cycloalkyl, 3 to 8 membered heterocyclyl, 3 to 8 membered heterocyclyloxy, 3 to 8 membered heterocyclylthio, C$_{5-10}$ aryl, C$_{5-10}$ aryloxy, C$_{5-10}$ arylthio, 5 to 10 membered heteroaryl, 5 to 10 membered heteroaryloxy, 5 to 10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$, and —N(R$_{12}$)—C(O)OR$_{10}$, provided that the substituents are not hydroxy, acetyl, C$_{1-3}$ alkyl or di C$_{1-3}$ alkylamino;

$R_6$, $R_7$ and $R_8$ are each independently selected from the group consisting of hydrogen, deuterium, halogen, hydroxy, thiol, cyano, nitro, azido, C$_{1-8}$ alkyl, haloC$_{1-8}$ alkyl, C$_{3-8}$ cycloalkyl, 3 to 8 membered heterocyclyl, 3 to 8 membered heterocyclyloxy, 3 to 8 membered heterocyclylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$, and —N(R$_{12}$)—C(O)OR$_{10}$;

$R_9$ is selected from the group consisting of hydrogen, deuterium, C$_{1-8}$ alkyl, C$_{2-8}$ alkenyl, C$_{1-8}$ alkyloxy substituted by C$_{1-8}$ alkyl, C$_{3-8}$ cycloalkyl, substituted or unsubstituted 3 to 8 membered heterocyclyl, haloC$_{1-8}$ alkyl, phenyl, p-methylphenyl, amino, mono C$_{1-8}$ alkylamino, di C$_{1-8}$ alkylamino and C$_{1-8}$ alkanoylamino;

$R_{10}$ is selected from the group consisting of hydrogen, deuterium, C$_{1-8}$ alkyl, C$_{3-8}$ cycloalkyl, C$_{1-8}$ alkyloxy substituted by C$_{1-8}$ alkyl, C$_{5-10}$ aryl, haloC$_{1-8}$ alkyl and hydroxyC$_{1-8}$ alkyl;

$R_{11}$ is selected from the group consisting of hydrogen, deuterium, C$_{1-8}$ alkyl, C$_{1-8}$ alkoxy, C$_{3-8}$ cycloalkyl, C$_{3-8}$ cycloalkoxy, haloC$_{1-8}$ alkyl, haloC$_{1-8}$ alkoxy, hydroxyC$_{1-8}$ alkyl and hydroxyC$_{1-8}$ alkoxy;

$R_{12}$ and $R_{13}$ are each independently selected from the group consisting of hydrogen, deuterium, C$_{1-8}$ alkyl, C$_{1-8}$ alkyloxy substituted by C$_{1-8}$ alkyl, C$_{1-8}$ alkyl substituted by C$_{1-8}$ alkoxy, C$_{1-8}$ alkyl substituted by C$_{3-8}$ cycloalkyl, C$_{2-8}$ alkenyl, C$_{2-8}$ alkynyl, C$_{3-8}$ cycloalkyl, substituted or unsubstituted 3 to 8 membered heterocyclyl, substituted or unsubstituted C$_{5-10}$ aryl, substituted or unsubstituted 5 to 10 membered heteroaryl and C$_{1-8}$ alkanoyl;

Y is selected from the group consisting of O and S; and r is 0, 1 or 2.

In a preferred embodiment, the compound of formula (I) is a compound of formula (I-a), a stereoisomer or a pharmaceutically acceptable salt thereof:

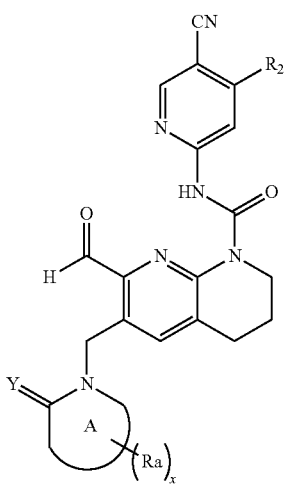

(I-a)

wherein:

A is 5 to 6 membered heterocyclyl or heteroaryl;

$R_a$ is a substituent selected from the group consisting of hydrogen, deuterium, halogen, thiol, cyano, nitro, azido, $C_{2-8}$ alkenyl, $C_{2-8}$ alkynyl, halo$C_{1-8}$ alkyl, $C_{3-8}$ cycloalkyl, 3 to 8 membered heterocyclyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$, and —N(R$_{12}$)—C(O)OR$_{10}$, provided that the substituent is not hydroxy, acetyl, or di $C_{1-3}$ alkylamino; and x is 0, 1, 2, or 3.

In a preferred embodiment, the compound of formula (I) is a compound of formula (I-a), a stereoisomer or a pharmaceutically acceptable salt thereof:

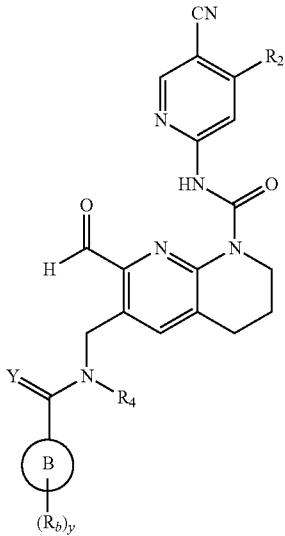

(I-b)

wherein:

B is 5 to 6 membered heterocyclyl, aryl or heteroaryl; $R_b$ is a substituent selected from the group consisting of hydro-gen, deuterium, halogen, thiol, cyano, nitro, azido, $C_{2-8}$ alkenyl, $C_{2-8}$ alkynyl, halo$C_{1-8}$ alkyl, $C_{3-8}$ cycloalkyl, 3 to 8 membered heterocyclyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$, provided that the substituent is not hydroxy, acetyl, or di $C_{1-3}$ alkylamino; and y is 0, 1, 2 or 3.

In a more preferred embodiment, the compound of formula (I), the stereoisomer or the pharmaceutically acceptable salt thereof is a compound of the following formula (IIa), (IIb), (IIc), (IId), (IIe), (IIf), (IIg), (IIh), (IIi), (IIj) or (IIk):

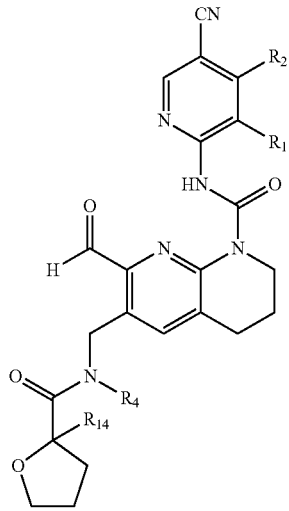

(IIa)

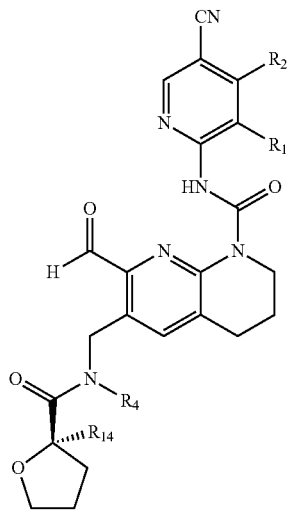

(IIb)

(IIc)
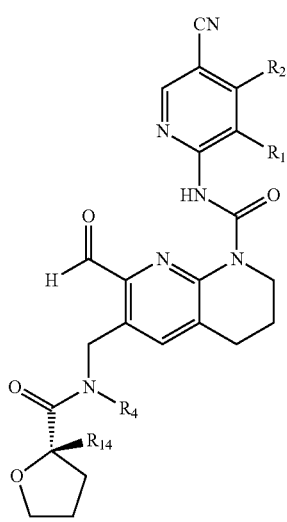
(IId)
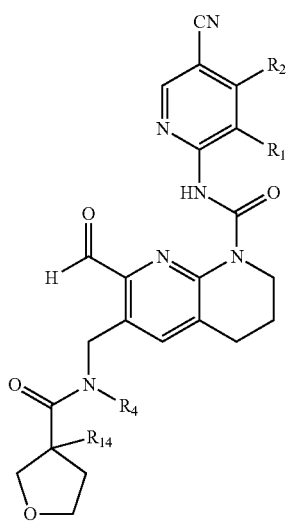
(IIe)
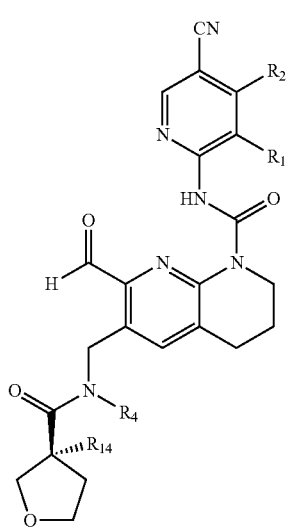
(IIf)
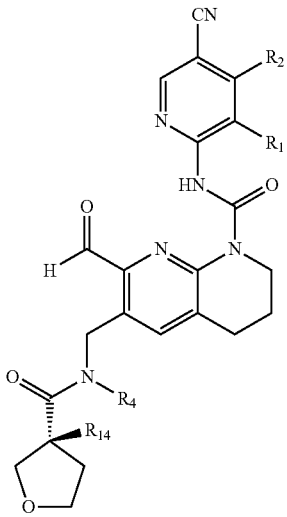
(IIg)
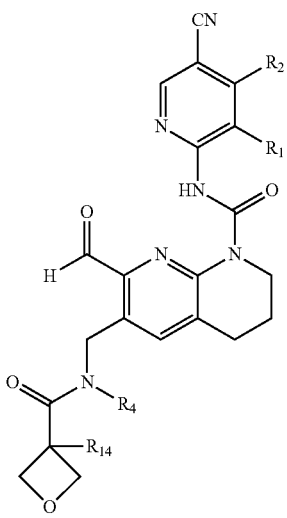
(IIh)
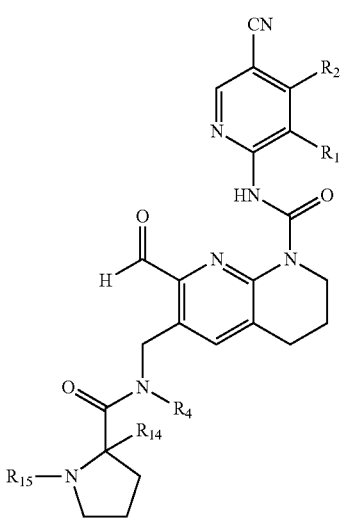

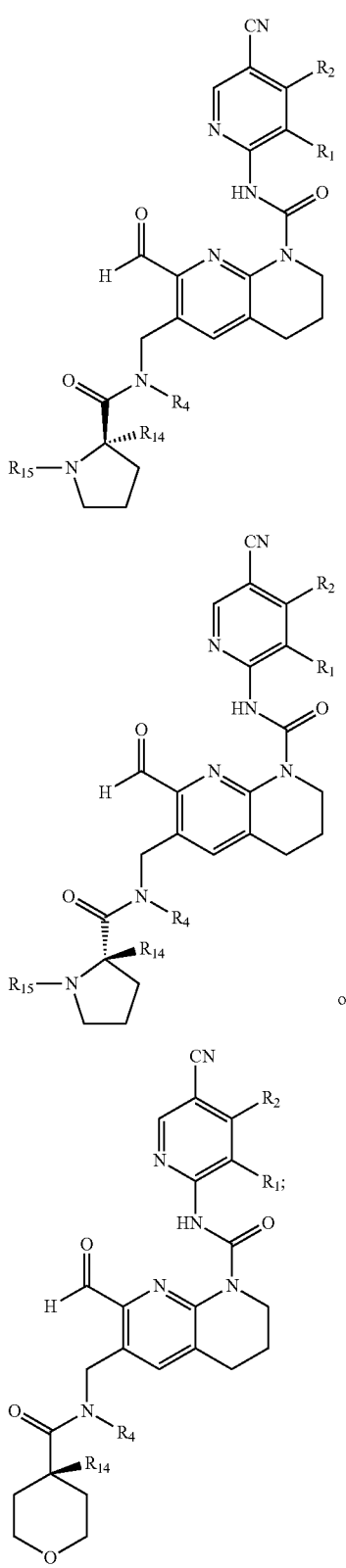

clyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, $—C_{0-8}—S(O)_rR_9$, $—C_{0-8}—O—R_{10}$, $—C_{0-8}—C(O)OR_{10}$, $—C_{0-8}—C(O)R_{11}$, $—C_{0-8}—O—C(O)R_{11}$, $—C_{0-8}—NR_{12}R_{13}$, $—C_{0-8}—C(O)NR_{12}R_{13}$, $—N(R_{12})—C(O)R_{11}$ and $—N(R_{12})—C(O)OR_{10}$;

$R_4$ is selected from the group consisting of hydrogen, deuterium, $C_{1-8}$ alkyl, $haloC_{1-8}$ alkyl, $—C_{0-8}—C(O)R_{11}$, $C_{1-8}$ alkyl substituted by $C_{1-8}$ alkoxy, $aminoC_{1-8}$ alkyl, $hydroxyC_{1-8}$ alkyl, $C_{1-8}$ alkyl substituted by $C_{3-8}$ cycloalkyl, $C_{1-8}$ alkyl substituted by 3 to 8 membered heterocyclyl, $C_{2-8}$ alkenyl, $C_{2-8}$ alkynyl, $C_{3-8}$ cycloalkyl and 3 to 8 membered heterocyclyl.

In a more preferred embodiment, $R_1$ is selected from the group consisting of hydrogen, deuterium, halogen, hydroxy, thiol, cyano, nitro, azido, methyl, ethyl, isopropyl, trifluoromethyl, cyclopropyl, 3-oxetanyl, methoxy, ethoxy, isopropoxy, acetoxy, amino and acetamido;

$R_2$ is selected from the group consisting of 3 to 8 membered heterocyclyl, 3 to 8 membered heterocyclyloxy, 3 to 8 membered heterocyclylthio, $—C_{0-8}—S(O)_rR_9$, $—C_{0-8}—O—R_{10}$ and $—C_{0-8}—NR_{12}R_{13}$, wherein the 3 to 8 membered heterocyclyl, 3 to 8 membered heterocyclyloxy, and 3 to 8 membered heterocyclylthio are each optionally substituted by one or more groups selected from the group consisting of hydrogen, halogen, hydroxy, $C_{1-8}$ alkyl, $C_{1-8}$ alkoxy, $haloC_{1-8}$ alkyl, $C_{3-8}$ cycloalkyl, 3 to 8 membered heterocyclyl, 3 to 8 membered heterocyclyloxy, 3 to 8 membered heterocyclylthio, $—C_{0-8}—S(O)_rR_9$, $—C_{0-8}—O—R_{10}$, $—C_{0-8}—C(O)OR_{10}$, $—C_{0-8}—C(O)R_{11}$, $—C_{0-8}—O—C(O)R_{11}$, $—C_{0-8}—NR_{12}R_{13}$, $—C_{0-8}—C(O)NR_{12}R_{13}$, $—N(R_{12})—C(O)R_{11}$, and $—N(R_{12})—C(O)OR_{10}$;

$R_9$ is selected from the group consisting of hydrogen, deuterium, $C_{1-8}$ alkyl, $C_{1-8}$ alkoxy and 3 to 8 membered heterocyclyl, wherein the $C_{1-8}$ alkyl, $C_{1-8}$ alkoxy and 3 to 8 membered heterocyclyl are each optionally substituted by one or more groups selected from the group consisting of hydrogen, halogen, $C_{1-8}$ alkyl, and $C_{1-8}$ alkoxy;

$R_{10}$ is selected from the group consisting of hydrogen, deuterium, $C_{1-8}$ alkyl, $C_{1-8}$ alkoxy, $C_{3-8}$ cycloalkyl and 3 to 8 membered heterocyclyl, wherein the $C_{1-8}$ alkyl, $C_{1-8}$ alkoxy, $C_{3-8}$ cycloalkyl and 3 to 8 membered heterocyclyl are each optionally substituted by one or more groups selected from the group consisting of hydrogen, halogen, $C_{1-8}$ alkyl, and $C_{1-8}$ alkoxy;

$R_{11}$ is selected from the group consisting of hydrogen, deuterium, $C_{1-8}$ alkyl, $C_{1-8}$ alkoxy, $C_{3-8}$ cycloalkyl, $C_{3-8}$ cycloalkyloxy, $haloC_{1-8}$ alkyl, $haloC_{1-8}$ alkoxy, $hydroxyC_{1-8}$ alkyl and $hydroxyC_{1-8}$ alkoxy;

$R_{12}$ and $R_{13}$ are each independently selected from hydrogen, deuterium, $C_{1-8}$ alkyl, $C_{1-8}$ alkoxy, $C_{3-8}$ cycloalkyl, and 3 to 8 membered heterocyclyl, wherein the $C_{1-8}$ alkyl, $C_{1-8}$ alkoxy, $C_{3-8}$ cycloalkyl and 3 to 8 membered heterocyclyl are each optionally substituted by one or more groups selected from the group consisting of hydrogen, halogen, $C_{1-8}$ alkyl, and $C_{1-8}$ alkoxy;

or, $R_1$ and $R_2$ together with the carbon atom to which they are directly attached form a 5 to 7 membered cycloalkyl or 5 to 7 membered heterocyclyl, wherein the 5 to 7 membered heterocyclyl is selected from the group consisting of:

$R_{14}$ and $R_{15}$ are each independently selected from the group consisting of hydrogen, halogen, hydroxy, thiol, cyano, nitro, azido, $C_{1-8}$ alkyl, $C_{2-8}$ alkenyl, $C_{2-8}$ alkynyl, $haloC_{1-8}$ alkyl, $C_{3-8}$ cycloalkyl, 3 to 8 membered heterocy-

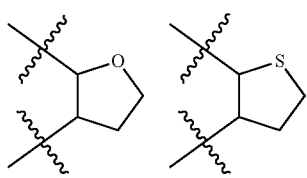 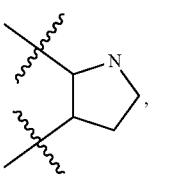

and optionally substituted by one or more groups selected from the group consisting of halogen, thiol, cyano, nitro, azido, $C_{1-8}$ alkyl, $C_{2-8}$ alkenyl, $C_{2-8}$ alkynyl, halo$C_{1-8}$ alkyl, $C_{3-8}$ cycloalkyl, 3 to 8 membered heterocyclyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$; and R$_4$ is selected from the group consisting of hydrogen, deuterium, methyl, ethyl, isopropyl, trifluoromethyl, ethoxyethyl, methoxymethyl, aminomethyl, hydroxymethyl, hydroxyethyl, aldehyde, methyl acetyl, cyclopropyl, cyclopropyl methyl, allyl, ethynyl and 3-oxetanyl.

In the most preferred embodiment, the compound of formula (I), the stereoisomer or the pharmaceutically acceptable salt thereof, includes but is not limited to:

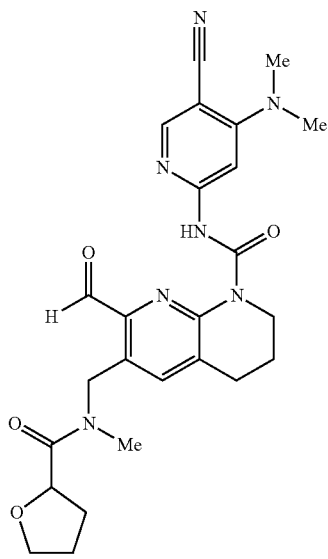

-continued

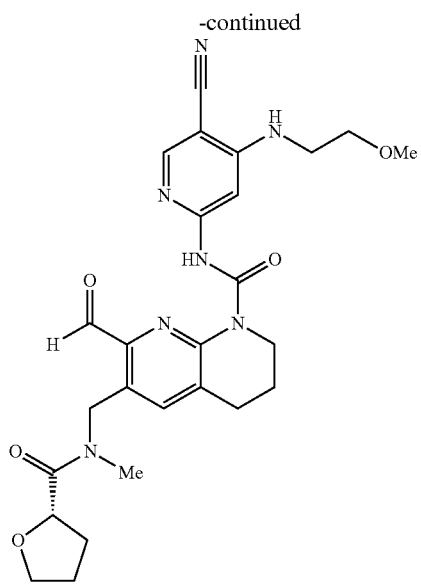

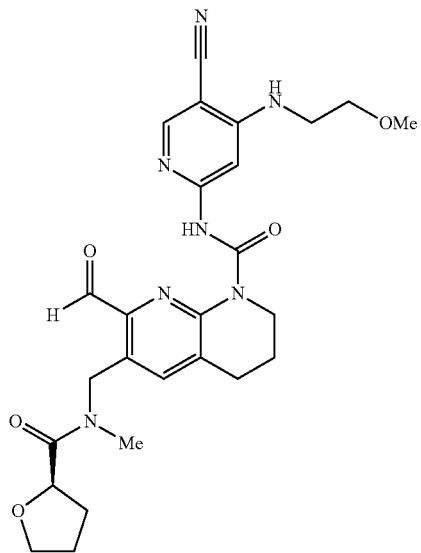

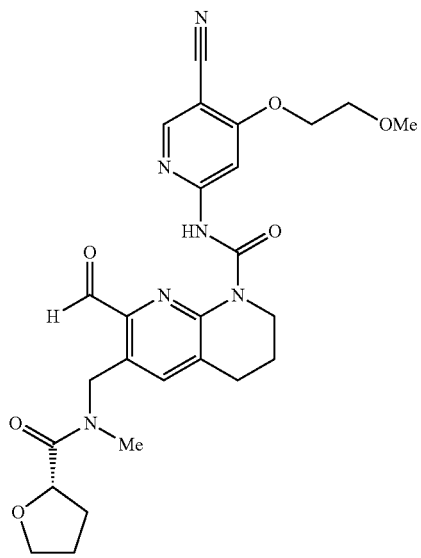

13
-continued
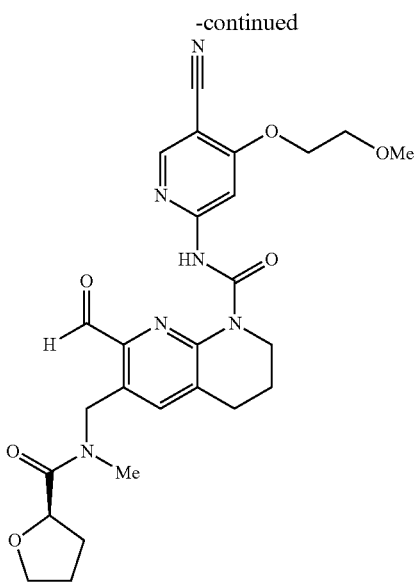
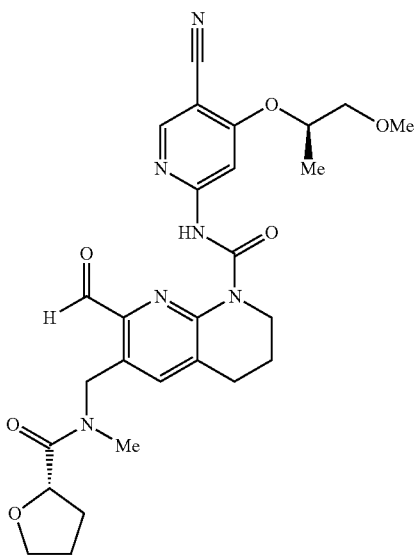
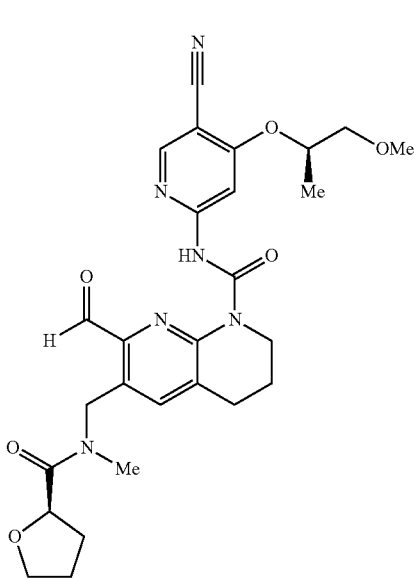
14
-continued
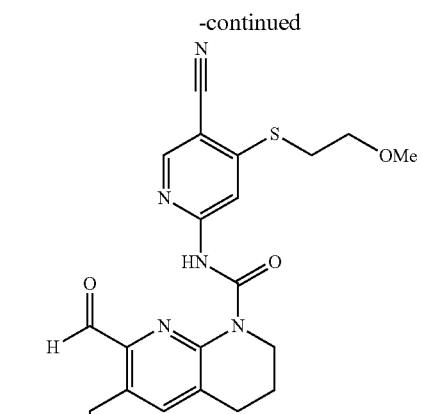
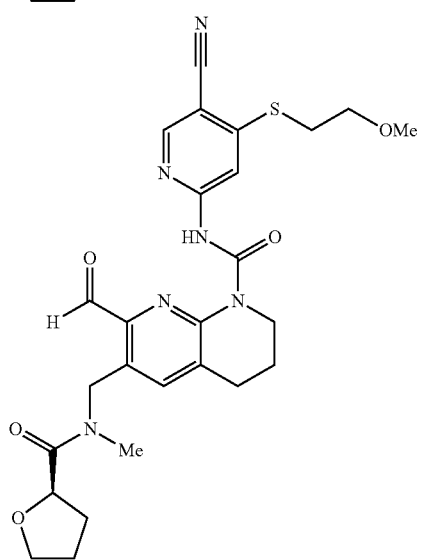
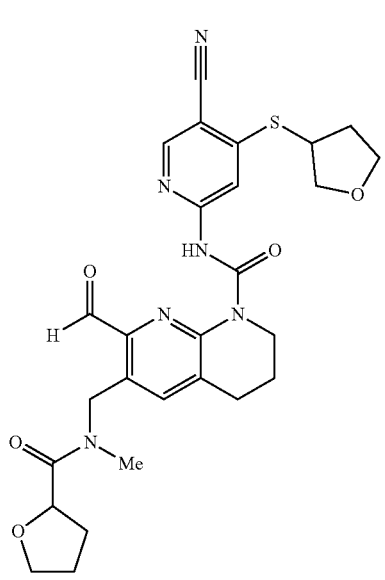

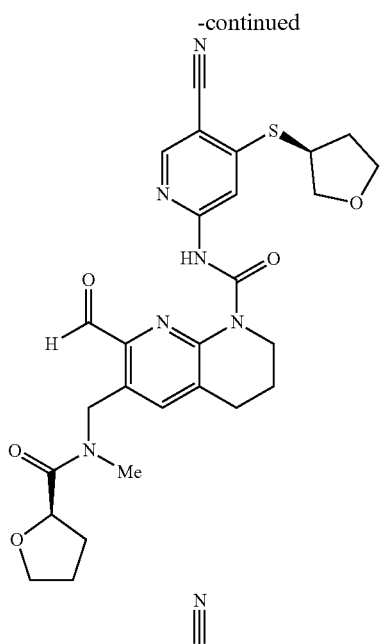
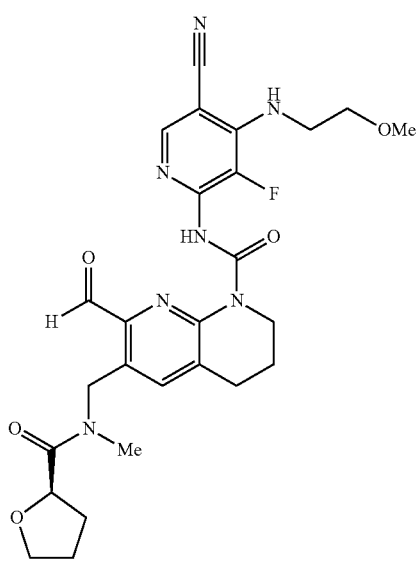
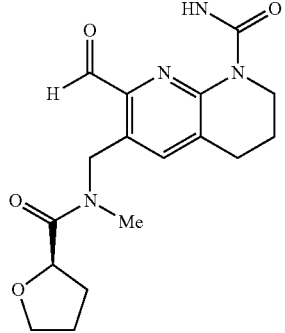
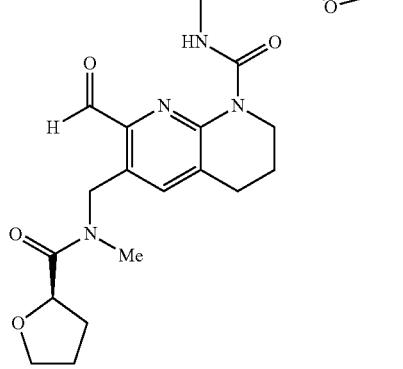
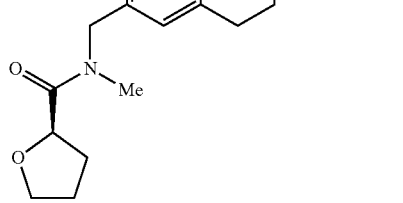

17
-continued
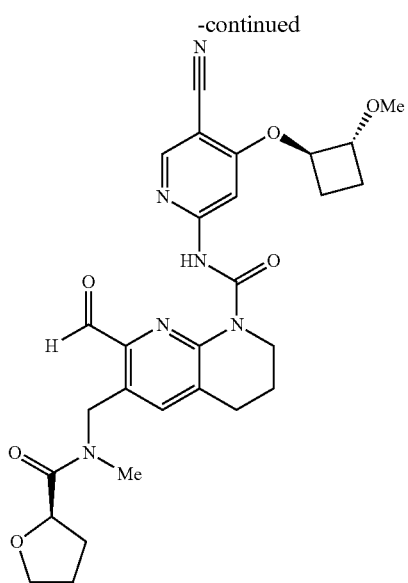
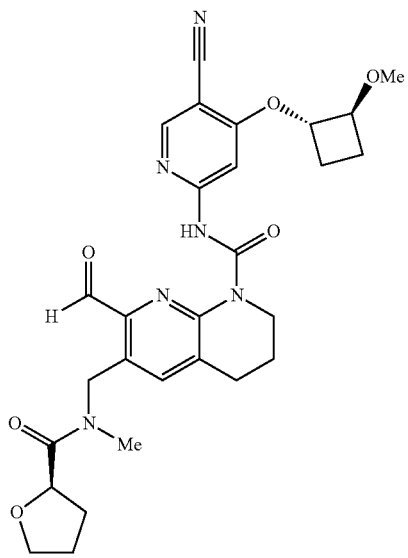
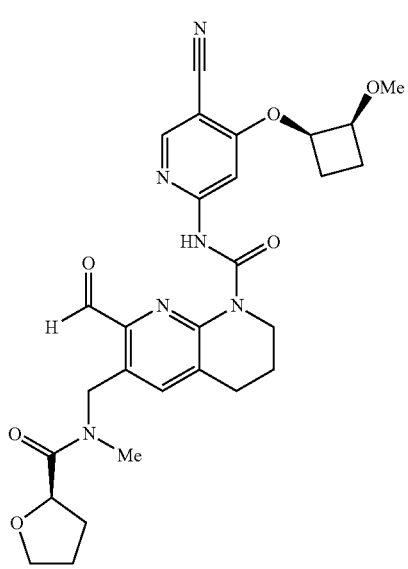
18
-continued
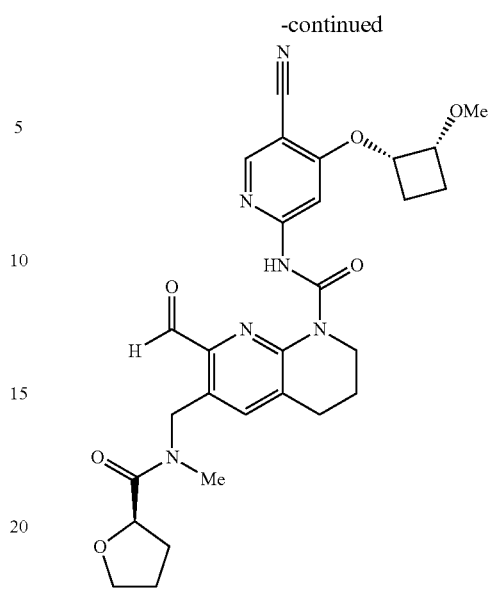
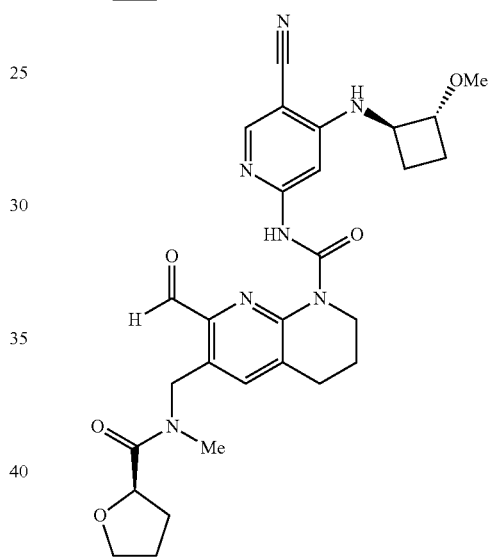
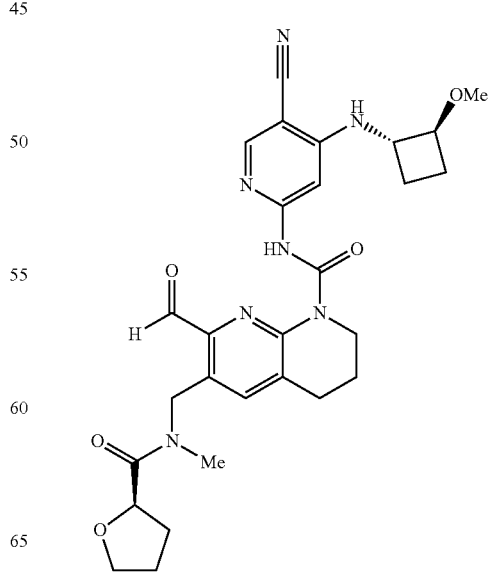

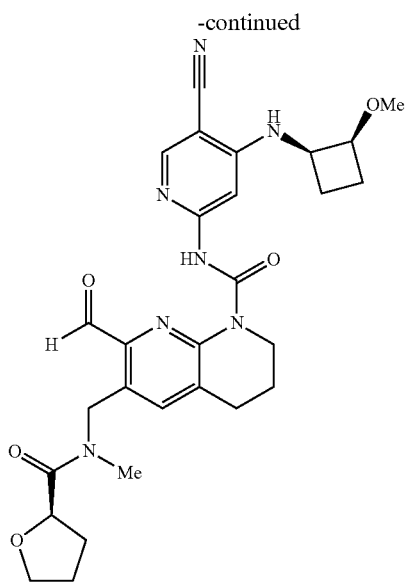
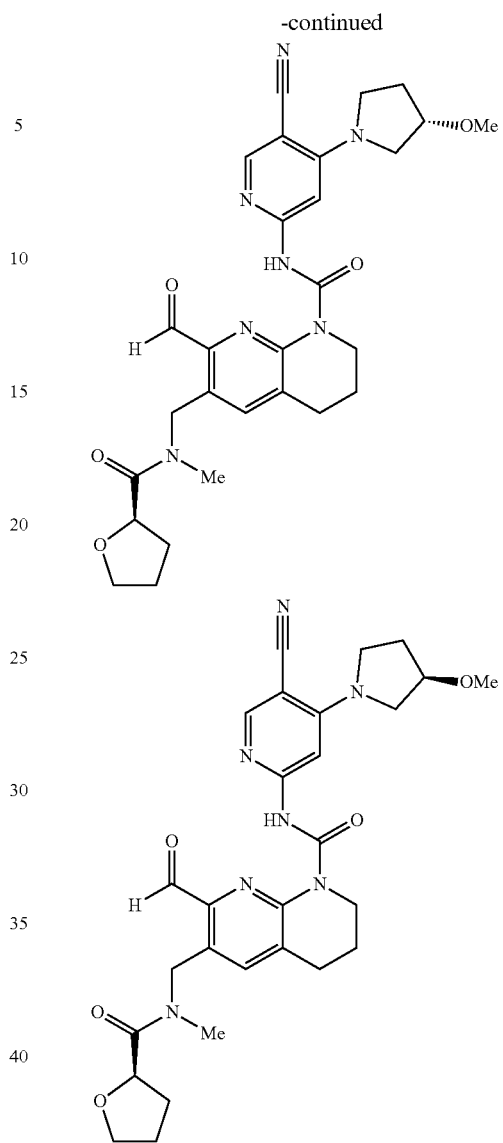
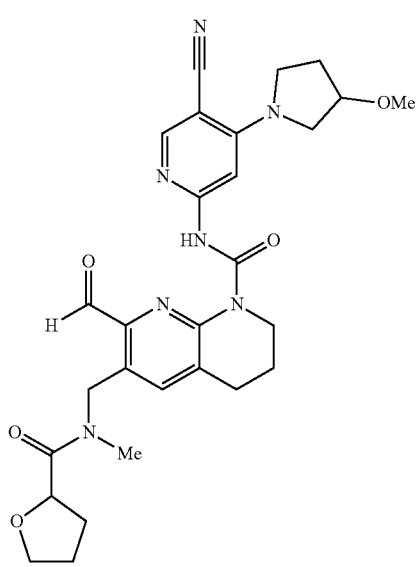

-continued
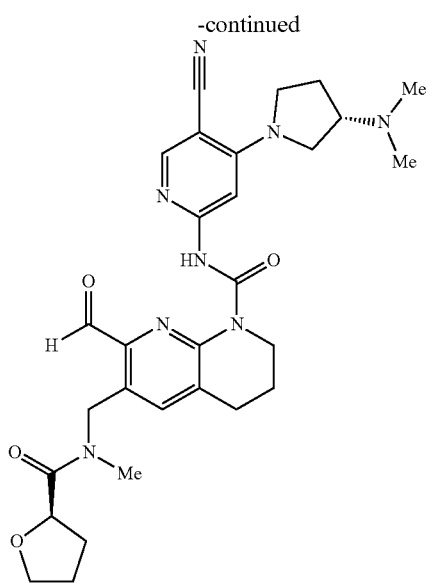
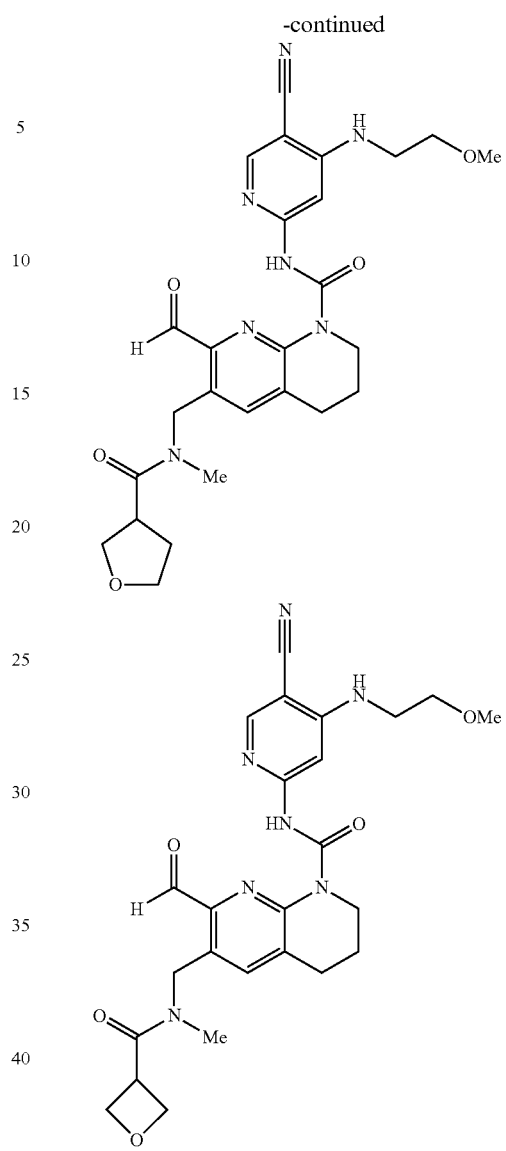
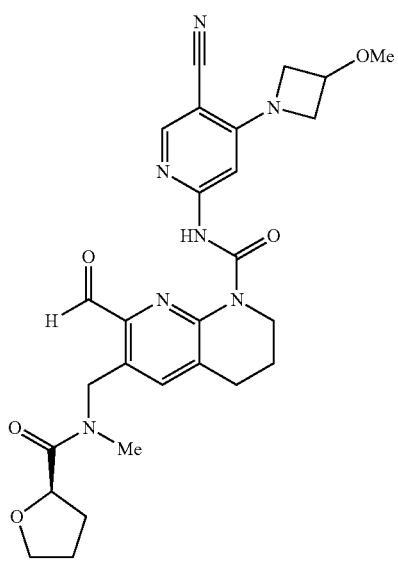

23
-continued
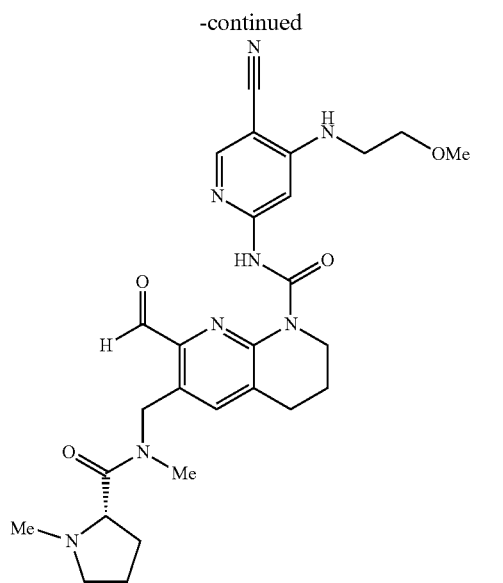
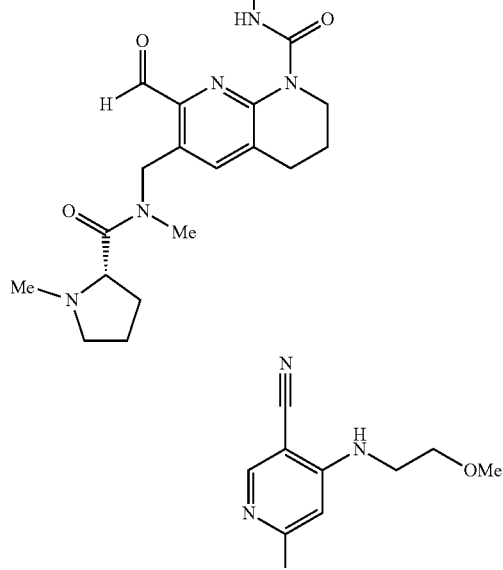
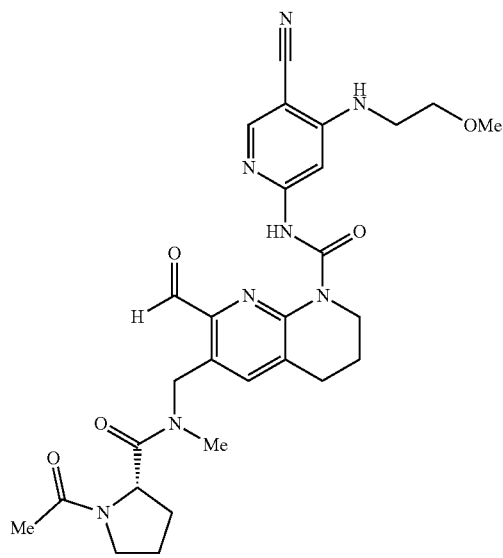
24
-continued
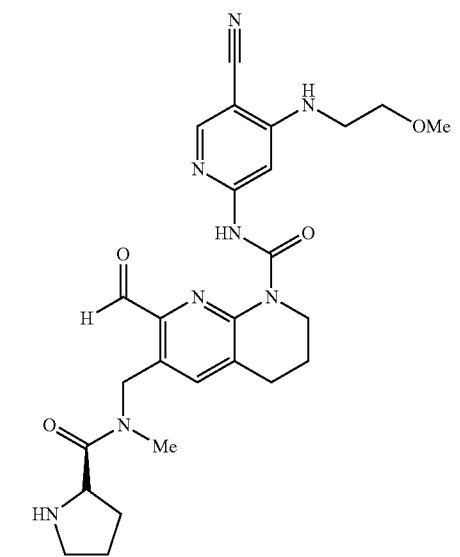
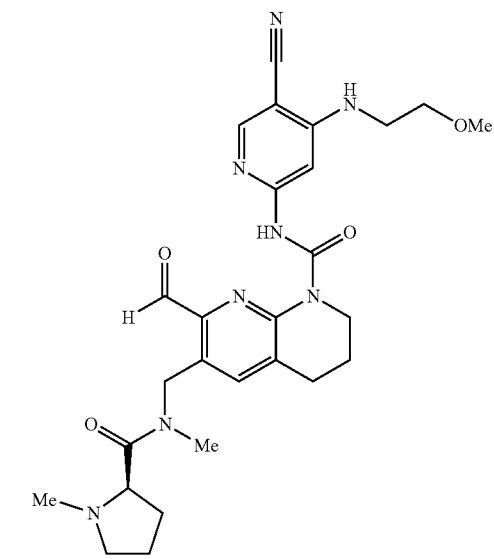
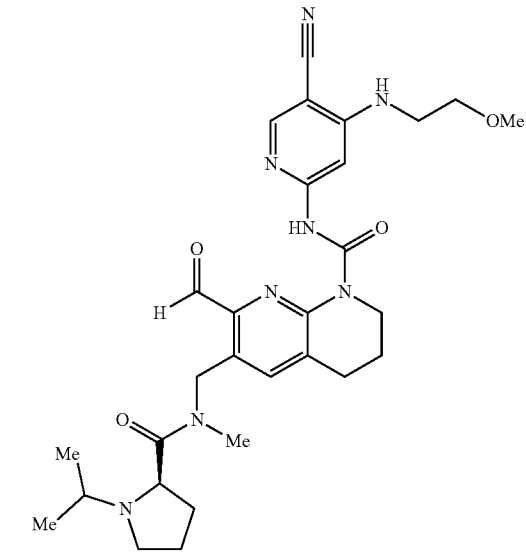

-continued
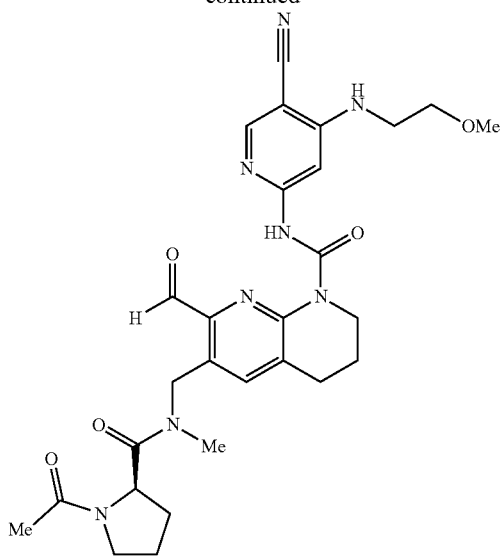
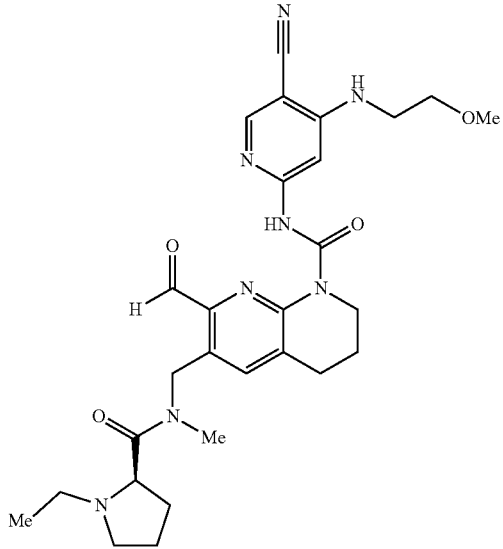
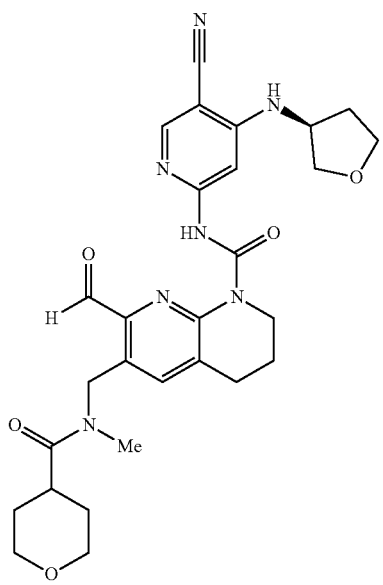
-continued
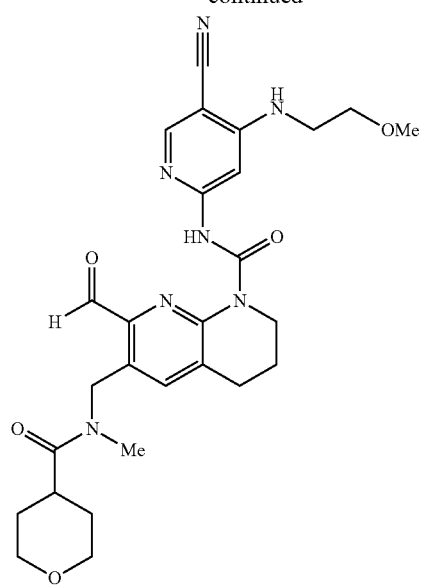
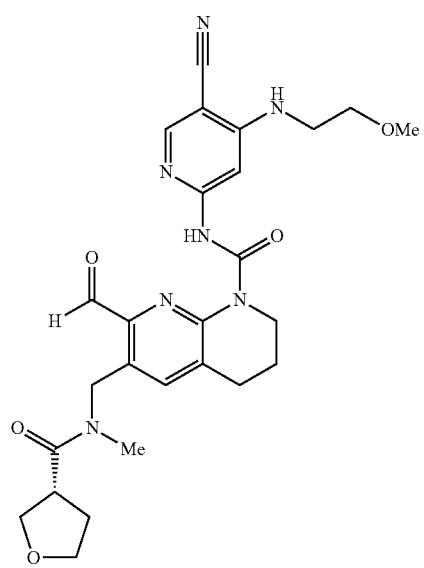
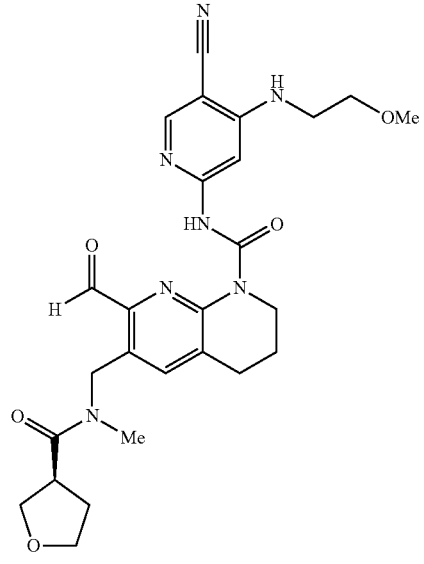

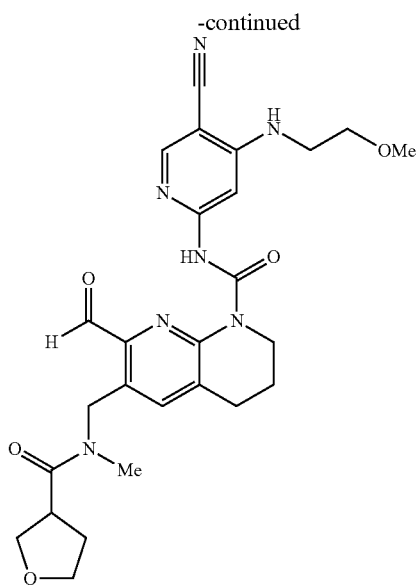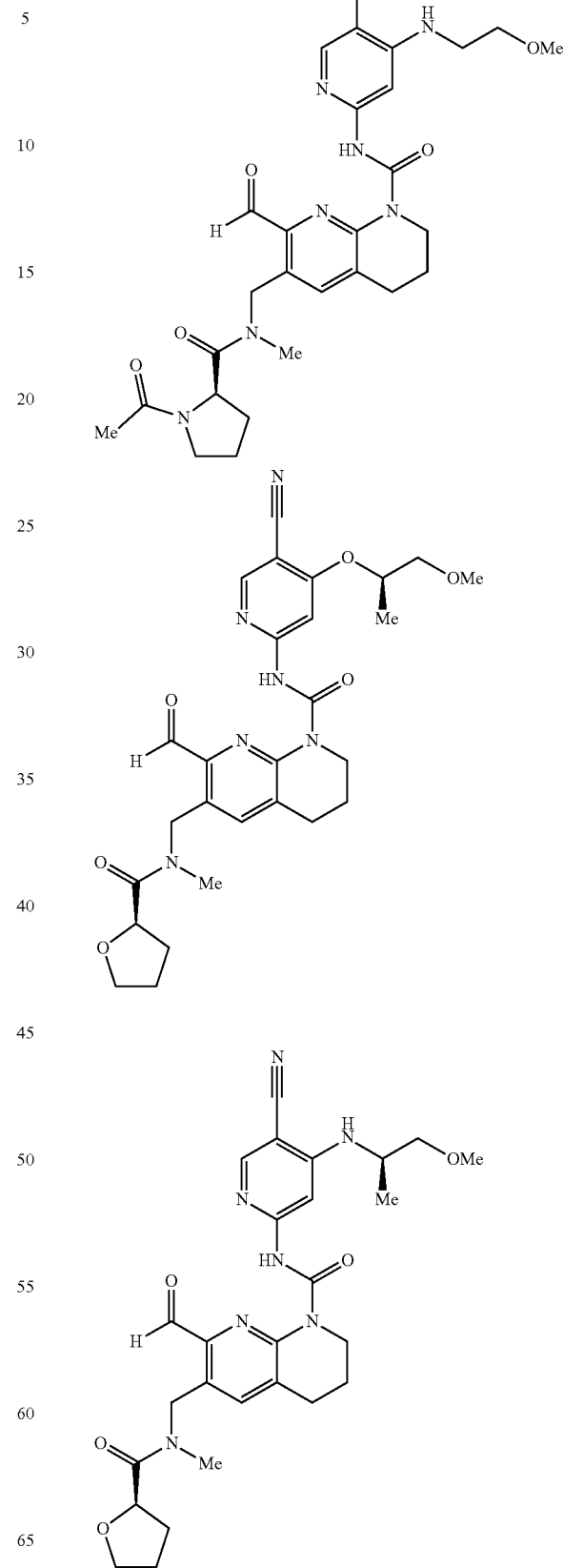

-continued
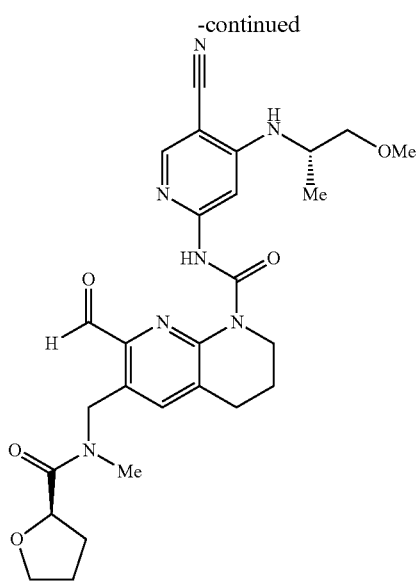
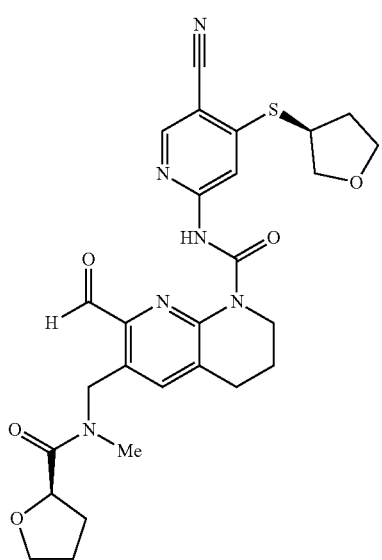
-continued
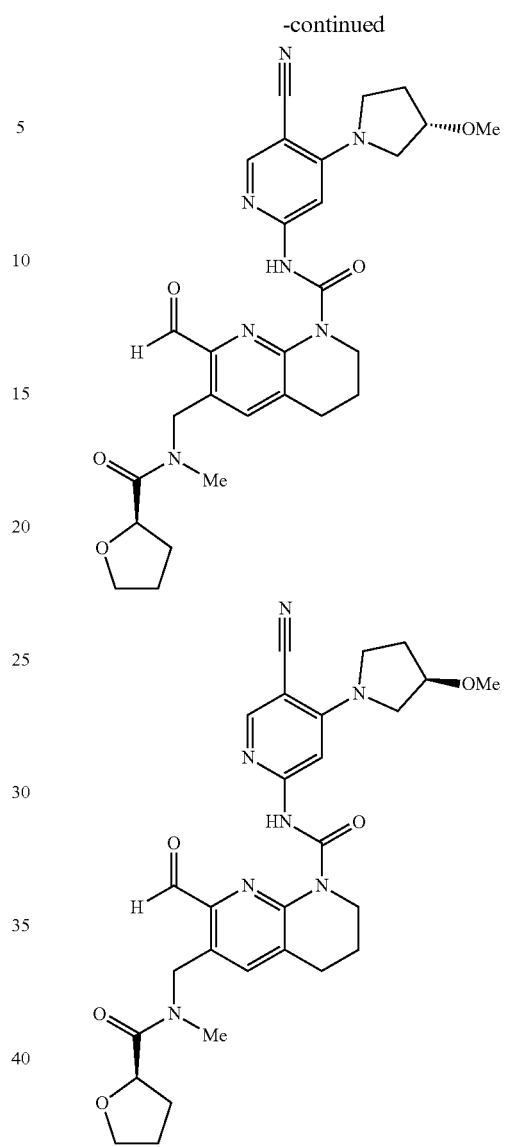

| 31 | 32 |
|---|---|
| -continued | -continued |
| 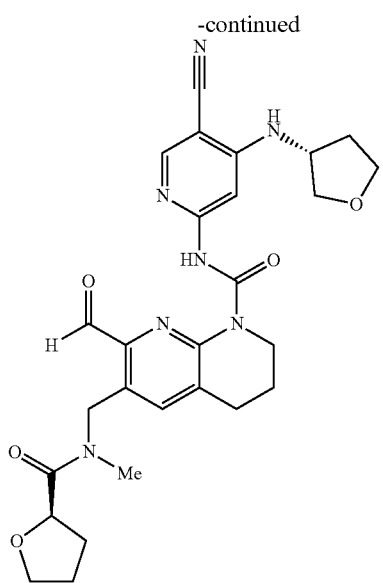 | 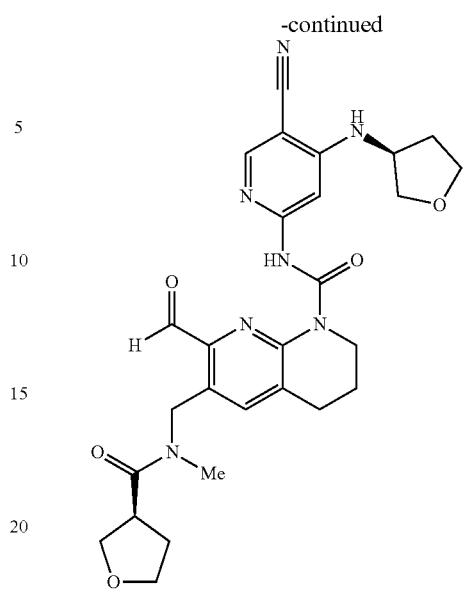 |
| 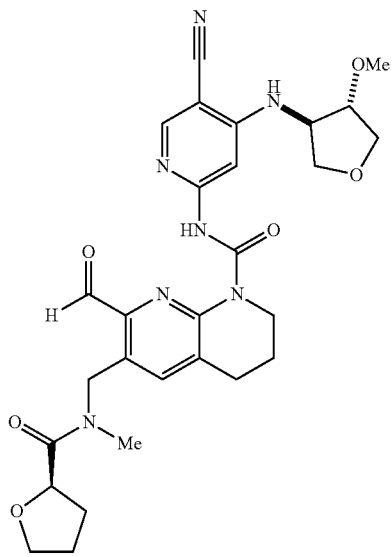 | 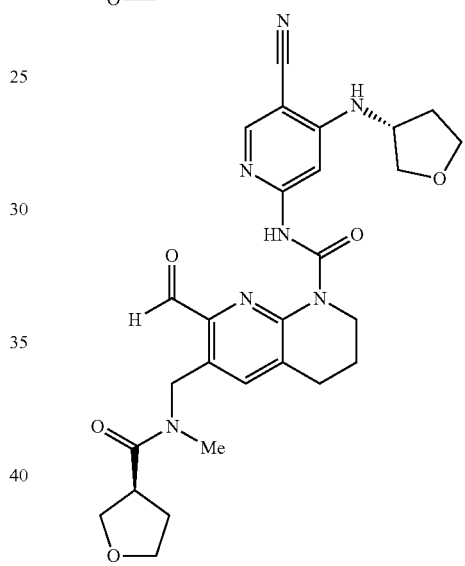 |
| 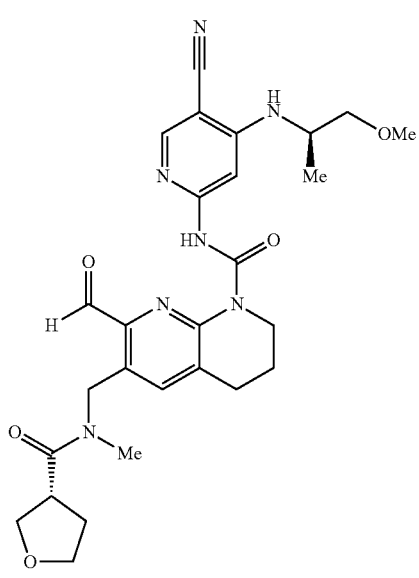 | 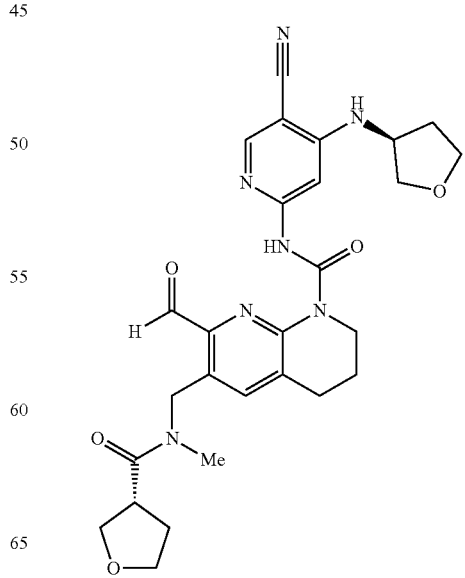 |

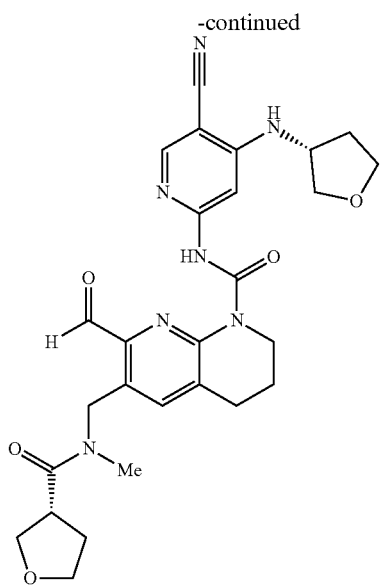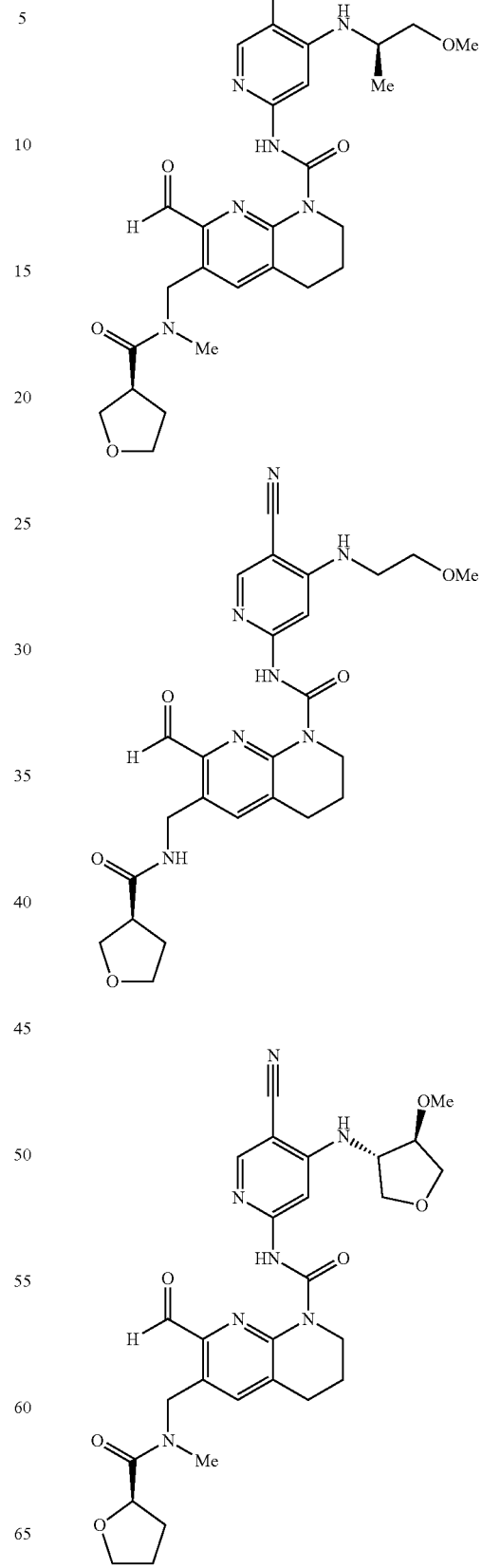

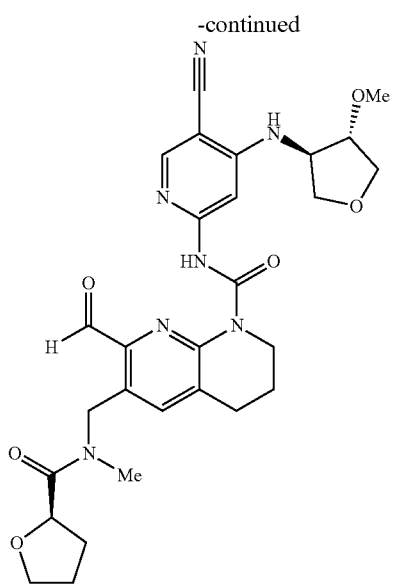
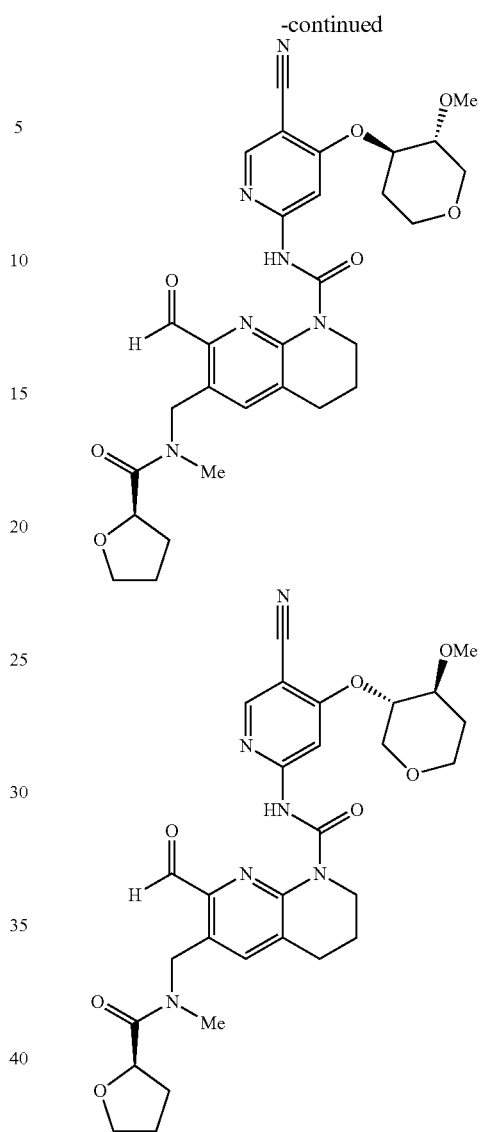
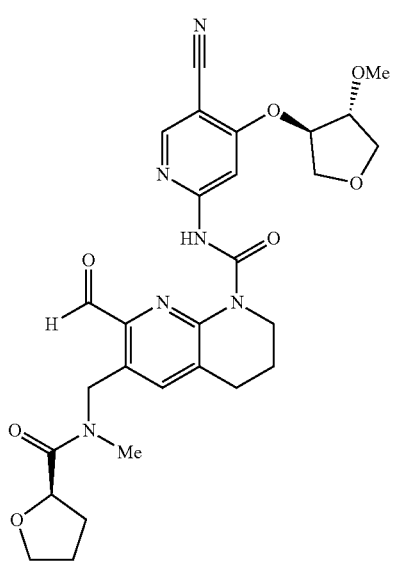
and

In a preferred embodiment, the compound of formula (I), the stereoisomer or the pharmaceutically acceptable salt thereof, is a compound of formula (III):

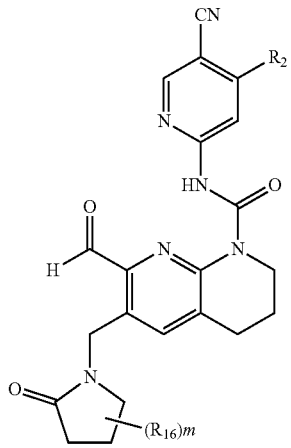

(III)

$R_{16}$ is a substituent selected from the group consisting of hydrogen, deuterium, halogen, thiol, cyano, $C_{1-8}$ alkyl, $C_{1-8}$ alkyloxy, nitro, azido, $C_{2-8}$ alkenyl, $C_{2-8}$ alkynyl, halo$C_{1-8}$ alkyl, $C_{3-8}$ cycloalkyl, 3 to 8 membered heterocyclyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, —$C_{0-8}$—$S(O)_rR_9$, —$C_{0-8}$—O—$R_{10}$, —$C_{0-8}$—$C(O)OR_{10}$, —$C_{0-8}$—$C(O)R_{11}$, —$C_{0-8}$—O—$C(O)R_{11}$, —$C_{0-8}$—$NR_{12}R_{13}$, —$C_{0-8}$—$C(O)NR_{12}R_{13}$, —$N(R_{12})$—$C(O)R_{11}$ and —$N(R_{12})$—$C(O)OR_{10}$, provided that the substituent is not hydroxy, acetyl, or di $C_{1-3}$ alkylamino; and m is 0, 1, 2, or 3.

In a further preferred embodiment, $R_{16}$ is selected from the group consisting of halogen, thiol, cyano, nitro, azido, allyl, alkynyl, trifluoromethyl, cyclopropyl, 3-oxetanyl, methoxy, ethoxy, isopropoxy, acetoxy, acetamido, amino, dimethylamino and ethoxycarbonyl.

In a preferred embodiment, the compound of formula (I), the stereoisomer or the pharmaceutically acceptable salt thereof, is a compound of the following formula (III-a), (III-b) or (III-c):

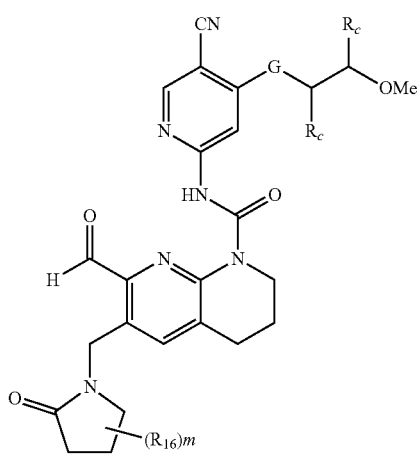

(III-a)

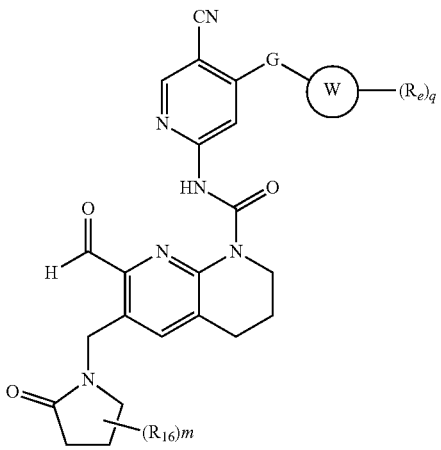

(III-b)

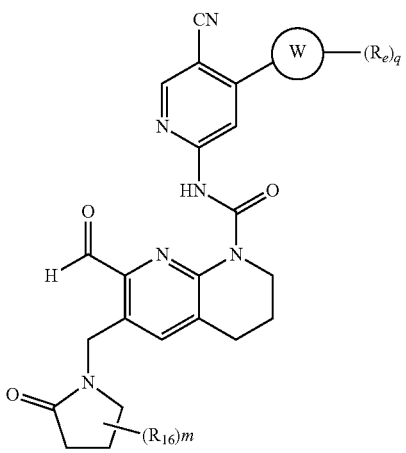

(III-c)

wherein:

G is selected from the group consisting of NH, O and S;

ring W is selected from the group consisting of $C_{3-8}$ cycloalkyl and 3 to 8 membered heterocyclyl, wherein the $C_{3-8}$ cycloalkyl and 3 to 8 membered heterocyclyl are each optionally substituted by one or more groups selected from the group consisting of hydrogen, halogen, $C_{1-8}$ alkyl, —$C_{0-8}$—$NR_{12}R_{13}$ and $C_{1-8}$ alkyloxy;

$R_c$ and $R_d$ are each independently selected from the group consisting of hydrogen, $C_{1-8}$ alkyl, $C_{1-8}$ alkyloxy and halogen;

$R_e$ is selected from the group consisting of hydrogen, halogen, $C_{1-8}$ alkyl, $C_{1-8}$ alkyloxy, and —$C_{0-8}$—$NR_{12}R_{13}$;

q is 0, 1, 2, or 3; and $R_{16}$ and m are as defined in formula (III)

In the most preferred embodiment, the compound of formula (I), the stereoisomer or the pharmaceutically acceptable salt thereof, includes but is not limited to:

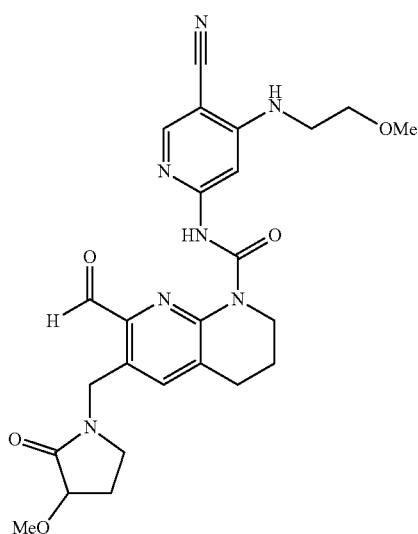
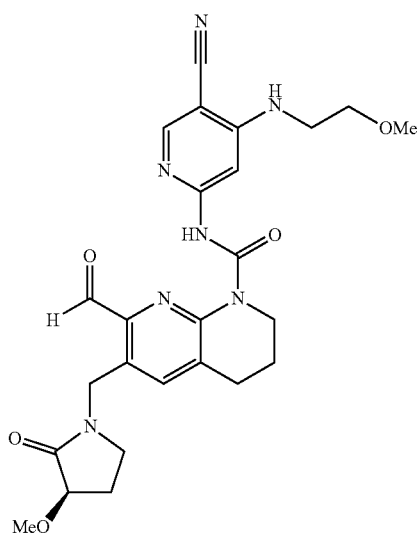
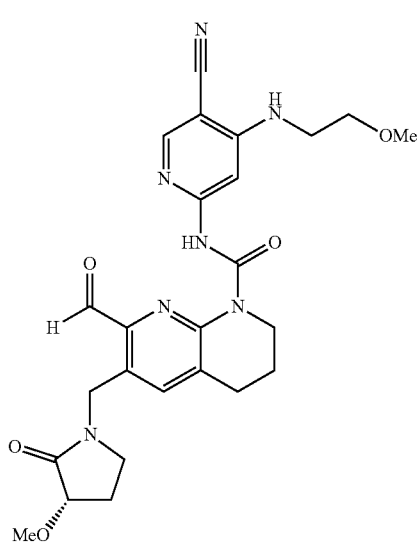
-continued
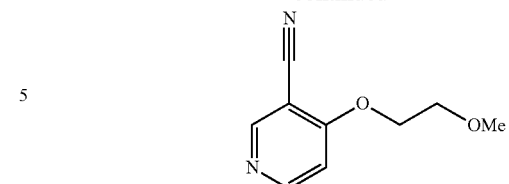
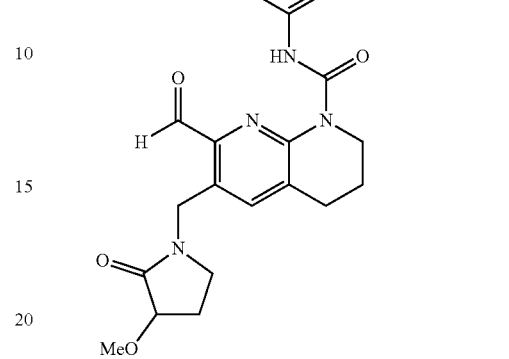
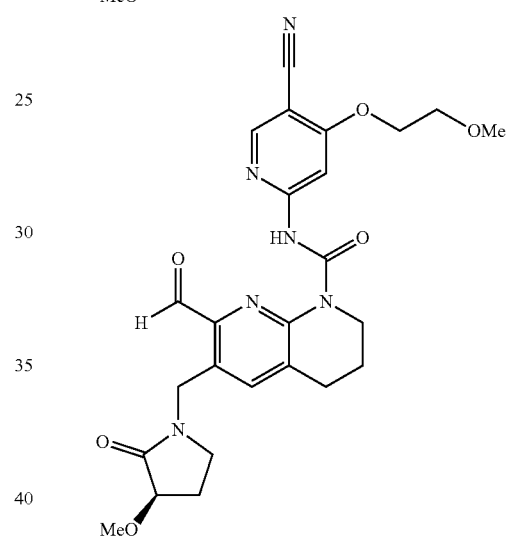
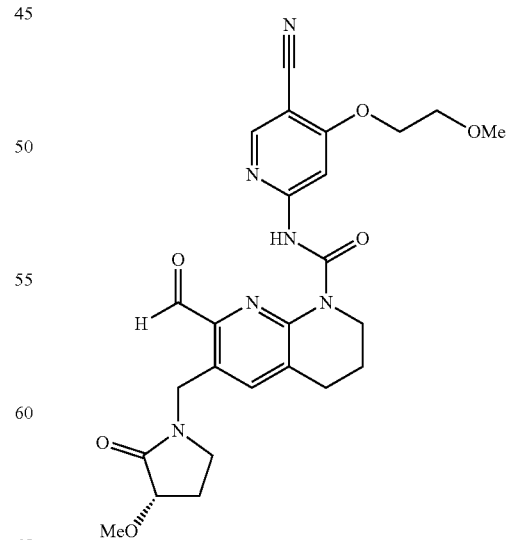

-continued
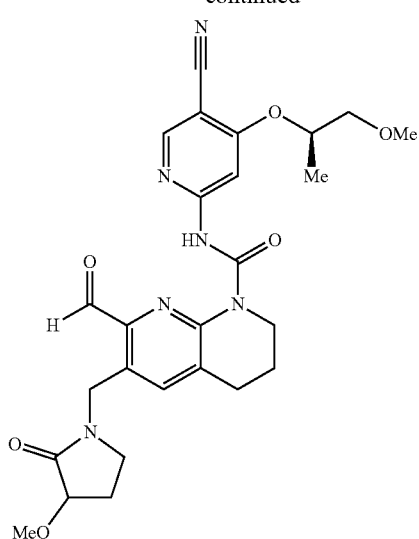
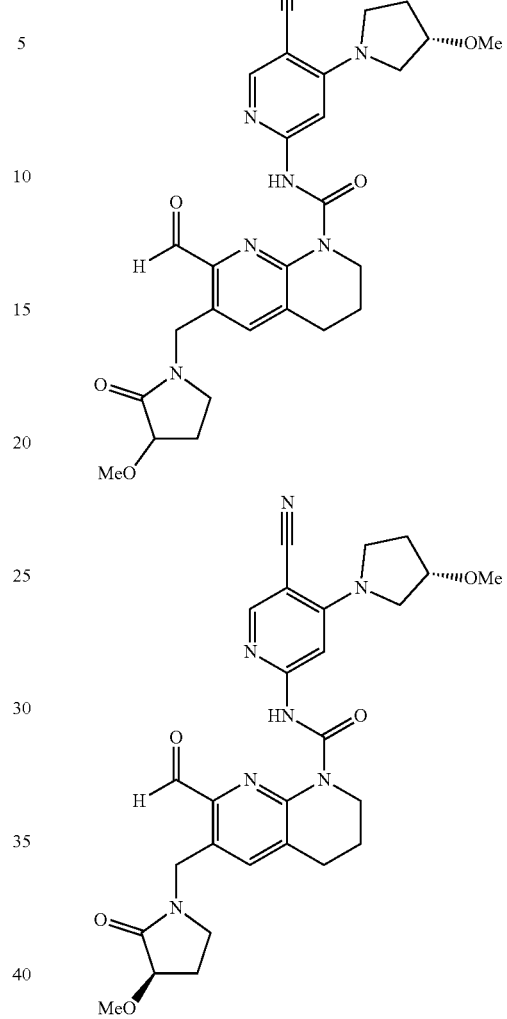
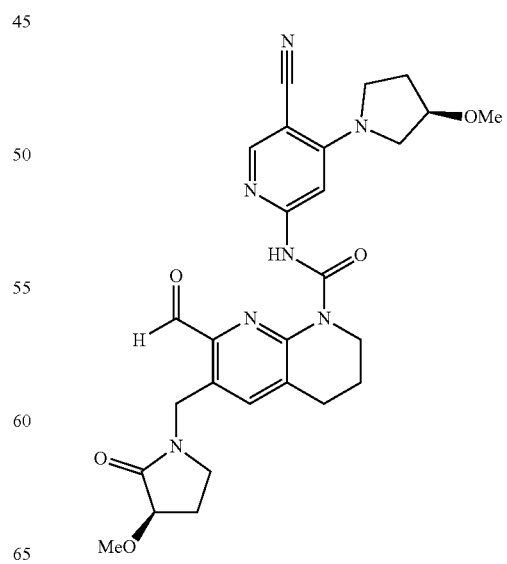

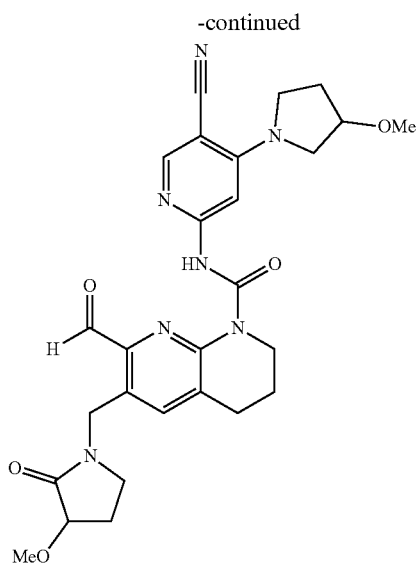
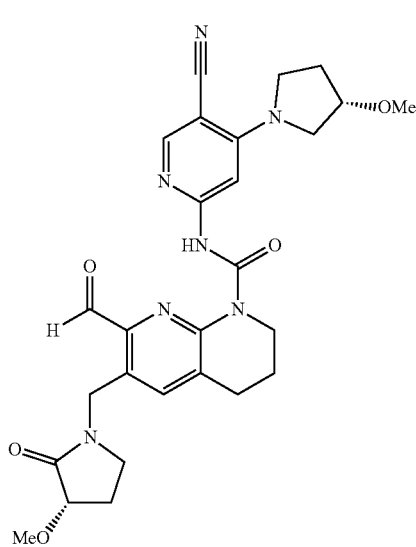
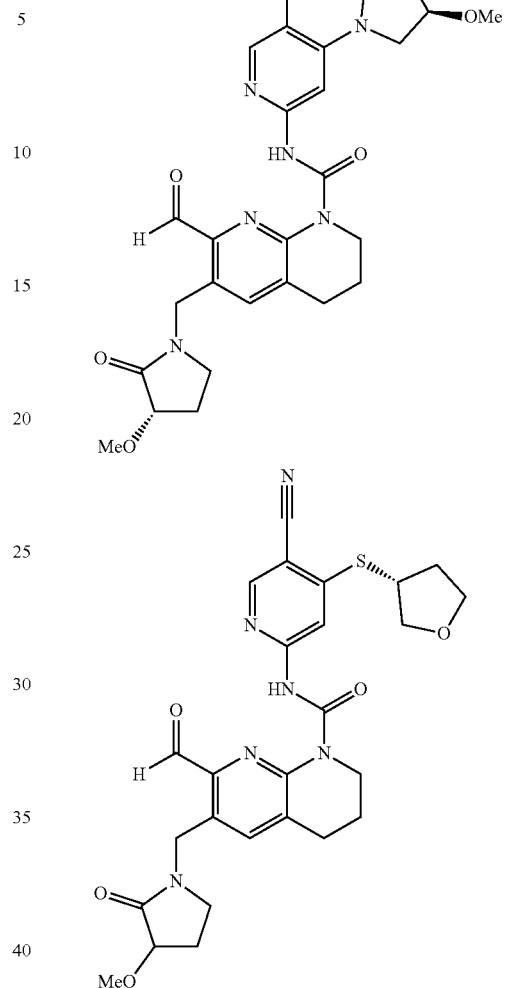
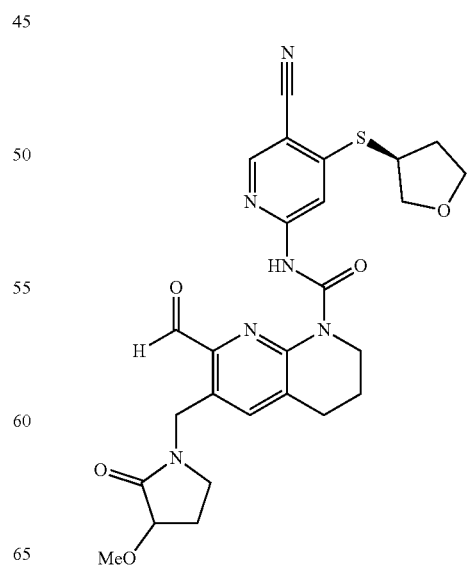

-continued
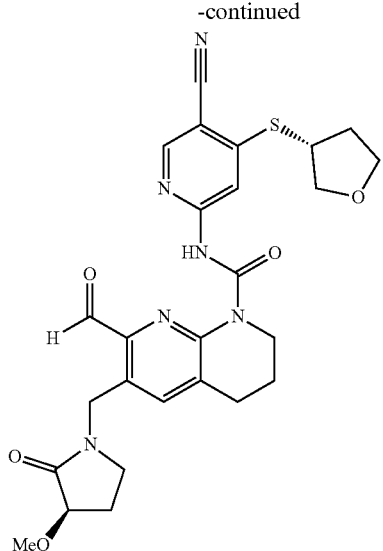
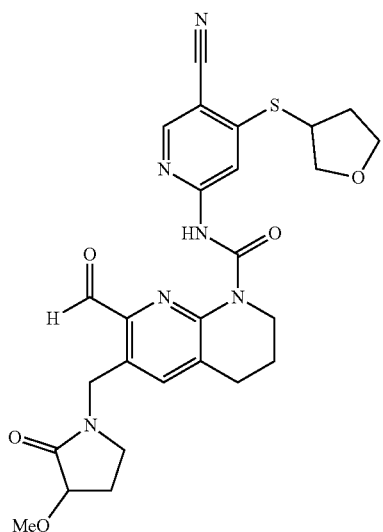
-continued
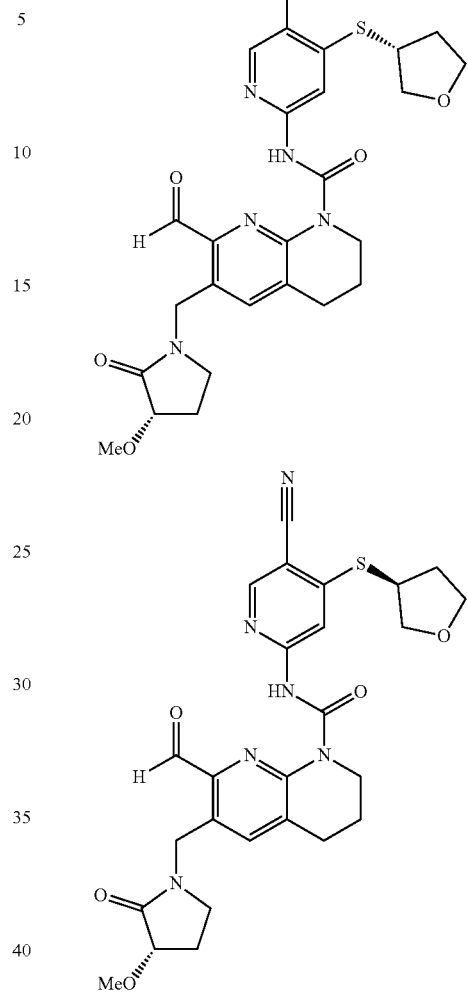
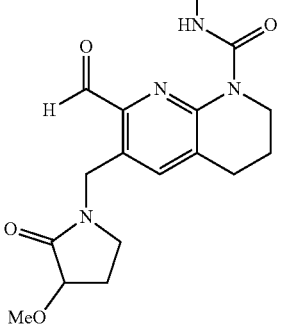

47
-continued
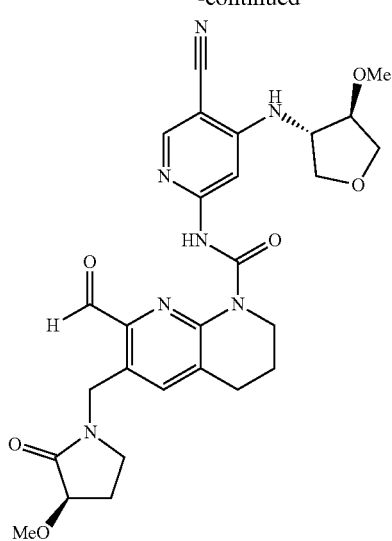
48
-continued
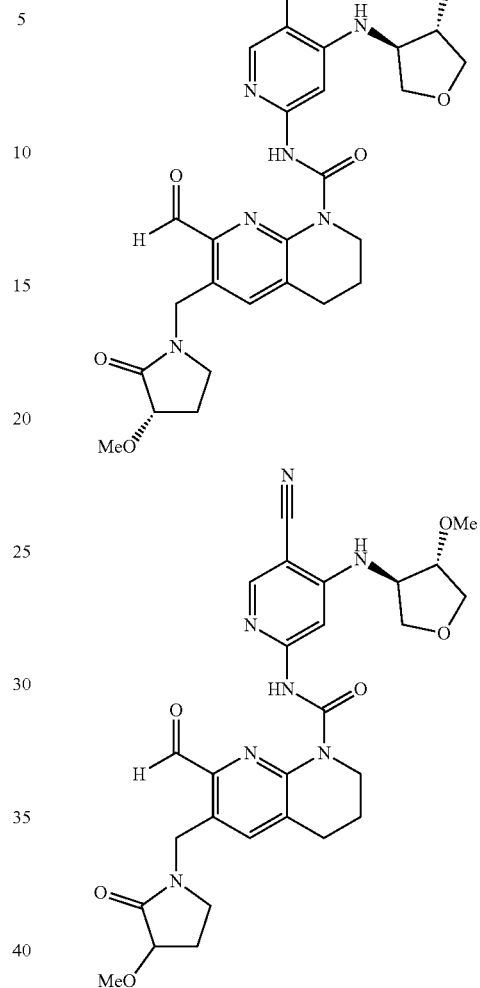
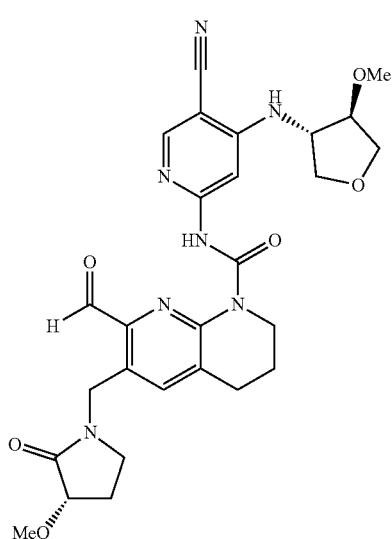
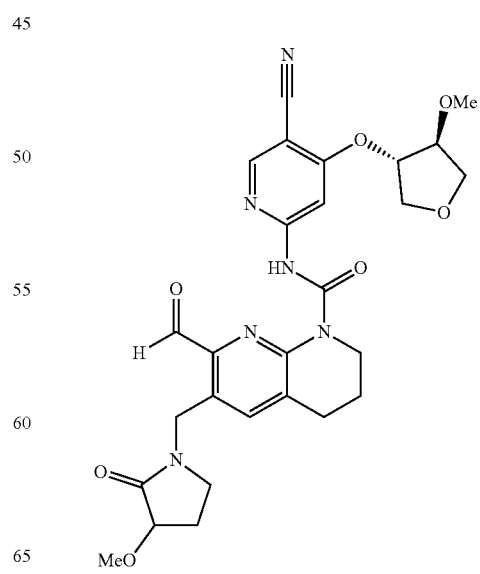

49
-continued
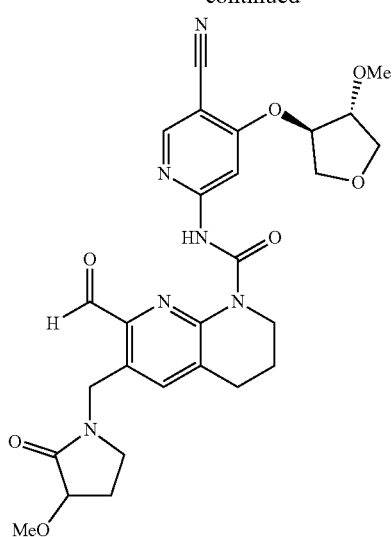
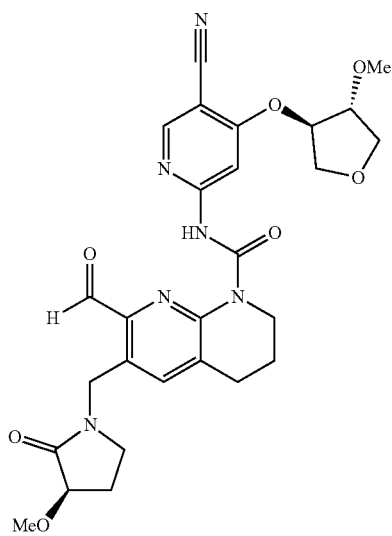
50
-continued
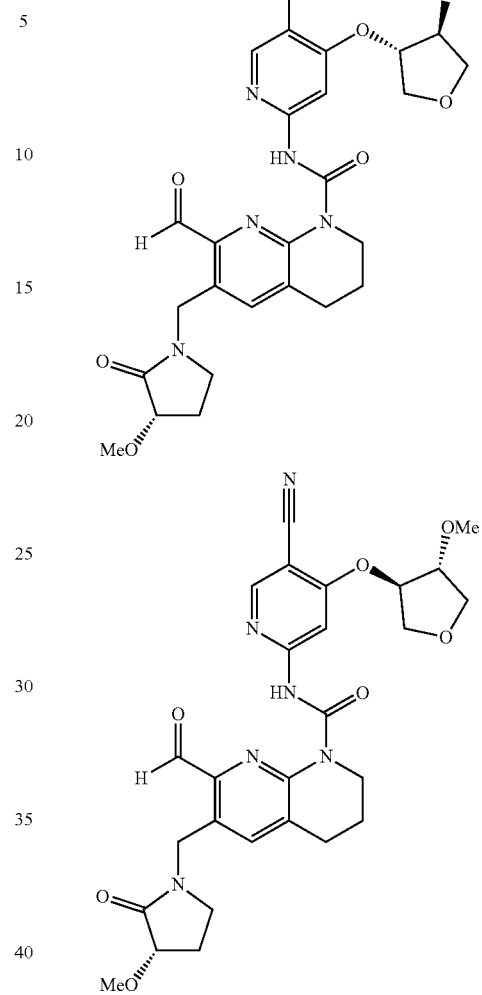
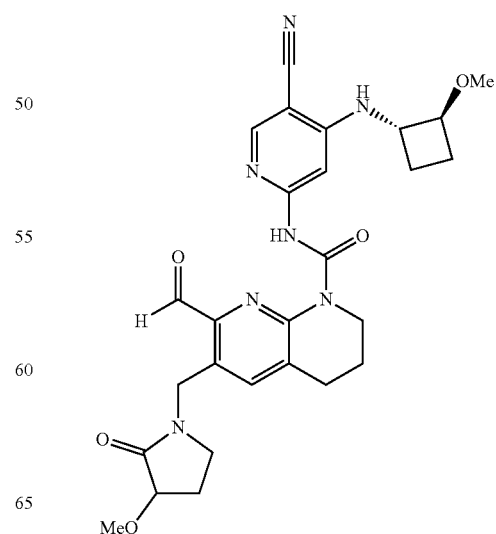

51
-continued
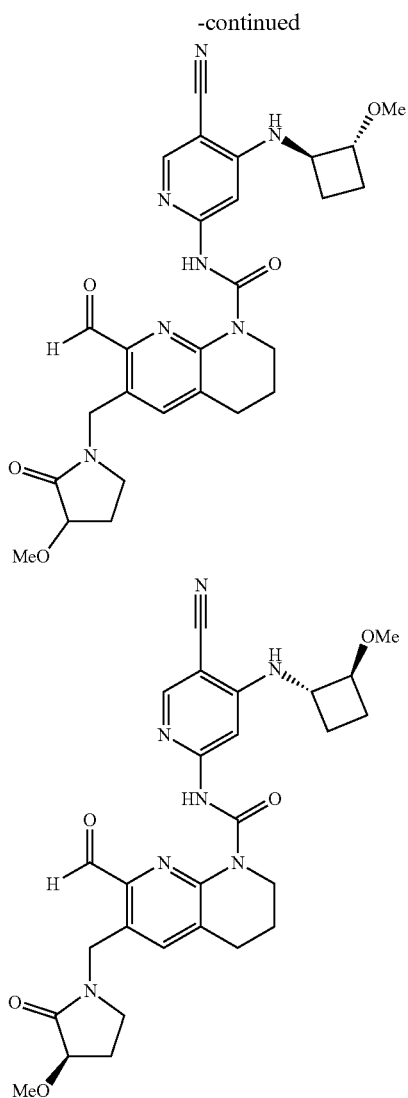
52
-continued
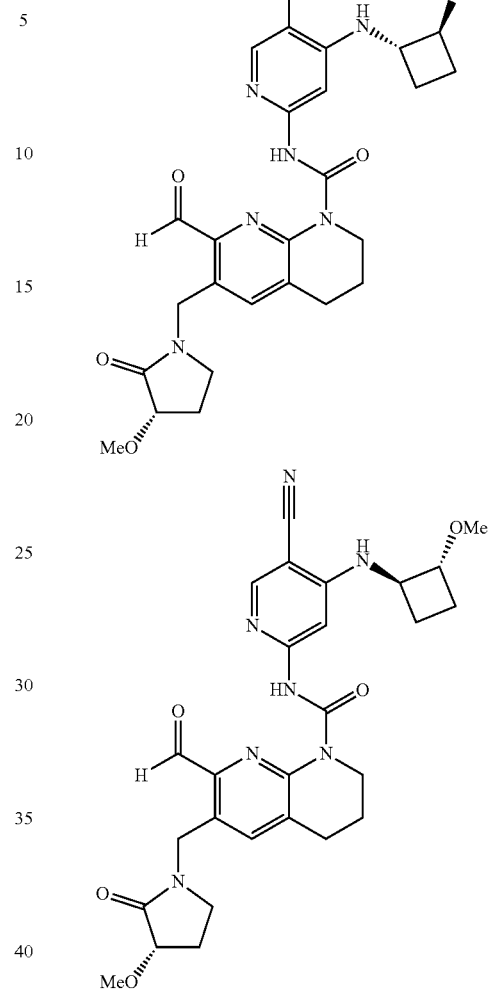
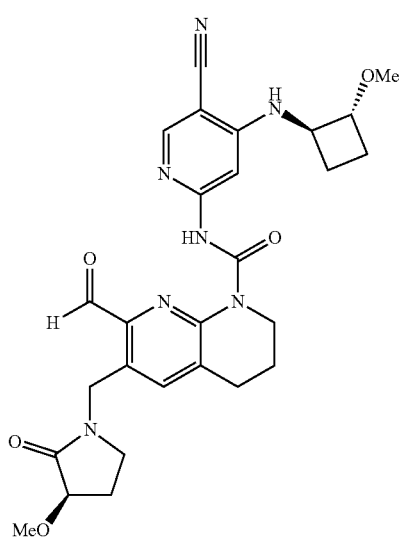
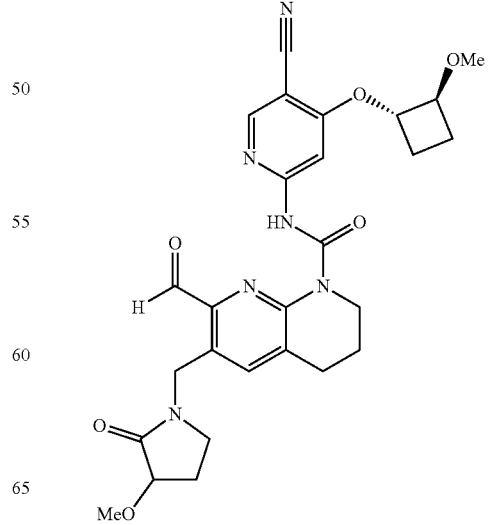

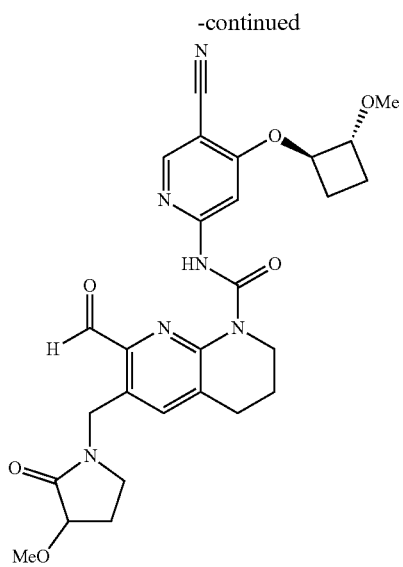
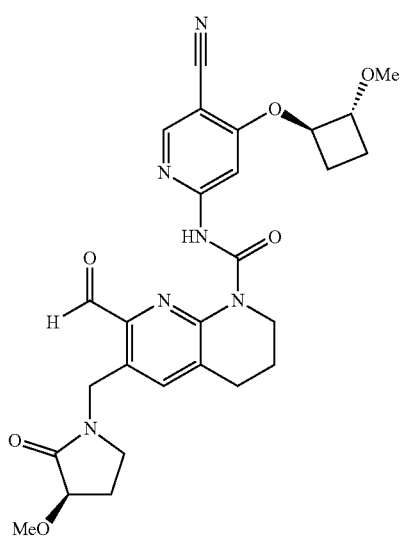
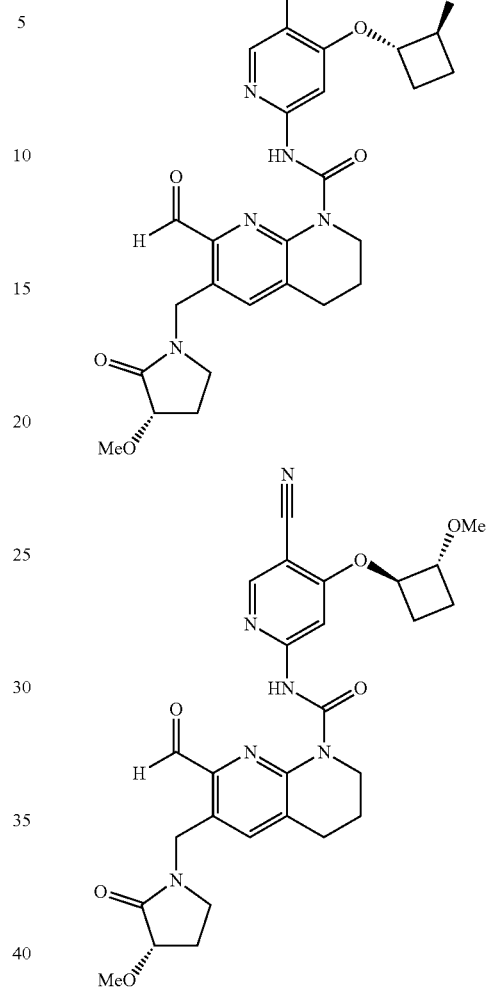

55
-continued
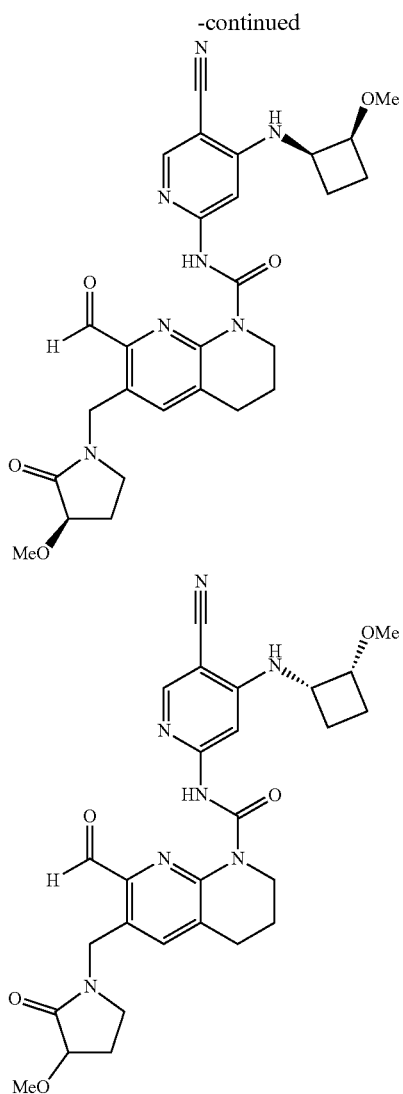
56
-continued
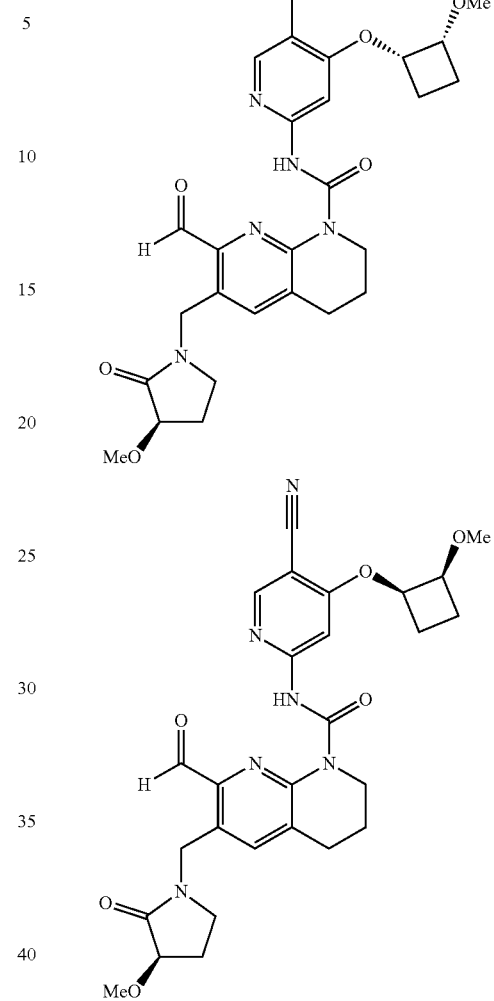
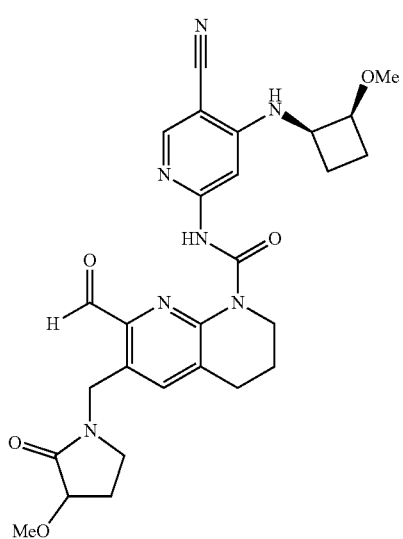
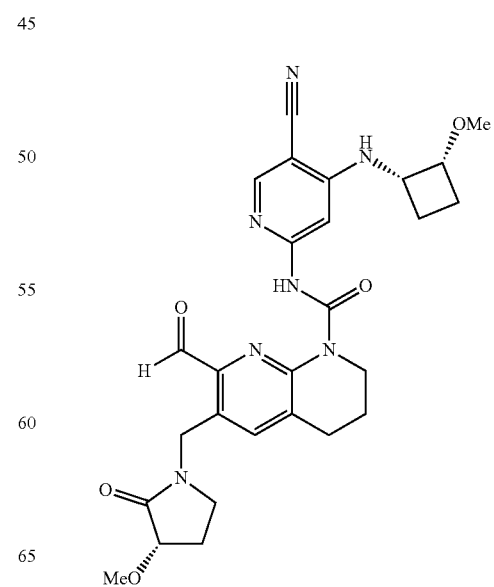

57
-continued
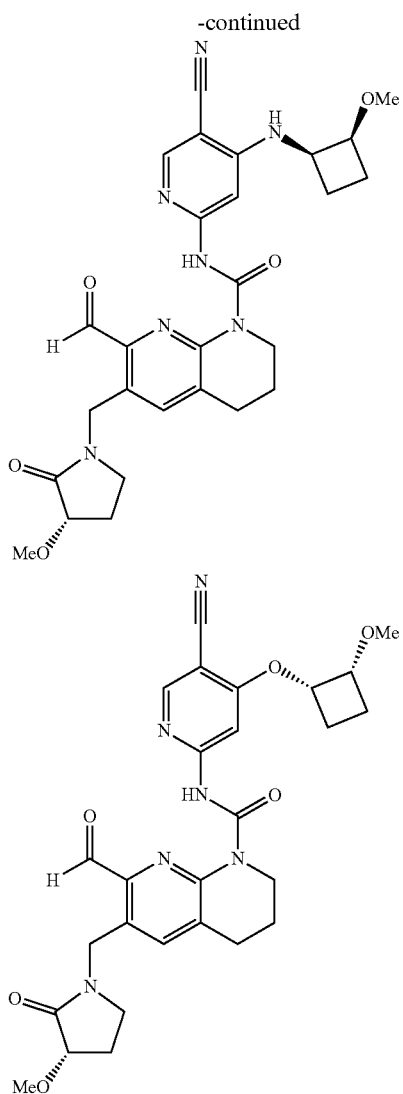
58
-continued
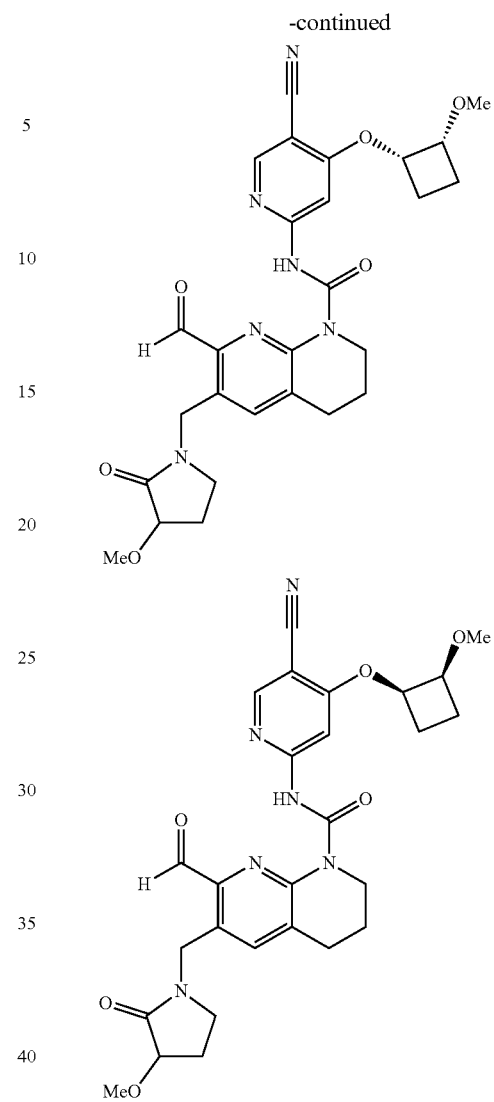
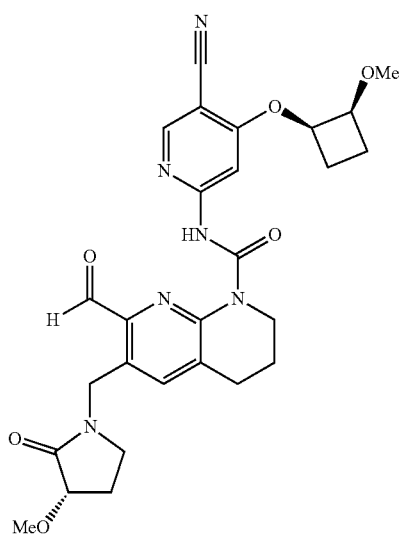
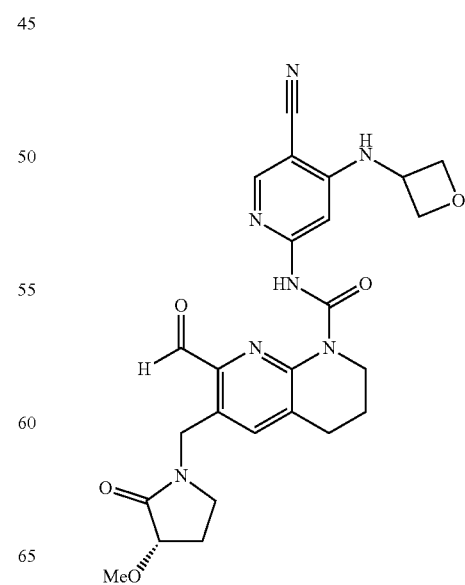

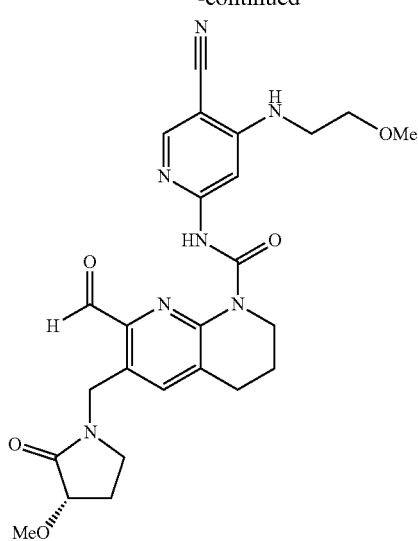
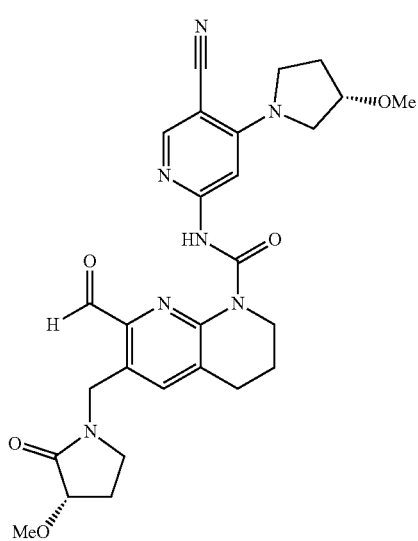
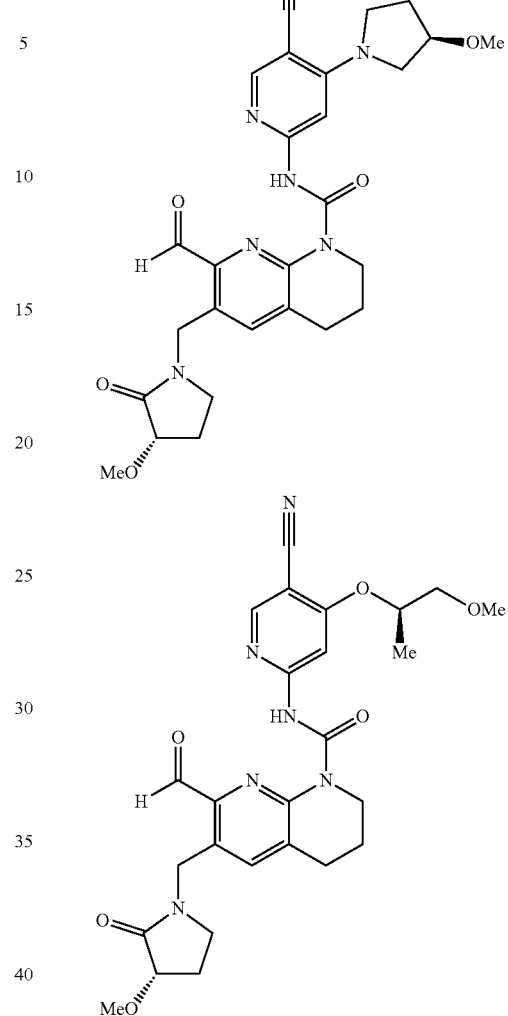
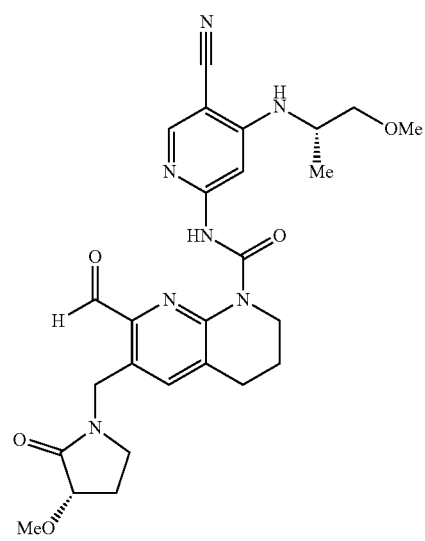

-continued
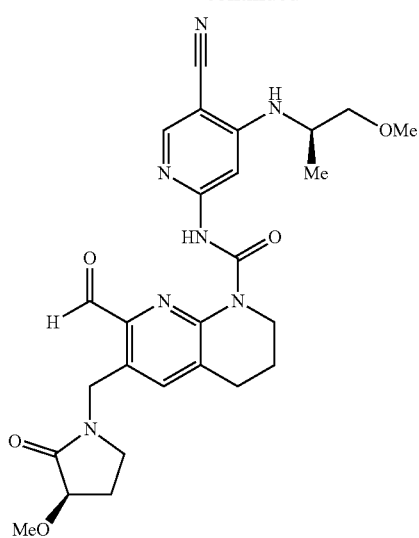
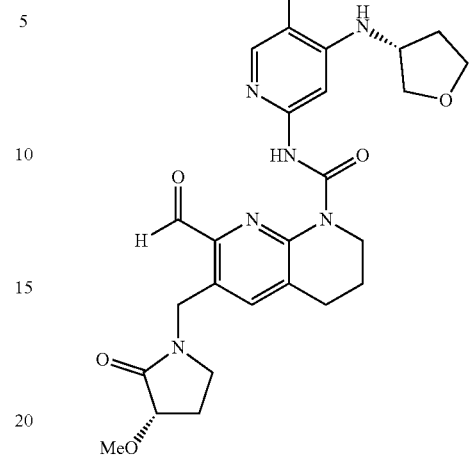
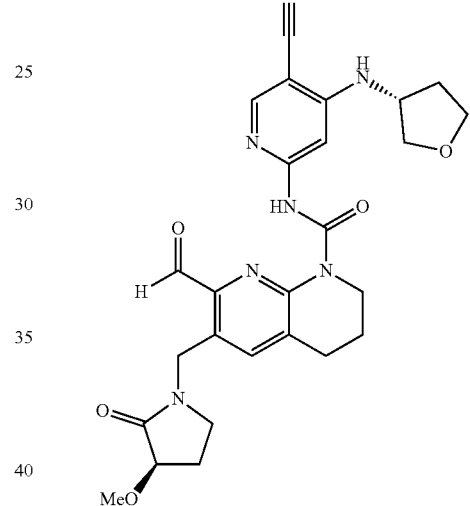
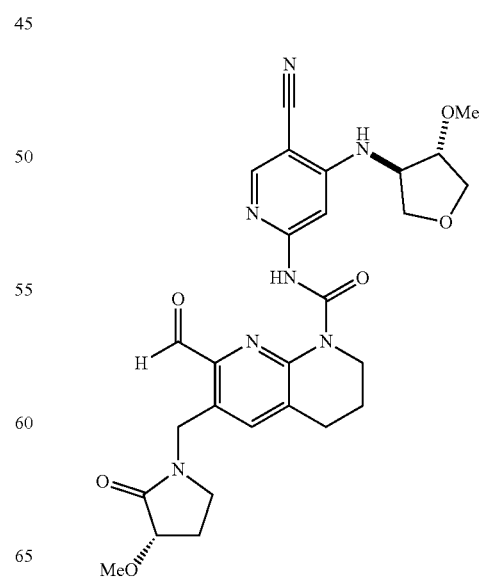
and

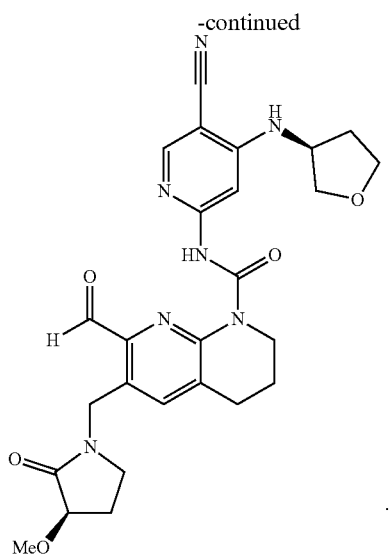

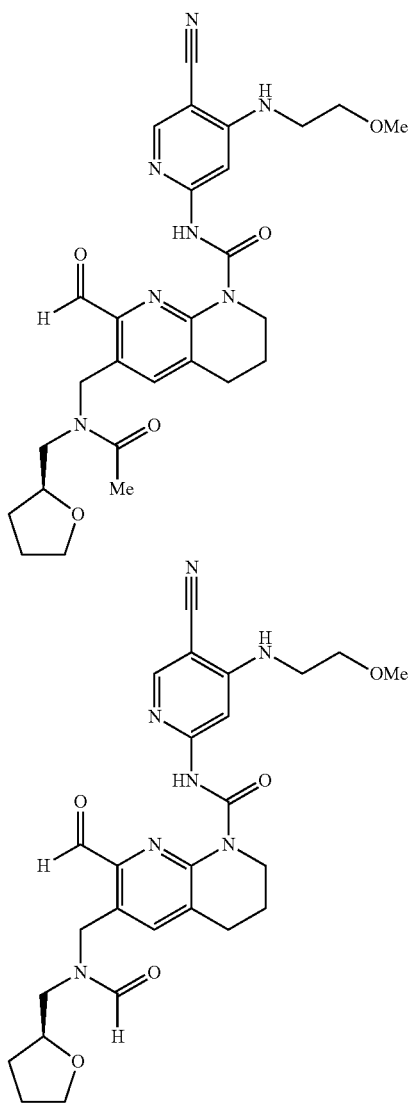

In a preferred embodiment, R₄ is selected from the group consisting of hydrogen, deuterium, $C_{1-8}$ alkyl, halo$C_{1-8}$ alkyl, $C_{1-8}$ alkyl substituted by $C_{1-8}$ alkyloxy, amino$C_{1-8}$ alkyl, hydroxy$C_{1-8}$ alkyl, $C_{1-8}$ alkyl substituted by $C_{3-8}$ cycloalkyl, $C_{1-8}$ alkyl substituted by 3 to 8 membered heterocyclyl, $C_{2-8}$ alkenyl, $C_{2-8}$ alkynyl, $C_{3-8}$ cycloalkyl, and 3 to 8 membered heterocyclyl; and R₅ is selected from the group consisting of hydrogen, $C_{1-8}$ alkyl, $C_{1-8}$ alkyl substituted by $C_{1-8}$ alkyloxy, halo$C_{1-8}$ alkyl, $C_{1-8}$ alkyl substituted by $C_{3-8}$ cycloalkyl$C_{1-8}$ alkyl substituted by 3 to 8 membered heterocyclyl, and hydroxy$C_{1-8}$ alkyl.

In a further preferred embodiment, R₄ is selected from the group consisting of hydrogen, deuterium, methyl, ethyl, isopropyl, trifluoromethyl, aminomethyl, cyclopropyl, cyclopropylmethyl, cyclobutyl, cyclobutylmethyl, cyclopentyl, cyclopentylmethyl, tetrahydrofuranyl, tetrahydrothienyl, tetrahydropyrrolyl, tetrahydroimidazolyl, tetrahydrofuranylmethyl, tetrahydrothienylmethyl, tetrahydropyrrolylmethyl, and tetrahydroimidazolylmethyl; and R₅ is selected from the group consisting of hydrogen, methyl, ethyl, isopropyl, trifluoromethyl, methoxymethyl, methoxyethyl, ethoxymethyl and ethoxyethyl.

In the most preferred embodiment, the compound of formula (I), the stereoisomer or the pharmaceutically acceptable salt thereof, includes is but not limited to:

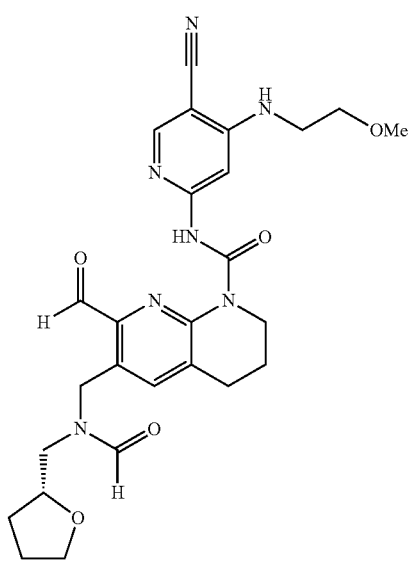

-continued
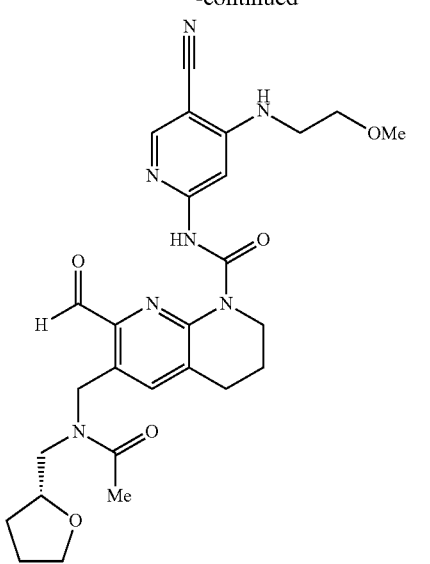
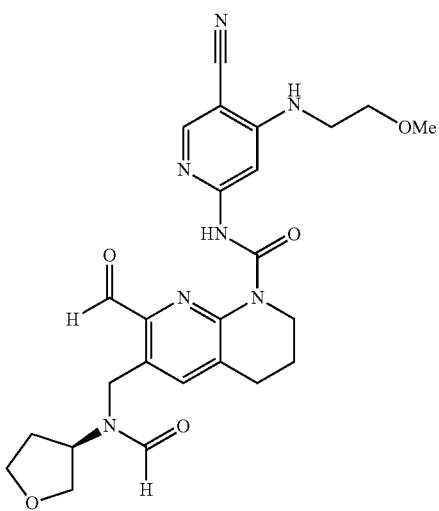
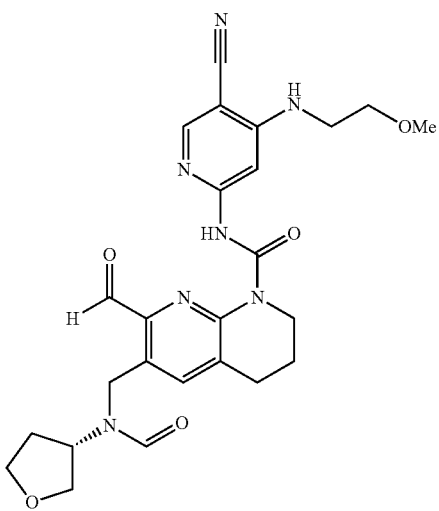
-continued
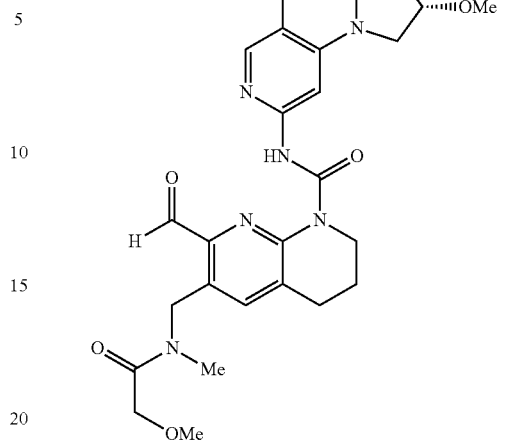
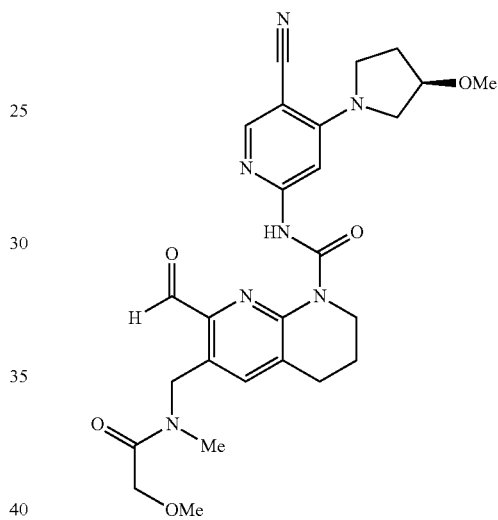
and
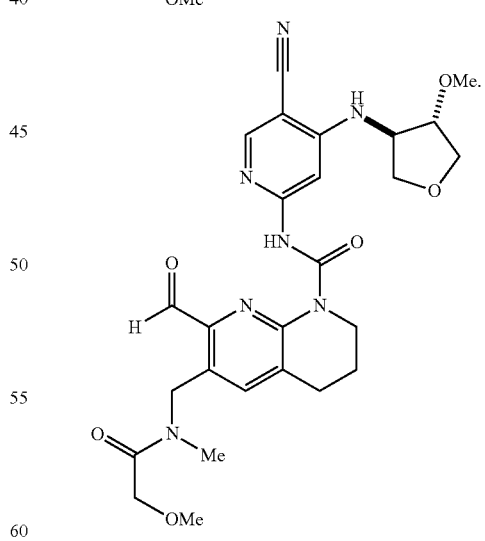
In the second aspect, the present invention provides a process for preparing the aforementioned compound of formula (I), the stereoisomer or the pharmaceutically acceptable salt thereof, comprising the steps of:

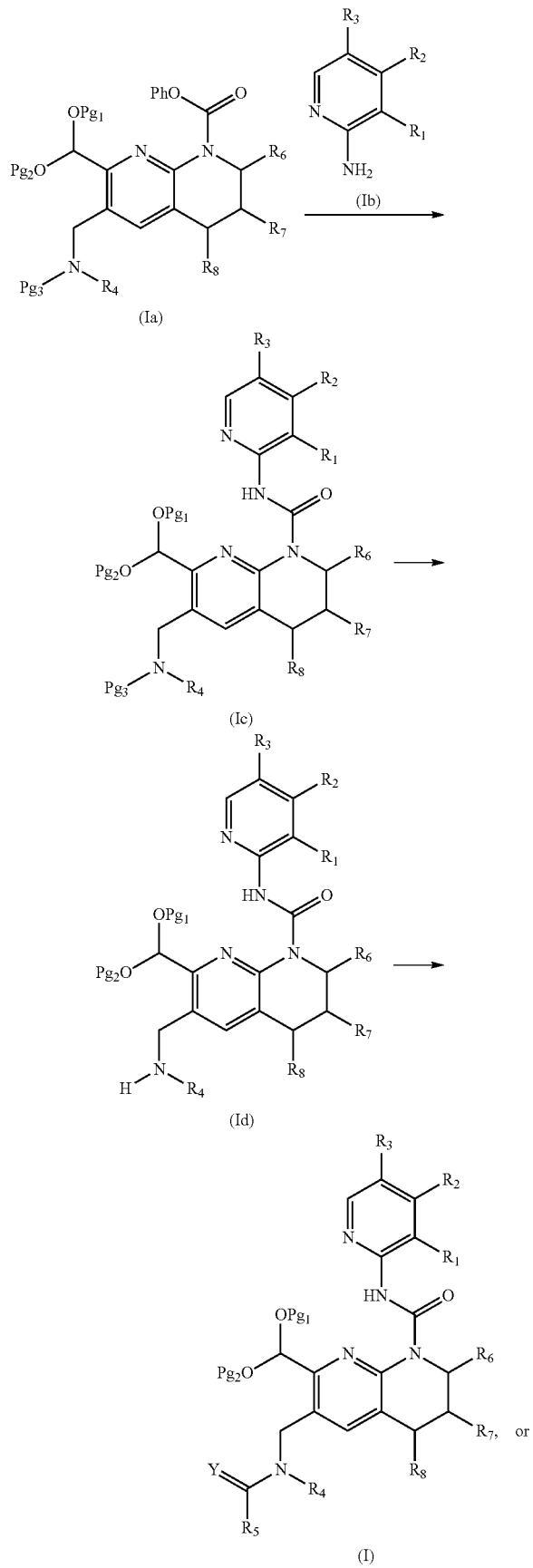
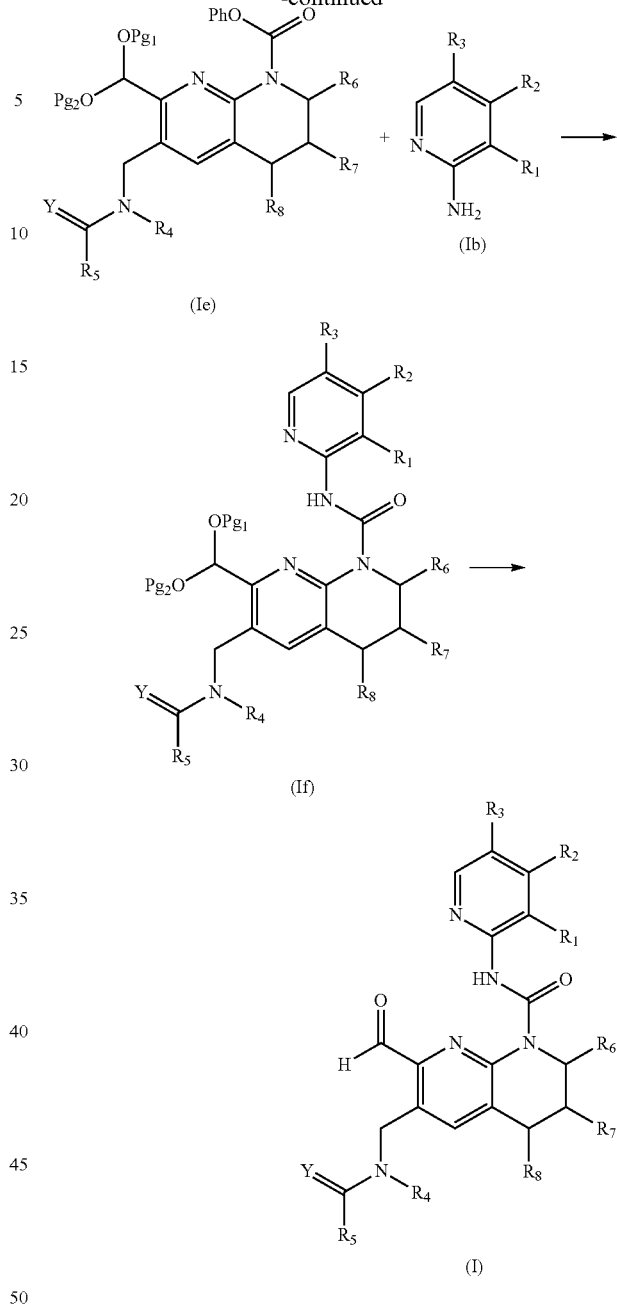

wherein: $R_1$, $R_2$, $R_3$, $R_4$, $R_5$, $R_6$, $R_7$, $R_8$, $R_9$, $R_{10}$, $R_{11}$, $R_{12}$, $R_{13}$, Y and r are as defined in formula (I);

$Pg_1$ and $Pg_2$ are hydroxy protecting groups, preferably, each is independently selected from the group consisting of benzyl, 2-tetrahydrofuranyl, methoxymethyl, ethoxyethyl, $C_{1-8}$ alkyl, allyl, trimethylsilyl, triethylsilyl, triisopropylsilyl, tert-butyldimethylsilyl, and tert-butyldiphenylsilyl, or, $Pg_1$ and $Pg_2$ are simultaneously selected from the group consisting of ethidene and propilidene, more preferably, $Pg_1$ and $Pg_2$ are each independently selected from the group consisting of methyl, ethyl and benzyl, or, $Pg_1$ and $Pg_2$ are simultaneously ethidene; and $Pg_3$ is an amino protecting group, preferably, tert-butoxycarbonyl, allylcarbonyl, fluorenylmethoxycarbonyl, methoxycarbonyl, ethoxycarbonyl, trimethylsilyl ethoxycarbonyl or benzyloxycarbonyl, and more preferably tert-butoxycarbonyl.

In another aspect, the present invention provides a pharmaceutical composition comprising a therapeutically effective amount of the compound of each aforementioned formula, a stereoisomer or a pharmaceutically acceptable salt thereof, and one or more pharmaceutically acceptable carriers, diluents or excipients. The present invention also relates to a method for preparing the aforementioned composition, comprising a step of mixing the compound of each aforementioned formula, a stereoisomer or a pharmaceutically acceptable salt thereof, with pharmaceutically acceptable carriers, diluents and excipients.

In the third aspect, the present invention provides a pharmaceutical composition comprising a therapeutically effective amount of the aforementioned compound of formula (I), the stereoisomer or the pharmaceutically acceptable salt thereof and a pharmaceutically acceptable carrier. In the fourth aspect, the present invention relates to a use of the aforementioned compound of formula (I), the stereoisomer or the pharmaceutically acceptable salt thereof, and the aforementioned pharmaceutical composition in the preparation of a FGFR4 inhibitor medicament.

The present invention also relates to a method for treating and/or preventing a disease having a pathological characteristic mediated by FGFR4 inhibitors, comprising administering to a patient a therapeutically effective amount of the compound of formula (I), the stereoisomer or the pharmaceutically acceptable salt thereof, or the pharmaceutical composition comprising the same.

In the fifth aspect, the present invention relates to a use of the aforementioned compound of formula (I), the stereoisomer or the pharmaceutically acceptable salt thereof, and the aforementioned pharmaceutical composition in the preparation of a medicament for treating cancer.

In another aspect, the present invention relates to a method for treating cancer, comprising administering to a patient a therapeutically effective amount of the compound of formula (I) of the present application, the stereoisomer or the pharmaceutically acceptable salt thereof. The method exhibits outstanding efficacy and fewer side effects, wherein the cancer can be selected from the group consisting of breast cancer, cervical cancer, colon cancer, lung cancer, gastric cancer, rectal cancer, pancreatic cancer, brain cancer, skin cancer, oral cancer, prostate cancer, bone cancer, kidney cancer, ovarian cancer, bladder cancer, liver cancer, tubal tumor, ovarian tumor, peritoneal cancer, phase IV melanoma, glioma, rhabdomyosarcoma, glioblastoma, hepatocellular carcinoma, papillomatosis, head and neck tumor, leukemia, lymphoma, myeloma and non-small cell lung cancer. In a preferred embodiment, the cancer is selected from the group consisting of liver cancer, gastric cancer, prostate cancer, skin cancer, ovarian cancer, lung cancer, breast cancer, colon cancer, glioma and rhabdomyosarcoma.

DETAILED DESCRIPTION OF THE INVENTION

Detailed description: unless otherwise stated, the following terms which are used in the description and the claims have the following meanings.

"$C_{1-8}$ alkyl" refers to a straight chain or branched chain alkyl group having 1 to 8 carbon atoms, alkyl refers to a saturated aliphatic hydrocarbon group, preferably an alkyl group having 1 to 6 carbon atoms, and more preferably an alkyl group having 1 to 3 carbon atoms, for example, methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl and various branched chain isomers thereof and the like.

"Cycloalkyl" refers to a saturated or partially unsaturated monocyclic or polycyclic hydrocarbon group, "$C_{3-8}$ cycloalkyl" refers to a cycloalkyl group having 3 to 8 carbon atoms, preferably having 3 to 6 carbon atoms, and more preferably having 4 to 6 carbon atoms, for example:

Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like.

Polycyclic cycloalkyl includes a cycloalkyl having a spiro ring, fused ring and bridged ring. "Spiro cycloalkyl" refers to a polycyclic group with rings connected through one common carbon atom (called a spiro atom), wherein these rings can contain one or more double bonds, but none of the rings has a completely conjugated π electronic system. According to the number of the spiro atoms shared between the rings, spiro cycloalkyl can be divided into mono-spiro cycloalkyl, di-spiro cycloalkyl or poly-spiro cycloalkyl. Non-limiting examples of spiro cycloalkyl include:

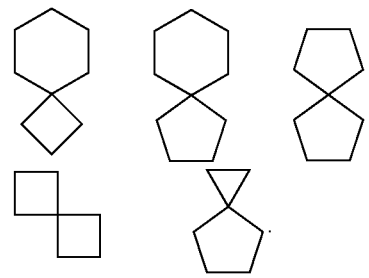

"Fused cycloalkyl" refers to an all-carbon polycyclic group in which each ring in the system shares an adjacent pair of carbon atoms with another ring, wherein one or more rings can contain one or more double bonds, but none of the rings has a completely conjugated 21 electronic system. According to the number of membered rings, fused-cycloalkyl can be divided into bicyclic, tricyclic, tetracyclic or polycyclic fused cycloalkyl. Non-limiting examples of fused cycloalkyl include:

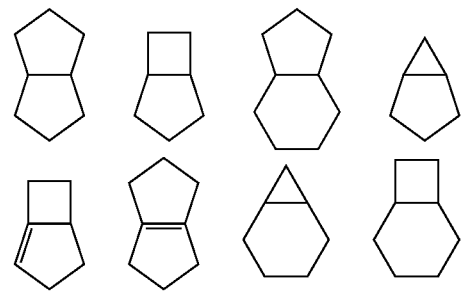

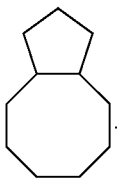

"Bridged cycloalkyl" refers to an all-carbon polycyclic group in which any two rings in the system share two disconnected carbon atoms, wherein these rings can contain one or more double bonds, but none of the rings has a completely conjugated π electronic system. According to the number of membered rings, bridged cycloalkyl can be divided into bicyclic, tricyclic, tetracyclic or polycyclic bridged cycloalkyl. Non-limiting examples of bridged cycloalkyl include:

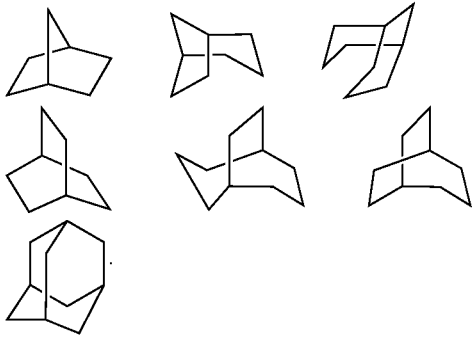

The cycloalkyl ring can be fused to the ring of aryl, heteroaryl or heterocyclyl, wherein the ring connected with the parent structure is the cycloalkyl. Non-limiting examples include indanyl, tetrahydronaphthyl, benzocycloheptylalkyl and the like.

The cycloalkyl can be optionally substituted or unsubstituted. When the cycloalkyl is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3 to 8 membered heterocyclyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$, and —N(R$_{12}$)—C(O)OR$_{10}$.

"Heterocyclyl" refers to a saturated or partially unsaturated monocyclic or polycyclic hydrocarbon group, wherein one or more ring atoms are heteroatoms selected from the group consisting of nitrogen, oxygen and S(O)$_r$ (wherein r is an integer of 0, 1, and 2), but the cyclic part does not include —O—O—, —O—S— or —S—S—, and the remaining ring atoms are carbon. "5 to 10 membered heterocyclyl" refers to a heterocyclyl group having 5 to 10 ring atoms, "3 to 8 membered heterocyclyl" refers to a heterocyclyl group having 3 to 8 ring atoms, preferably 5 to 6 membered heterocyclyl.

Non-limiting examples of monocyclic heterocyclyl include pyrrolidinyl, tetrahydrofuranyl, piperidinyl, pyranyl, piperazinyl, morpholinyl, thiomorpholinyl, homopiperazinyl and the like, preferably pyrrolidinyl, tetrahydrofuranyl and pyranyl.

Polycyclic heterocyclyl includes a heterocyclyl having a spiro ring, fused ring and bridged ring. "Spiro heterocyclyl" refers to a polycyclic heterocyclyl group with rings connected through one common atom (called a spiro atom), wherein one or more ring atoms are heteroatoms selected from the group consisting of nitrogen, oxygen and S(O)$_r$ (wherein r is an integer of 0, 1, and 2), and the remaining ring atoms are carbon. These rings can contain one or more double bonds, but none of the rings has a completely conjugated π electronic system. According to the number of the spiro atoms shared between the rings, spiro cycloalkyl can be divided into mono-spiro heterocyclyl, di-spiro heterocyclyl or poly-spiro heterocyclyl. Non-limiting examples of spiro heterocyclyl include:

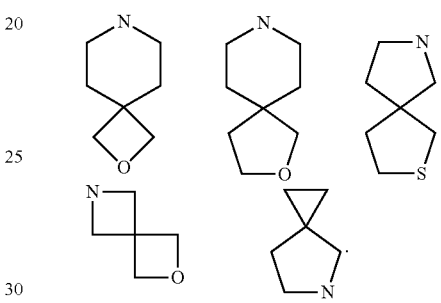

"Fused heterocyclyl" refers to a polycyclic heterocyclyl group in which each ring in the system shares an adjacent pair of atoms with another ring, wherein one or more rings can contain one or more double bonds, but none of the rings has a completely conjugated π electronic system, and wherein one or more ring atoms are heteroatoms selected from the group consisting of nitrogen, oxygen and S(O)$_r$ (wherein r is an integer of 0, 1 and 2), and the remaining ring atoms are carbon. According to the number of membered rings, fused heterocyclyl can be divided into bicyclic, tricyclic, tetracyclic or polycyclic fused heterocyclyl. Non-limiting examples of fused heterocyclyl include:

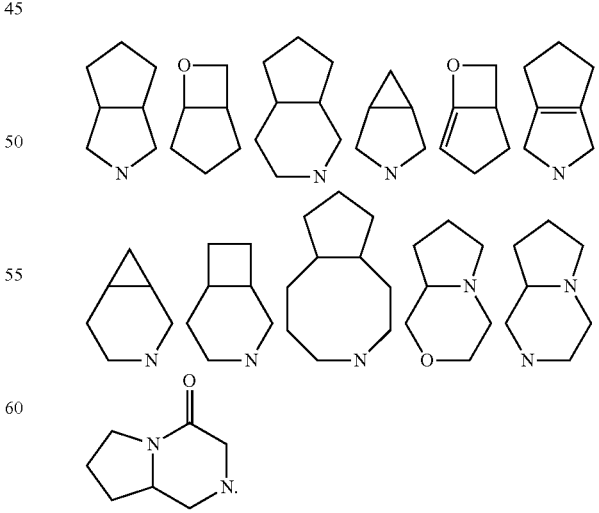

"Bridged heterocyclyl" refers to a polycyclic heterocyclic group in which any two rings in the system share two disconnected atoms, wherein the rings can contain one or more double bonds, but none of the rings has a completely conjugated π electronic system, and one or more ring atoms are heteroatoms selected from the group consisting of nitrogen, oxygen and S(O)$_r$ (wherein r is an integer of 0, 1 and 2), and the remaining ring atoms are carbon. According to the number of membered rings, bridged heterocyclyl can be divided into bicyclic, tricyclic, tetracyclic or polycyclic bridged heterocyclyl. Non-limiting examples of bridged heterocyclyl include:

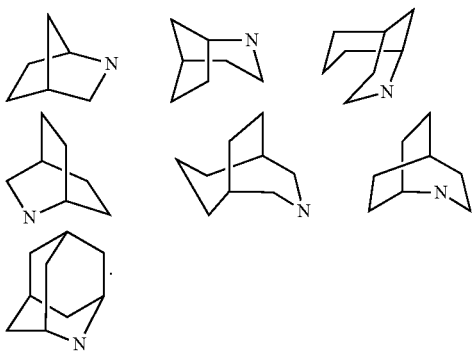

The heterocyclyl ring can be fused to the ring of aryl, heteroaryl or cycloalkyl, wherein the ring connected with the parent structure is the heterocyclyl. Non-limiting examples include:

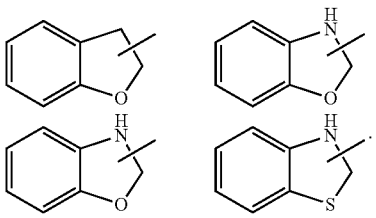

The heterocyclyl can be optionally substituted or unsubstituted. When the heterocyclyl is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3 to 8 membered heterocyclyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$.

"Aryl" refers to an all-carbon monocycle or fused polycycle (i.e, a ring in the system shares an adjacent pair of carbon atoms with another ring) with a conjugated π electronic system. "$C_{5-10}$ aryl" refers to an all-carbon aryl group having 5 to 10 carbon atoms, "5 to 10 membered aryl" refers to an all-carbon aryl group having 5 to 10 carbon atoms, preferably 5 to 8 membered aryl, and more preferably 5 to 6 membered aryl, for example, phenyl and naphthyl. The aryl ring can be fused to the ring of heteroaryl, heterocyclyl or cycloalkyl, wherein the ring connected with the parent structure is aryl. Non-limiting examples include:

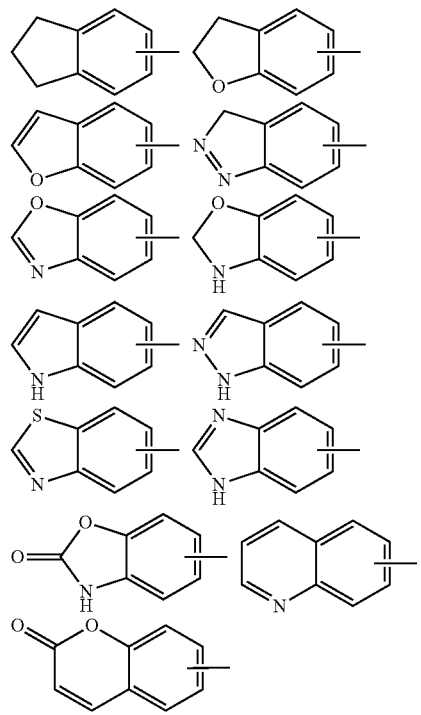

The aryl can be substituted or unsubstituted. When the alkyl is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3 to 8 membered heterocyclyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$.

"Heteroaryl" refers to a heteroaromatic system having 1 to 4 heteroatoms, wherein the heteroatoms include nitrogen, oxygen and S(O)r (wherein r is an integer of 0, 1, and 2). 5 to 7 membered heteroaryl refers to a heteroaromatic system having 5 to 7 ring atoms, 5 to 10 membered heteroaryl refers to a heteroaromatic system having 5 to 10 ring atoms, preferably 5 to 6 membered heteroaryl, for example, furanyl, thienyl, pyridyl, pyrrolyl, N-alkyl pyrrolyl, pyrimidinyl, pyrazinyl, imidazolyl, tetrazolyl and the like. The heteroaryl ring can be fused to the ring of aryl, heterocyclyl or cycloalkyl, wherein the ring connected with the parent structure is heteroaryl. Non-limiting examples include:

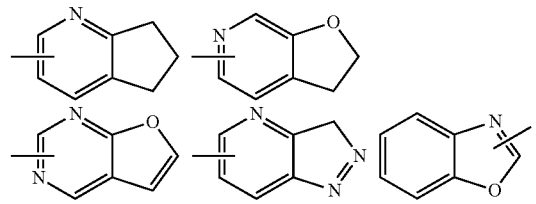

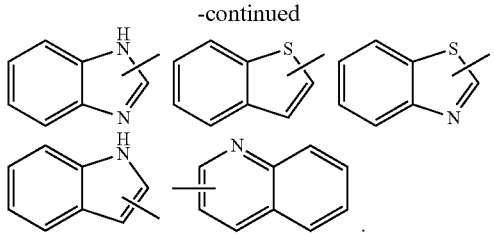

The heteroaryl can be optionally substituted or unsubstituted. When the heteroaryl is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3 to 8 membered heterocyclyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-N(R_{12})-C(O)R_{11}$, and $-N(R_{12})-C(O)OR_{10}$.

"Alkenyl" refers to an alkyl group as defined above that has at least two carbon atoms and at least one carbon-carbon double bond. $C_{2-8}$ alkenyl refers to a straight chain or branched chain alkenyl group having 2 to 8 carbon atoms, for example, vinyl, 1-propenyl, 2-propenyl, 1-, 2- or 3-butenyl and the like.

The alkenyl can be substituted or unsubstituted. When the alkenyl is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3 to 8 membered heterocyclyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-N(R_{12})-C(O)R_1$, and $-N(R_{12})-C(O)OR_{10}$.

"Alkynyl" refers to an alkyl group as defined above that has at least two carbon atoms and at least one carbon-carbon triple bond. $C_{2-8}$ alkynyl refers to a straight chain or branched chain alkynyl group having 2 to 8 carbon atoms, for example, ethynyl, 1-propynyl, 2-propynyl, 1-, 2- or 3-butynyl and the like.

The alkynyl can be substituted or unsubstituted. When the alkynyl is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3 to 8 membered heterocyclyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-N(R_{12})-C(O)R_1$, and $-N(R_{12})-C(O)OR_{10}$.

"Alkoxy" refers to an —O-(alkyl) group, wherein the alkyl is as defined above. "$C_{1-8}$ alkoxy" refers to an alkoxy group having 1 to 8 carbon atoms, preferably having 1 to 6 carbon atoms, and more preferably having 1 to 3 carbon atoms. Non-limiting examples include methoxy, ethoxy, propoxy, butoxy and the like.

The alkoxy can be optionally substituted or unsubstituted. When the alkoxy is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3 to 8 membered heterocyclyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-N(R_{12})-C(O)R_1$, and $N(R_{12})-C(O)OR_{10}$.

"Cycloalkoxy" refers to an —O-(unsubstituted cycloalkyl) group, wherein the cycloalkyl is as defined above. "$C_{3-8}$ cycloalkoxy" refers to a cycloalkoxy group having 3 to 8 carbon atoms. Non-limiting examples include cyclopropoxy, cyclobutyloxy, cyclopentyloxy, cyclohexyloxy and the like.

The cycloalkoxy can be optionally substituted or unsubstituted. When the cycloalkoxy is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3 to 8 membered heterocyclyl, 3 to 8 membered heterocyclyloxy, 3 to 8 membered heterocyclylthio, $C_{5-10}$ aryl, $C_{5-10}$ aryloxy, $C_{5-10}$ arylthio, 5 to 10 membered heteroaryl, 5 to 10 membered heteroaryloxy, 5 to 10 membered heteroarylthio, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(O)NR_{12}R_{13}$, $-N(R_{12})-C(O)R_{11}$, and $-N(R_{12})-C(O)OR_{10}$.

"Halo$C_{1-8}$ alkyl" refers to a $C_{1-8}$ alkyl group, wherein hydrogen(s) in the alkyl is substituted by fluorine, chlorine, bromine and/or iodine atom(s), for example, difluoromethyl, dichloromethyl, dibromomethyl, trifluoromethyl, trichloromethyl, tribromomethyl and the like.

"Halo $C_{1-8}$ alkoxy" refers to a $C_{1-8}$ alkoxy group, wherein hydrogen(s) in the alkyl is substituted by fluorine, chlorine, bromine and/or iodine atom(s), for example, difluoromethoxy, dichloromethoxy, dibromomethoxy, trifluoromethoxy, trichloromethoxy, tribromomethoxy and the like.

"Halogen" refers to fluorine, chlorine, bromine or iodine.
"THF" refers to tetrahydrofuran.
"EtOAc" refers to ethyl acetate.
"MeOH" refers to methanol.
"DMF" refers to N,N-dimethylformamide.
"TFA" refers to trifluoroacetic acid.
"MeCN" refers to acetonitrile.
"DMA" refers to N,N-dimethylacetamide.
"$Et_2O$" refers to diethyl ether.
"DCE" refers to 1, 2-dichloroethane.
"DIPEA" refers to N,N-diisopropylethylamine.
"NBS" refers to N-bromosuccinimide.
"NIS" refers to N-iodosuccinimide.
"Cbz-Cl" refers to benzyl chloroformate.
"$Pd_2(dba)_3$" refers to tris (dibenzylideneacetone) dipalladium.
"Dppf" refers to 1,1'-bisdiphenylphosphinoferrocene.
"HATU" refers to 2-(7-oxobenzotriazole)-N,N,N',N'-tetramethyluronium hexafluorophosphate.
"KHMDS" refers to potassium hexamethyldisilazide.
"LiHMDS" refers to lithium bis(trimethylsilyl)amide.
"MeLi" refers to methyl lithium.
"n-BuLi" refers to n-butyl lithium.

"NaBH(OAc)₃" refers to sodium triacetoxyborohydride.
"NaBH(CN)₃" refers to sodium trisocyanateborohydride.

Different terms such as "X is selected from the group consisting of A, B or C", "X is selected from the group consisting of A, B and C", "X is A, B or C", and "X is A, B and C" express the same meaning, that is, X can be any one or more of A, B, and C.

"Stereoisomerism" includes three types: geometric isomerism (cis-trans isomerization), optical isomerism, and conformational isomerism.

The hydrogen atom of the present invention can be substituted by its isotope deuterium, and any one of the hydrogen atoms in the compounds of the examples of the present invention can also be substituted by a deuterium atom.

"Optional" or "optionally" means that the subsequently described event or the circumstance can, but need not occur, and such a description includes the instances in which the event or the circumstance does or does not occur. For example, "heterocyclyl optionally substituted by alkyl" means that the alkyl group can be, but need not be present, and such a description includes the instances in which the heterocyclyl group is substituted by alkyl and the heterocyclyl group is not substituted by alkyl.

"Substituted" means that one or more hydrogen atoms in the group are each independently substituted by the corresponding number of the substituents.

Apparently, the substituents are only positioned at their possible chemical positions, and the possible or impossible substitutions can be determined (through experiments or theory) by those skilled in the art without paying excessive efforts. For example, the combination of amino or hydroxy having free hydrogen and carbon atoms having unsaturated bonds (such as olefin) can be unstable.

"Pharmaceutical composition" refers to a mixture comprising one or more of the compounds described herein or the physiological/pharmaceutical salts or prodrugs thereof and other chemical components, and other components such as physiological/pharmaceutical carriers and excipients. The purpose of a pharmaceutical composition is to facilitate administration of a compound to an organism, which will help absorption of the active ingredient, thereby realizing biological activity.

The following examples serve to illustrate the present invention in detail and completely, but these examples should not be considered as limiting the scope of the present invention, and the present invention is not limited to the examples.

The structures of compounds in the present invention were identified by nuclear magnetic resonance (NMR) and/or liquid chromatography-mass spectrometry (LC-MS). The chemical shift of NMR is given in $10^{-6}$ (ppm). NMR was determined by a Bruker AVANCE-400 machine, the solvents for determination are deuterated dimethylsulfoxide (DMSO-d6), deuterated methanol (CD₃OD) and deuterated chloroform (CDCl₃), and the internal standard is tetramethylsilane (TMS).

Liquid chromatography-mass spectrometry (LC-MS) was determined by an Agilent 1200 Infinity Series mass spectrometer. HPLC was determined on an Agilent 1200DAD high pressure liquid chromatographic instrument (Sunfire C18 150×4.6 mm chromatographic column) and a Waters 2695-2996 high pressure liquid chromatographic instrument (Gimini C18 150×4.6 mm chromatographic column).

For thin-layer silica gel chromatography (TLC), Yantai Huanghai HSGF254 or Qingdao GF254 silica gel plate was used. The dimension of the plates used in TLC was 0.15 mm to 0.20 mm, and the dimension of the plates used in product purification was 0.4 mm to 0.5 mm. Column chromatography generally used Yantai Huanghai 200 to 300 mesh silica gel as carrier.

The starting materials used in the examples of the present invention are known and commercially available, or can be synthesized by adopting or according to known methods in the art.

Unless otherwise stated, all reactions of the present invention are carried out under continuous magnetic stirring in a dry nitrogen or argon atmosphere, the solvent is dry, and the reaction temperature is in degrees Celsius.

PREPARATION OF INTERMEDIATE

Intermediate 1: Preparation of 6-amino-4-fluoronicotinonitrile

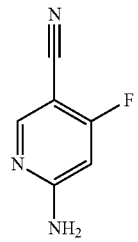

Step 1: Preparation of 4-fluoro-5-iodopyridin-2-amine

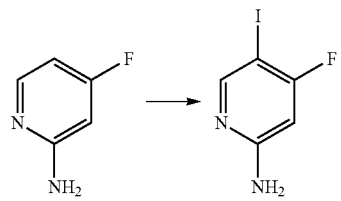 [SMILES: Nc1cc(F)ccn1 ; Nc1cc(F)c(I)cn1]

4-Fluoropyridin-2-amine (9 g, 80 mmol), NIS (19.8 g, 88 mmol) and TFA (3.65 g, 32 mmol) were mixed in MeCN (290 mL), and then the reaction was carried out at room temperature overnight. The reaction solution was diluted with ethyl acetate (300 mL), and washed with saturated aqueous Na₂SO₃ solution (150 mL×2). The organic phase was washed with saturated brine, dried over anhydrous sodium sulfate and concentrated to obtain the title compound 4-fluoro-5-iodopyridin-2-amine (15.8 g, 83%).

MS m/z (ESI): 238.9 [M+H]⁺.

Step 2: Preparation of 6-amino-4-fluoronicotinonitrile

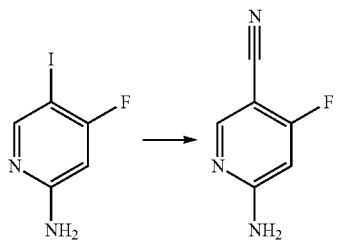 [SMILES: Nc1cc(F)c(I)cn1 ; N#Cc1cnc(N)cc1F]

4-Fluoro-5-iodopyridin-2-amine (15.8 g, 66.4 mmol), Zn(CN)₂ (8.2 g, 69.8 mmol) and Zn (0.87 g, 13.3 mmol) were mixed in DMA (55 mL), followed by addition of Pd₂(dba)₃ (2.4 g, 2.62 mmol) and dppf (7.4 g, 13.35 mmol) in a nitrogen atmosphere. The reaction system was purged 3 times with nitrogen, and then warmed up to 110° C. for 3 hours in the nitrogen atmosphere. Then the reaction solution was cooled to room temperature, and diluted with ethyl acetate (100 mL), followed by addition of saturated aqueous NaHCO₃ solution (200 mL). Two phases were separated, and the aqueous phase was extracted with ethyl acetate (150 mL×3). The organic phases were combined, washed with saturated brine, dried over anhydrous sodium sulfate and concentrated to obtain the title compound 6-amino-4-fluoronicotinonitrile (7.3 g, 80%).

MS m/z (ESI): 138.1 [M+H]⁺.

Intermediate 2: Preparation of 6-amino-4-((2-methoxyethyl)amino)nicotinonitrile

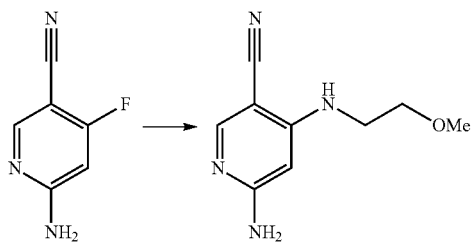 [SMILES: N#Cc1cnc(N)cc1F ; COCCNc1cc(N)ncc1C#N]

6-amino-4-fluoronicotinonitrile (4.11 g, 30 mmol), 2-methoxyethane-1-amine (4.5 g, 60 mmol), and DIPEA (1.16 g, 90 mmol) were mixed in DMF(120 mL). The mixture was stirred at 60° C. overnight. Then the reaction solution was concentrated. The resulting residue was dissolved in dichloromethane (100 mL), followed by addition of saturated aqueous NaHCO₃ solution (100 mL) to separate phases. Two phases were separated, and the organic phase was washed with saturated aqueous NaCl solution (50 mL×2), dried over anhydrous sodium sulfate, and concentrated. The resulting residue was subjected to column chromatography to obtain the title compound 6-amino-4-((2-methoxyethyl)amino)nicotinonitrile (3.84 g, 67%).

1H NMR (400 MHz, DMSO) δ 7.93 (s, 1H), 6.39 (S, 2H), 6.14 (t, J=5.6 Hz, 1H), 5.62 (s, 1H), 3.47 (t, J=6.0 Hz, 2H), 3.29-3.22 (m, 5H);

MS m/z (ESI): 193.1 [M+H]⁺.

Intermediate 3: Preparation of 6-amino-4-(dimethylamino)nicotinonitrile

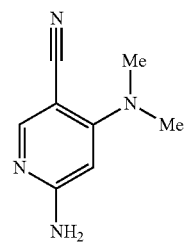 [SMILES: CN(C)c1cc(N)ncc1C#N]

6-amino-4-(dimethylamino)nicotinonitrile was prepared in accordance with the method of intermediate 2.

MS m/z (ESI): 163.2 [M+H]⁺.

Intermediate 4: Preparation of 6-amino-4-(2-methoxyethoxy)nicotinonitrile

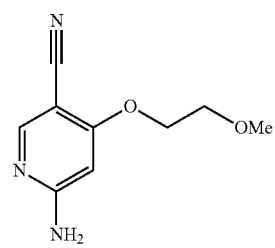 [SMILES: COCCOc1cc(N)ncc1C#N]

6-amino-4-(2-methoxyethoxy)nicotinonitrile was prepared in accordance with the method of intermediate 2.

MS m/z (ESI): 194.2 [M+H]⁺.

Intermediate 5: Preparation of (R)-6-amino-4-((1-methoxypropan-2-yl)oxy)nicotinonitrile

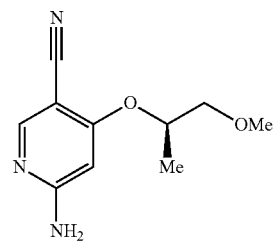 [SMILES: COC[C@@H](C)Oc1cc(N)ncc1C#N]

(R)-6-amino-4-((1-methoxypropan-2-yl)oxy)nicotinonitrile was prepared in accordance with the method of intermediate 2.

MS m/z (ESI): 208.2 [M+H]⁺.

Intermediate 6: Preparation of 6-amino-4-(2-methoxyethyl)thio)nicotinonitrile

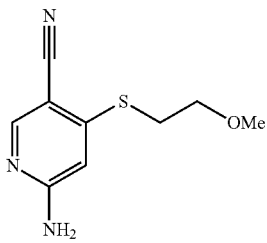 [SMILES: COCCSc1cc(N)ncc1C#N]

6-amino-4-(2-methoxyethyl)thio)nicotinonitrile was prepared in accordance with the method of intermediate 2.

MS m/z (ESI): 210.3 [M+H]⁺.

Intermediate 7: Preparation of (S)-6-amino-4-(3-methoxypyrrolidin-1-yl))nicotinonitrile

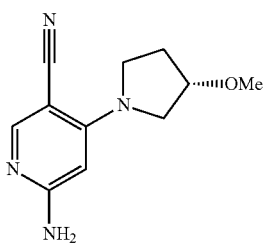 [SMILES: CO[C@H]1CCN(c2cc(N)ncc2C#N)C1]

(S)-6-amino-4-(3-methoxypyrrolidin-1-yl))nicotinonitrile was prepared in accordance with the method of intermediate 2.

MS m/z (ESI): 219.3 [M+H]⁺

Intermediate 8: Preparation of (S)-6-amino-4-(tetrahydrofuran-3-yl)thio)nicotinonitrile

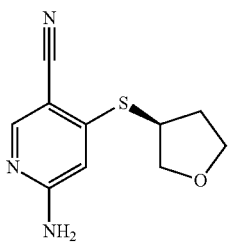 [SMILES: N#Cc1cnc(N)cc1S[C@H]1CCOC1]

(S)-6-amino-4-(tetrahydrofuran-3-yl)thio)nicotinonitrile was prepared in accordance with the method of intermediate 2.

MS m/z (ESI): 222.3 [M+H]⁺.

Intermediate 9: Preparation of (S)-6-amino-4-(3-(dimethylamino)pyrrolidin-1-yl)nicotinonitrile

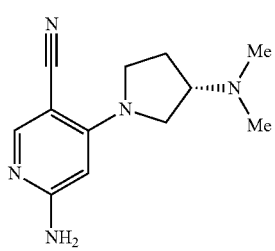 [SMILES: CN(C)[C@H]1CCN(c2cc(N)ncc2C#N)C1]

(S)-6-amino-4-(3-(dimethylamino)pyrrolidin-1-yl)nicotinonitrile was prepared in accordance with the method of intermediate 2.

MS m/z (ESI): 232.3 [M+H]⁺.

Intermediate 10: Preparation of 6-amino-4-(3-methyoxyazetidin-1-yl)nicotinonitrile

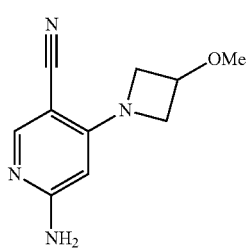 [SMILES: COC1CN(c2cc(N)ncc2C#N)C1]

6-amino-4-(3-methyoxyazetidin-1-yl)nicotinonitrile was prepared in accordance with the method of intermediate 2.

MS m/z (ESI): 205.2 [M+H]⁺.

Intermediate 11: Preparation of 6-amino-4-(((3S,4R)-4-methyoxy tetrahydrofuran-3-yl)amino)nicotinonitrile

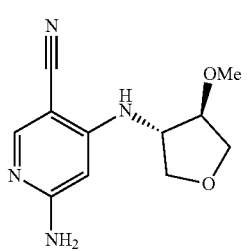 [SMILES: CO[C@H]1COC[C@@H]1Nc1cc(N)ncc1C#N]

6-amino-4-(((3S,4R)-4-methyoxytetrahydrofuran-3-yl)amino)nicotinonitrile was prepared in accordance with the method of intermediate 2.

MS m/z (ESI): 235.3 [M+H]⁺.

Intermediate 12: Preparation of 6-amino-4-(((3S,4S)-4-methyoxy tetrahydrofuran-3-yl)oxy)nicotinonitrile

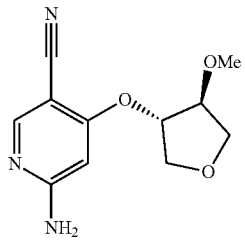 [SMILES: CO[C@H]1COC[C@@H]1Oc1cc(N)ncc1C#N]

6-amino-4-(((3S,4S)-4-methyoxytetrahydrofuran-3-yl)oxy)nicotinonitrile was prepared in accordance with the method of intermediate 2.

MS m/z (ESI): 236.2 [M+H]$^+$.

Intermediate 13: Preparation of 6-amino-4-(((3S,4S)-3-methoxytetrahydro-2H-pyran-4-yl)oxy)nicotinonitrile

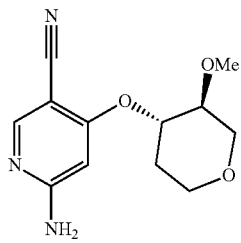 [SMILES: CO[C@H]1COCC[C@@H]1Oc1cc(N)ncc1C#N]

6-amino-4-(((3S,4S)-3-methoxytetrahydro-2H-pyran-4-yl)oxy)nicotinonitrile was prepared in accordance with the method of intermediate 2.

MS m/z (ESI): 250.3 [M+H]$^+$.

Intermediate 14: Preparation of 6-amino-4-(((3S,4S)-4-methoxytetrahydro-2H-pyran-3-yl)oxy)nicotinonitrile

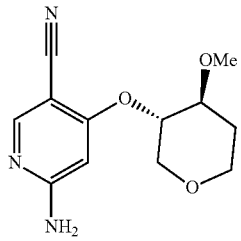

6-amino-4-(((3S,4S)-4-methoxytetrahydro-2H-pyran-3-yl)oxy)nicotinonitrile was prepared in accordance with the method of intermediate 2.

MS m/z (ESI): 250.3 [M+H]$^+$.

Intermediate 15: Preparation of 6-amino-4-(((3S,4S)-4-methoxytetrahydro-2H-pyran-3-yl)amino)nicotinonitrile

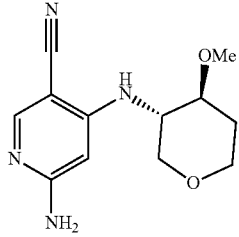 [SMILES: CO[C@H]1CCOC[C@@H]1Nc1cc(N)ncc1C#N]

6-amino-4-(((3S,4S)-4-methoxytetrahydro-2H-pyran-3-yl)amino)nicotinonitrile was prepared in accordance with the method of intermediate 2.

MS m/z (ESI): 249.2 [M+H]$^+$.

Intermediate 16: Preparation of 6-amino-4-(((1R,2R)-2-methoxycyclobutoxy)nicotinonitrile

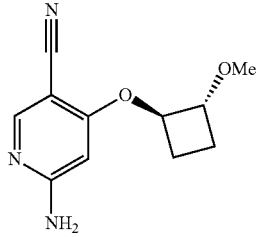 [SMILES: CO[C@@H]1CC[C@H]1Oc1cc(N)ncc1C#N]

Preparation of 6-amino-4-(((1R,2R)-2-methoxycyclobutoxy)nicotinonitrile was prepared in accordance with the method of intermediate 2.

MS m/z (ESI): 220.2 [M+H]$^+$.

Intermediate 17: Preparation of 6-amino-4-((1R,2S)-2-methoxycyclobutoxy)nicotinonitrile

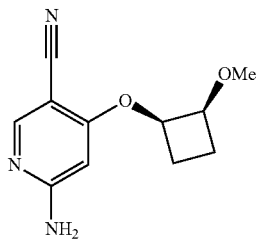 [SMILES: CO[C@H]1CC[C@H]1Oc1cc(N)ncc1C#N]

Preparation of 6-amino-4-((1R,2S)-2-methoxycyclobutoxy)nicotinonitrile was prepared in accordance with the method of intermediate 2.

MS m/z (ESI): 220.2 [M+H]$^+$.

Intermediate 18: Preparation of 6-amino-4-(((1R,2R)-2-methoxycyclobutoxy)amino)nicotinonitrile

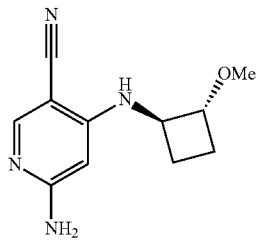 [SMILES: CO[C@@H]1CC[C@H]1Nc1cc(N)ncc1C#N]

Preparation of 6-amino-4-(((1R,2R)-2-methoxycyclobutoxy)amino)nicotinonitrile was prepared in accordance with the method of intermediate 2.

MS m/z (ESI): 219.2 [M+H]⁺.

Intermediate 19: Preparation of 6-amino-4-(((1R,2S)-2-methoxycyclobutoxy)amino)nicotinonitrile

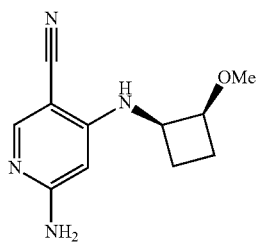 [SMILES: CO[C@H]1CC[C@H]1Nc1cc(N)ncc1C#N]

Preparation of 6-amino-4-(((1R,2S)-2-methoxycyclobutoxy)amino)nicotinonitrile was prepared in accordance with the method of intermediate 2.

MS m/z (ESI): 219.2 [M+H]⁺.

Intermediate 20: Preparation of 2-(dimethoxymethyl)-5,6,7,8-tetrahydro-1,8-naphthyridin-3-carbaldehyde

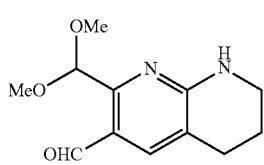

Step 1: Preparation of 2-(dimethoxymethyl)-1,8-naphthyridine

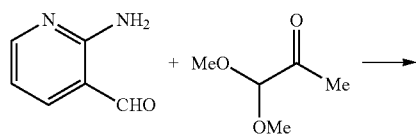

2-Aminonicotine aldehyde (25.0 g, 205 mmol) and 1,1-dimethoxypropan-2-one (31.4 g, 266 mmol) were mixed and dissolved in a mixed solvent of ethanol (500 mL) and water (50 mL), followed by addition of aqueous NaOH solution (3M, 88.7 mL, 266 mmol). The reaction solution was stirred at room temperature for 3 hours, and then concentrated. The resulting residue was dissolved in EtOAc, washed twice with saturated brine, dried over anhydrous sodium sulfate, and concentrated to obtain the title compound 2-(dimethoxymethyl)-1,8-naphthyridine (42.3 g), which was directly used in the next step.

Step 2: Preparation of 7-(dimethoxymethyl)-1,2,3,4-tetrahydro-1,8-naphthyridine

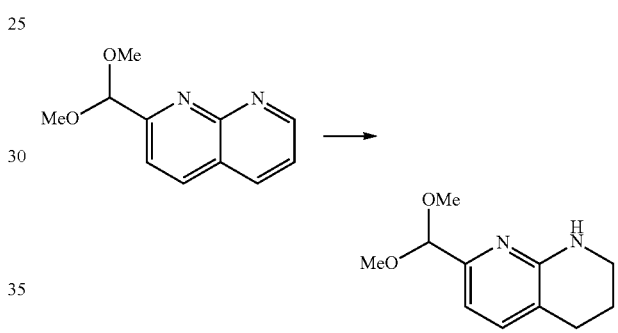

PtO₂ (1.25 g) was added to a solution of 2-(dimethoxymethyl)-1,8-naphthyridine (42.3 g, 205 mmol) in ethanol (600 mL). After stirring for 36 hours in a hydrogen atmosphere at room temperature and normal pressure, the reaction was filtered with diatomite to remove the catalyst. The filtrate was concentrated to obtain the title compound 7-(dimethoxymethyl)-1,2,3,4-tetrahydro-1,8-naphthyridine (42.7 g), which was directly used in the next step.

Step 3: Preparation of 6-bromo-7-(dimethoxymethyl)-1,2,3,4-tetrahydro-1,8-naphthyridine

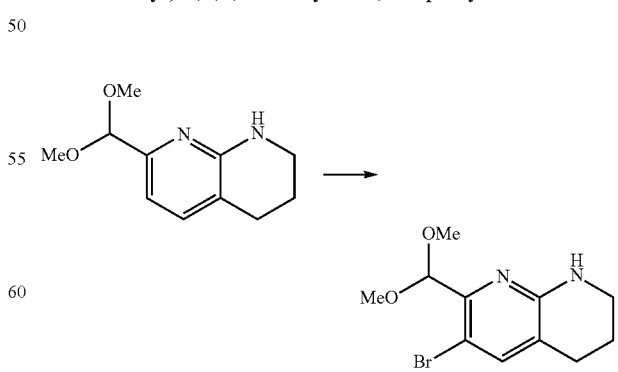

NBS (38.3 g, 215 mmol) was added in batches to a solution of 7-(dimethoxymethyl)-1,2,3,4-tetrahydro-1,8-naphthyridine (42.7 g, 205 mmol) in MeCN (1 L) at room temperature. The reaction solution was stirred for 1 hour and concentrated. The resulting residue was dissolved in CH₂Cl₂, washed with 1 M aqueous NaOH solution and saturated brine successively, dried over anhydrous sodium sulfate and concentrated. The resulting residue was subjected to column chromatography to obtain the title compound 6-bromo-7-(dimethoxymethyl)-1,2,3,4-tetrahydro-1,8-naphthyridine (47.5 g, total yield of three steps: 81%).

¹H NMR (400 MHz, CDCl₃): δ 7.27 (s, 1H), 5.55 (s, 1H), 5.39 (br s, 1H), 3.45 (s, 6H), 3.38 (m, 2H), 2.70 (t, J=6.0 Hz, 2H), 1.88 (m, 2H);

MS m/z (ESI): 287.0 [M+H]⁺.

Step 4: Preparation of 2-(dimethoxymethyl)-5,6,7,8-tetrahydro-1,8-naphthyridin-3-carbaldehyde

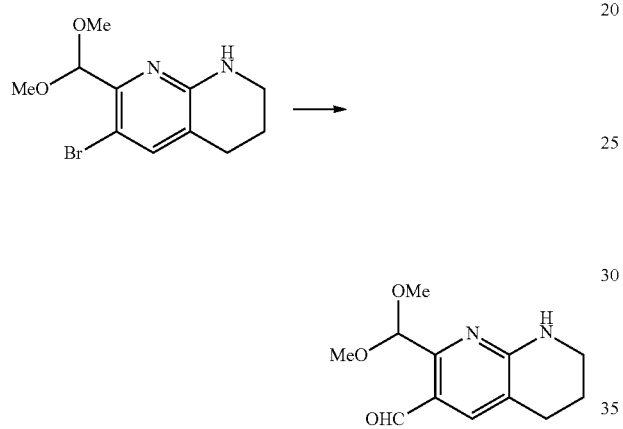

MeLi (1.6 M THF solution, 0.30 mL, 0.48 mmol) was added dropwise to a solution of 6-bromo-7-(dimethoxymethyl)-1,2,3,4-tetrahydro-1,8-naphthyridine (114 mg, 0.397 mmol) in THF (3 mL) at −78° C. After the reaction solution was stirred at this temperature for 5 minutes, n-BuLi (1.6 M THF solution, 0.50 mL, 0.80 mmol) was added dropwise, and then the reaction solution was stirred for another 15 minutes. The reaction solution was warmed up slowly to room temperature and stirred for 30 minutes after dry DMF (0.12 mL, 1.6 mmol) was added dropwise and slowly. Saturated aqueous NH₄Cl solution was added, and then the reaction solution was stirred for 5 minutes and extracted twice with CH₂Cl₂. The organic phases were combined, dried over anhydrous magnesium sulfate, and concentrated. The resulting residue was subjected to column chromatography to obtain the title compound 2-(dimethoxymethyl)-5,6,7,8-tetrahydro-1,8-naphthyridin-3-carbaldehyde (73 mg, 78%).

¹H NMR (400 MHz, CDCl3): δ 10.32 (s, 1H), 7.75 (s, 1H), 5.93 (br s, 1H), 5.44 (s, 1H), 3.49 (m, 8H), 2.76 (t, J=6.0 Hz, 2H), 1.91 (m, 2H);

MS m/z (ESI): 237.1 [M+H]⁺.

Intermediate 21: Preparation of 1-((2-(dimethoxymethyl)-5,6,7,8-tetrahydro-1,8-naphthyridin-3-yl)methyl)-3-methoxypyrrolidin-2-one

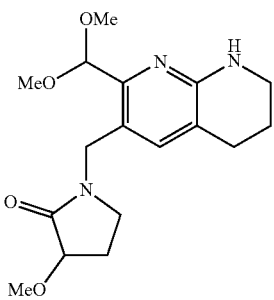 [SMILES: COC1CCN(Cc2cc3c(nc2C(OC)OC)NCCC3)C1=O]

Step 1: Preparation of 4-((tert-butyoxycarbonyl)amino)-2-hydroxybutyric acid

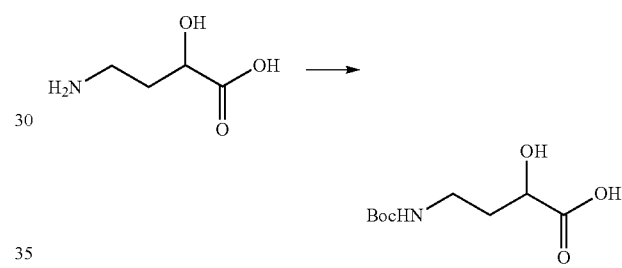

A solution of Boc₂O (20 g, 84 mmol) in 1,4-dioxane (30 mL) was added dropwise and slowly to a solution of 4-amino-2-hydroxybutyric acid (10 g, 84 mmol) and K₂CO₃ (34.8 g, 252 mmol) solution in H₂O (80 mL) in an ice water bath. The reaction solution was stirred overnight at room temperature, and then washed with Et₂O (30 mL×2). The aqueous phase was adjusted to pH 4 to 5 with hydrochloric acid (2 N) and extracted with EtOAc (100 mL×3). The organic phase was washed with saturated brine, dried over anhydrous sodium sulfate, and concentrated to obtain the title compound 4-((tert-butoxycarbonyl)amino)-2-hydroxybutyric acid (12.2 g, 66%).

MS m/z (ESI): 220.2 [M+H]⁺.

Step 2: Preparation of methyl 4-((tert-butyoxycarbonyl)amino)-2-methoxybutyrate

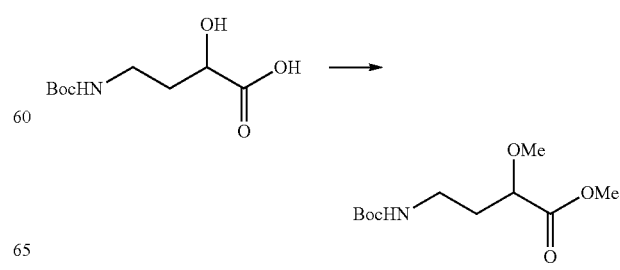

MeI (6.5 g, 45.6 mmol) was added dropwise and slowly to a solution of 4-((tert-butoxycarbonyl)amino)-2-hydroxybutyric acid (1 g, 4.6 mmol) and Ag₂O (4.23 g, 18.3 mmol) in anhydrous DMF (10 mL) in an ice water bath. The reaction solution was stirred overnight in an ice water bath in the dark, and then diluted with ethyl acetate (500 mL). The organic phase was washed with saturated brine (50 mL×5), dried over anhydrous sodium sulfate, and concentrated. The resulting residue was subjected to column chromatography to obtain the title compound methyl 4-((tert-butoxycarbonyl)amino)-2-methoxybutyrate (0.33 g, 29%).

MS m/z (ESI): 248.3 [M+H]⁺.

Step 3: Preparation of methyl 4-amino-2-methoxybutyrate Hydrochloride

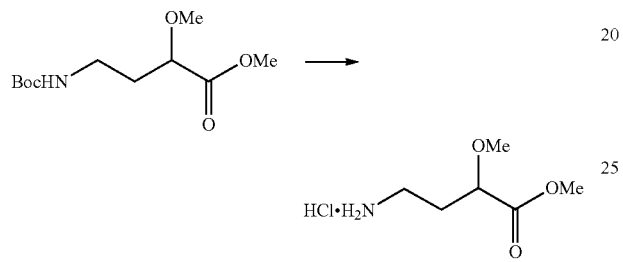

Hydrochloride in dioxane (5 mL) was added to a solution of methyl 4-((tert-butoxycarbonyl)amino)2-methoxybutyrate (0.33 g, 1.33 mmol) in CH₂Cl₂ (2 mL) in an ice water bath. The reaction solution was slowly warmed up to room temperature, stirred for 2 hours, and then concentrated to obtain the title compound methyl 4-amino-2-methoxybutyrate hydrochloride, which was directly used in the next step.

MS m/z (ESI): 148.2 [M+H]⁺.

Step 4: Preparation of 1-((2-(dimethoxymethyl)-5,6,7,8-tetrahydro-1,8-naphthyridin-3-yl)methyl)-3-methoxypyrrolidin-2-one

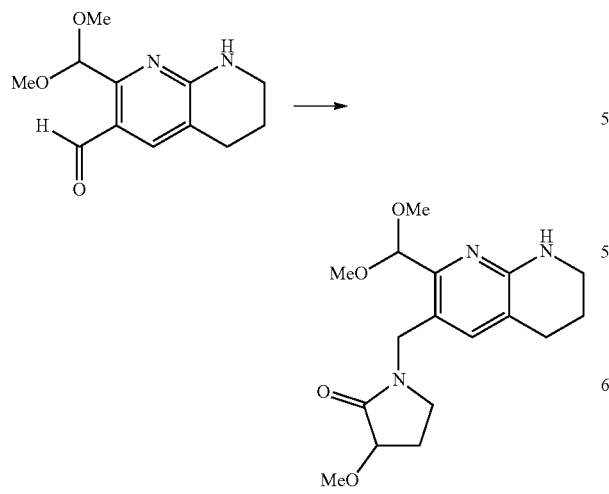

2-(Dimethoxymethyl)-5,6,7,8-tetrahydro-1,8-naphthyridin-3-carbaldehyde (130 mg, 0.55 mmol) and 4-amino-2-methoxybutyrate hydrochloride (121 mg, 0.66 mmol) were dissolved in a solution of 1,2-dichloroethane (5 mL) at room temperature. Then triethylamine (73 mg, 0.72 mmol) was added, followed by addition of anhydrous acetic acid (6.6 mg, 0.11 mmol) and sodium triacetylborohydride (175 mg, 0.83 mmol). The reaction solution was stirred overnight at room temperature, and then concentrated the next day. The resulting residue was subjected to column chromatography to obtain the title compound 1-((2-(dimethoxymethyl)-5,6,7,8-tetrahydro-1,8-naphthyridin-3-yl)methyl)-3-methoxypyrrolidin-2-one (91 mg, 49%).

¹H NMR (400 MHz, CDCl₃) δ 7.38 (s, 1H), 5.42 (s, 1H), 5.31 (s, 1H), 4.68 (d, J=14.8 Hz, 1H), 4.63 (d, J=14.8 Hz, 1H), 4.11 (t, J=7.4 Hz, 1H), 3.70 (s, 3H), 3.55 (s, 3H), 3.54 (s, 3H), 3.53-3.50 (m, 1H), 3.39-3.35 (m, 1H), 3.26-3.20 (m, 1H), 2.81 (t, J=6.2 Hz, 2H), 2.57-2.32 (m, 1H), 2.21 (s, 1H), 2.06-1.88 (m, 3H);

MS m/z (ESI): 336.2 [M+H]⁺.

Intermediate 22: Preparation of (R)-6-amino-4-((1-methoxypropan-2-yl)amino)nicotinonitrile

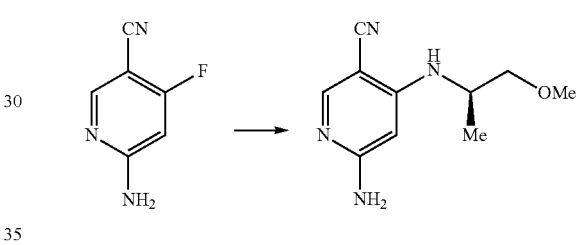

6-Amino-4-fluoronicotinonitrile (1.5 g, 10.9 mmol) and (R)-1-methoxypropan-2-amine (1.2 g, 13 mmol) were dissolved in DMA (10 mL) at room temperature, followed by addition of DIPEA (4.2 g, 33 mmol). The reaction solution was warmed up to 130° C., stirred for 12 hours at this temperature and concentrated. The resulting residue was subjected to column chromatography to obtain the compound (R)-6-amino-4-((1-methoxypropan-2-yl)amino)nicotinonitrile (2 g, 89%).

MS m/z (ESI): 207.1 [M+H]⁺.

Intermediate 23: Preparation of (R)-1-((2-(dimethoxymethyl)-5,6,7,8-tetrahydro-1,8-naphthyridin-3-yl)methyl)-3-methoxypyrrolidin-2-one

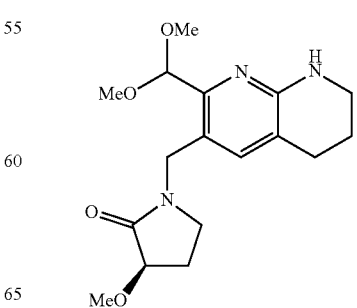

Step 1: Preparation of methyl (R)-4-((tert-butyoxy-carbonyl)amino)-2-methoxybutyrate

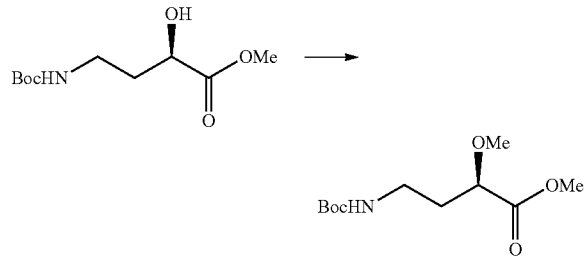

Methyl (R)-4-((tert-butoxycarbonyl)amino)-2-hydroxybutyrate (6.0 g, 25.7 mmol) was dissolved in dry DMF(200 mL), and cooled to 8° C. Ag$_2$O was added in batches (23.8 g, 102.9 mmol) in a nitrogen atmosphere, followed by dropwise addition of MeI (36.5 g, 257.2 mmol). The reaction solution was stirred at 8° C. for 18 hours in dark, and then diluted with EtOAc (200 mL), filtered with diatomite, and concentrated. The resulting residue was subjected to column chromatography to obtain the compound methyl (R)-4-(tert-butoxycarbonyl)amino)-2-methoxybutyrate (3.9 g, 61%)

$^1$H NMR (400 MHz, CDCl$_3$) δ 4.80 (s, 1H), 3.86-3.83 (m, 1H), 3.77 (s, 3H), 3.41 (s, 3H), 3.34-3.28 (m, 1H), 3.21-3.17 (m, 1H), 1.99-1.85 (m, 2H), 1.44 (s, 9H).

Step 2: Preparation of methyl (R)-4-amino-2-methoxybutyrate

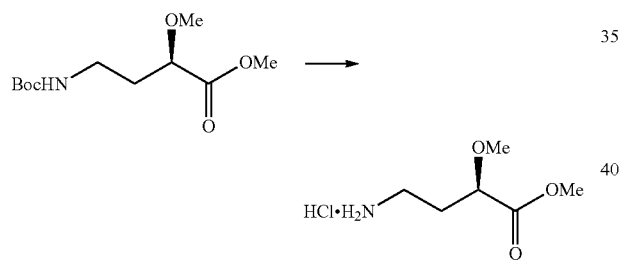

Methyl (R)-4-(tert-butoxycarbonyl)amino)-2-methoxybutyrate (1.5 g, 6.1 mmol) 15 was dissolved in CH$_2$Cl$_2$ (5 mL) and cooled to 5° C. A solution of hydrochloride in dioxane (8 mL) was added in a nitrogen atmosphere, and then the reaction solution was gradually warmed up to room temperature, stirred for 2.5 hours at this temperature, and concentrated to obtain the compound methyl (R)-4-(tert-butoxycarbonyl)amino)-2-methoxybutyrate hydrochloride, which was directly used in the next step.

MS m/z (ESI): 148.1 [M+H]$^+$.

Step 3: Preparation of (R)-1-((2-(dimethoxymethyl)-5,6,7,8-tetrahydro-1,8-naphthyridin-3-yl)methyl)-3-met hoxypyrrolidin-2-one

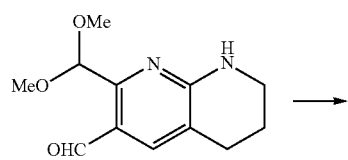

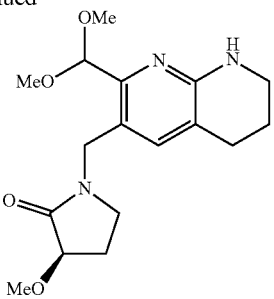

2-(dimethoxymethyl)-5,6,7,8-tetrahydro-1,8-naphthyridin-3-carbaldehyde (1.0 g, 4.2 mmol) and methyl (R)-4 ((tert-butoxycarbonyl)amino)-2-methoxybutyrate hydrochloride (0.75 g, 5.1 mmol) were dissolved in DCE (15 mL). Trimethylamine (0.56 g, 5.5 mmol) was added, followed by addition of anhydrous acetic acid (63.5 mg, 1.06 mmol). The reaction solution was stirred for 12 hours at room temperature, and then diluted with CH$_2$Cl$_2$ (100 mL). The organic phase was washed with water (10 mL) and saturated brine (15 mL) successively, dried over anhydrous sodium sulfate, and concentrated. The resulting residue was subjected to column chromatography to obtain the compound (R)-1-((2-(dimethoxymethyl)-5,6,7,8-tetrahydro-1,8-naphthyridin-3-yl)methyl)-3-met hoxypyrrolidin-2-one (1.1 g, 77%).

$^1$H NMR (400 MHz, CDCl$_3$) δ 7.38 (s, 1H), 5.42 (s, 1H), 5.31 (s, 1H), 4.68 (d, J=14.8 Hz, 1H), 4.63 (d, J=14.8 Hz, 1H), 4.11 (t, J=7.4 Hz, 1H), 3.70 (s, 3H), 3.55 (s, 3H), 3.54 (s, 3H), 3.53-3.50 (m, 1H), 3.39-3.35 (m, 1H), 3.26-3.20 (m, 1H), 2.81 (t, J=6.2 Hz, 2H), 2.57-2.32 (m, 1H), 2.21 (s, 1H), 2.06-1.88 (m, 3H);

MS m/z (ESI): 336.2 [M+H]$^+$.

Intermediate 24: Preparation of (S)-6-amino-4-((tetrahydrofuran-3-yl)amino)nicotinonitrile

6-Amino-4-fluoronicotinenitrile (2.54 g, 20 mmol), (S)-tetrahydrofuran-3-amine hydrochloride (4.94 g, 40 mmol) and DIPEA (0.77 g, 60 mmol) were mixed in DMF (60 mL) and stirred overnight at 110° C. The reaction solution was concentrated, and then the resulting residue was dissolved in dichloromethane (100 mL), followed by addition of saturated aqueous NaHCO$_3$ (100 mL) solution. Two phases were separated, and then the organic phase was washed with saturated aqueous NaCl solution (50 mL×2), dried over anhydrous sodium sulfate, and concentrated. The resulting residue was subjected to column chromatography to obtain the title compound (S)-6-amino-4-((tetrahydrofuran-3-yl)amino)nicotinonitrile (2.85 g, 70%).

MS m/z (ESI): 205.1 [M+H]$^+$.

Intermediate 25: Preparation of (R)-6-amino-4-((tetrahydrofuran-3-yl)amino)nicotinonitrile

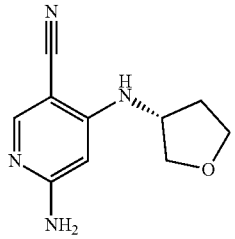 [SMILES: N#Cc1cnc(N)cc1N[C@@H]1CCOC1]

6-Amino-4-fluoronicotinenitrile (2.54 g, 20 mmol), (R)-tetrahydrofuran-3-amine hydrochloride (4.94 g, 40 mmol) and DIPEA (0.77 g, 60 mmol) were mixed in DMF (60 mL) and stirred overnight at 110° C. The reaction solution was concentrated, and then the residue was dissolved in dichloromethane (100 mL), followed by addition of saturated aqueous NaHCO$_3$ (100 mL) solution. Two phases were separated, and then the organic phase was washed with saturated aqueous NaCl solution (50 mL×2), dried over anhydrous sodium sulfate, and concentrated. The resulting residue was subjected to column chromatography to obtain the title compound (R)-6-amino-4-((tetrahydrofuran-3-yl)amino)nicotinenitrile (2.68 g, 66%).

MS m/z (ESI): 205.1 [M+H]+

PREPARATION OF EXAMPLE COMPOUNDS

Example 1

(R)—N-(5-Cyano-4-((2-methoxyethyl)amino)pyridin-2-yl)-7-formyl-6-((N-methyltetrahydrofuran-2-carboxamido)methyl)-3,4-dihydro-1,8-naphthyridin-1(2H)-carboxamide

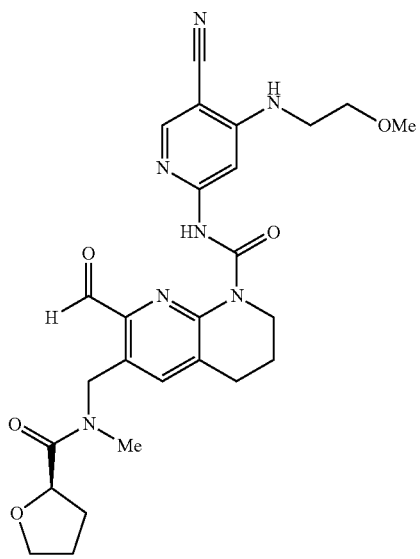 [SMILES: COCCNc1cc(NC(=O)N2CCCc3cc(CN(C)C(=O)[C@H]4CCCO4)c(C=O)nc32)ncc1C#N]

Step 1: Preparation of 1-(2-(dimethoxymethyl)-5,6,7,8-tetrahydro-1,8-naphthyridin-3-yl)-N-methylmethylamine

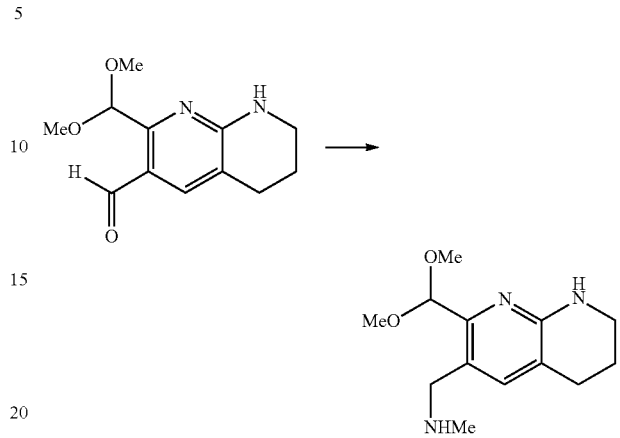

NaBH$_3$CN (1.32 g, 21.1 mmol) was added in one batch to a solution of 2-(dimethoxymethyl)-5,6,7,8-tetrahydro-1,8-naphthyridin-3-carbaldehyde (2.00 g, 8.44 mmol) and methylamine hydrochloride (5.60 g, 84.4 mmol) in MeOH (60 mL). Then the reaction solution was stirred overnight at room temperature, concentrated under reduced pressure, dissolved with CH$_2$Cl$_2$, washed with aqueous 1 M KOH solution and saturated brine successively. The organic phase was dried over anhydrous sodium sulfate, and concentrated under reduced pressure to obtain a crude product, which was directly used in the next step. MS m/z (ESI): 252.2 [M+H]+.

Step 2: Preparation of tertbutyl ((2-(dimethoxymethyl)-5,6,7,8-tetrahydro-1,8-naphthyridin-3-yl)methyl(methyl)carbamate

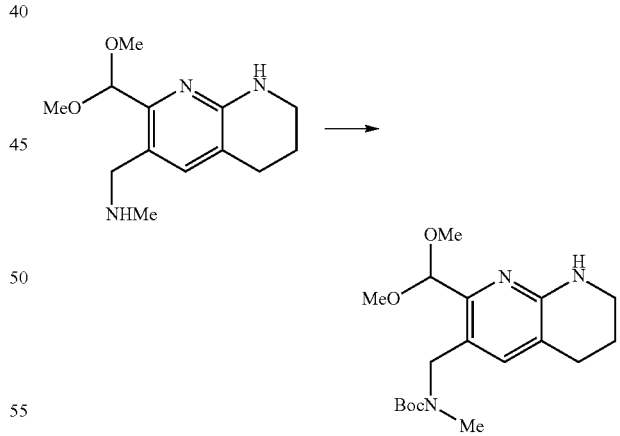

Boc$_2$O (2.20 mL, 9.55 mmol) was added dropwise to a solution of 1-(2-(dimethoxymethyl)-5,6,7,8-tetrahydro-1,8-naphthyridin-3-yl)-N-methylmethylamine (the crude product of the previous step, about 8.44 mmol) and DIPEA (2.36 mL, 14.3 mmol) in CH$_2$Cl$_2$ (50 mL) in an ice water bath. The reaction solution was stirred overnight at room temperature, concentrated and subjected to column chromatography to obtain the title compound tertbutyl 2-(dimethoxymethyl)-5,6,7,8-tetrahydro-1,8-naphthyridin-3-yl)methyl(methyl)carbamate (2.20 g, yield of two steps: 74%).

$^1$H NMR (400 MHz, CDCl$_3$): δ7.03 (s, 1H), 5.24 (m, 1H), 4.89 (s, 1H), 4.49 (S, 2H), 3.40 (m, 8H), 2.70 (m, 5H), 1.90 (m, 2H), 1.26 (s, 9H);

MS m/z (ESI): 252.1 [M+H]$^+$.

Step 3: Preparation of phenyl 6-((tertbutoxycarbonyl)(methyl)amino)methyl)-7-(dimethoxymethyl)-3,4-dihydro-1,8-naphthyridin-1(2H)-carboxylate

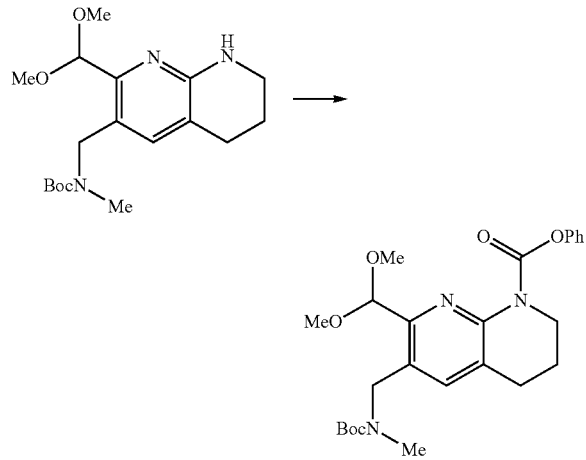

A solution of LiHMDS in THF (1M, 6.01 mL, 6.01 mmol) was added dropwise to a solution of tertbutyl ((2-(dimethoxymethyl)-5,6,7,8-tetrahydro-1,8-naphthyridin-3-yl)methyl)(methyl)carbamate (1.92 g, 5.46 mmol) and diphenyl carbonate (1.40 g, 6.56 mmol) in THF (40 mL) in a dry ice-acetone bath. After completion of the addition, the reaction solution was slowly warmed up to room temperature and stirred for 30 minutes. After the reaction was quenched with saturated aqueous ammonium chloride solution, it was extracted with CH$_2$Cl$_2$. The organic phase was washed with saturated brine, dried over anhydrous sodium sulfate, and concentrated. The resulting residue was subjected to column chromatography to obtain phenyl 6-((tertbutoxycarbonyl)(methyl)amino)methyl)-7-(dimethoxymethyl)-3,4-dihydro-1,8-naphthyridin-1(2H)-carboxylate (1.80 g, 70%). MS m/z (ESI): 472.2 [M+H]$^+$.

Step 4: Preparation of tertbutyl ((8-((5-cyano-4-((2-methoxyethyl)amino)pyridin-2-yl)carbamoyl)-2-(dimethoxymethyl)-5,6,7,8-tetrahydro-1,8-naphthyridin-3-yl)methyl(methyl)carbamate

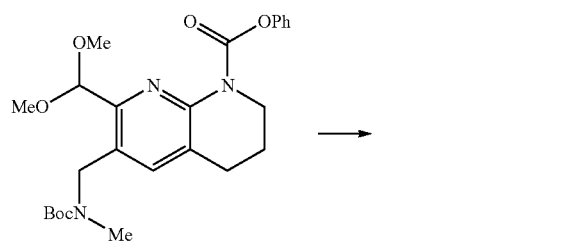

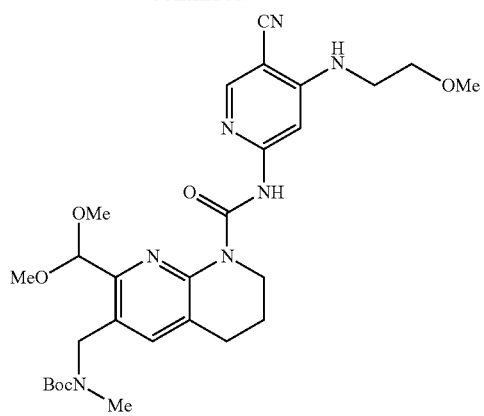

LiHMDS (1 M, 6.11 mL, 6.11 mmol) was added dropwise to a solution of phenyl 6-((((tertbutoxycarbonyl)(methyl)amino)methyl)-7-(dimethoxymethyl)-3,4-dihydro-1,8-naphthyridin-1(2H)-carboxylate (1.80 g, 3.82 mmol) and 6-amino-4-((2-methoxyethyl)amino)nicotinenitrile (1.00 g, 5.00 mmol) in THF in a dry ice-acetone bath. After completion of the addition, the reaction solution was slowly warmed up to room temperature and stirred overnight. After the reaction solution was quenched with saturated aqueous ammonium chloride solution, it was extracted with CH$_2$Cl$_2$. The organic phase was washed with saturated brine, dried over anhydrous sodium sulfate, and concentrated. The resulting residue was subjected to column chromatography to obtain the compound tertbutyl ((8-((5-cyano-4-((2-methoxyethyl)amino)pyridin-2-yl)carbamoyl)-2-(dimethoxymethyl)-5,6,7,8-tetrahydro-1,8-naphthyridin-3-yl)methyl)(methyl)carbamate (1.95 g, 90%).

$^1$H NMR (400 MHz, CDCl$_3$): δ13.72 (br s, 1H), 8.20 (s, 1H), 7.58 (s, 1H), 7.37 (br s, 1H), 5.42 (m, 1H), 5.23 (m, 1H), 4.64 (S, 2H), 4.03 (m, 2H), 3.63 (m, 2H), 3.47 (m, 8H), 3.38 (s, 3H), 2.81 (m, 5H), 2.00 (m, 2H), 1.50 (m, 9H);

MS m/z (ESI): 570.2 [M+H]$^+$.

Step 5: Preparation of N-(5-cyano-4-((2-methoxyethyl)amino)pyridin-2-yl)-7-(dimethoxymethyl)-6-((methyl amino)methyl)-3,4-dihydro-1,8-naphthyridin-1(2H)-carboxamide

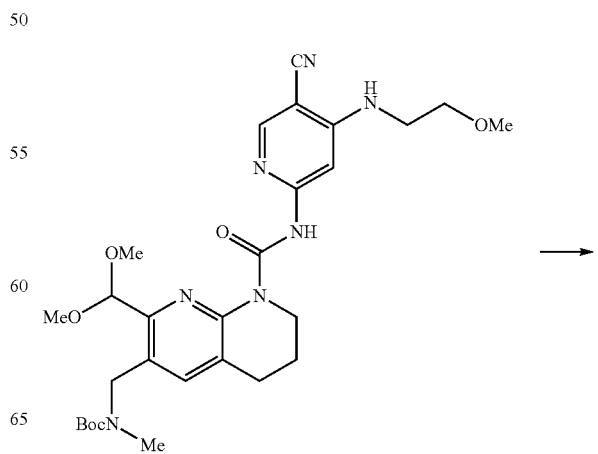

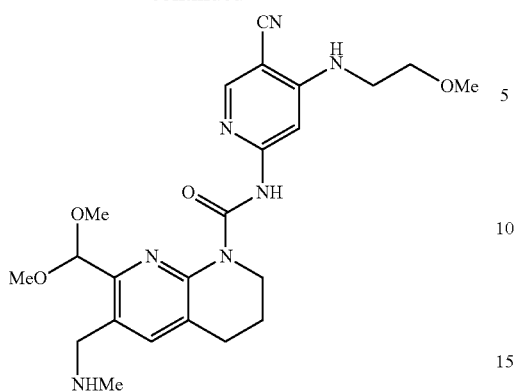

Tertbutyl ((8-(((5-cyano-4-((2-methoxyethyl)amino)pyridin-2-yl)carbamoyl)-2-(dimethoxymethyl)-5,6,7,8-tetrahydro-1,8-naphthyridin-3-yl)methyl(methyl)carbamate (2.00 g, 3.51 mmol) was dissolved in a 0.3 M solution of hydrochloric acid in methanol, and the resulting mixture was stirred for 4 days at room temperature. Triethylamine was added dropwise in ice water bath until the reaction solution was alkaline. After the reaction solution was concentrated, the residue was dissolved in $CH_2Cl_2$, washed twice with saturated brine, dried over anhydrous sodium sulfate, and concentrated under reduced pressure. The resulting residue was subjected to column chromatography to obtain N-(5-cyano-4-((2-methoxyethyl)amino)pyridin-2-yl)-7-(dimethoxymethyl)-6-((methyl amino)methyl)-3,4-dihydro-1,8-naphthyridin-1(2H)-carboxamide (1.00 g, 61%).

$^1$H NMR (400 MHz, $CDCl_3$): δ13.55 (s, 1H), 8.18 (s, 1H), 7.87 (s, 1H), 7.56 (s, 1H), 5.40 (s, 1H), 5.27 (m, 1H), 4.23 (S, 2H), 4.03 (m, 2H), 3.63 (t, J=5.2 Hz, 2H), 3.58 (s, 6H), 3.49 (t, J=5.2 Hz, 2H), 3.41 (s, 3H), 2.88 (t, J=6.0 Hz, 2H), 2.66 (s, 3H), 1.99 (m, 2H);

MS m/z (ESI): 470.2 $[M+H]^+$.

Step 6: Preparation of (R)—N-(5-cyano-4-((2-methoxyethyl)amino)pyridin-2-yl)-7-formyl-6-((N-methyltetrahydrofuran-2-carboxamido)methyl)-3,4-dihydro-1,8-naphthyridin-1(2H)-carboxamide

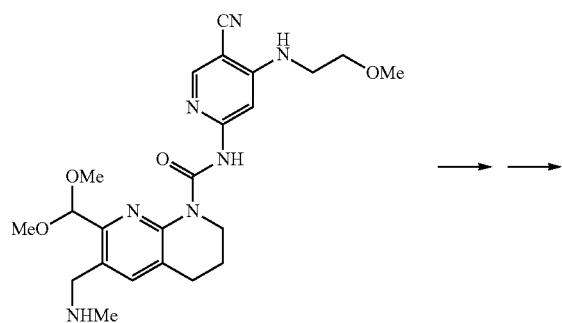

→ →

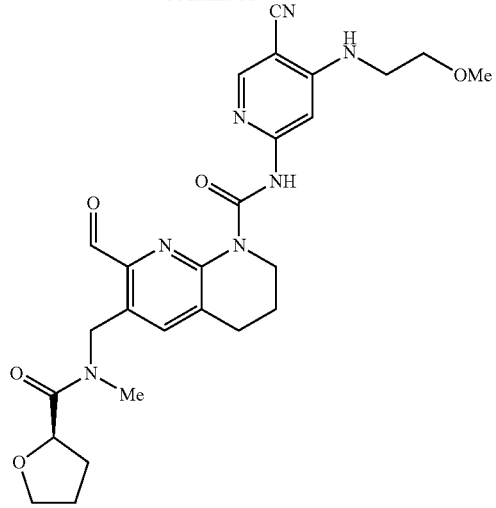

A solution of N-(5-cyano-4-((2-methoxyethyl)amino)pyridin-2-yl)-7-(dimethoxymethyl)-6-((methyl amino)methyl)-3,4-dihydro-1,8-naphthyridin-1(2H)-carboxamide (270 mg, 0.575 mmol), (R)-tetrahydrofuran-2-carboxylic acid (80 mg, 0.690 mmol), DIPEA (0.190 mL, 1.15 mmol), and HATU (284 mg, 0.748 mmol) in $CH_2Cl_2$ (5 mL) was stirred for one hour at room temperature. The reaction solution was washed once with saturated aqueous sodium bicarbonate solution and saturated brine successively, dried over anhydrous sodium sulfate, and concentrated. The crude product was dissolved in THF (11 mL), followed by addition of water (4 mL) and concentrated hydrochloric acid (1.5 mL) successively. The reaction solution was stirred for one hour at room temperature, and then saturated aqueous sodium bicarbonate solution was carefully added dropwise until no bubbles occurred and a large number of insoluble substances appeared. The reaction solution was extracted twice with $CH_2Cl_2$, and the organic phases were combined. The organic phase was washed with saturated brine, dried over anhydrous sodium sulfate, and concentrated under reduced pressure. The resulting residue was subjected to column chromatography to obtain (R)—N-(5-cyano-4-((2-methoxyethyl)amino)pyridin-2-yl)-7-formyl-6-((N-methyltetrahydrofuran-2-carboxamido)methyl)-3,4-dihydro-1,8-naphthyridin-1(2H)-carboxamide (226 mg, 75%).

$^1$H NMR (400 MHz, $CDCl_3$): δ 13.60 (m, 1H), 10.27 (m, 1H), 8.18 (m, 1H), 7.50 (m, 2H), 5.40 (m, 1H), 5.20 (m, 2H), 4.70 (m, 1H), 4.00 (m, 4H), 3.65 (m, 2H), 3.50 (m, 2H), 3.42 (s, 3H), 3.10 (S, 2H), 2.90 (m, 3H), 2.00 (m, 6H);

MS m/z (ESI): 522.2 $[M+H]^+$.

Example 2

(S)—N-(5-Cyano-4-((2-methoxyethyl)amino)pyridin-2-yl)-7-formyl-6-((N-methyltetrahydrofuran-2-carboxamido)methyl)-3,4-dihydro-1,8-naphthyridin-1(2H)-carboxamide

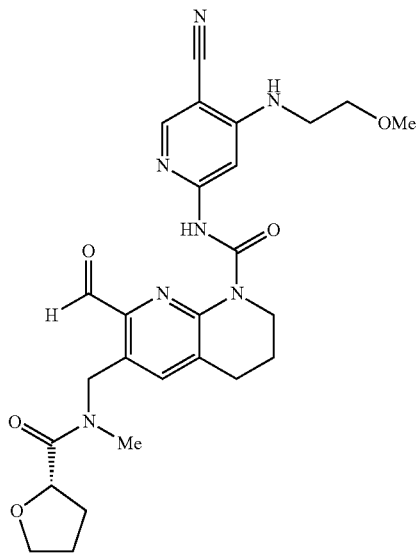 [SMILES: COCCNc1cc(NC(=O)N2CCCc3cc(CN(C)C(=O)[C@@H]4CCCO4)c(C=O)nc32)ncc1C#N]

(S)—N-(5-Cyano-4-((2-methoxyethyl)amino)pyridin-2-yl)-7-formyl-6-((N-methyl tetrahydrofuran-2-carboxamido)methyl)-3,4-dihydro-1,8-naphthyridin-1(2H)-carboxamide was prepared in accordance with the method of Example 1.

$^1$H NMR (400 MHz, CDCl$_3$): δ 13.64 (m, 1H), 10.28 (m, 1H), 8.19 (m, 1H), 7.56 (m, 2H), 5.44 (m, 1H), 5.10 (m, 2H), 4.73 (m, 1H), 4.00 (m, 4H), 3.65 (m, 2H), 3.50 (m, 2H), 3.42 (s, 3H), 3.09 (S, 2H), 2.92 (m, 3H), 2.00 (m, 6H);

MS m/z (ESI): 522.2 [M+H]$^+$.

Example 3

N-(5-Cyano-4-((2-methoxyethyl)amino)pyridin-2-yl)-7-formyl-6-((N-methyloxetane-3-carboxamido)methyl)-3,4-dihydro-1,8-naphthyridin-1(2H)-carboxamide

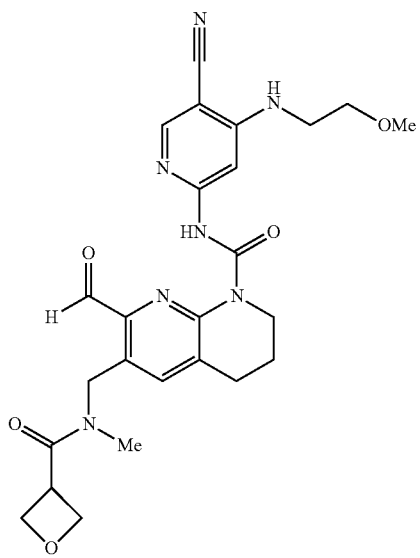 [SMILES: COCCNc1cc(NC(=O)N2CCCc3cc(CN(C)C(=O)C4COC4)c(C=O)nc32)ncc1C#N]

N-(5-Cyano-4-((2-methoxyethyl)amino)pyridin-2-yl)-7-formyl-6-((N-methyloxetane-3-carboxamido)methyl)-3,4-dihydro-1,8-naphthyridin-1(2H)-carboxamide was prepared in accordance with the method of Example 1.

$^1$H NMR (400 MHz, CDCl$_3$): δ 13.60 (m, 1H), 10.23 (m, 1H), 8.17 (m, 1H), 7.57 (m, 2H), 5.35 (m, 1H), 5.07 (s, 1H), 4.85 (m, 4H), 4.08 (m, 2H), 3.85 (m, 1H), 3.64 (m, 2H), 3.50 (m, 3H), 3.41 (s, 3H), 3.02 (s, 1H), 2.93 (m, 2H), 2.82 (S, 2H), 2.05 (m, 2H);

MS m/z (ESI): 508.2 [M+H]$^+$.

Example 4

N-(5-Cyano-4-(dimethylamino)pyridin-2-yl)-7-formyl-6-((N-methyltetrahydrofuran-2-carboxamido)methyl)-3,4-dihydro-1,8-naphthyridin-1(2H)-carboxamide

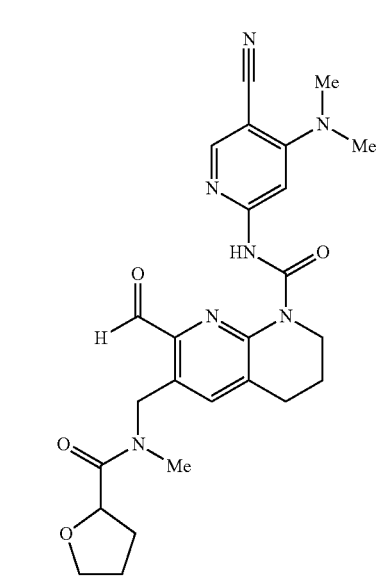 [SMILES: CN(Cc1cc2c(nc1C=O)N(C(=O)Nc1cc(N(C)C)c(C#N)cn1)CCC2)C(=O)C1CCCO1]

N-(5-Cyano-4-(dimethylamino)pyridin-2-yl)-7-formyl-6-((N-methyltetrahydrofuran-2-carboxamido)methyl)-3,4-dihydro-1,8-naphthyridin-1(2H)-carboxamide was prepared in accordance with the method of Example 1.

$^1$H NMR (400 MHz, CDCl$_3$): δ 13.57 (m, 1H), 10.25 (m, 1H), 8.23 (m, 1H), 7.55 (m, 2H), 5.00 (m, 3H), 4.00 (m, 4H), 3.27 (s, 6H), 3.09 (S, 2H), 2.90 (m, 3H), 2.04 (m, 6H);

MS m/z (ESI): 492.2 [M+H]$^+$.

Example 5

N-(5-Cyano-4-((2-methoxyethyl)amino)pyridin-2-yl)-7-formyl-6-((N-methyltetrahydrofuran-3-carboxamido)methyl)-3,4-dihydro-1,8-naphthyridin-1(2H)-carboxamide

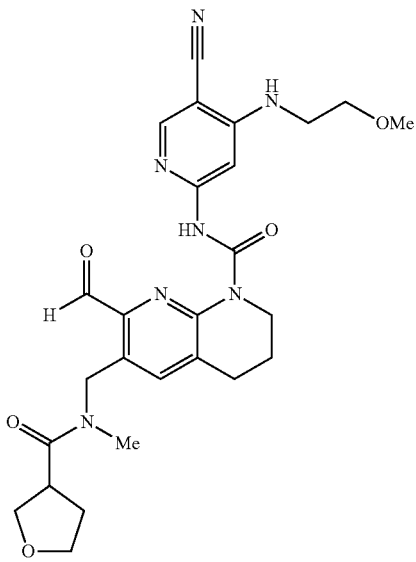

N-(5-Cyano-4-((2-methoxyethyl)amino)pyridin-2-yl)-7-formyl-6-((N-methyltetrahydrofuran-3-carboxamido)methyl)-3,4-dihydro-1,8-naphthyridin-1(2H)-carboxamide was prepared in accordance with the method of Example 1.

$^1$H NMR (400 MHz, CDCl$_3$): δ13.61 (m, 1H), 10.28 (m, 1H), 8.19 (m, 1H), 7.55 (m, 2H), 5.50 (m, 1H), 5.07 (m, 2H), 4.08 (m, 3H), 3.93 (m, 3H), 3.65 (m, 2H), 3.50 (m, 2H), 3.42 (s, 3H), 3.35 (m, 1H), 3.04 (m, 3H), 2.90 (m, 2H), 2.00 (m, 4H);

MS m/z (ESI): 522.2 [M+H]$^+$.

Example 6

(S)—N-(5-Cyano-4-((2-methoxyethyl)amino)pyridin-2-yl)-7-formyl-6-((N-methyltetrahydrofuran-3-carboxamido)methyl)-3,4-dihydro-1,8-naphthyridin-1(2H)-carboxamide

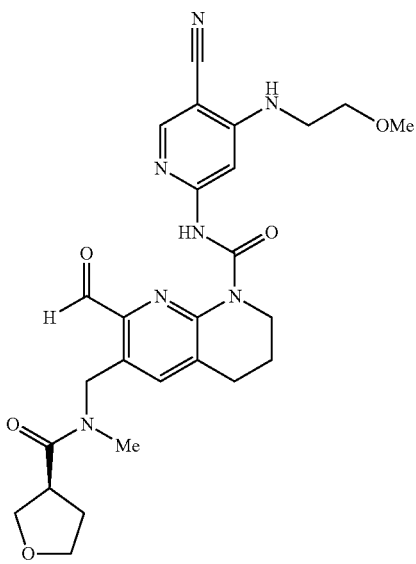 [SMILES: COCCNc1cc(NC(=O)N2CCCc3cc(CN(C)C(=O)[C@H]4CCOC4)c(C=O)nc32)ncc1C#N]

(S)—N-(5-Cyano-4-((2-methoxyethyl)amino)pyridin-2-yl)-7-formyl-6-((N-methyl tetrahydrofuran-3-carboxamido)methyl)-3,4-dihydro-1,8-naphthyridin-1(2H)-carboxamide was prepared in accordance with the method of Example 1.

$^1$H NMR (400 MHz, CDCl$_3$): δ 13.59 (m, 1H), 10.25 (m, 1H), 8.17 (m, 1H), 7.52 (m, 2H), 5.30 (m, 1H), 5.06 (m, 2H), 4.00 (m, 6H), 3.65 (m, 2H), 3.49 (m, 2H), 3.41 (s, 3H), 3.30 (m, 1H), 3.00 (m, 5H), 2.05 (m, 4H);

MS m/z (ESI): 522.2 [M+H]$^+$.

Example 7

(R)—N-(5-Cyano-4-((2-methoxyethyl)amino)pyridin-2-yl)-7-formyl-6-((N-methyltetrahydrofuran-3-carboxamido)methyl)-3,4-dihydro-1,8-naphthyridin-1(2H)-carboxamide

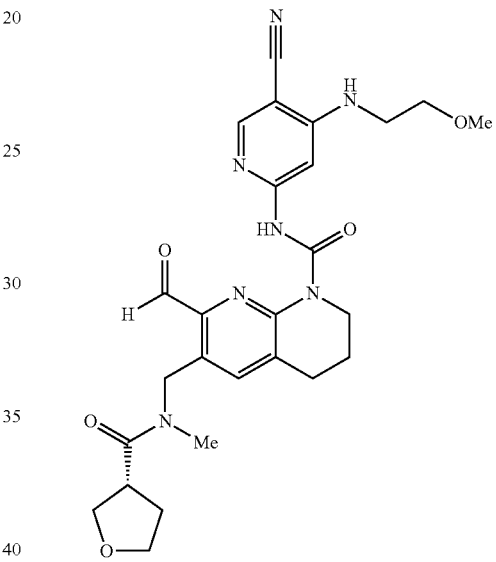

(R)—N-(5-Cyano-4-((2-methoxyethyl)amino)pyridin-2-yl)-7-formyl-6-((N-methyl tetrahydrofuran-3-carboxamido)methyl)-3,4-dihydro-1,8-naphthyridin-1(2H)-carboxamide was prepared in accordance with the method of Example 1.

$^1$H NMR (400 MHz, CDCl$_3$): δ 13.60 (m, 1H), 10.24 (m, 1H), 8.17 (m, 1H), 7.52 (m, 2H), 5.30 (m, 1H), 5.07 (m, 2H), 4.09 (m, 3H), 3.91 (m, 3H), 3.60 (m, 5H), 3.41 (s, 3H), 3.00 (m, 5H), 2.08 (m, 4H);

MS m/z (ESI): 522.2 [M+H]$^+$.

Example 8

(R)—N-(5-Cyano-4-((2-methoxyethyl)amino)pyridin-2-yl)-7-formyl-6-((N-methylpyrrolidin-2-carboxamido)methyl)-3,4-dihydro-1,8-naphthyridin-1(2H)-carboxamide

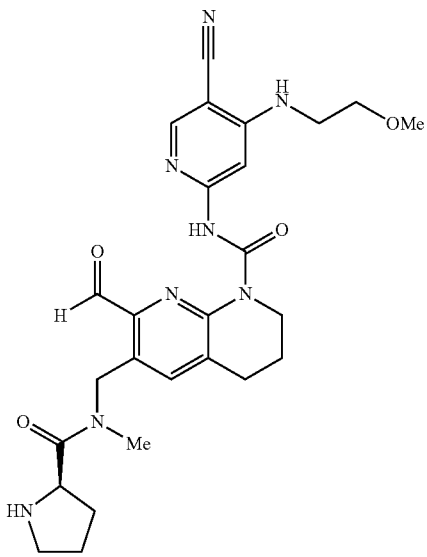 [SMILES: COCCNc1cc(NC(=O)N2CCCc3cc(CN(C)C(=O)[C@H]4CCCN4)c(C=O)nc32)ncc1C#N]

(R)—N-(5-Cyano-4-((2-methoxyethyl)amino)pyridin-2-yl)-7-formyl-6-((N-methyl pyrrolidin-2-carboxamido)methyl)-3,4-dihydro-1,8-naphthyridin-1(2H)-carboxamide was prepared in accordance with the method of Example 1.
MS m/z (ESI): 521.2 [M+H]$^+$.

Example 9

(R)—N-(5-Cyano-4-((2-methoxyethyl)amino)pyridin-2-yl)-6-((N,1-dimethylpyrrolidin-2-carboxamido)methyl)-7-formyl-3,4-dihydro-1,8-naphthyridin-1(2H)-carboxamide

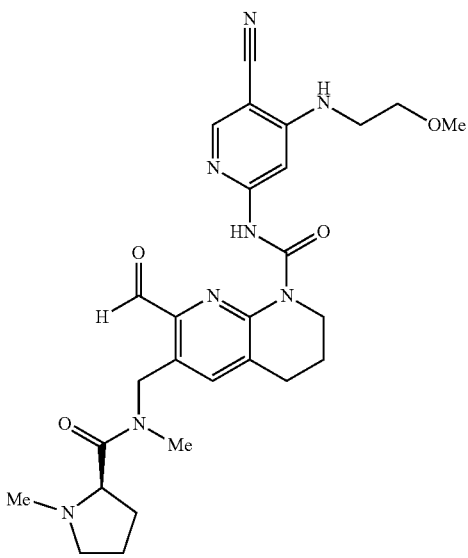 [SMILES: COCCNc1cc(NC(=O)N2CCCc3cc(CN(C)C(=O)[C@H]4CCCN4C)c(C=O)nc32)ncc1C#N]

(R)—N-(5-Cyano-4-((2-methoxyethyl)amino)pyridin-2-yl)-6-((N,1-dimethylpyrrolidin-2-carboxamido)methyl)-7-formyl-3,4-dihydro-1,8-naphthyridin-1(2H)-carboxamide was prepared in accordance with the method of Example 1.
$^1$H NMR (400 MHz, CDCl$_3$): δ 13.61 (m, 1H), 10.25 (m, 1H), 8.18 (m, 1H), 7.56 (m, 2H), 5.31 (m, 1H), 5.08 (m, 2H), 4.10 (m, 2H), 3.64 (m, 2H), 3.50 (m, 2H), 3.41 (s, 3H), 3.25 (m, 1H), 3.00 (m, 5H), 2.20 (m, 11H);
MS m/z (ESI): 535.2 [M+H]$^+$.

Example 10

(R)-6-((1-Acetyl-N-methylpyrrolidin-2-carboxamido)methyl)-N-(5-cyano-4-((2-m ethoxyethyl)amino)pyridin-2-yl)-7-formyl-3,4-dihydro-1,8-naphthyridin-1(2H)-carboxamide

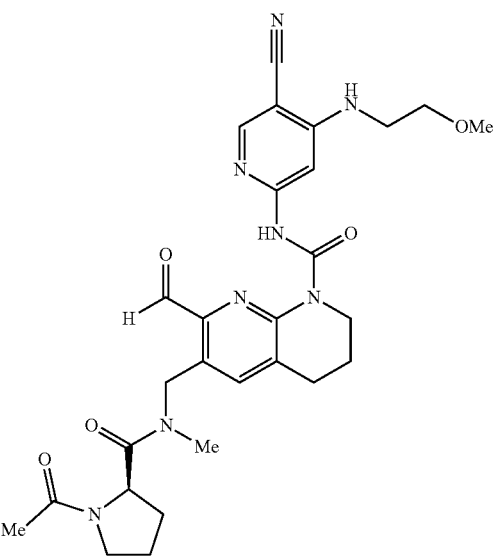 [SMILES: COCCNc1cc(NC(=O)N2CCCc3cc(CN(C)C(=O)[C@H]4CCCN4C(C)=O)c(C=O)nc32)ncc1C#N]

(R)-6-((1-Acetyl-N-methylpyrrolidin-2-carboxamido)methyl)-N-(5-cyano-4-((2-methoxyethyl)amino)pyridin-2-yl)-7-formyl-3,4-dihydro-1,8-naphthyridin-1(2H)-carboxamide was prepared in accordance with the method of Example 1.
$^1$H NMR (400 MHz, CDCl$_3$): δ 13.40 (m, 1H), 10.25 (m, 1H), 8.17 (m, 1H), 7.79 (m, 1H), 7.57 (s, 1H), 5.39 (m, 4H), 4.11 (m, 2H), 3.48 (m, 6H), 3.18 (s, 3H), 2.98 (m, 5H), 2.04 (m, 9H);
MS m/z (ESI): 563.3 [M+H]$^+$.

Example 11

(R)—N-(5-Cyano-4-((2-methoxyethyl)amino)pyridin-2-yl)-7-formyl-6-((tetrahydro furan-2-carboxamido)methyl)-3,4-dihydro-1,8-naphthyridin-1(2H)-carboxamide

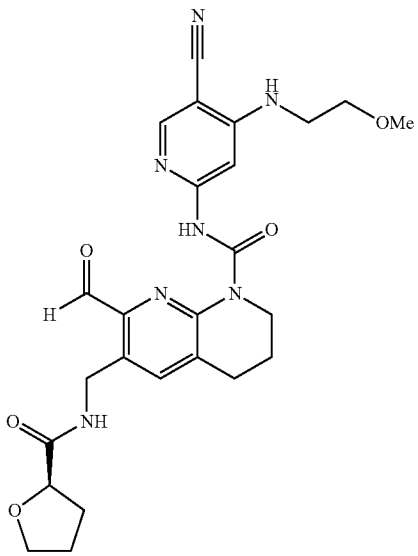 [SMILES: COCCNc1cc(NC(=O)N2CCCc3cc(CNC(=O)[C@H]4CCCO4)c(C=O)nc32)ncc1C#N]

(R)—N-(5-Cyano-4-((2-methoxyethyl)amino)pyridin-2-yl)-7-formyl-6-((tetrahydrofuran-2-carboxamido)methyl)-3,4-dihydro-1,8-naphthyridin-1(2H)-carboxamide was prepared in accordance with the method of Example 1.
MS m/z (ESI): 508.2 [M+H]$^+$.

Example 12

(S)—N-(5-Cyano-4-(2-methoxyethoxy)pyridin-2-yl)-7-formyl-6-((N-methyltetrahydrofuran-2-carboxamido)methyl)-3,4-dihydro-1,8-naphthyridin-1(2H)-carboxamide

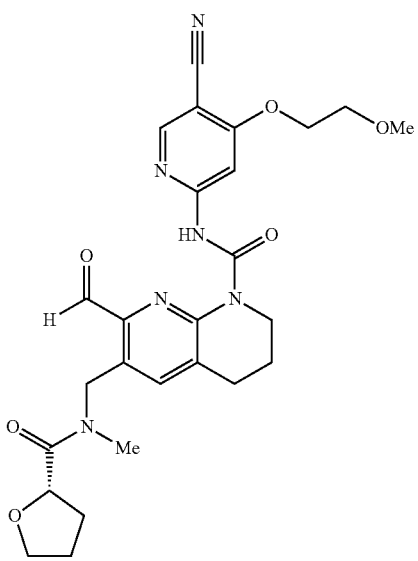 [SMILES: COCCOc1cc(NC(=O)N2CCCc3cc(CN(C)C(=O)[C@@H]4CCCO4)c(C=O)nc32)ncc1C#N]

(S)—N-(5-Cyano-4-(2-methoxyethoxy)pyridin-2-yl)-7-formyl-6-((N-methyltetrahydrofuran-2-carboxamido)methyl)-3,4-dihydro-1,8-naphthyridin-1(2H)-carboxamide was prepared in accordance with the method of Example 1.
MS m/z (ESI): 523.2 [M+H]$^+$.

Example 13

(R)—N-(5-Cyano-4-(2-methoxyethoxy)pyridin-2-yl)-7-formyl-6-((N-methyltetrahydrofuran-2-carboxamido)methyl)-3,4-dihydro-1,8-naphthyridin-1(2H)-carboxamide

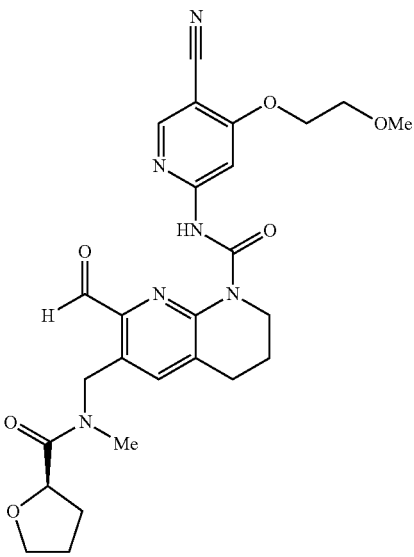

(R)—N-(5-Cyano-4-(2-methoxyethoxy)pyridin-2-yl)-7-formyl-6-((N-methyltetrahydrofuran-2-carboxamido)methyl)-3,4-dihydro-1,8-naphthyridin-1(2H)-carboxamide was prepared in accordance with the method of Example 1.
MS m/z (ESI): 523.2 [M+H]$^+$.

Example 14

N-(5-Cyano-4-(((R)-1-methoxypropan-2-yl)oxy)pyridin-2-yl)-7-formyl-6-(((S)—N-methyltetrahydrofuran-2-carboxamido)methyl)-3,4-dihydro-1,8-naphthyridin-1(2H)-carboxamide

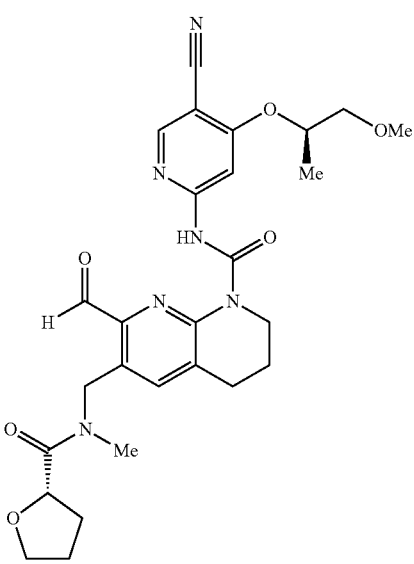 [SMILES: COC[C@@H](C)Oc1cc(NC(=O)N2CCCc3cc(CN(C)C(=O)[C@@H]4CCCO4)c(C=O)nc32)ncc1C#N]

N-(5-Cyano-4-(((R)-1-methoxypropan-2-yl)oxy)pyridin-2-yl)-7-formyl-6-(((S)—N-methyltetrahydrofuran-2-carboxamido)methyl)-3,4-dihydro-1,8-naphthyridin-1(2H)-carboxamide was prepared in accordance with the method of Example 1.

MS m/z (ESI): 536.2 [M+H]⁺.

Example 15

N-(5-Cyano-4-(((R)-1-methoxypropan-2-yl)oxy)pyridin-2-yl)-7-formyl-6-(((R)—N-methyltetrahydrofuran-2-carboxamido)methyl)-3,4-dihydro-1,8-naphthyridin-1(2H)-carboxamide

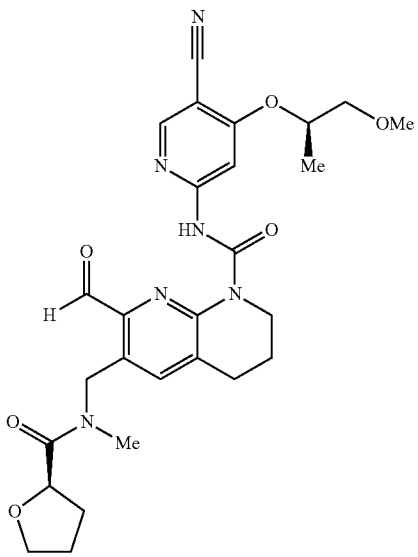 [SMILES: COC[C@@H](C)Oc1cc(NC(=O)N2CCCc3cc(CN(C)C(=O)[C@H]4CCCO4)c(C=O)nc32)ncc1C#N]

N-(5-Cyano-4-(((R)-1-methoxypropan-2-yl)oxy)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

¹H NMR (400 MHz, CDCl₃): δ 14.20-13.80 (m, 1H), 10.50-10.30 (m, 1H), 8.50-8.35 (m, 2H), 7.65-7.45 (m, 1H), 5.28-4.88 (m, 2H), 4.78-4.45 (m, 1H), 4.17-3.84 (m, 4H), 3.71-3.55 (m, 3H), 3.42 (s, 3H), 3.16-3.06 (m, 2H), 2.95 (s, 3H), 2.65-1.80 (m, 6H), 1.47 (s, 3H);

MS m/z (ESI): 537.2 [M+H]⁺.

Example 16

(R)—N-(5-Cyano-4-((2-methoxyethyl)thio)pyridin-2-yl)-7-formyl-6-((N-methyltetrahydrofuran-2-carboxamido)methyl)-3,4-dihydro-1,8-naphthyridin-1(2H)-carboxamide

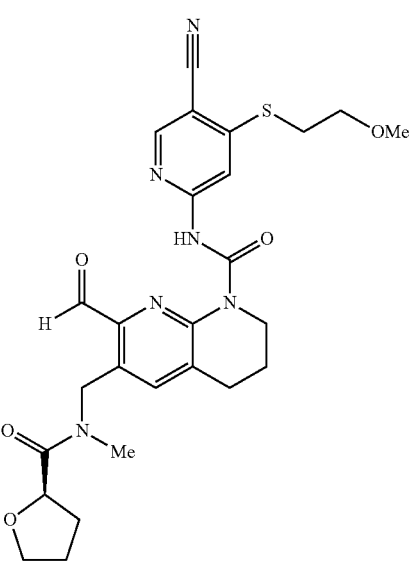 [SMILES: COCCSc1cc(NC(=O)N2CCCc3cc(CN(C)C(=O)[C@H]4CCCO4)c(C=O)nc32)ncc1C#N]

(R)—N-(5-Cyano-4-((2-methoxyethyl)thio)pyridin-2-yl)-7-formyl-6-((N-methyltetrahydrofuran-2-carboxamido)methyl)-3,4-dihydro-1,8-naphthyridin-1(2H)-carboxamide was prepared in accordance with the method of Example 1.

¹H NMR (400 MHz, CDCl₃): δ14.20-13.80 (m, 1H), 10.50-10.25 (m, 1H), 8.50-8.35 (m, 2H), 7.65-7.45 (m, 1H), 5.25-4.85 (m, 2H), 4.77-4.45 (m, 1H), 4.15-3.83 (m, 4H), 3.77 (m, 2H), 3.45 (s, 3H), 3.35 (m, 2H), 3.15-2.78 (m, 5H), 2.55-1.70 (m, 6H);

MS m/z (ESI): 539.2 [M+H]⁺.

Example 17

N-(5-Cyano-4-((S)-3-methoxypyrrolidin-1-yl)pyridin-2-yl)-7-formyl-6-(((R)—N-methyltetrahydrofuran-2-carboxamido)methyl)-3,4-dihydro-1,8-naphthyridin-1(2H)-carboxamide

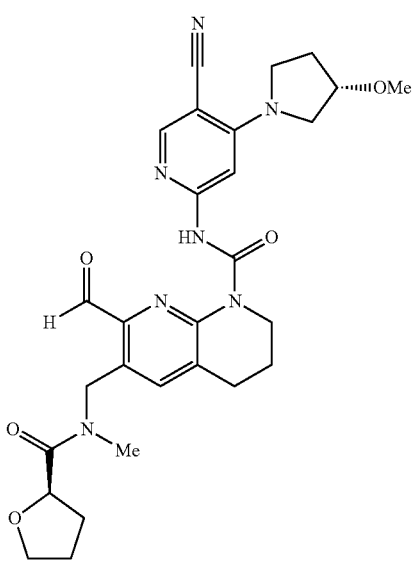 [SMILES: CO[C@H]1CCN(c2cc(NC(=O)N3CCCc4cc(CN(C)C(=O)[C@H]5CCCO5)c(C=O)nc43)ncc2C#N)C1]

N-(5-cyano-4-((S)-3-methoxypyrrolidin-1-yl)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

$^1$H NMR (400 MHz, CDCl$_3$): δ14.20-13.80 (m, 1H), 10.50-10.25 (m, 1H), 8.50-8.35 (m, 2H), 7.65-7.45 (m, 1H), 5.25-4.85 (m, 2H), 4.77-4.45 (m, 1H), 4.20-3.74 (m, 9H), 3.38 (s, 3H), 3.15-2.78 (m, 5H), 2.55-1.70 (m, 8H);

MS m/z (ESI): 548.2 [M+H]$^+$.

Example 18

N-(5-Cyano-4-((R)-3-methoxypyrrolidin-1-yl)pyridin-2-yl)-7-formyl-6-(((R)—N-methyltetrahydrofuran-2-carboxamido)methyl)-3,4-dihydro-1,8-naphthyridin-1(2H)-carboxamide N-(5-Cyano-4-((R)-3-methoxypyrrolidin-1-yl)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

$^1$H NMR (400 MHz, CDCl$_3$): 314.20-13.80 (m, 1H), 10.50-10.25 (m, 1H), 8.50-8.35 (m, 2H), 7.65-7.45 (m, 1H), 5.25-4.85 (m, 2H), 4.77-4.45 (m, 1H), 4.20-3.74 (m, 9H), 3.38 (s, 3H), 3.15-2.78 (m, 5H), 2.55-1.70 (m, 8H);

MS m/z (ESI): 548.2 [M+H]$^+$.

Example 19

N-(5-Cyano-4-(((S)-tetrahydrofuran-3-yl)thio)pyridin-2-yl)-7-formyl-6-(((R)—N-m ethyltetrahydrofuran-2-carboxamido)methyl)-3,4-dihydro-1,8-naphthyridin-1(2H)-carboxamide

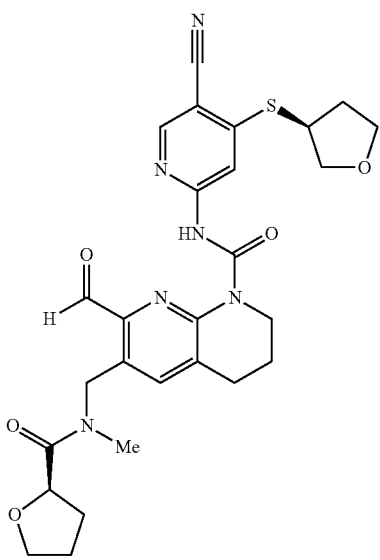 [SMILES: CN(Cc1cc2c(nc1C=O)N(C(=O)Nc1cc(S[C@H]3CCOC3)c(C#N)cn1)CCC2)C(=O)[C@H]1CCCO1]

N-(5-Cyano-4-(((S)-tetrahydrofuran-3-yl)thio)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

¹H NMR (400 MHz, CDCl₃): δ 14.20-13.80 (m, 1H), 10.50-10.25 (m, 1H), 8.50-8.35 (m, 2H), 7.65-7.45 (m, 1H), 5.25-4.85 (m, 2H), 4.77-4.45 (m, 1H), 4.45-4.33 (m, 1H), 4.20-3.74 (m, 8H), 3.15-2.78 (m, 5H), 2.55-1.70 (m, 8H); MS m/z (ESI): 551.2 [M+H]⁺.

Example 20

N-(5-Cyano-4-(((R)-tetrahydrofuran-3-yl)thio)pyridin-2-yl)-7-formyl-6-(((R)—N-methyltetrahydrofuran-2-carboxamido)methyl)-3,4-dihydro-1,8-naphthyridin-1(2H)-carboxamide

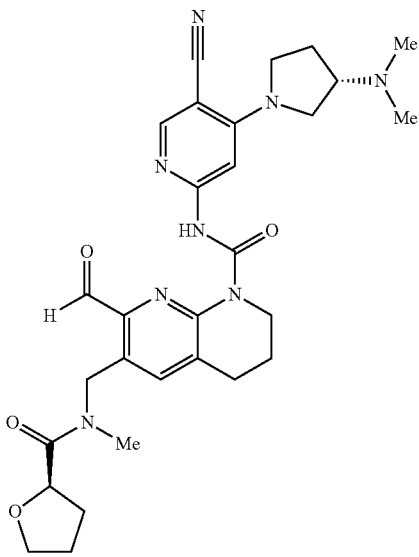 [SMILES: CN(Cc1cc2c(nc1C=O)N(C(=O)Nc1cc(N3CC[C@H](N(C)C)C3)c(C#N)cn1)CCC2)C(=O)[C@H]1CCCO1]

N-(5-Cyano-4-(((R)-tetrahydrofuran-3-yl)thio)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 551.2 [M+H]⁺.

Example 21

N-(5-Cyano-4-((S)-3-(dimethylamino)pyrrolidin-1-yl)pyridin-2-yl)-7-formyl-6-(((R)—N-methyltetrahydrofuran-2-carboxamido)methyl)-3,4-dihydro-1,8-naphthyridin-1(2H)-carboxamide N-(5-Cyano-4-((S)-3-(dimethylamino)pyrrolidin-1-yl)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 561.3 [M+H]⁺.

Example 22

N-(5-Cyano-4-((R)-3-(dimethylamino)pyrrolidin-1-yl)pyridin-2-yl)-7-formyl-6-(((R)—N-methyltetrahydrofuran-2-carboxamido)methyl)-3,4-dihydro-1,8-naphthyridin-1(2H)-carboxamide

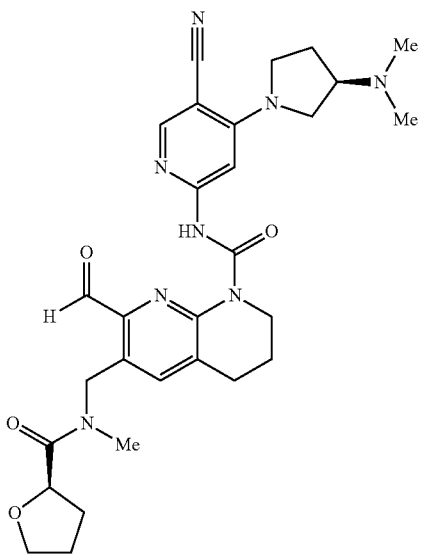 [SMILES: CN(Cc1cc2c(nc1C=O)N(C(=O)Nc1cc(N3CC[C@@H](N(C)C)C3)c(C#N)cn1)CCC2)C(=O)[C@H]1CCCO1]

N-(5-Cyano-4-((R)-3-(dimethylamino)pyrrolidin-1-yl)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 561.3 [M+H]⁺.

Example 23

(R)—N-(5-Cyano-4-(3-methoxyazetidin-1-yl)pyridin-2-yl)-7-formyl-6-((N-methyltetrahydrofuran-2-carboxamido)methyl)-3,4-dihydro-1,8-naphthyridin-1(2H)-carboxamide

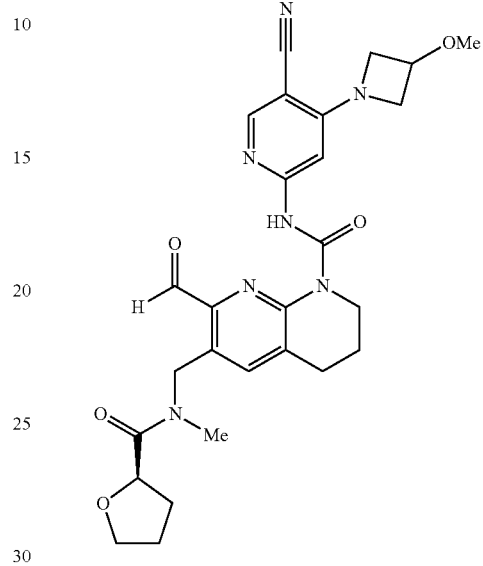

(R)—N-(5-Cyano-4-(3-methoxyazetidin-1-yl)pyridin-2-yl)-7-formyl-6-((N-methyl tetrahydrofuran-2-carboxamido)methyl)-3,4-dihydro-1,8-naphthyridin-1(2H)-carboxamide was prepared in accordance with the method of Example 1.
MS m/z (ESI): 534.2 [M+H]⁺.

Example 24

N-(5-Cyano-4-(((3S,4R)-4-methoxytetrahydrofuran-3-yl)amino)pyridin-2-yl)-7-formyl-6-(((R)—N-methyltetrahydrofuran-2-carboxamido)methyl)-3,4-dihydro-1,8-naphthyridin-1(2H)-carboxamide

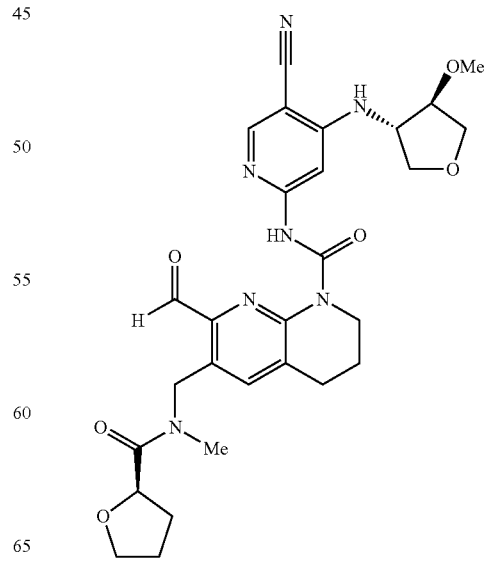

N-(5-Cyano-4-(((3S,4R)-4-methoxytetrahydrofuran-3-yl)amino)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 564.2 [M+H]⁺.

Example 25

N-(5-Cyano-4-(((3R,4S)-4-methoxytetrahydrofuran-3-yl)amino)pyridin-2-yl)-7-formyl-6-(((R)—N-methyltetrahydrofuran-2-carboxamido)methyl)-3,4-dihydro-1,8-naphthyridin-1(2H)-carboxamide

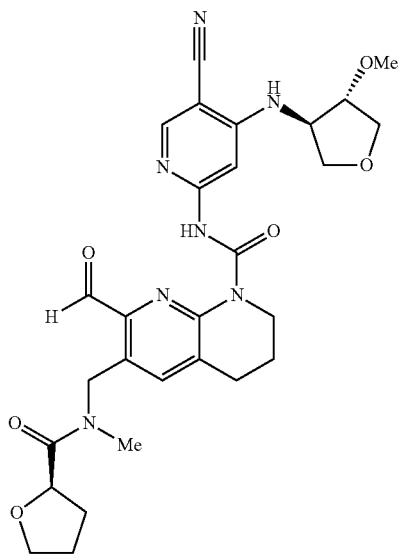 [SMILES: CO[C@@H]1COC[C@H]1Nc1cc(NC(=O)N2CCCc3cc(CN(C)C(=O)[C@H]4CCCO4)c(C=O)nc32)ncc1C#N]

N-(5-Cyano-4-(((3R,4S)-4-methoxytetrahydrofuran-3-yl)amino)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 564.2 [M+H]⁺.

Example 26

N-(5-Cyano-4-(((3S,4S)-4-methoxytetrahydrofuran-3-yl)oxy)pyridin-2-yl)-7-formyl-6-(((R)—N-methyltetrahydrofuran-2-carboxamido)methyl)-3,4-dihydro-1,8-naphthyridin-1(2H)-carboxamide

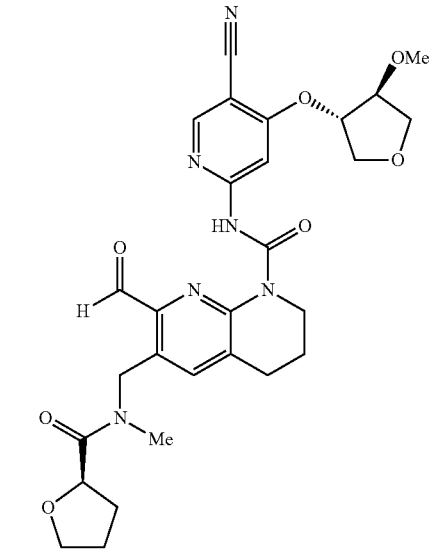 [SMILES: CO[C@H]1COC[C@@H]1Oc1cc(NC(=O)N2CCCc3cc(CN(C)C(=O)[C@H]4CCCO4)c(C=O)nc32)ncc1C#N]

N-(5-Cyano-4-(((3S,4S)-4-methoxytetrahydrofuran-3-yl)oxy)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 565.2 [M+H]⁺.

Example 27

N-(5-Cyano-4-(((3R,4R)-4-methoxytetrahydrofuran-3-yl)oxy)pyridin-2-yl)-7-formyl-6-(((R)—N-methyltetrahydrofuran-2-carboxamido)methyl)-3,4-dihydro-1,8-naphthyridin-1(2H)-carboxamide

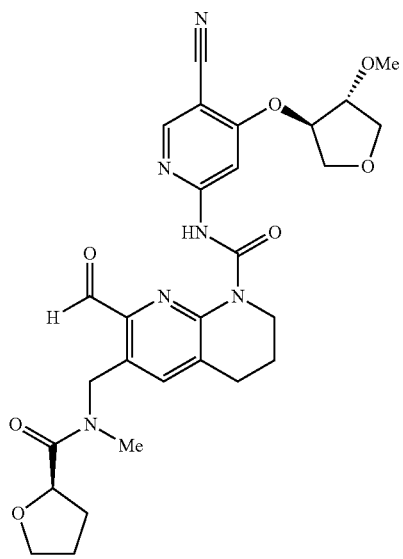 [SMILES: CO[C@@H]1COC[C@H]1Oc1cc(NC(=O)N2CCCc3cc(CN(C)C(=O)[C@H]4CCCO4)c(C=O)nc32)ncc1C#N]

N-(5-Cyano-4-(((3R,4R)-4-methoxytetrahydrofuran-3-yl)oxy)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 565.2 [M+H]⁺.

Example 28

N-(5-Cyano-4-(((3R,4R)-3-methoxytetrahydro-2H-pyran-4-yl)oxy)pyridin-2-yl)-7-formyl-6-(((R)—N-methyltetrahydrofuran-2-carboxamido)-3,4-dihydro-1,8-naphthyridin-1(2H)-carboxamide

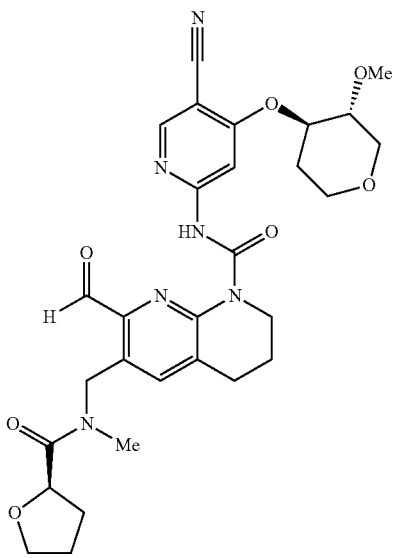 [SMILES: CO[C@@H]1COCC[C@H]1Oc1cc(NC(=O)N2CCCc3cc(CN(C)C(=O)[C@H]4CCCO4)c(C=O)nc32)ncc1C#N]

N-(5-Cyano-4-(((3R,4R)-3-methoxytetrahydro-2H-pyran-4-yl)oxy)pyridin-2-yl)-7-formyl-6-(((R)—N-methyltetrahydrofuran-2-carboxamido)-3,4-dihydro-1,8-naphthyridin-1(2H)-carboxamide was prepared in accordance with the method of Example 1.

MS m/z (ESI): 579.2 [M+H]⁺.

Example 29

N-(5-Cyano-4-(((3S,4S)-4-methoxytetrahydro-2H-pyran-3-yl)oxy)pyridin-2-yl)-7-formyl-6-(((R)—N-methyltetrahydrofuran-2-carboxamido)methyl)-3,4-dihydro-1,8-naphthyridin-1(2H)-carboxamide

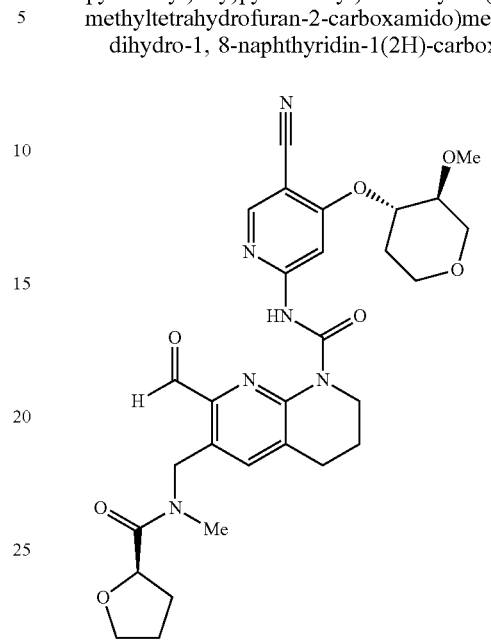

N-(5-Cyano-4-(((3S,4S)-4-methoxytetrahydro-2H-pyran-3-yl)oxy)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 579.2 [M+H]⁺.

Example 30

N-(5-Cyano-4-(((3R,4R)-4-methoxytetrahydro-2H-pyran-3-yl)oxy)pyridin-2-yl)-7-formyl-6-(((R)—N-methyltetrahydrofuran-2-carboxamido)methyl)-3,4-dihydro-1,8-naphthyridin-1(2H)-carboxamide

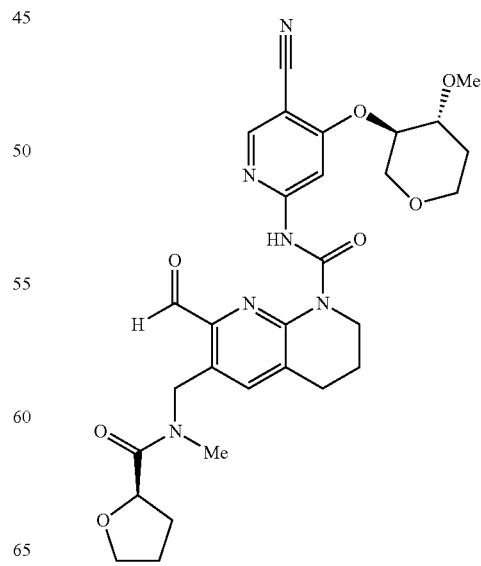

N-(5-Cyano-4-(((3R,4R)-4-methoxytetrahydro-2H-pyran-3-yl)oxy)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 579.2 [M+H]$^+$.

Example 31

N-(5-Cyano-4-(((3S,4S)-4-methoxytetrahydro-2H-pyran-3-yl)amino)pyridin-2-yl)-7-formyl-6-(((R)—N-methyltetrahydrofuran-2-carboxamido)methyl)-3,4-dihydro-1,8-naphthyridin-1(2H)-carboxamide

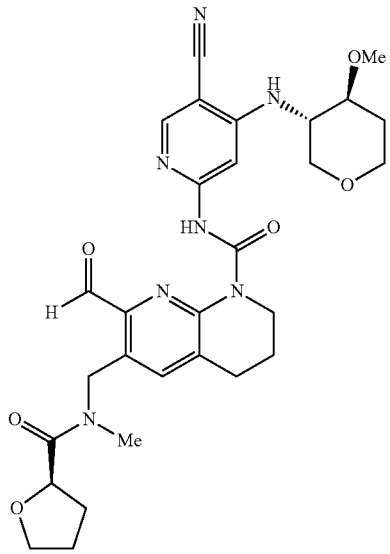 [SMILES: CO[C@H]1CCOC[C@@H]1Nc1cc(NC(=O)N2CCCc3cc(CN(C)C(=O)[C@H]4CCCO4)c(C=O)nc32)ncc1C#N]

N-(5-Cyano-4-(((3S,4S)-4-methoxytetrahydro-2H-pyran-3-yl)amino)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 578.2 [M+H]$^+$.

Example 32

N-(5-Cyano-4-(((3R,4R)-4-methoxytetrahydro-2H-pyran-3-yl)amino)pyridin-2-yl)-7-formyl-6-(((R)—N-methyltetrahydrofuran-2-carboxamido)methyl)-3,4-dihydro-1,8-naphthyridin-1(2H)-carboxamide

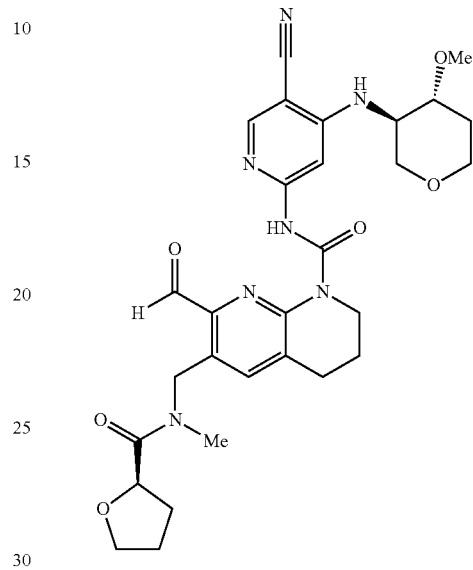

N-(5-Cyano-4-(((3R,4R)-4-methoxytetrahydro-2H-pyran-3-yl)amino)pyridin-2-y 1)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 578.2 [M+H]$^+$.

Example 33

N-(5-Cyano-4-((1R,2R)-2-methoxycyclobutoxy)pyridin-2-yl)-7-formyl-6-(((R)—N-methyltetrahydrofuran-2-carboxamido)methyl)-3,4-dihydro-1,8-naphthyridin-1(2H)-carboxamide

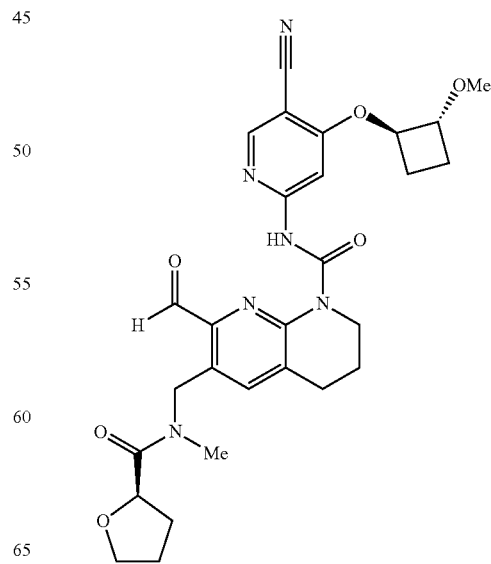

121

N-(5-Cyano-4-(((1R,2R)-2-methoxycyclobutoxy)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 549.2 [M+H]⁺.

Example 34

N-(5-Cyano-4-(((1S,2S)-2-methoxycyclobutoxy)pyridin-2-yl)-7-formyl-6-(((R)—N-methyltetrahydrofuran-2-carboxamido)methyl)-3,4-dihydro-1,8-naphthyridin-1(2H)-carboxamide

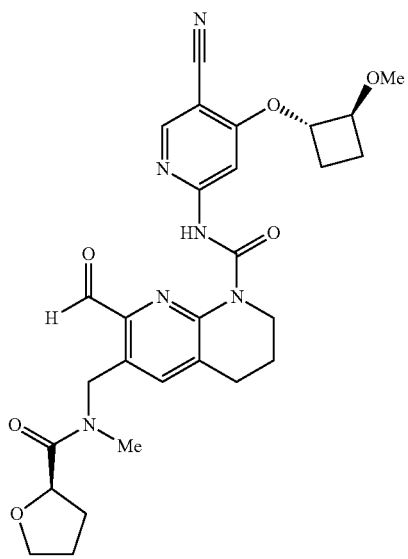 [SMILES: CO[C@H]1CC[C@@H]1Oc1cc(NC(=O)N2CCCc3cc(CN(C)C(=O)[C@H]4CCCO4)c(C=O)nc32)ncc1C#N]

N-(5-Cyano-4-(((1S,2S)-2-methoxycyclobutoxy)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 549.2 [M+H]⁺.

122

Example 35

N-(5-Cyano-4-(((1R,2S)-2-methoxycyclobutoxy)pyridin-2-yl)-7-formyl-6-(((R)—N-methyltetrahydrofuran-2-carboxamido)methyl)-3,4-dihydro-1,8-naphthyridin-1(2H)-carboxamide

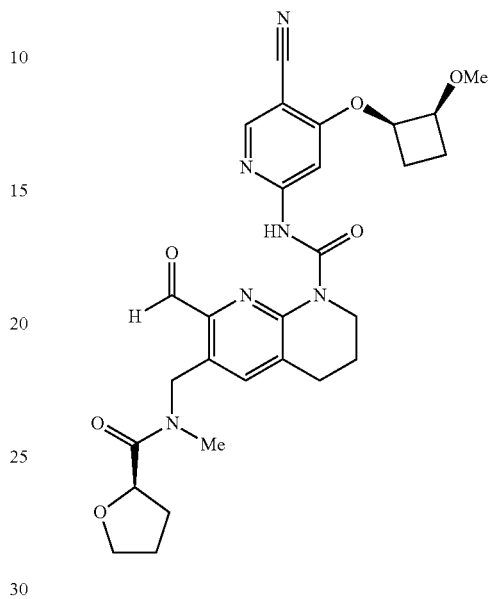

N-(5-Cyano-4-(((1R,2S)-2-methoxycyclobutoxy)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 549.2 [M+H]⁺.

Example 36

N-(5-Cyano-4-(((1S,2R)-2-methoxycyclobutoxy)pyridin-2-yl)-7-formyl-6-(((R)—N-methyltetrahydrofuran-2-carboxamido)methyl)-3,4-dihydro-1,8-naphthyridin-1(2H)-carboxamide

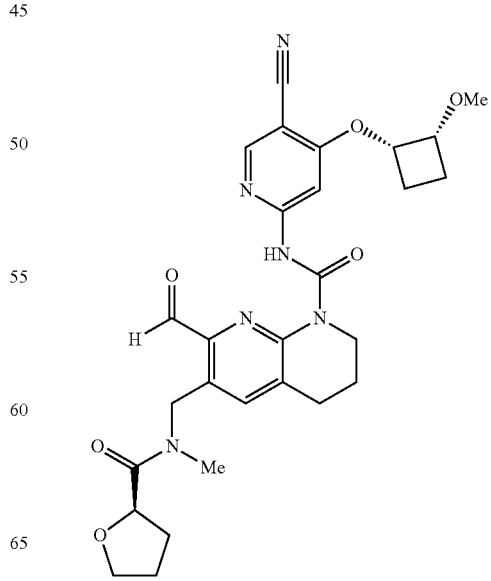

N-(5-Cyano-4-((1S,2R)-2-methoxycyclobutoxy)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 549.2 [M+H]⁺.

Example 37

N-(5-Cyano-4-(((1R,2R)-2-methoxycyclobutyl)amino)pyridin-2-yl)-7-formyl-6-(((R)—N-methyltetrahydrofuran-2-carboxamido)methyl)-3,4-dihydro-1,8-naphthyridin-1(2H)-carboxamide

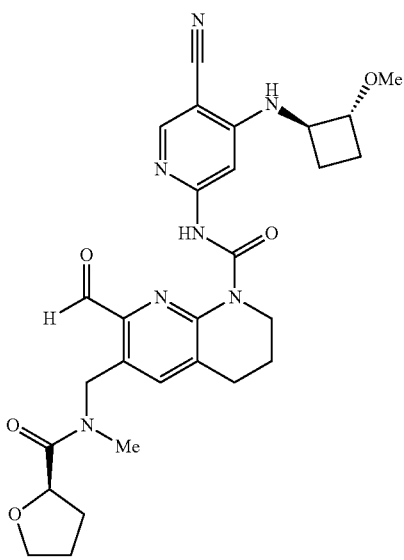 [SMILES: CO[C@@H]1CC[C@H]1Nc1cc(NC(=O)N2CCCc3cc(CN(C)C(=O)[C@H]4CCCO4)c(C=O)nc32)ncc1C#N]

N-(5-Cyano-4-(((1R,2R)-2-methoxycyclobutyl)amino)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 548.2 [M+H]⁺.

Example 38

N-(5-Cyano-4-(((1S,2S)-2-methoxycyclobutyl)amino)pyridin-2-yl)-7-formyl-6-(((R)—N-methyltetrahydrofuran-2-carboxamido)methyl)-3,4-dihydro-1,8-naphthyridin-1(2H)-carboxamide

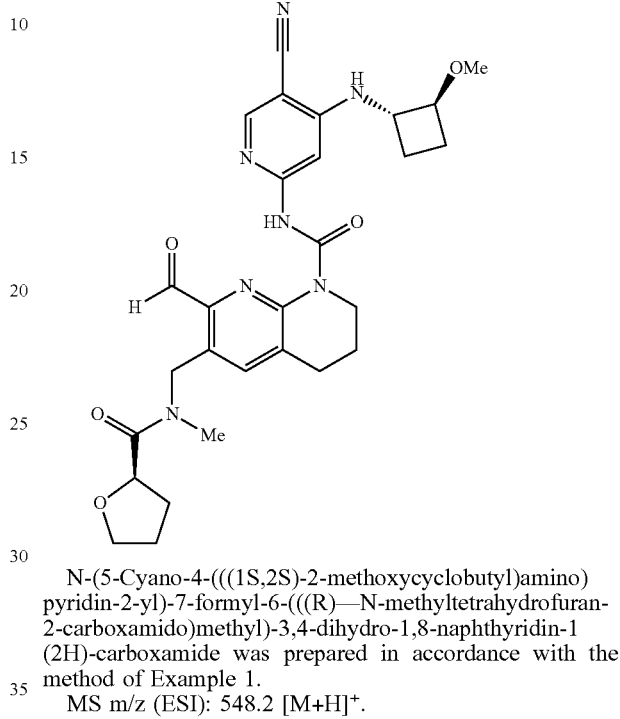

N-(5-Cyano-4-(((1S,2S)-2-methoxycyclobutyl)amino)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 548.2 [M+H]⁺.

Example 39

N-(5-Cyano-4-(((1R,2S)-2-methoxycyclobutyl)amino)pyridin-2-yl)-7-formyl-6-(((R)—N-methyltetrahydrofuran-2-carboxamido)methyl)-3,4-dihydro-1,8-naphthyridin-1(2H)-carboxamide

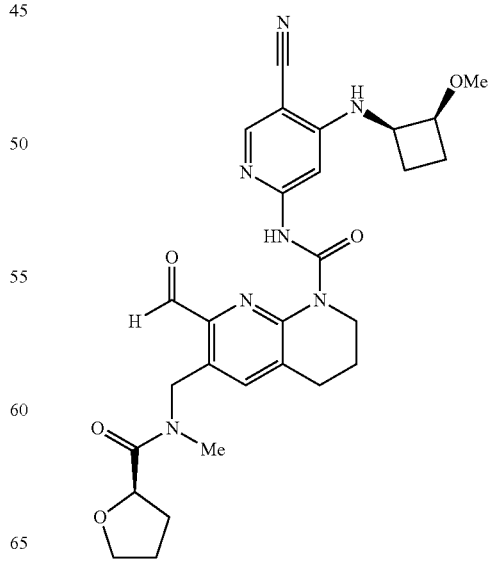

N-(5-Cyano-4-(((1R,2S)-2-methoxycyclobutyl)amino)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 548.2 [M+H]⁺.

Example 40

N-(5-Cyano-4-(((1S,2R)-2-methoxycyclobutyl)amino)pyridin-2-yl)-7-formyl-6-(((R)—N-methyltetrahydrofuran-2-carboxamido)methyl)-3,4-dihydro-1,8-naphthyridin-1(2H)-carboxamide

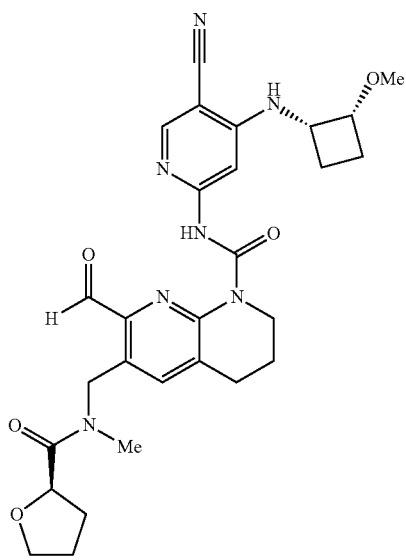 [SMILES: CO[C@@H]1CC[C@@H]1Nc1cc(NC(=O)N2CCCc3cc(CN(C)C(=O)[C@H]4CCCO4)c(C=O)nc32)ncc1C#N]

N-(5-Cyano-4-(((1S,2R)-2-methoxycyclobutyl)amino)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 548.2 [M+H]⁺.

Example 41

(R)—N-(5-Cyano-3-fluoro-4-((2-methoxyethyl)amino)pyridin-2-yl)-7-formyl-6-((N-methyltetrahydrofuran-2-carboxamido)methyl)-3,4-dihydro-1,8-naphthyridin-1(2H)-carboxamide

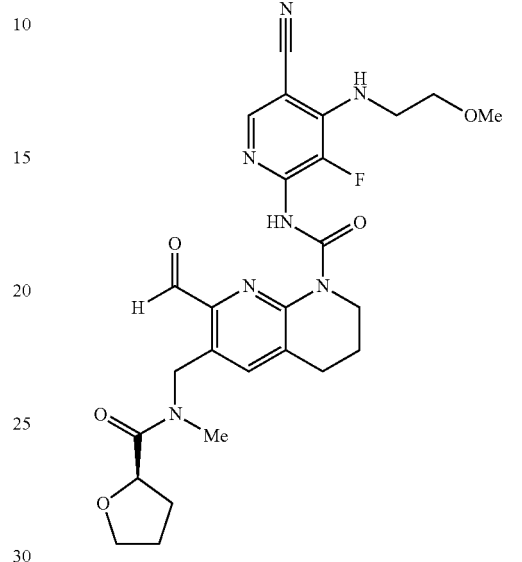

(R)—N-(5-Cyano-3-fluoro-4-((2-methoxyethyl)amino)pyridin-2-yl)-7-formyl-6-((N-methyltetrahydrofuran-2-carboxamido)methyl)-3,4-dihydro-1,8-naphthyridin-1(2H)-carboxamide was prepared in accordance with the method of Example 1.

MS m/z (ESI): 540.2 [M+H]⁺.

Example 42

N—((R)-7-Cyano-2-(methoxymethyl)-2,3-dihydrofuran[3,2-c]pyridin-4-yl)-7-formyl-6-(((R)—N-methyltetrahydrofuran-2-carboxamido)methyl)-3,4-dihydro-1,8-naphthyridin-1(2H)-carboxamide

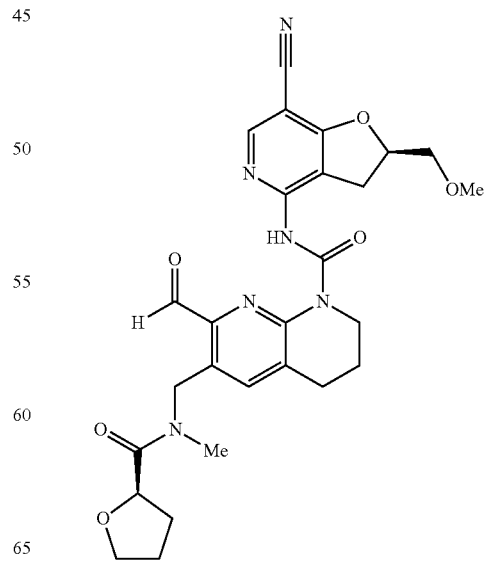

N—((R)-7-Cyano-2-(methoxymethyl)-2,3-dihydrofuran[3,2-c]pyridin-4-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 535.2 [M+H]⁺.

Example 43

N—((S)-7-Cyano-2-(methoxymethyl)-2,3-dihydrofuran[3,2-c]pyridin-4-yl)-7-formyl-6-(((R)—N-methyltetrahydrofuran-2-carboxamido)methyl)-3,4-dihydro-1,8-naphthyridin-1(2H)-carboxamide

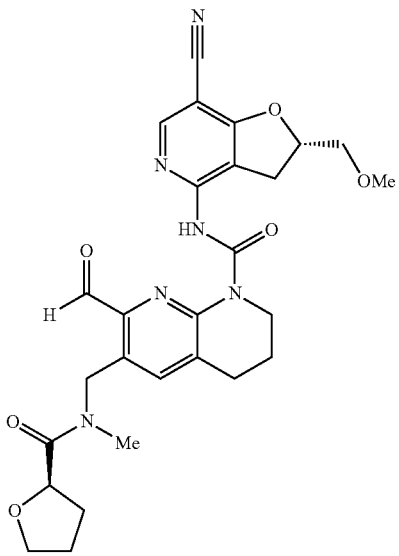 [SMILES: COC[C@@H]1Cc2c(NC(=O)N3CCCc4cc(CN(C)C(=O)[C@H]5CCCO5)c(C=O)nc43)ncc(C#N)c2O1]

N—((S)-7-Cyano-2-(methoxymethyl)-2,3-dihydrofuran[3,2-c]pyridin-4-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

MS m/z (ESI): 535.2 [M+H]⁺.

Example 44

N-(5-Cyano-4-((2-methoxyethyl)amino)pyridin-2-yl)-7-formyl-6-((3-methoxy-2-carbonylpyrrolidin-1-yl)methyl)-3,4-dihydro-1,8-naphthyridin-1(2H)-carboxamide

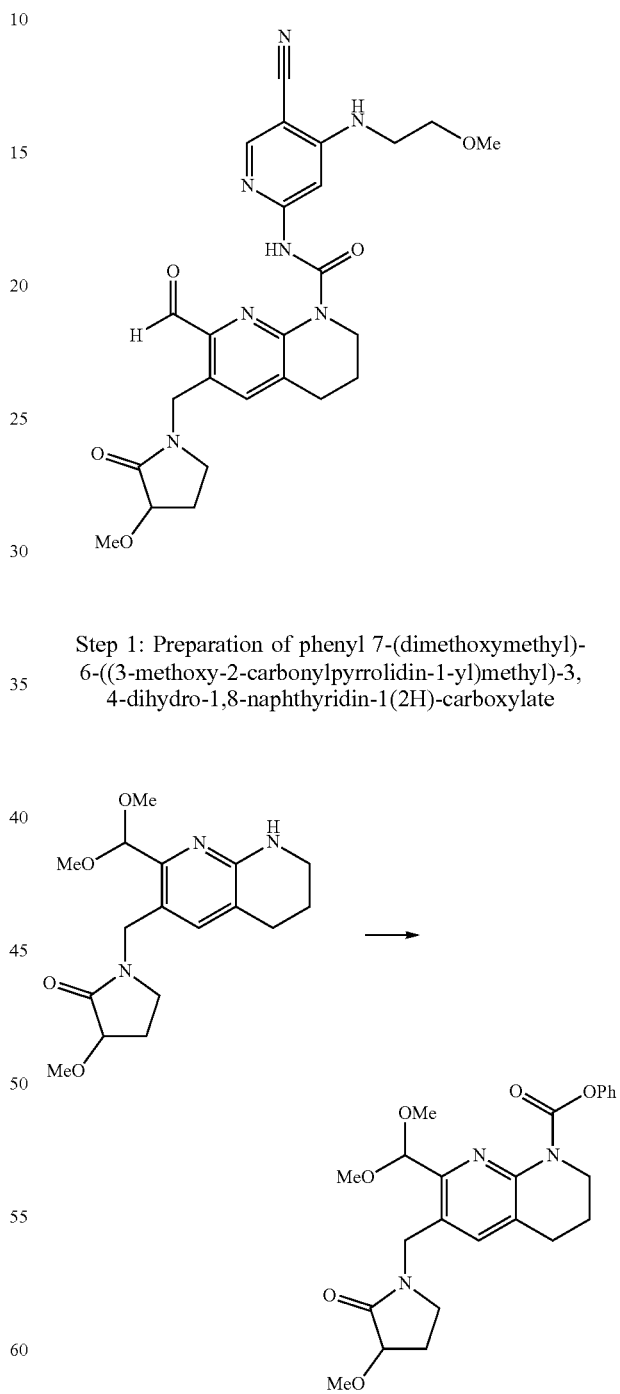

Step 1: Preparation of phenyl 7-(dimethoxymethyl)-6-((3-methoxy-2-carbonylpyrrolidin-1-yl)methyl)-3,4-dihydro-1,8-naphthyridin-1(2H)-carboxylate 1-((2-(dimethoxymethyl)-5,6,7,8-tetrahydro-1,8-naphthyridin-3-yl)methyl)-3-methoxypyrrolidin-2-one (91 mg, 0.27 mmol) and diphenylcarbonate (70 mg, 0.33 mmol) were mixed in THF (5 mL), cooled to −78° C., and then added dropwise with a solution of LiHMDS (0.54 mL, 0.54 mmol) in THF in a $N_2$ atmosphere. The reaction solution was naturally warmed up to room temperature and stirred overnight. Saturated aqueous $NH_4Cl$ solution (2 mL) was added, and then the reaction solution was extracted with EtOAc (50 mL×2). The organic phase was washed with saturated brine, dried over anhydrous sodium sulfate, and concentrated. The resulting residue was subjected to column chromatography to obtain the title compound phenyl 7-(dimethoxymethyl)-6-((3-methoxy-2-carbonylpyrrolidin-1-yl)methyl)-3,4-dihydro-1,8-naphthyridin-1(2H)-carboxylate (61 mg, 49%).

$^1$H NMR (400 MHz, $CDCl_3$) δ 7.37 (s, 1H), 7.34-7.22 (m, 2H), 7.17-7.04 (m, 3H), 5.22 (S, 2H), 5.14 (s, 1H), 4.65 (q, J=15.2 Hz, 2H), 3.94 (t, J=7.3 Hz, 1H), 3.86 (m, 2H), 3.52 (s, 3H), 3.31 (d, J=3.9 Hz, 6H), 3.19-3.00 (m, 1H), 2.74 (t, J=6.6 Hz, 2H), 2.25 (m, 1H), 2.03-1.89 (m, 2H);

MS m/z (ESI): 456.1 [M+H]$^+$.

Step 2: Preparation of N-(5-cyano-4-((2-methoxyethyl)amino)pyridin-2-yl)-7-(dimethoxymethyl)-6-((3-methoxy-2-carbonylpyrrolidin-1-yl)methyl)-3,4-dihydro-1,8-naphthyridin-1(2H)-carboxamide

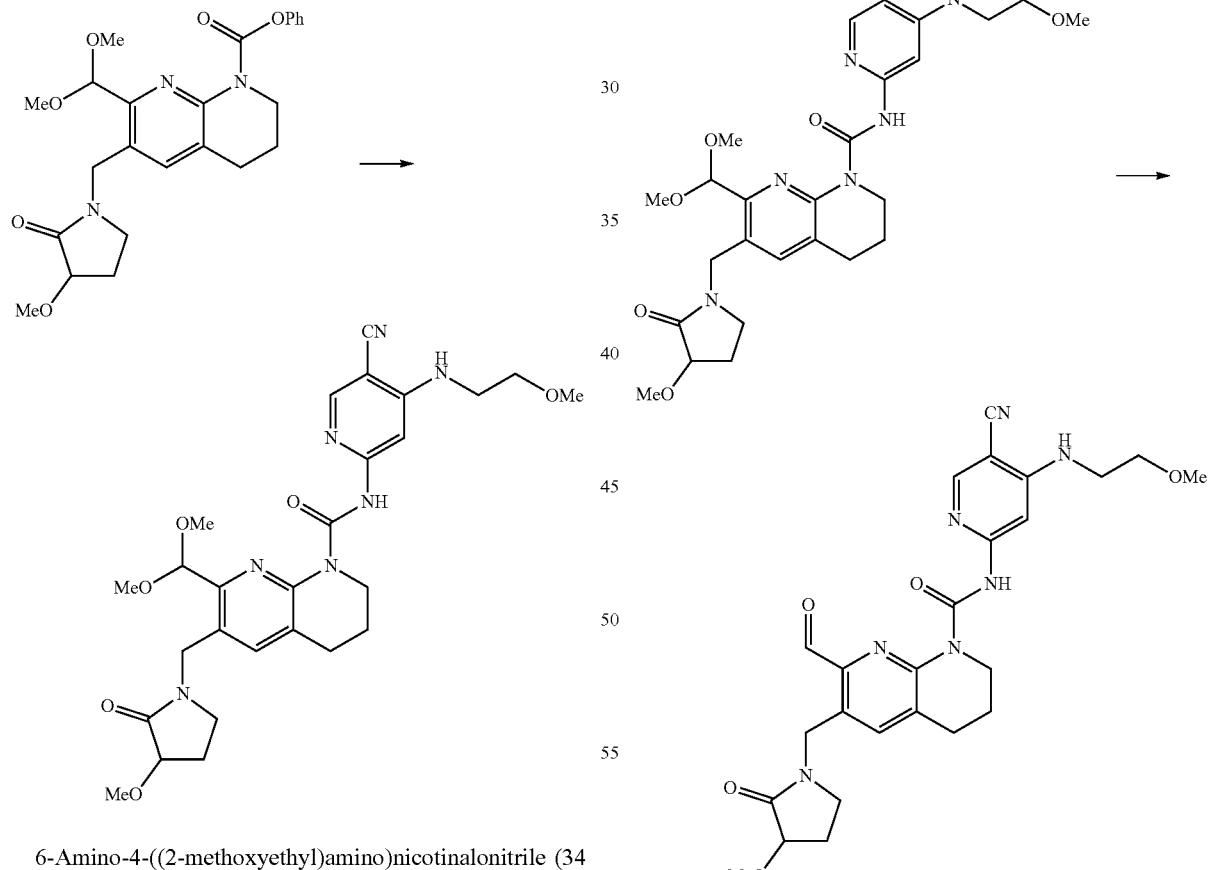

6-Amino-4-((2-methoxyethyl)amino)nicotinalonitrile (34 mg, 0.18 mmol) and phenyl 7-(dimethoxymethyl)-6-((3-methoxy-2-carbonylpyrrolidin-1-yl)methyl)-3,4-dihydro-1,8-naphthyridin-1(2H)-carboxylate (68 mg, 0.15 mmol) were mixed in THF (5 mL), cooled to −78° C., and then added dropwise with a solution of LiHMDS (0.33 mL, 0.33 mmol) in THF in a $N_2$ atmosphere. The reaction solution was naturally warmed up to room temperature and stirred overnight. Saturated aqueous $NH_4Cl$ solution (50 mL) was added, and then the reaction solution was extracted with EtOAc (50 mL×2). The organic phase was washed with saturated brine, dried over anhydrous sodium sulfate, and concentrated. The resulting residue was subjected to column chromatography to obtain the title compound N-(5-cyano-4-((2-methoxyethyl)amino)pyridin-2-yl)-7-(dimethoxymethyl)-6-((3-methoxy-2-carbonylpyrrolidin-1-yl)methyl)-3, 4-dihydro-1,8-naphthyridin-1(2H)-carboxamide (51 mg, 46%).

$^1$H NMR (400 MHz, $CDCl_3$) δ13.63 (s, 1H), 8.13 (s, 1H), 7.49 (s, 1H), 7.41 (s, 1H), 5.36 (s, 1H), 5.18 (dd, J=12.5, 7.5 Hz, 1H), 4.61 (m, 2H), 4.03-3.87 (m, 3H), 3.56 (t, J=5.1 Hz, 2H), 3.52 (s, 3H), 3.42 (t, J=5.3 Hz, 8H), 3.34 (s, 3H), 3.24 (m, 1H), 3.10 (dm, 1H), 2.74 (t, J=6.2 Hz, 2H), 2.26 (m, 1H), 1.90 (m, 2H), 1.88-1.83 (m, 1H);

MS m/z (ESI): 554.2 [M+H]$^+$.

Step 3: Preparation of N-(5-cyano-4-((2-methoxyethyl)amino)pyridin-2-yl)-7-formyl-6-((3-methoxy-2-carbo nylpyrrolidin-1-yl)methyl)-3,4-dihydro-1,8-naphthyridin-1(2H)-carboxamide

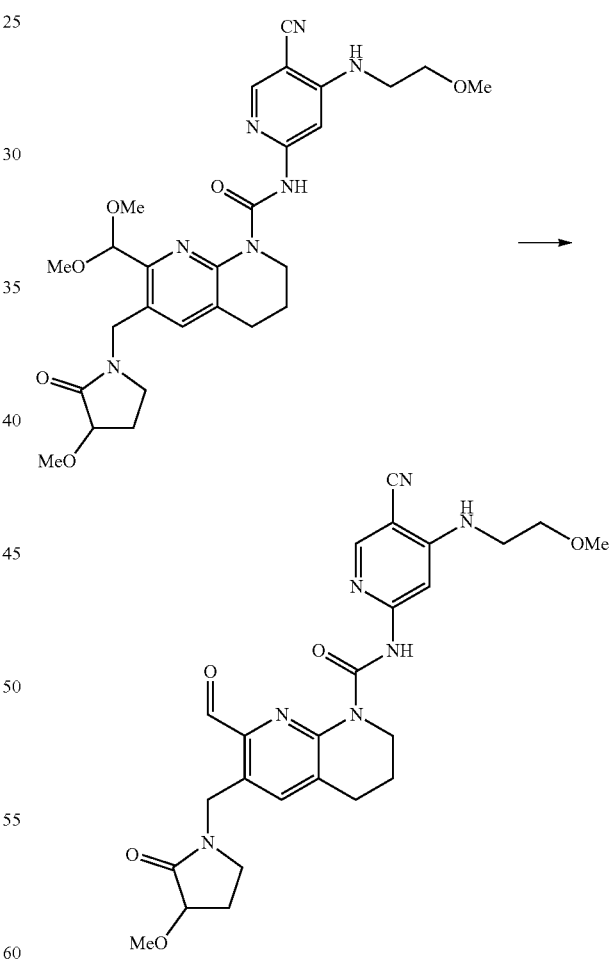

N-(5-Cyano-4-((2-methoxyethyl)amino)pyridin-2-yl)-7-(dimethoxymethyl)-6-((3-methoxy-2-carbonylpyrrolidin-1-yl)methyl)-3,4-dihydro-1,8-naphthyridin-1(2H)-carboxamide (51 mg, 0.09 mmol) was dissolved in THF/water (volume ratio: 11/4, 1.5 mL). Concentrated HCl (0.15 ml, 1.8 mmol) was added, and then the reaction solution was stirred for 2 hours at room temperature. Saturated aqueous NaHCO₃ solution (5 mL) was added, and then the reaction solution was extracted with ethyl acetate (50 mL×2). The organic phase was washed with saturated brine, dried over anhydrous sodium sulfate, and concentrated. The resulting residue was subjected to column chromatography to obtain the title compound N-(5-cyano-4-((2-methoxyethyl)amino)pyridin-2-yl)-7-formyl-6-((3-methoxy-2-carbo nylpyrrolidin-1-yl)methyl)-3,4-dihydro-1,8-naphthyridin-1(2H)-carboxamide (15 mg, 32%).

1H NMR (400 MHz, CDCl3) δ 13.58 (s, 1H), 10.24 (s, 1H), 8.18 (s, 1H), 7.63 (s, 1H), 7.58 (s, 1H), 5.34 (s, 1H), 4.97 (d, J=15.4 Hz, 1H), 4.90 (d, J=15.4 Hz, 1H), 4.13-4.04 (m, 2H), 4.04-3.93 (m, 1H), 3.64 (t, J=5.1 Hz, 2H), 3.59 (s, 3H), 3.51-3.47 (m, 2H), 3.42 (s, 3H), 3.41-3.35 (m, 1H), 3.34-3.22 (m, 1H), 2.92 (t, J=6.3 Hz, 2H), 2.39-2.35 (m, 1H), 2.06-2.02 (m, 2H), 1.98-1.88 (m, 1H);

MS m/z (ESI): 508.2 [M+H]⁺.

Example 45

(R)—N-(5-Cyano-4-((2-methoxyethyl)amino)pyridin-2-yl)-7-formyl-6-((3-methoxy-2-carbonylpyrrolidin-1-yl)methyl)-3,4-dihydro-1,8-naphthyridin-1(2H)-carboxamide

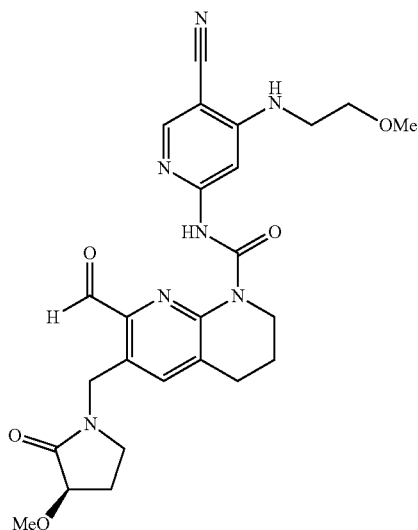 [SMILES: COCCNc1cc(NC(=O)N2CCCc3cc(CN4CC[C@@H](OC)C4=O)c(C=O)nc32)ncc1C#N]

Step 1: Preparation of (R)—N-(5-cyano-4-((2-methoxyethyl)amino)pyridin-2-yl)-7-(dimethoxymethyl)-6-((3-methoxy-2-carbonylpyrrolidin-1-yl)methyl)-3,4-dihydro-1,8-naphthyridin-1(2H)-carb oxamide

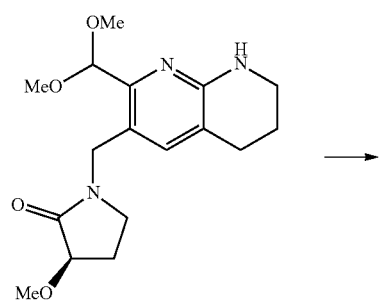

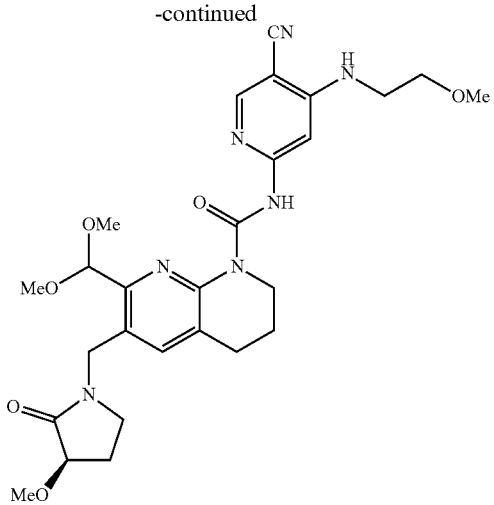

A solution of 6-amino-4-((2-methoxyethyl)amino)nicotinonitrile (358 mg, 1.9 mmol) in DMF (2.5 mL) was slowly added dropwise to a solution of N,N'-carbonyl di(1,2,4-triazole) (306 mg, 1.9 mmol) in DMF (2 mL) at 5° C., and the resulting mixture was stirred for 1 hour at 5° C. Then the reaction solution was slowly warmed up to room temperature, and stirred for 1.5 hours. A solution of (R)-1-((2-(dimethoxymethyl)-5,6,7,8-tetrahydro-1,8-naphthyridin-3-yl)methyl)-3-met hoxypyrrolidin-2-one (250 mg, 0.75 mmol) in DMF (2 mL) was added dropwise, and then the reaction solution was stirred overnight at room temperature. Water (20 mL) was added dropwise, and then the solid precipitated in the reaction solution was filtered, and dried to obtain (R)—N-(5-cyano-4-((2-methoxyethyl)amino)pyridin-2-yl)-7-(dimethoxymethyl)-6-((3-methoxy-2-carbonylpyrrolidin-1-yl)methyl)-3,4-dihydro-1, 8-naphthyridin-1(2H)-carboxamide (0.28 g, 67%).

MS m/z (ESI): 554.2 [M+H]⁺.

Step 2: Preparation of (R)—N-(5-cyano-4-((2-methoxyethyl)amino)pyridin-2-yl)-7-formyl-6-((3-methoxy-2-carbonylpyrrolidin-1-yl)methyl)-3,4-dihydro-1,8-naphthyridin-1(2H)-carboxamide

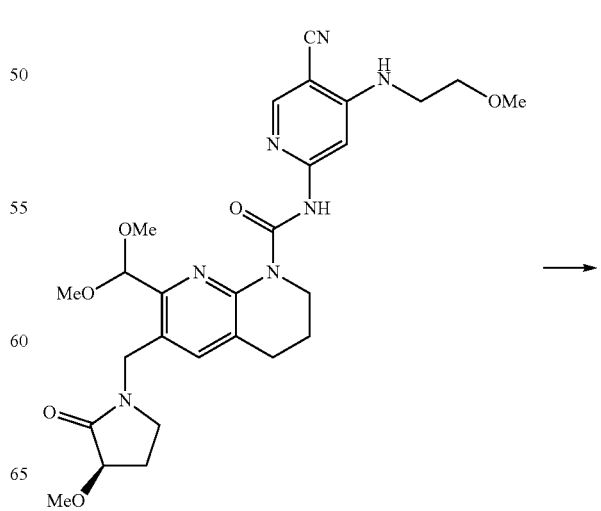

-continued

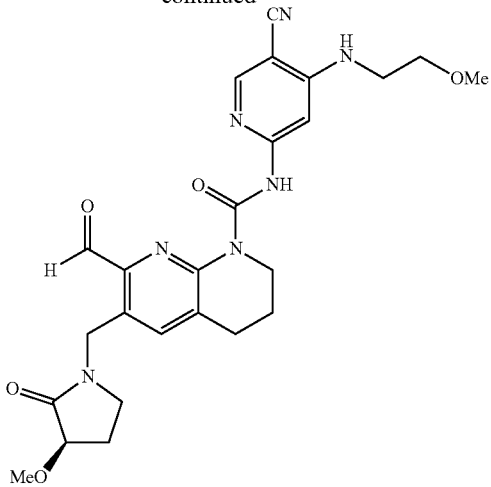

(R)—N-(5-Cyano-4-((2-methoxyethyl)amino)pyridin-2-yl)-7-formyl-6-((3-methoxy-2-carbonylpyrrolidin-1-yl)methyl)-3,4-dihydro-1,8-naphthyridin-1(2H)-carboxamide was prepared in accordance with the method of Step 3 of Example 44.

1H NMR (400 MHz, CDCl3) δ 13.58 (s, 1H), 10.24 (s, 1H), 8.18 (s, 1H), 7.63 (s, 1H), 7.58 (s, 1H), 5.34 (s, 1H), 4.97 (d, J=15.4 Hz, 1H), 4.90 (d, J=15.4 Hz, 1H), 4.13-4.04 (m, 2H), 4.04-3.93 (m, 1H), 3.64 (t, J=5.1 Hz, 2H), 3.59 (s, 3H), 3.51-3.47 (m, 2H), 3.42 (s, 3H), 3.41-3.35 (m, 1H), 3.34-3.22 (m, 1H), 2.92 (t, J=6.3 Hz, 2H), 2.39-2.35 (m, 1H), 2.06-2.02 (m, 2H), 1.98-1.88 (m, 1H);

MS m/z (ESI): 508.2 [M+H]+.

Example 46

(S)—N-(5-Cyano-4-((2-methoxyethyl)amino)pyridin-2-yl)-7-formyl-6-((3-methoxy-2-carbonylpyrrolidin-1-yl)methyl)-3,4-dihydro-1,8-naphthyridin-1(2H)-carboxamide

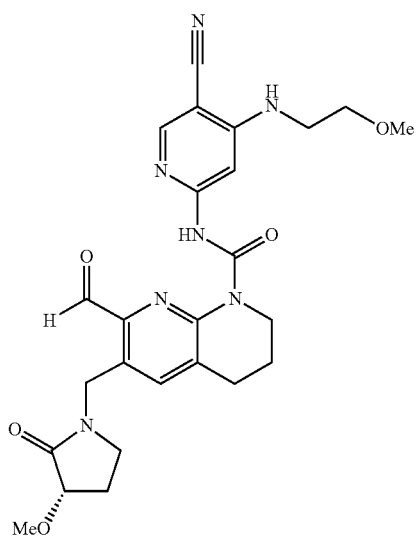 [SMILES: COCCNc1cc(NC(=O)N2CCCc3cc(CN4CC[C@H](OC)C4=O)c(C=O)nc32)ncc1C#N]

(S)—N-(5-Cyano-4-((2-methoxyethyl)amino)pyridin-2-yl)-7-formyl-6-((3-methoxy-2-carbonylpyrrolidin-1-yl)methyl)-3,4-dihydro-1,8-naphthyridin-1(2H)-carboxamide was prepared in accordance with the method of Example 44.

$^1$H NMR (400 MHz, CDCl$_3$) δ 13.58 (s, 1H), 10.24 (s, 1H), 8.18 (s, 1H), 7.63 (s, 1H), 7.58 (s, 1H), 5.34 (s, 1H), 4.97 (d, J=15.4 Hz, 1H), 4.90 (d, J=15.4 Hz, 1H), 4.13-4.04 (m, 2H), 4.04-3.93 (m, 1H), 3.64 (t, J=5.1 Hz, 2H), 3.59 (s, 3H), 3.51-3.47 (m, 2H), 3.42 (s, 3H), 3.41-3.35 (m, 1H), 3.34-3.22 (m, 1H), 2.92 (t, J=6.3 Hz, 2H), 2.39-2.35 (m, 1H), 2.06-2.02 (m, 2H), 1.98-1.88 (m, 1H);

MS m/z (ESI): 508.2 [M+H]+.

Example 47

(R)—N-(5-Cyano-4-(2-methoxyethoxy)pyridin-2-yl)-7-formyl-6-((3-methoxy-2-carbonylpyrrolidin-1-yl)methyl)-3,4-dihydro-1,8-naphthyridin-1(2H)-carboxamide

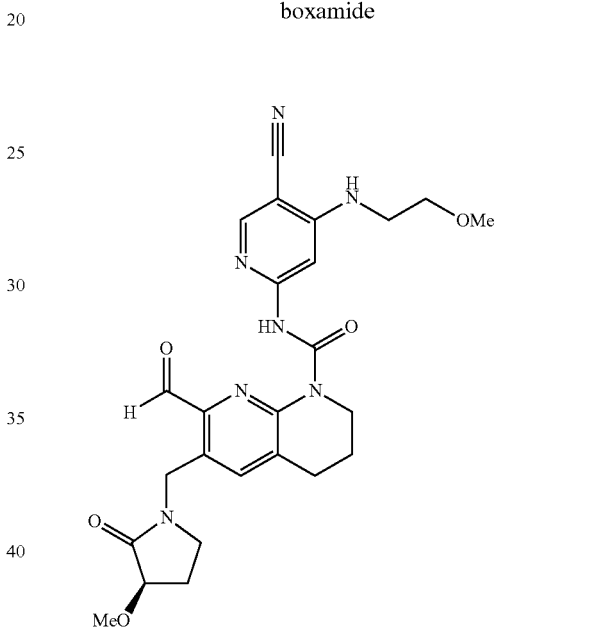

(R)—N-(5-Cyano-4-(2-methoxyethoxy)pyridin-2-yl)-7-formyl-6-((3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 509.1 [M+H]+.

Example 48

(S)—N-(5-Cyano-4-(2-methoxyethoxy)pyridin-2-yl)-7-formyl-6-((3-methoxy-2-carbonylpyrrolidin-1-yl)methyl)-3,4-dihydro-1,8-naphthyridin-1(2H)-carboxamide

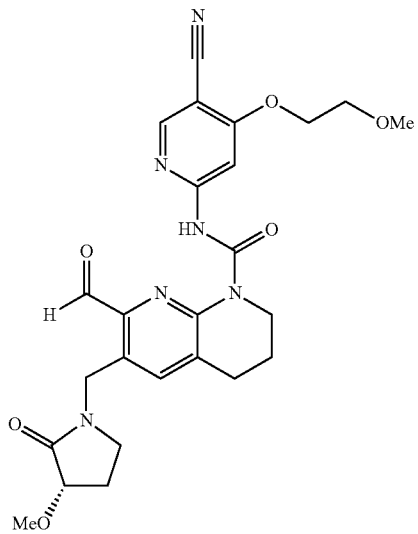 [SMILES: COCCOc1cc(NC(=O)N2CCCc3cc(CN4CC[C@H](OC)C4=O)c(C=O)nc32)ncc1C#N]

(S)—N-(5-Cyano-4-(2-methoxyethoxy)pyridin-2-yl)-7-formyl-6-((3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 509.1 [M+H]$^+$.

Example 49

N-(5-Cyano-4-(((R)-1-methoxypropan-2-yl)oxy)pyridin-2-yl)-7-formyl-6-(((R)-3-methoxy-2-carbonylpyrrolidin-1-yl)methyl)-3,4-dihydro-1,8-naphthyridin-1(2H)-carboxamide

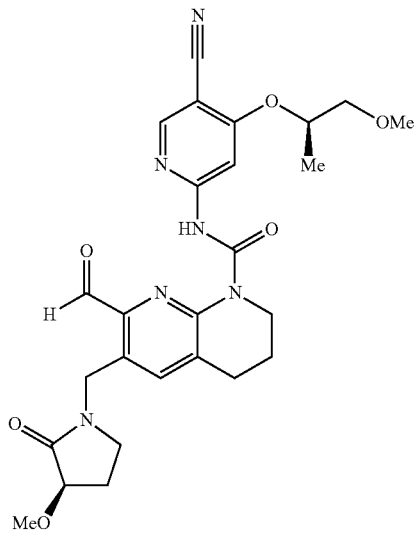 [SMILES: COC[C@@H](C)Oc1cc(NC(=O)N2CCCc3cc(CN4CC[C@@H](OC)C4=O)c(C=O)nc32)ncc1C#N]

N-(5-Cyano-4-(((R)-1-methoxypropan-2-yl)oxy)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 523.1 [M+H]$^+$.

Example 50

N-(5-Cyano-4-(((R)-1-methoxypropan-2-yl)oxy)pyridin-2-yl)-7-formyl-6-(((S)-3-methoxy-2-carbonylpyrrolidin-1-yl)methyl)-3,4-dihydro-1,8-naphthyridin-1(2H)-carboxamide

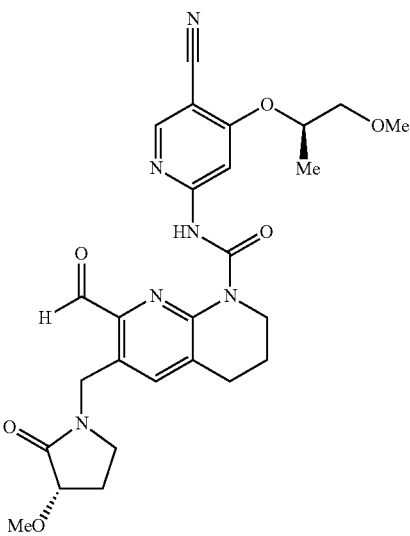 [SMILES: COC[C@@H](C)Oc1cc(NC(=O)N2CCCc3cc(CN4CC[C@H](OC)C4=O)c(C=O)nc32)ncc1C#N]

N-(5-Cyano-4-(((R)-1-methoxypropan-2-yl)oxy)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

1H NMR (400 MHz, CDCl3) δ 13.82 (s, 1H), 10.24 (s, 1H), 8.35 (s, 1H), 8.02 (s, 1H), 7.64 (s, 1H), 4.97 (d, J=15.4 Hz, 1H), 4.90 (d, J=15.4 Hz, 1H), 4.88-4.82 (m, 1H), 4.14-4.05 (m, 2H), 4.01 (dd, J=13.5, 6.3 Hz, 1H), 3.66 (dd, J=10.7, 6.6 Hz, 1H), 3.62-3.54 (m, 4H), 3.46-3.36 (m, 4H), 3.28 (m, 1H), 2.93 (t, J=6.0 Hz, 2H), 2.43-2.32 (m, 1H), 2.09-2.00 (m, 2H), 1.95 (m, 1H), 1.41 (d, J=6.3 Hz, 3H);

MS m/z (ESI): 523.2 [M+H]$^+$.

Example 51

N-(5-Cyano-4-((S)-3-methoxypyrrolidin-1-yl)pyridin-2-yl)-7-formyl-6-(((R)-3-methoxy-2-carbonylpyrrolidin-1-yl)methyl)-3,4-dihydro-1,8-naphthyridin-1(2H)-carboxamide

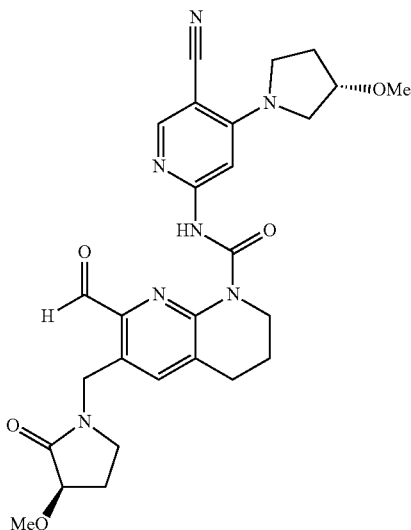 [SMILES: CO[C@H]1CCN(c2cc(NC(=O)N3CCCc4cc(CN5CC[C@@H](OC)C5=O)c(C=O)nc43)ncc2C#N)C1]

N-(5-Cyano-4-((S)-3-methoxypyrrolidin-1-yl)pyridin-2-yl)-7-formyl-6-(((R)-3-methoxy-2-carbonylpyrrolidin-1-yl)methyl)-3,4-dihydro-1,8-naphthyridin-1(2H)-carb oxamide was prepared in accordance with the method of Example 44.
MS m/z (ESI): 534.1 [M+H]$^+$.

Example 52

N-(5-Cyano-4-((R)-3-methoxypyrrolidin-1-yl)pyridin-2-yl)-7-formyl-6-(((R)-3-methoxy-2-carbonylpyrrolidin-1-yl)methyl)-3,4-dihydro-1,8-naphthyridin-1(2H)-carboxamide

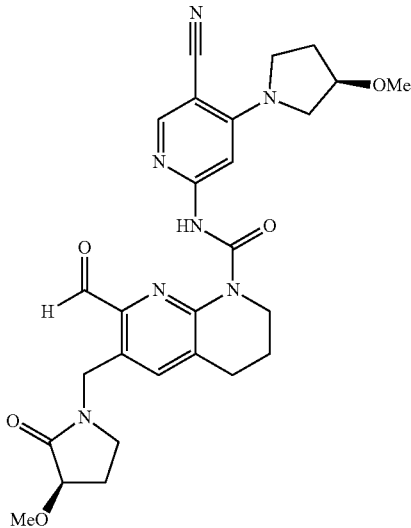 [SMILES: CO[C@@H]1CCN(c2cc(NC(=O)N3CCCc4cc(CN5CC[C@@H](OC)C5=O)c(C=O)nc43)ncc2C#N)C1]

N-(5-Cyano-4-((R)-3-methoxypyrrolidin-1-yl)pyridin-2-yl)-7-formyl-6-(((R)-3-methoxy-2-carbonylpyrrolidin-1-yl)methyl)-3,4-dihydro-1,8-naphthyridin-1(2H)-carb oxamide was prepared in accordance with the method of Example 44.
MS m/z (ESI): 534.1 [M+H]$^+$.

Example 53

N-(5-Cyano-4-((S)-3-methoxypyrrolidin-1-yl)pyridin-2-yl)-7-formyl-6-(((S)-3-methoxy-2-carbonylpyrrolidin-1-yl)methyl)-3,4-dihydro-1,8-naphthyridin-1(2H)-carboxamide

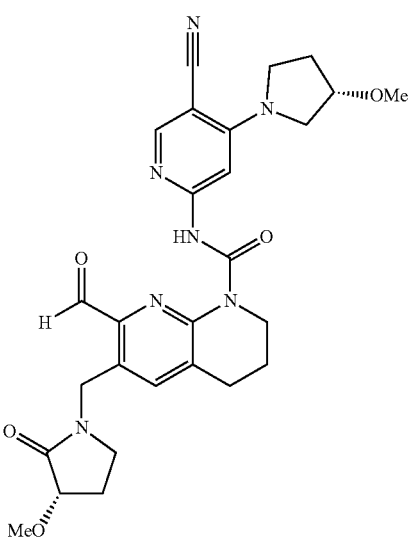 [SMILES: CO[C@H]1CCN(c2cc(NC(=O)N3CCCc4cc(CN5CC[C@H](OC)C5=O)c(C=O)nc43)ncc2C#N)C1]

N-(5-Cyano-4-((S)-3-methoxypyrrolidin-1-yl)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.
$^1$H NMR (400 MHz, CDCl$_3$) δ 13.50 (s, 1H), 10.22 (s, 1H), 8.19 (s, 1H), 7.62 (s, 1H), 7.46 (s, 1H), 4.97 (d, J=15.4 Hz, 1H), 4.90 (d, J=15.4 Hz, 1H), 4.11-4.05 (m, 3H), 4.03-3.98 (m, 1H), 3.86-3.78 (m, 4H), 3.58 (s, 3H), 3.40-3.36 (m, 4H), 3.31-3.26 (m, 1H), 2.92 (t, J=6.2 Hz, 2H), 2.42-2.33 (m, 1H), 2.25-2.19 (m, 1H), 2.05-1.92 (m, 4H);
MS m/z (ESI): 534.2 [M+H]$^+$.

Example 54

N-(5-Cyano-4-((R)-3-methoxypyrrolidin-1-yl)pyridin-2-yl)-7-formyl-6-(((S)-3-methoxy-2-carbonylpyrrolidin-1-yl)methyl)-3,4-dihydro-1,8-naphthyridin-1(2H)-carboxamide

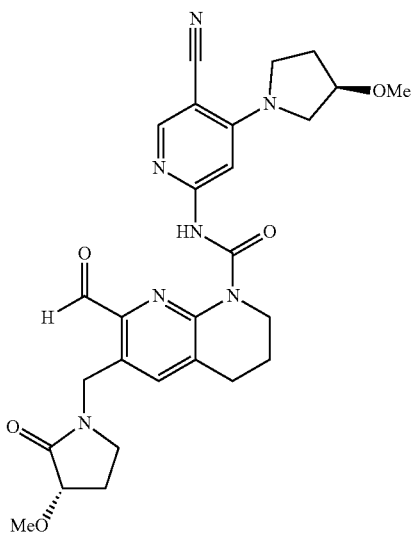 [SMILES: CO[C@@H]1CCN(c2cc(NC(=O)N3CCCc4cc(CN5CC[C@H](OC)C5=O)c(C=O)nc43)ncc2C#N)C1]

N-(5-Cyano-4-((R)-3-methoxypyrrolidin-1-yl)pyridin-2-yl)-7-formyl-6-(((S)-3-methoxy-2-carbonylpyrrolidin-1-yl)methyl)-3,4-dihydro-1,8-naphthyridin-1(2H)-carb oxamide was prepared in accordance with the method of Example 44.
$^1$H NMR (400 MHz, CDCl$_3$) δ 13.50 (s, 1H), 10.22 (s, 1H), 8.20 (s, 1H), 7.62 (s, 1H), 7.47 (s, 1H), 4.97 (d, J=15.4 Hz, 1H), 4.90 (d, J=15.4 Hz, 1H), 4.13-4.06 (m, 3H), 4.03-3.98 (m, 1H), 3.86-3.78 (m, 4H), 3.58 (s, 3H), 3.44-3.34 (m, 4H), 3.31-3.26 (m, 1H), 2.92 (t, J=6.2 Hz, 2H), 2.41-2.34 (m, 1H), 2.25-2.20 (m, 1H), 2.05-1.93 (m, 4H); MS m/z (ESI): 534.2 [M+H]$^+$.

Example 55

N-(5-Cyano-4-(((R)-tetrahydrofuran-3-yl)thio)pyridin-2-yl)-7-formyl-6-(((R)-3-methoxy-2-carbonylpyrrolidin-1-yl)methyl)-3,4-dihydro-1,8-naphthyridin-1(2H)-carboxamide

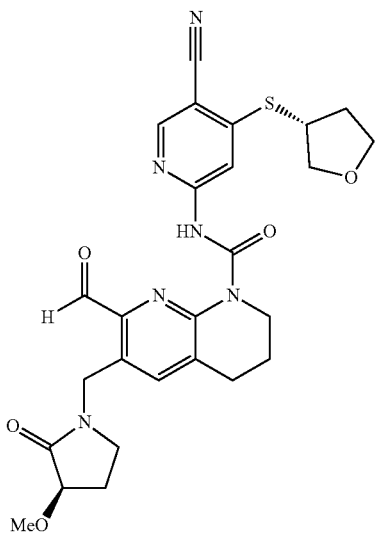 [SMILES: CO[C@@H]1CCN(Cc2cc3c(nc2C=O)N(C(=O)Nc2cc(S[C@@H]4CCOC4)c(C#N)cn2)CCC3)C1=O]

N-(5-Cyano-4-(((R)-tetrahydrofuran-3-yl)thio)pyridin-2-yl)-7-formyl-6-(((R)-3-methoxy-2-carbonylpyrrolidin-1-yl)methyl)-3,4-dihydro-1,8-naphthyridin-1(2H)-carb oxamide was prepared in accordance with the method of Example 44.
MS m/z (ESI): 537.1 [M+H]$^+$.

Example 56

N-(5-Cyano-4-(((S)-tetrahydrofuran-3-yl)thio)pyridin-2-yl)-7-formyl-6-(((R)-3-methoxy-2-carbonylpyrrolidin-1-yl)methyl)-3,4-dihydro-1,8-naphthyridin-1(2H)-carboxamide

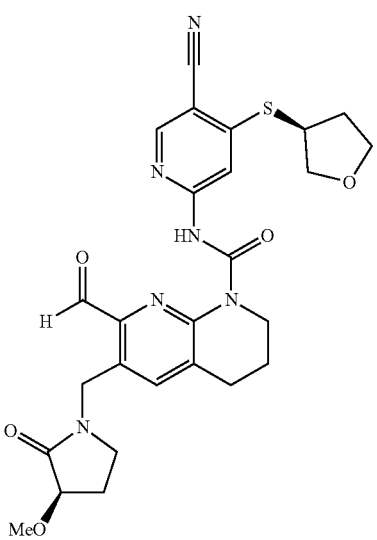 [SMILES: CO[C@@H]1CCN(Cc2cc3c(nc2C=O)N(C(=O)Nc2cc(S[C@H]4CCOC4)c(C#N)cn2)CCC3)C1=O]

N-(5-Cyano-4-(((S)-tetrahydrofuran-3-yl)thio)pyridin-2-yl)-7-formyl-6-(((R)-3-methoxy-2-carbonylpyrrolidin-1-yl)methyl)-3,4-dihydro-1,8-naphthyridin-1(2H)-carb oxamide was prepared in accordance with the method of Example 44.
MS m/z (ESI): 537.1 [M+H]$^+$.

Example 57

N-(5-Cyano-4-(((R)-tetrahydrofuran-3-yl)thio)pyridin-2-yl)-7-formyl-6-(((S)-3-methoxy-2-carbonylpyrrolidin-1-yl)methyl)-3,4-dihydro-1,8-naphthyridin-1(2H)-carboxamide

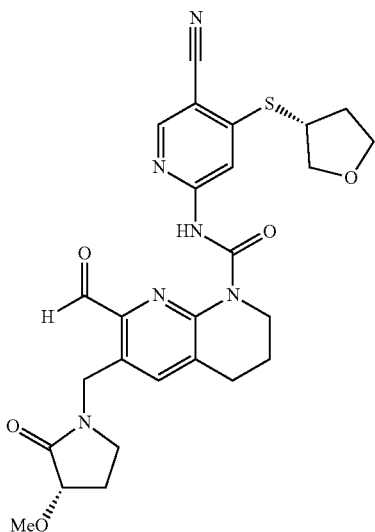 [SMILES: CO[C@H]1CCN(Cc2cc3c(nc2C=O)N(C(=O)Nc2cc(S[C@@H]4CCOC4)c(C#N)cn2)CCC3)C1=O]

N-(5-Cyano-4-(((R)-tetrahydrofuran-3-yl)thio)pyridin-2-yl)-7-formyl-6-(((S)-3-methoxy-2-carbonylpyrrolidin-1-yl)methyl)-3,4-dihydro-1,8-naphthyridin-1(2H)-carb oxamide was prepared in accordance with the method of Example 44.
MS m/z (ESI): 537.1 [M+H]$^+$.

Example 58

N-(5-Cyano-4-(((S)-tetrahydrofuran-3-yl)thio)pyridin-2-yl)-7-formyl-6-(((S)-3-methoxy-2-carbonylpyrrolidin-1-yl)methyl)-3,4-dihydro-1,8-naphthyridin-1(2H)-carboxamide

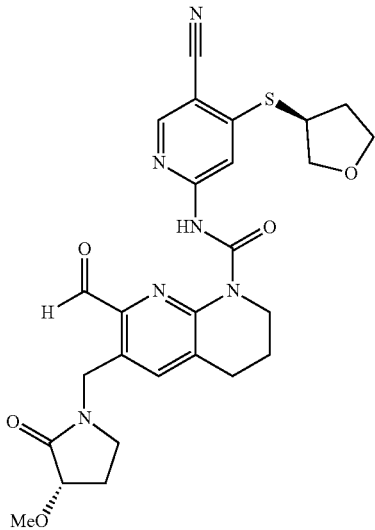 [SMILES: CO[C@H]1CCN(Cc2cc3c(nc2C=O)N(C(=O)Nc2cc(S[C@H]4CCOC4)c(C#N)cn2)CCC3)C1=O]

N-(5-Cyano-4-(((S)-tetrahydrofuran-3-yl)thio)pyridin-2-yl)-7-formyl-6-(((S)-3-methoxy-2-carbonylpyrrolidin-1-yl)methyl)-3,4-dihydro-1,8-naphthyridin-1(2H)-carb oxamide was prepared in accordance with the method of Example 44.
MS m/z (ESI): 537.1 [M+H]$^+$.

Example 59

N-(5-Cyano-4-(((3S,4R)-4-methoxytetrahydrofuran-3-yl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide

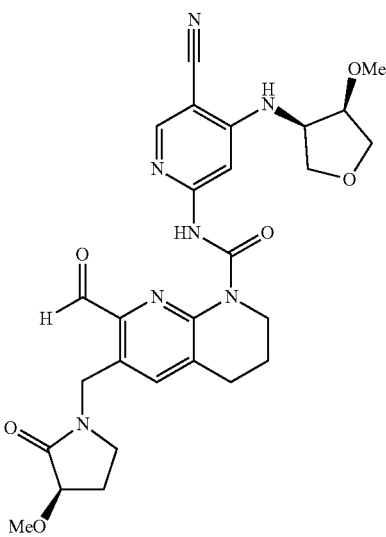 [SMILES: CO[C@H]1COC[C@H]1Nc1cc(NC(=O)N2CCCc3cc(CN4CC[C@@H](OC)C4=O)c(C=O)nc32)ncc1C#N]

N-(5-Cyano-4-(((3S,4R)-4-methoxytetrahydrofuran-3-yl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.
MS m/z (ESI): 550.1 [M+H]$^+$.

Example 60

N-(5-Cyano-4-(((3R,4S)-4-methoxytetrahydrofuran-3-yl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide

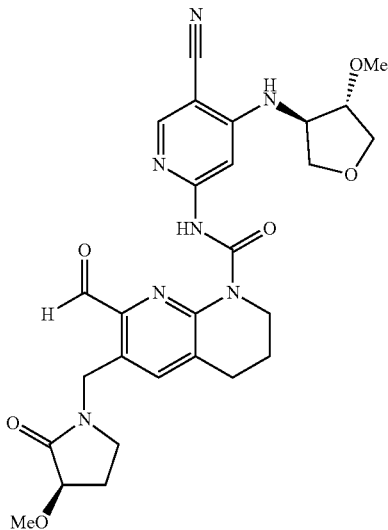 [SMILES: CO[C@@H]1CCN(Cc2cc3c(nc2C=O)N(C(=O)Nc2cc(N[C@@H]4COC[C@H]4OC)c(C#N)cn2)CCC3)C1=O]

N-(5-Cyano-4-(((3R,4S)-4-methoxytetrahydrofuran-3-yl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 550.1 [M+H]$^+$.

Example 61

N-(5-Cyano-4-(((3S,4S)-4-methoxytetrahydrofuran-3-yl)oxy)pyridin-2-yl)-7-formyl-6-(((R)-3-methoxy-2-carbonylpyrrolidin-1-yl)methyl)-3,4-dihydro-1,8-naphthyridin-1(2H)-carboxamide

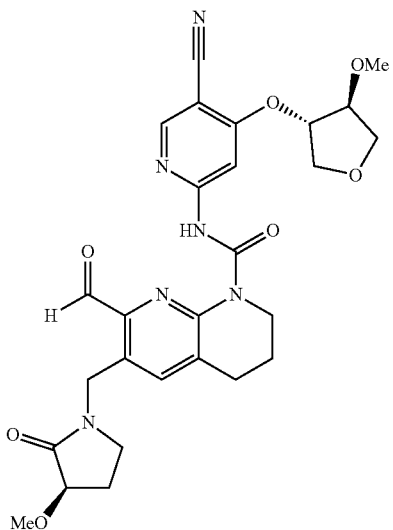 [SMILES: CO[C@H]1COC[C@@H]1Oc1cc(NC(=O)N2CCCc3cc(CN4CC[C@@H](OC)C4=O)c(C=O)nc32)ncc1C#N]

N-(5-Cyano-4-(((3S,4S)-4-methoxytetrahydrofuran-3-yl)oxy)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 551.1 [M+H]$^+$.

Example 62

N-(5-Cyano-4-(((3R,4R)-4-methoxytetrahydrofuran-3-yl)oxy)pyridin-2-yl)-7-formyl-6-(((R)-3-methoxy-2-carbonylpyrrolidin-1-yl)methyl)-3,4-dihydro-1,8-naphthyridin-1(2H)-carboxamide

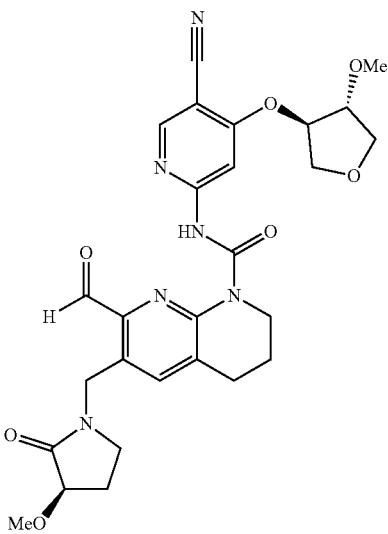 [SMILES: CO[C@@H]1CCN(Cc2cc3c(nc2C=O)N(C(=O)Nc2cc(O[C@@H]4COC[C@H]4OC)c(C#N)cn2)CCC3)C1=O]

N-(5-Cyano-4-(((3R,4R)-4-methoxytetrahydrofuran-3-yl)oxy)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 551.1 [M+H]$^+$.

Example 63

N-(5-Cyano-4-(((3S,4R)-4-methoxytetrahydrofuran-3-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide

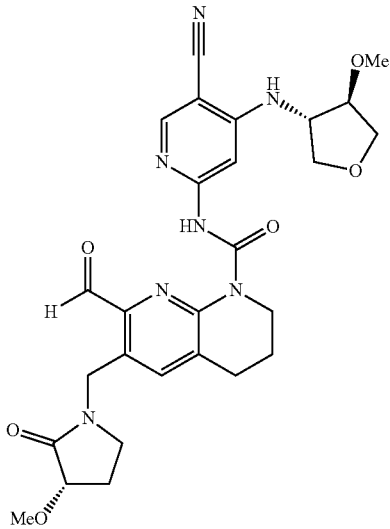 [SMILES: CO[C@H]1CCN(Cc2cc3c(nc2C=O)N(C(=O)Nc2cc(N[C@H]4COC[C@@H]4OC)c(C#N)cn2)CCC3)C1=O]

N-(5-Cyano-4-(((3S,4R)-4-methoxytetrahydrofuran-3-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 550.1 [M+H]$^+$.

Example 64

N-(5-Cyano-4-(((3R,4S)-4-methoxytetrahydrofuran-3-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide

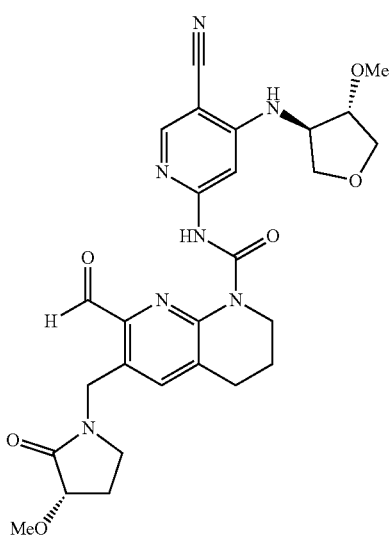 [SMILES: CO[C@H]1CCN(Cc2cc3c(nc2C=O)N(C(=O)Nc2cc(N[C@@H]4COC[C@H]4OC)c(C#N)cn2)CCC3)C1=O]

N-(5-Cyano-4-(((3R,4S)-4-methoxytetrahydrofuran-3-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 550.1 [M+H]$^+$.

Example 65

N-(5-Cyano-4-(((3S,4S)-4-methoxytetrahydrofuran-3-yl)oxy)pyridin-2-yl)-7-formyl-6-(((S)-3-methoxy-2-carbonylpyrrolidin-1-yl)methyl)-3,4-dihydro-1,8-naphthyridin-1(2H)-carboxamide

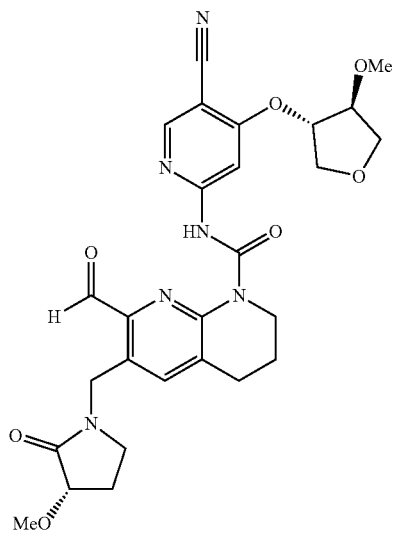 [SMILES: CO[C@H]1CCN(Cc2cc3c(nc2C=O)N(C(=O)Nc2cc(O[C@H]4COC[C@@H]4OC)c(C#N)cn2)CCC3)C1=O]

N-(5-Cyano-4-(((3S,4S)-4-methoxytetrahydrofuran-3-yl)oxy)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 551.1 [M+H]$^+$.

Example 66

N-(5-Cyano-4-(((3R,4R)-4-methoxytetrahydrofuran-3-yl)oxy)pyridin-2-yl)-7-formyl-6-(((S)-3-methoxy-2-carbonylpyrrolidin-1-yl)methyl)-3,4-dihydro-1,8-naphthyridin-1(2H)-carboxamide

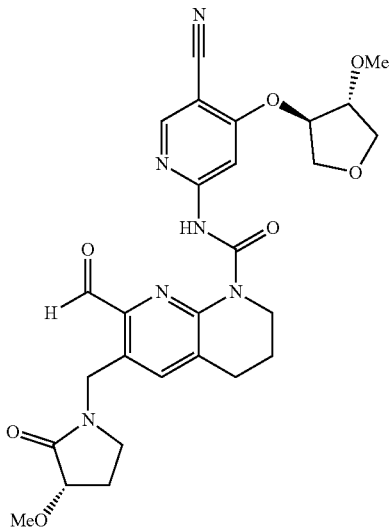 [SMILES: CO[C@H]1CCN(Cc2cc3c(nc2C=O)N(C(=O)Nc2cc(O[C@@H]4COC[C@H]4OC)c(C#N)cn2)CCC3)C1=O]

N-(5-Cyano-4-(((3R,4R)-4-methoxytetrahydrofuran-3-yl)oxy)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 551.1 $[M+H]^+$.

Example 67

N-(5-Cyano-4-(((1S,2S)-2-methoxycyclobutyl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide

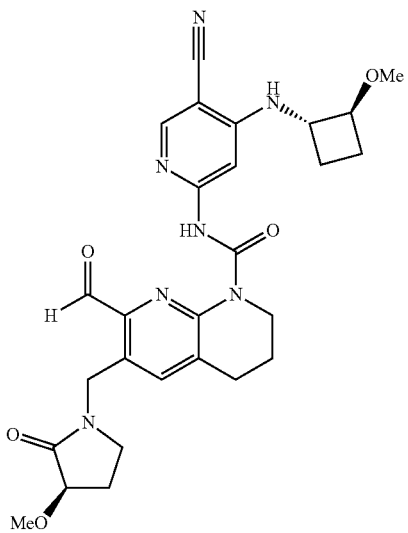 [SMILES: CO[C@H]1CC[C@@H]1Nc1cc(NC(=O)N2CCCc3cc(CN4CC[C@@H](OC)C4=O)c(C=O)nc32)ncc1C#N]

N-(5-Cyano-4-(((1S,2S)-2-methoxycyclobutyl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 534.1 $[M+H]^+$.

Example 68

N-(5-Cyano-4-(((1R,2R)-2-methoxycyclobutyl)amino)pyridin-2-yl)-7-formyl-6-(((R)-3-methoxy-2-carbonylpyrrolidin-1-yl)methyl)-3,4-dihydro-1,8-naphthyridin-1 (2H)-carboxamide

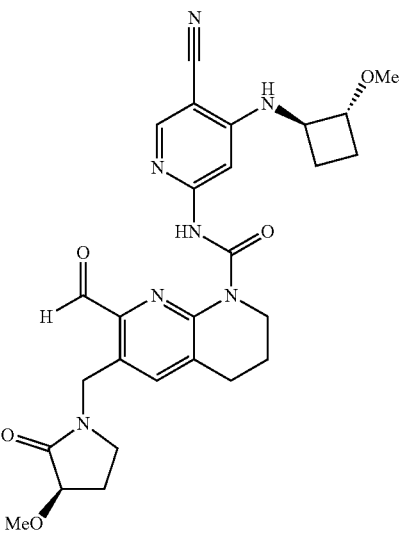 [SMILES: CO[C@@H]1CCN(Cc2cc3c(nc2C=O)N(C(=O)Nc2cc(N[C@@H]4CC[C@H]4OC)c(C#N)cn2)CCC3)C1=O]

N-(5-Cyano-4-(((1R,2R)-2-methoxycyclobutyl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 534.1 $[M+H]^+$.

Example 69

N-(5-Cyano-4-((1S,2S)-2-methoxycyclobutoxy)pyridin-2-yl)-7-formyl-6-(((R)-3-methoxy-2-carbonylpyrrolidin-1-yl)methyl)-3,4-dihydro-1,8-naphthyridin-1(2H)-carboxamide

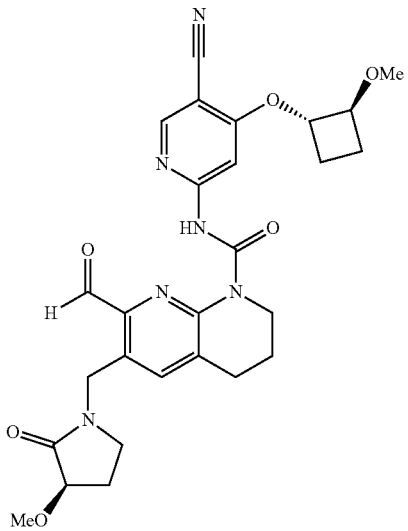 [SMILES: CO[C@H]1CC[C@@H]1Oc1cc(NC(=O)N2CCCc3cc(CN4CC[C@@H](OC)C4=O)c(C=O)nc32)ncc1C#N]

N-(5-Cyano-4-((1S,2S)-2-methoxycyclobutoxy)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 535.1 [M+H]$^+$.

Example 70

N-(5-Cyano-4-((1R,2R)-2-methoxycyclobutoxy)pyridin-2-yl)-7-formyl-6-(((R)-3-methoxy-2-carbonylpyrrolidin-1-yl)methyl)-3,4-dihydro-1,8-naphthyridin-1(2H)-carboxamide

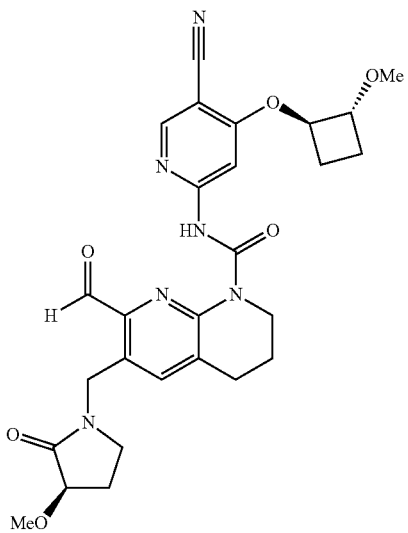 [SMILES: CO[C@@H]1CCN(Cc2cc3c(nc2C=O)N(C(=O)Nc2cc(O[C@@H]4CC[C@H]4OC)c(C#N)cn2)CCC3)C1=O]

N-(5-Cyano-4-((1R,2R)-2-methoxycyclobutoxy)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 535.1 [M+H]$^+$.

Example 71

N-(5-Cyano-4-(((1S,2S)-2-methoxycyclobutyl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide

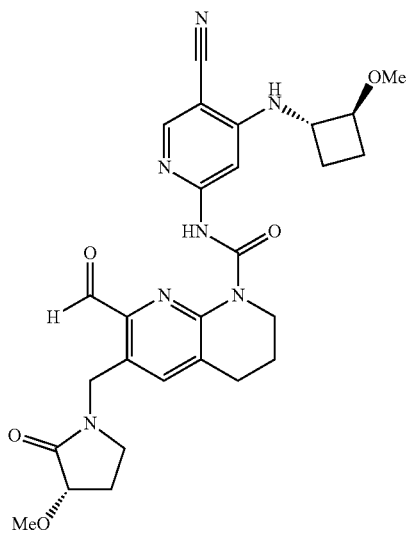 [SMILES: CO[C@H]1CCN(Cc2cc3c(nc2C=O)N(C(=O)Nc2cc(N[C@H]4CC[C@@H]4OC)c(C#N)cn2)CCC3)C1=O]

N-(5-Cyano-4-(((1S,2S)-2-methoxycyclobutyl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 534.1 [M+H]$^+$.

Example 72

N-(5-Cyano-4-(((1R,2R)-2-methoxycyclobutyl)amino)pyridin-2-yl)-7-formyl-6-(((S)-3-methoxy-2-carbonylpyrrolidin-1-yl)methyl)-3,4-dihydro-1,8-naphthyridin-1 (2H)-carboxamide

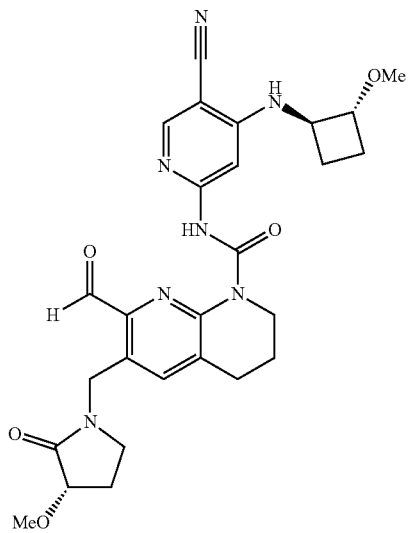 [SMILES: CO[C@H]1CCN(Cc2cc3c(nc2C=O)N(C(=O)Nc2cc(N[C@@H]4CC[C@H]4OC)c(C#N)cn2)CCC3)C1=O]

N-(5-Cyano-4-(((1R,2R)-2-methoxycyclobutyl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 534.1 [M+H]$^+$.

Example 73

N-(5-Cyano-4-((1S,2S)-2-methoxycyclobutoxy)pyridin-2-yl)-7-formyl-6-(((S)-3-methoxy-2-carbonylpyrrolidin-1-yl)methyl)-3,4-dihydro-1,8-naphthyridin-1(2H)-carboxamide

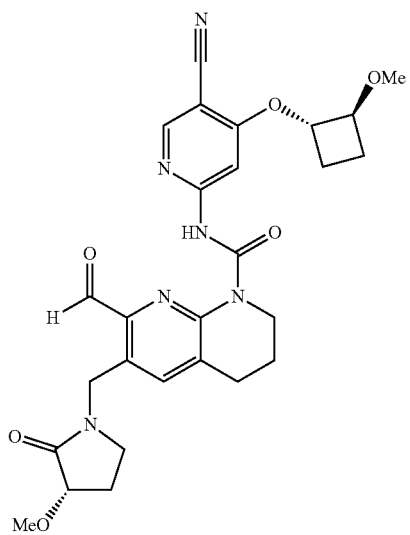 [SMILES: CO[C@H]1CCN(Cc2cc3c(nc2C=O)N(C(=O)Nc2cc(O[C@H]4CC[C@@H]4OC)c(C#N)cn2)CCC3)C1=O]

N-(5-Cyano-4-((1S,2S)-2-methoxycyclobutoxy)pyridin-2-yl)-7-formyl-6-(((S)-3-methoxy-2-carbonylpyrrolidin-1-yl)methyl)-3,4-dihydro-1,8-naphthyridin-1(2H)-carb oxamide was prepared in accordance with the method of Example 44.

MS m/z (ESI): 534.1 [M+H]$^+$.

Example 74

N-(5-Cyano-4-((1R,2R)-2-methoxycyclobutoxy)pyridin-2-yl)-7-formyl-6-(((S)-3-methoxy-2-carbonylpyrrolidin-1-yl)methyl)-3,4-dihydro-1,8-naphthyridin-1(2H)-carboxamide

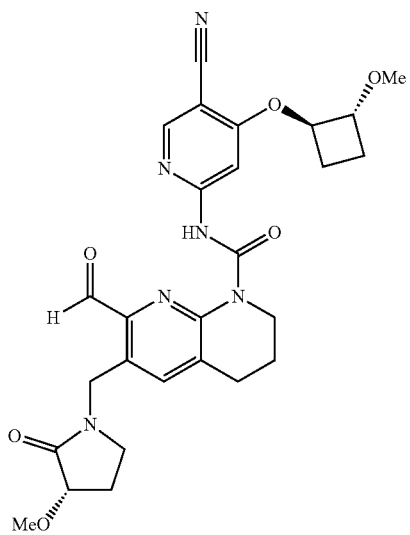 [SMILES: CO[C@H]1CCN(Cc2cc3c(nc2C=O)N(C(=O)Nc2cc(O[C@@H]4CC[C@H]4OC)c(C#N)cn2)CCC3)C1=O]

N-(5-Cyano-4-((1R,2R)-2-methoxycyclobutoxy)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 535.1 [M+H]$^+$.

Example 75

N-(5-Cyano-4-(((1S,2R)-2-methoxycyclobutyl) amino)pyridin-2-yl)-7-formyl-6-(((R)-3-methoxy-2-carbonylpyrrolidin-1-yl)methyl)-3,4-dihydro-1,8-naphthyridin-1(2H)-carboxamide

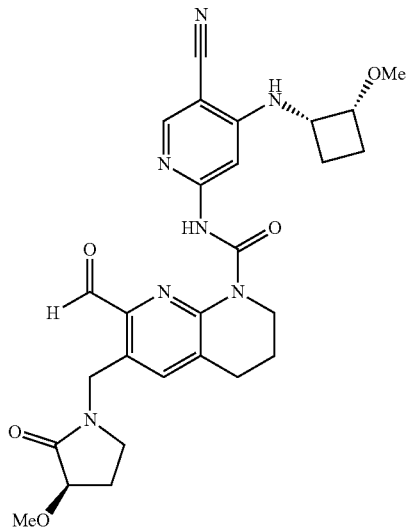 [SMILES: CO[C@@H]1CCN(Cc2cc3c(nc2C=O)N(C(=O)Nc2cc(N[C@H]4CC[C@H]4OC)c(C#N)cn2)CCC3)C1=O]

N-(5-Cyano-4-(((1S,2R)-2-methoxycyclobutyl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 534.1 [M+H]$^+$.

Example 76

N-(5-Cyano-4-(((1R,2S)-2-methoxycyclobutyl) amino)pyridin-2-yl)-7-formyl-6-(((R)-3-methoxy-2-carbonylpyrrolidin-1-yl)methyl)-3,4-dihydro-1,8-naphthyridin-1 (2H)-carboxamide

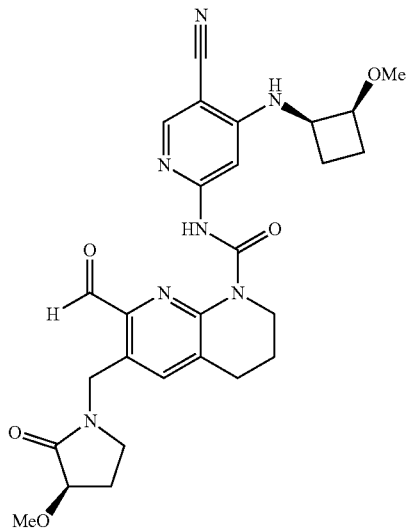 [SMILES: CO[C@H]1CC[C@H]1Nc1cc(NC(=O)N2CCCc3cc(CN4CC[C@@H](OC)C4=O)c(C=O)nc32)ncc1C#N]

N-(5-Cyano-4-(((1R,2S)-2-methoxycyclobutyl)amino) pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 534.1 [M+H]$^+$.

Example 77

N-(5-Cyano-4-((1S,2R)-2-methoxycyclobutoxy) pyridin-2-yl)-7-formyl-6-(((R)-3-methoxy-2-carbonylpyrrolidin-1-yl)methyl)-3,4-dihydro-1,8-naphthyridin-1(2H)-carboxamide

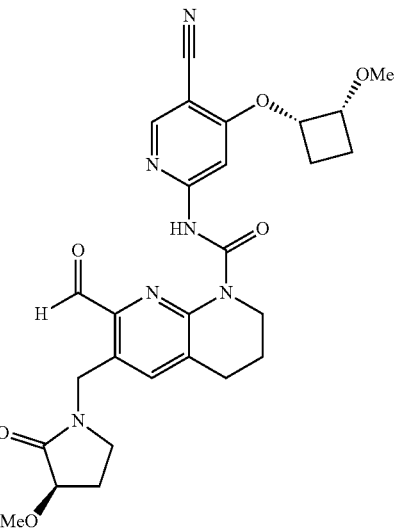

N-(5-Cyano-4-((1S,2R)-2-methoxycyclobutoxy)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 535.1 [M+H]$^+$.

Example 78

N-(5-Cyano-4-(((1S,2R)-2-methoxycyclobutyl)amino)pyridin-2-yl)-7-formyl-6-(((S)-3-methoxy-2-carbonylpyrrolidin-1-yl)methyl)-3,4-dihydro-1,8-naphthyridin-1 (2H)-carboxamide

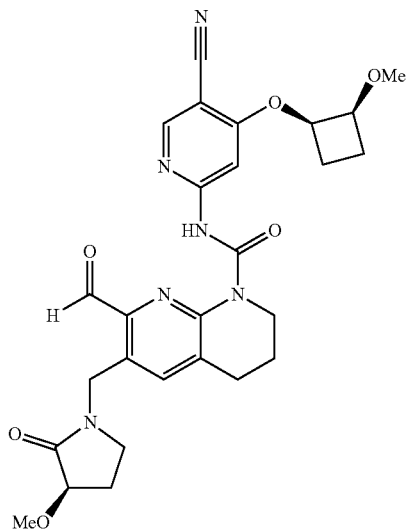 [SMILES: CO[C@H]1CC[C@H]1Oc1cc(NC(=O)N2CCCc3cc(CN4CC[C@@H](OC)C4=O)c(C=O)nc32)ncc1C#N]

N-(5-Cyano-4-(((1S,2R)-2-methoxycyclobutyl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 535.1 [M+H]$^+$.

Example 79

N-(5-Cyano-4-(((1S,2R)-2-methoxycyclobutyl)amino)pyridin-2-yl)-7-formyl-6-(((S)-3-methoxy-2-carbonylpyrrolidin-1-yl)methyl)-3,4-dihydro-1,8-naphthyridin-1 (2H)-carboxamide

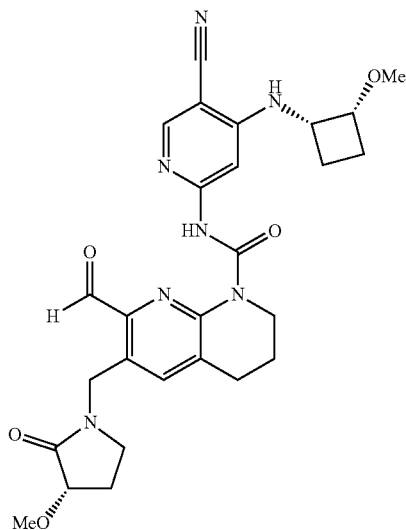 [SMILES: CO[C@H]1CCN(Cc2cc3c(nc2C=O)N(C(=O)Nc2cc(N[C@H]4CC[C@H]4OC)c(C#N)cn2)CCC3)C1=O]

N-(5-Cyano-4-(((1S,2R)-2-methoxycyclobutyl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 534.1 [M+H]$^+$.

Example 80

N-(5-Cyano-4-(((1R,2S)-2-methoxycyclobutyl)amino)pyridin-2-yl)-7-formyl-6-(((S)-3-methoxy-2-carbonylpyrrolidin-1-yl)methyl)-3,4-dihydro-1,8-naphthyridin-1 (2H)-carboxamide

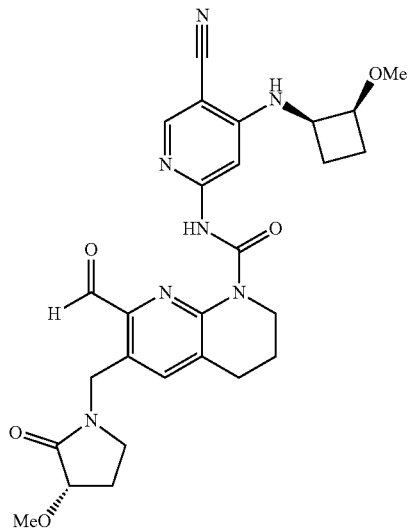 [SMILES: CO[C@H]1CCN(Cc2cc3c(nc2C=O)N(C(=O)Nc2cc(N[C@@H]4CC[C@@H]4OC)c(C#N)cn2)CCC3)C1=O]

N-(5-Cyano-4-(((1R,2S)-2-methoxycyclobutyl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 534.1 [M+H]$^+$.

Example 81

N-(5-Cyano-4-(((1S,2R)-2-methoxycyclobutoxy)pyridin-2-yl)-7-formyl-6-(((S)-3-methoxy-2-carbonylpyrrolidin-1-yl)methyl)-3,4-dihydro-1,8-naphthyridin-1(2H)-carboxamide

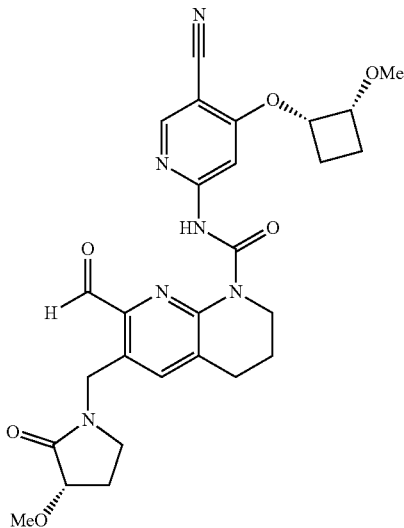 [SMILES: CO[C@H]1CCN(Cc2cc3c(nc2C=O)N(C(=O)Nc2cc(O[C@H]4CC[C@H]4OC)c(C#N)cn2)CCC3)C1=O]

N-(5-Cyano-4-(((1S,2R)-2-methoxycyclobutoxy)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 535.1 [M+H]$^+$.

Example 82

N-(5-Cyano-4-((1R,2S)-2-methoxycyclobutoxy)pyridin-2-yl)-7-formyl-6-(((S)-3-methoxy-2-carbonylpyrrolidin-1-yl)methyl)-3,4-dihydro-1,8-naphthyridin-1(2H)-carboxamide

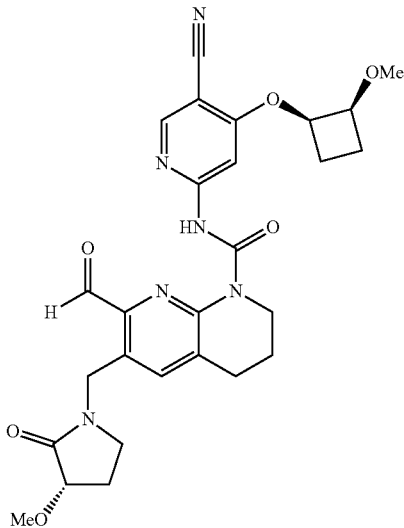 [SMILES: CO[C@H]1CCN(Cc2cc3c(nc2C=O)N(C(=O)Nc2cc(O[C@@H]4CC[C@@H]4OC)c(C#N)cn2)CCC3)C1=O]

N-(5-Cyano-4-((1R,2S)-2-methoxycyclobutoxy)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 535.1 [M+H]$^+$.

Example 83

(S)—N-(5-Cyano-4-(oxetan-3-ylamino)pyridin-2-yl)-7-formyl-6-((3-methoxy-2-carbonylpyrrolidin-1-yl)methyl)-3,4-dihydro-1,8-naphthyridin-1(2H)-carboxamide

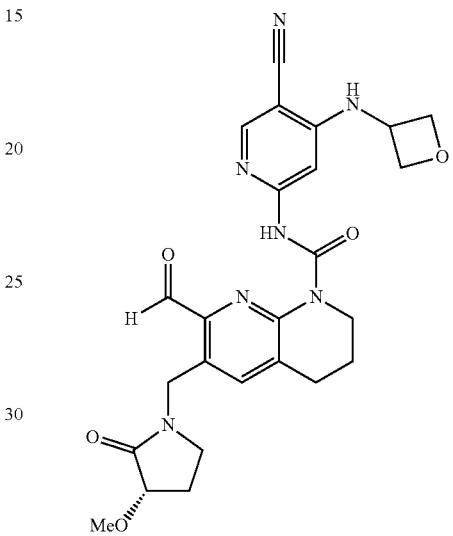

(S)—N-(5-Cyano-4-(oxocyclobutane-3-yl)amino)pyridin-2-yl)-7-formyl-6-((3-methoxy-2-carbonylpyrrolidin-1-yl)methyl)-3,4-dihydro-1,8-naphthyridin-1(2H)-carboxamide was prepared in accordance with the method of Example 44.

$^1$H NMR (400 MHz, CDCl$_3$): δ13.66 (s, 1H), 10.22 (s, 1H), 8.23 (s, 1H), 7.63 (s, 1H), 7.36 (s, 1H), 5.40 (d, J=5.7 Hz, 1H), 5.08 (t, J=6.8 Hz, 2H), 4.97 (d, J=14.8 Hz1H), 4.89 (d, J=14.8 Hz1H), 4.87-4.81 (m, 1H), 4.63 (t, J=6.2 Hz, 2H), 4.13-4.03 (m, 2H), 3.99 (t, J=7.2 Hz, 1H), 3.58 (s, 3H), 3.42-3.37 (m, 1H), 3.31-3.25 (m, 1H), 2.92 (t, J=6.1 Hz, 2H), 2.39-2.35 (m, 1H), 2.08-2.01 (m, 2H), 1.98-1.91 (m, 1H);

MS m/z (ESI): 506.2 [M+H]$^+$.

Example 84

N-(5-Cyano-4-(((S)-tetrahydrofuran-3-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide

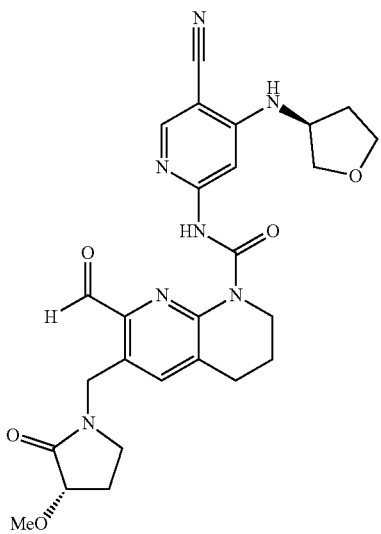 [SMILES: CO[C@H]1CCN(Cc2cc3c(nc2C=O)N(C(=O)Nc2cc(N[C@H]4CCOC4)c(C#N)cn2)CCC3)C1=O]

Example 85

N-(5-Cyano-4-(((R)-tetrahydrofuran-3-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide

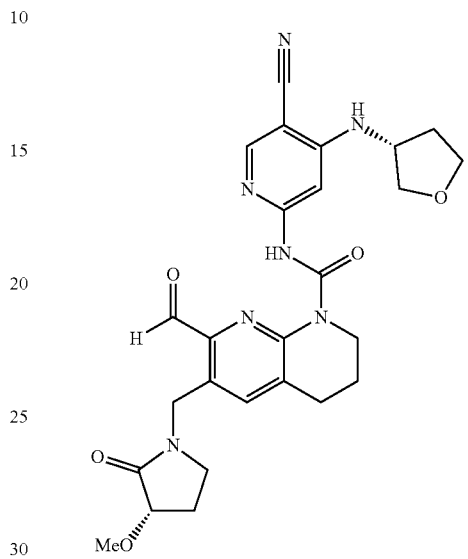

N-(5-Cyano-4-(((S)-tetrahydrofuran-3-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

$^1$H NMR (400 MHz, CDCl$_3$):δ 13.64 (s, 1H), 10.24 (s, 1H), 8.20 (s, 1H), 7.63 (d, J=6.1 Hz, 2H), 5.09 (s, 1H), 4.97 (d, J=14.8 Hz 1H), 4.90 (d, J=14.8 Hz, 1H), 4.34-4.25 (m, 1H), 4.11-3.97 (m, 5H), 3.91-3.86 (m, 1H), 3.80 (dd, J=9.6, 2.8 Hz, 1H), 3.58 (s, 3H), 3.42-3.37 (m, 1H), 3.32-3.26 (m, 1H), 2.92 (t, J=6.2 Hz, 2H), 2.48-2.33 (m, 2H), 2.07-2.01 (m, 2H), 1.99-1.89 (m, 2H).

MS m/z (ESI): 520.2 [M+H]$^+$.

N-(5-Cyano-4-(((R)-tetrahydrofuran-3-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

$^1$H NMR (400 MHz, CDCl3):δ 13.64 (s, 1H), 10.25 (s, 1H), 8.20 (s, 1H), 7.64 (d, J=4.4 Hz, 2H), 5.13 (s, 1H), 4.97 (d, J=14.8 Hz 1H), 4.90 (d, J=14.8 Hz, 1H), 4.34-4.25 (m, 1H), 4.11-3.97 (m, 5H), 3.91-3.86 (m, 1H), 3.81 (dd, J=9.6, 2.8 Hz, 1H), 3.58 (s, 3H), 3.44-3.36 (m, 1H), 3.32-3.26 (m, 1H), 2.92 (t, J=6.2 Hz, 2H), 2.50-2.32 (m, 2H), 2.01-2.07 (m, 2H), 1.99-1.91 (m, 2H);

MS m/z (ESI): 520.2 [M+H]$^+$.

Example 86

N-(5-Cyano-4-((trans)-4-methoxytetrahydrofuran-3-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide

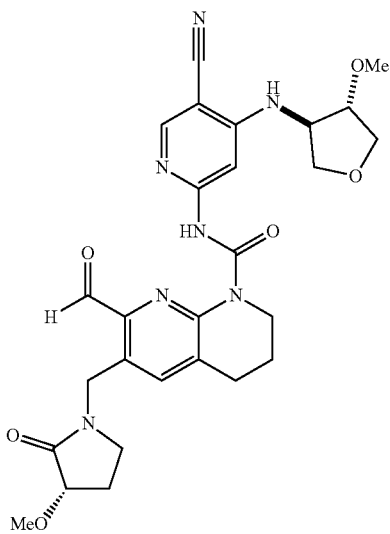 [SMILES: CO[C@H]1CCN(Cc2cc3c(nc2C=O)N(C(=O)Nc2cc(N[C@@H]4COC[C@H]4OC)c(C#N)cn2)CCC3)C1=O]

N-(5-Cyano-4-((trans)-4-methoxytetrahydrofuran-3-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

$^1$H NMR (400 MHz, CDCl$_3$) δ 13.65 (s, 1H), 10.23 (s, 1H), 8.21 (s, 1H), 7.77 (s, 1H), 7.63 (s, 1H), 5.02-4.88 (m, 3H), 4.16-4.06 (m, 5H), 4.00 (t, J=7.2 Hz, 1H), 3.92-3.88 (m, 1H), 3.85-3.80 (m, 2H), 3.58 (s, 3H), 3.54 (s, 3H), 3.42-3.36 (m, 1H), 3.32-3.25 (m, 1H), 2.92 (t, J=6.3 Hz, 2H), 2.43-2.35 (m, 1H), 2.05-1.93 (m, 3H);

MS m/z (ESI): 550.2 [M+H]$^+$.

Example 87

N-(5-Cyano-4-(((R)-tetrahydrofuran-3-yl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide

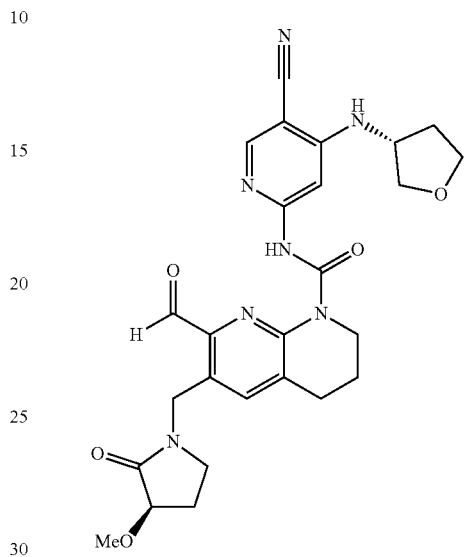

N-(5-Cyano-4-(((R)-tetrahydrofuran-3-yl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

$^1$H NMR (400 MHz, CDCl$_3$) δ 13.63 (s, 1H), 10.22 (s, 1H), 8.19 (s, 1H), 7.63 (s, 1H), 7.60 (s, 1H), 5.11 (d, J=6.5 Hz, 1H), 4.96 (d, J=15.2 Hz, 1H), 4.88 (d, J=15.2 Hz, 1H), 4.42-4.20 (m, 1H), 4.12-4.06 (m, 2H), 4.06-3.96 (m, 3H), 3.91-3.88 (m, 1H), 3.82-3.79 (m, 1H), 3.58 (s, 3H), 3.47-3.34 (m, 1H), 3.32-3.26 (m, 1H), 2.93 (t, J=6.2 Hz, 2H), 2.45-2.36 (m, 2H), 2.15-1.88 (m, 4H);

MS m/z (ESI): 520.2 [M+H]$^+$.

Example 88

N-(5-Cyano-4-(((S)-tetrahydrofuran-3-yl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide

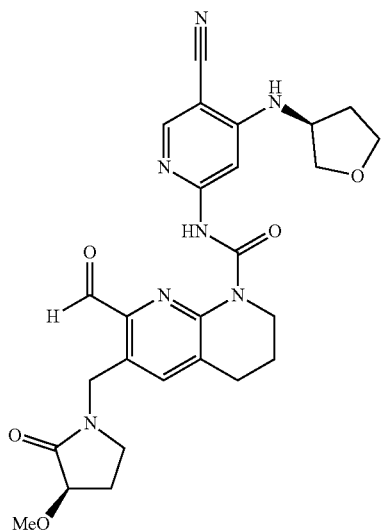 [SMILES: CO[C@@H]1CCN(Cc2cc3c(nc2C=O)N(C(=O)Nc2cc(N[C@H]4CCOC4)c(C#N)cn2)CCC3)C1=O]

N-(5-Cyano-4-(((S)-tetrahydrofuran-3-yl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method of Example 44.

MS m/z (ESI): 520.2 [M+H]$^+$.

Example 89

N-(5-Cyano-4-(((R)-1-methoxypropan-2-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide

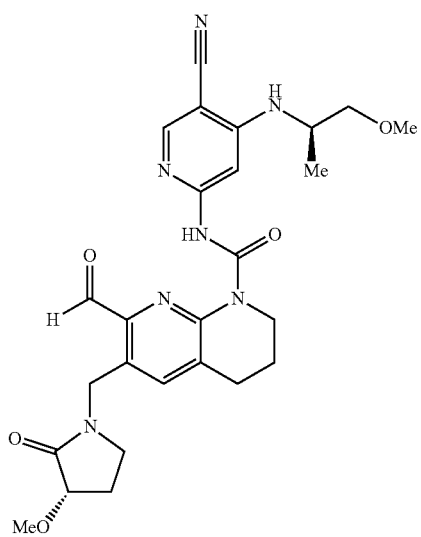 [SMILES: COC[C@@H](C)Nc1cc(NC(=O)N2CCCc3cc(CN4CC[C@H](OC)C4=O)c(C=O)nc32)ncc1C#N]

N-(5-Cyano-4-(((R)-1-methoxypropan-2-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

$^1$H NMR (400 MHz, CDCl$_3$) δ 13.55 (s, 1H), 10.22 (s, 1H), 8.17 (s, 1H), 7.63 (s, 1H), 7.60 (s, 1H), 5.20-5.14 (m, 1H), 4.97 (d, J=15.4 Hz, 1H), 4.90 (d, J=15.4 Hz, 1H), 4.10-4.05 (m, 2H), 4.02-3.98 (m, 1H), 3.96-3.90 (m, 1H), 3.58 (s, 3H), 3.53-3.48 (m, 1H), 3.47-3.43 (m, 1H), 3.41-3.36 (m, 4H), 3.31-3.26 (m, 1H), 2.92 (t, J=6.3 Hz, 2H), 2.41-2.32 (m, 1H), 2.06-1.93 (m, 3H), 1.32 (d, J=6.6 Hz, 3H);

MS m/z (ESI): 522.2 [M+H]$^+$.

Example 90

N-(5-Cyano-4-(((S)-1-methoxypropan-2-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide

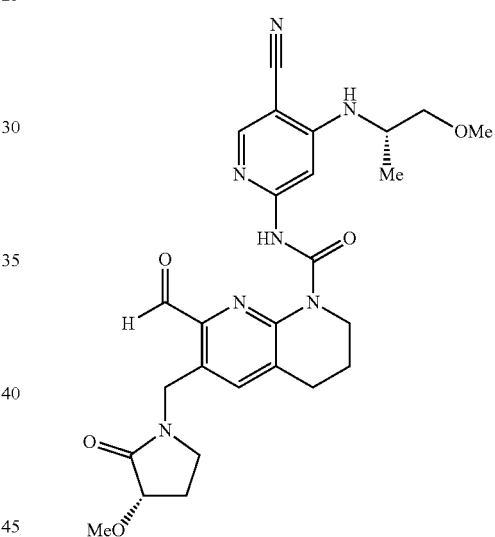

N-(5-Cyano-4-(((S)-1-methoxypropan-2-yl)amino)pyridin-2-yl)-7-formyl-6-(((S)-3-methoxy-2-carbonylpyrrolidin-1-yl)methyl)-3,4-dihydro-1,8-naphthyridin-1(2H)-carboxamide was prepared in accordance with the method of Example 44.

$^1$H NMR (400 MHz, CDCl$_3$) δ 13.55 (s, 1H), 10.21 (s, 1H), 8.15 (s, 1H), 7.61 (s, 1H), 7.59 (s, 1H), 5.18 (d, J=7.8 Hz, 1H), 4.90 (d, J=15.6 Hz, 1H), 4.88 (d, J=15.6 Hz, 1H), 4.16-3.87 (m, 4H), 3.58 (s, 3H), 3.49-3.43 (m, 2H), 3.39 (s, 3H), 3.34-3.21 (m, 2H), 2.91 (t, J=6.2 Hz, 2H), 2.45-2.36 (m, 1H), 2.20-1.86 (m, 3H), 1.32-1.30 (d, J=6.8 Hz, 3H);

MS m/z (ESI): 522.2 [M+H]$^+$.

Example 91

Preparation of N-(5-cyano-4-(((R)-1-methoxypropan-2-yl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide

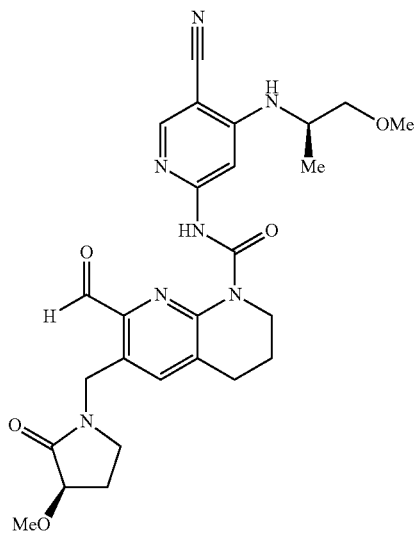 [SMILES: COC[C@@H](C)Nc1cc(NC(=O)N2CCCc3cc(CN4CC[C@@H](OC)C4=O)c(C=O)nc32)ncc1C#N]

Step 1: Preparation of diphenyl (R)-(5-cyano-4-((1-methoxypropan-2-yl)amino)pyridin-2-yl)aminodicarboxylate

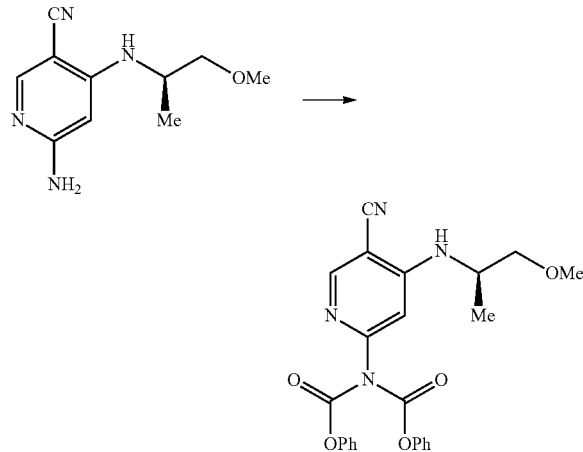

(R)-6-Amino-4-((1-methoxypropan-2-yl)amino)nicotinonitrile (1 g, 4.9 mmol) was dissolved in CH₂Cl₂ (10 mL) at room temperature. Pyridine (1.92 g, 24 mmol) and benzyl chloroformate (1.9 g, 12 mmol) were added successively, and the resulting mixture was stirred for 5 hours at room temperature. The reaction solution was diluted with CH₂Cl₂ (100 mL). The organic phase was washed with water (10 mL) and saturated brine (15 mL) successively, dried over anhydrous sodium sulfate, and concentrated. The resulting residue was subjected to column chromatography to obtain the compound diphenyl (R)-(5-cyano-4-((1-methoxypropan-2-yl)amino)pyridin-2-yl)aminodicarboxylate (1.56 g, 72%).

MS m/z (ESI): 447.2 [M+H]$^+$.

Step 2: Preparation of N-(5-cyano-4-(((R)-1-methoxypropan-2-yl)amino)pyridin-2-yl)-7-(dimethoxymethyl)-6-(((R)-3-methoxy-2-carbonylpyrrolidin-1-yl)methyl)-3,4-dihydro-1,8-naphthyridin-1(2H)-carboxamide

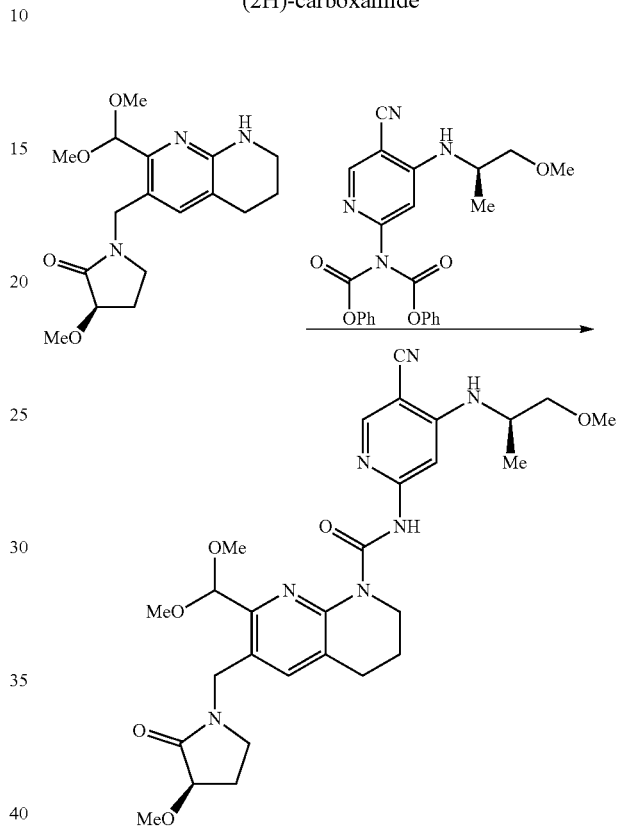

(R)-1-((2-(dimethoxymethyl)-5,6,7,8-tetrahydro-1,8-naphthyridin-3-yl)methyl)-3-methoxypyrrolidin-2-one (0.3 g, 0.9 mmol) and diphenyl (R)-(5-cyano-4-((1-methoxypropan-2-yl)amino)pyridin-2-yl)aminodicarboxylate (0.64 g, 1.3 mmol) were dissolved in toluene (10 mL) at room temperature. The reaction solution was warmed up to 105° C., stirred for 8 hours at this temperature, and then cooled to room temperature. The reaction solution was diluted with CH₂Cl₂ (100 mL), and then the organic phase was washed with water (10 mL) and saturated brine (15 mL) successively, dried over anhydrous sodium sulfate, and concentrated. The resulting residue was subjected to column chromatography to obtain the compound N-(5-cyano-4-(((R)-1-methoxypropan-2-yl)amino)pyridin-2-yl)-7-(dimethoxymethyl)-6-(((R)-3-methoxy-2-carbonylpyrrolidin-1-yl)methyl)-3,4-dihydro-1,8-naphthyridin-1(2H)-carboxamide (0.23 g, 45%).

$^1$H NMR (400 MHz, CDCl₃) δ 13.70 (s, 1H), 8.23 (s, 1H), 7.61 (s, 1H), 7.47 (s, 1H), 5.43 (s, 1H), 5.12 (m, 1H), 4.73 (d, J=15.2 Hz, 1H), 4.64 (d, J=15.2 Hz, 1H), 4.01-3.99 (m, 3H), 3.96-3.91 (m, 1H), 3.59 (s, 3H), 3.53-3.51 (m, 1H), 3.50 (s, 3H), 3.49 (s, 3H), 3.46-3.42 (m, 1H), 3.40 (s, 3H), 3.34-3.28 (m, 1H), 3.21-3.14 (m, 1H), 2.82 (t, J=6.2 Hz, 2H), 2.37-2.12 (m, 1H), 2.05-1.87 (m, 3H), 1.30 (d, J=6.6 Hz, 3H);

MS m/z (ESI): 568.2 [M+H]$^+$.

Step 3: Preparation of N-(5-cyano-4-(((R)-1-methoxypropan-2-yl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide

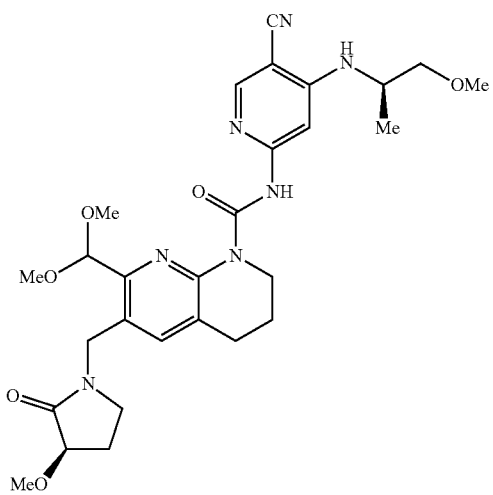

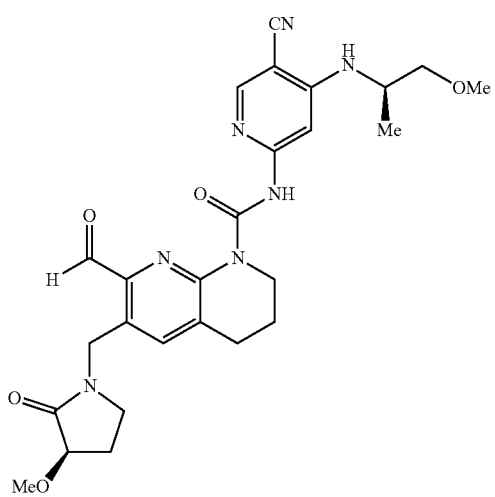

N-(5-Cyano-4-(((R)-1-methoxypropan-2-yl)amino)pyridin-2-yl)-7-formyl-6-(((R)-3-methoxy-2-carbonylpyrrolidin-1-yl)methyl)-3,4-dihydro-1,8-naphthyridin-1(2H)-carboxamide was prepared in accordance with the method in Step 3 of Example 44.

$^1$H NMR (400 MHz, CDCl$_3$) δ 13.55 (s, 1H), 10.21 (s, 1H), 8.15 (s, 1H), 7.61 (s, 1H), 7.59 (s, 1H), 5.18 (d, J=7.8 Hz, 1H), 4.90 (d, J=15.6 Hz, 1H), 4.88 (d, J=15.6 Hz, 1H), 4.16-3.87 (m, 4H), 3.58 (s, 3H), 3.49-3.43 (m, 2H), 3.39 (s, 3H), 3.34-3.21 (m, 2H), 2.91 (t, J=6.2 Hz, 2H), 2.45-2.36 (m, 1H), 2.20-1.86 (m, 3H), 1.32-1.30 (d, J=6.8 Hz, 3H);

MS m/z (ESI): 522.2 [M+H]$^+$.

Example 92

N-(5-Cyano-4-(((S)-1-methoxypropan-2-yl)amino)pyridin-2-yl)-7-formyl-6-(((R)—N-methyltetrahydrofuran-2-carboxamido)methyl)-3,4-dihydro-1,8-naphthyridin-1(2H)-carboxamide

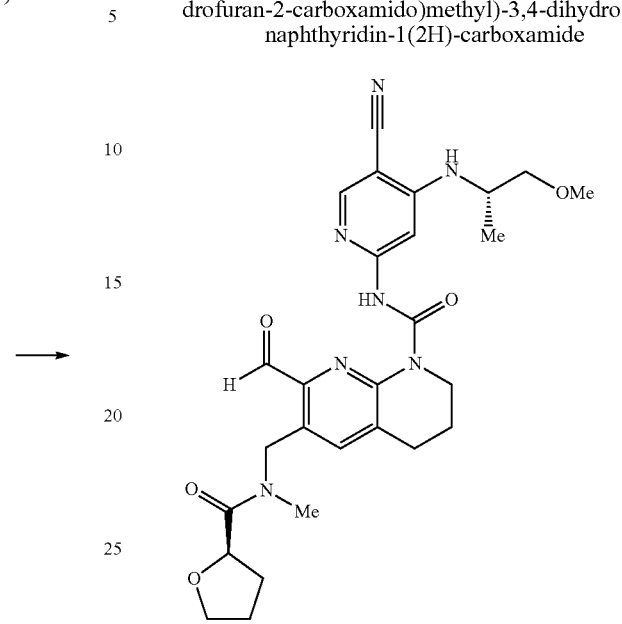

N-(5-Cyano-4-(((S)-1-methoxypropan-2-yl)amino)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

$^1$H NMR (400 MHz, CDCl$_3$): δ14.20-13.80 (m, 1H), 10.50-10.30 (m, 1H), 8.50-8.35 (m, 2H), 7.65-7.45 (m, 1H), 5.18-4.80 (m, 2H), 4.70-4.40 (m, 1H), 4.10-3.80 (m, 4H), 3.45-3.25 (m, 6H), 3.05-2.75 (m, 5H), 2.35-1.70 (m, 6H), 1.25 (d, J=6.4 Hz, 3H);

MS m/z (ESI): 536.2 [M+H]$^+$.

Example 93

N-(5-Cyano-4-(((R)-1-methoxypropan-2-yl)amino)pyridin-2-yl)-7-formyl-6-(((R)—N-methyltetrahydrofuran-2-carboxamido)methyl)-3,4-dihydro-1,8-naphthyridin-1(2H)-carboxamide

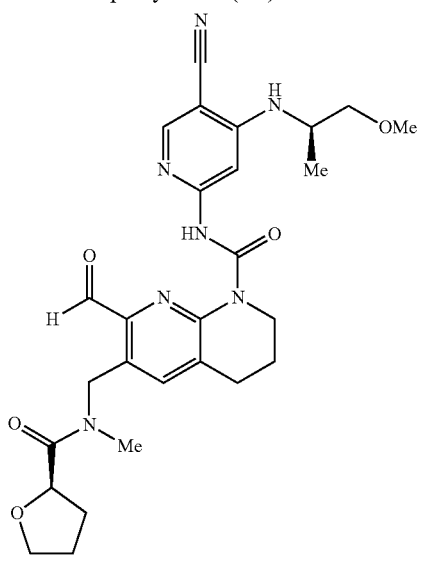

N-(5-Cyano-4-(((R)-1-methoxypropan-2-yl)amino)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

$^1$H NMR (400 MHz, CDCl$_3$): δ 14.20-13.80 (m, 1H), 10.50-10.30 (m, 1H), 8.50-8.35 (m, 2H), 7.65-7.45 (m, 1H), 5.18-4.80 (m, 2H), 4.70-4.40 (m, 1H), 4.10-3.80 (m, 4H), 3.45-3.25 (m, 6H), 3.05-2.75 (m, 5H), 2.3-1.705 (m, 6H), 1.25 (d, J=6.4 Hz, 3H);

MS m/z (ESI): 536.2 [M+H]$^+$.

Example 94

N-(5-Cyano-4-(((S)-tetrahydrofuran-3-yl)amino)pyridin-2-yl)-7-formyl-6-(((R)—N-methyltetrahydrofuran-2-carboxamido)methyl)-3,4-dihydro-1,8-naphthyridin-1 (2H)-carboxamide

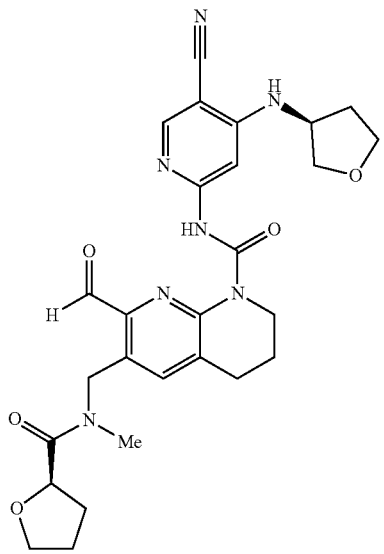 [SMILES: CN(Cc1cc2c(nc1C=O)N(C(=O)Nc1cc(N[C@H]3CCOC3)c(C#N)cn1)CCC2)C(=O)[C@H]1CCCO1]

N-(5-Cyano-4-(((S)-tetrahydrofuran-3-yl)amino)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

$^1$H NMR (400 MHz, CDCl$_3$): δ 13.61 (m, 1H), 10.25 (m, 1H), 8.20 (s, 1H), 7.55 (m, 2H), 4.75 (m, 4H), 4.30 (m, 1H), 4.00 (m, 8H), 3.00 (m, 5H), 2.04 (m, 8H);

MS m/z (ESI): 534.2 [M+H]$^+$.

Example 95

N-(5-Cyano-4-(((R)-tetrahydrofuran-3-yl)amino)pyridin-2-yl)-7-formyl-6-(((R)—N-methyltetrahydrofuran-2-carboxamido)methyl)-3,4-dihydro-1,8-naphthyridin-1 (2H)-carboxamide

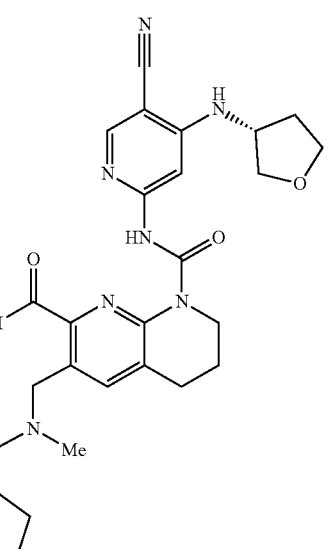

N-(5-Cyano-4-(((R)-tetrahydrofuran-3-yl)amino)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

$^1$H NMR (400 MHz, CDCl$_3$): δ 13.60 (m, 1H), 10.25 (s, 1H), 8.21 (s, 1H), 7.59 (m, 2H), 5.10 (m, 3H), 4.80 (m, 1H), 4.30 (m, 1H), 4.00 (m, 9H), 3.00 (m, 6H), 2.10 (m, 6H);

MS m/z (ESI): 534.2 [M+H]$^+$.

Example 96

N-(5-Cyano-4-(((trans)-4-methoxytetrahydrofuran-3-yl)amino)pyridin-2-yl)-7-formyl-6-(((R)—N-methyl-tetrahydrofuran-2-carboxamido)methyl)-3,4-dihydro-1,8-naphthyridin-1(2H)-carboxamide

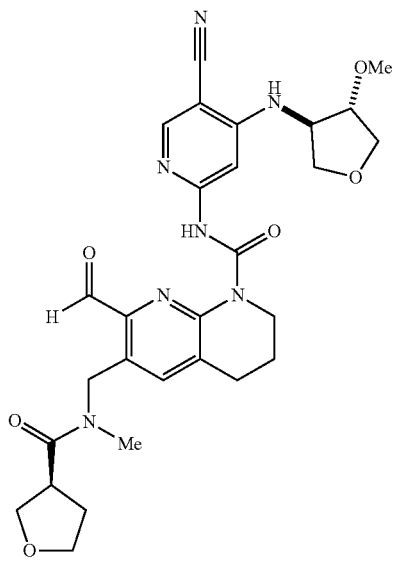

N-(5-Cyano-4-(((trans)-4-methoxytetrahydrofuran-3-yl)amino)pyridin-2-yl)-7-formyl-6-(((R)—N-methyltetrahydrofuran-2-carboxamido)methyl)-3,4-dihydro-1,8-naphthyridin-1(2H)-carboxamide was prepared in accordance with the method of Example 1.

$^1$H NMR (400 MHz, CDCl$_3$) δ 13.70-13.58 (m, 1H), 10.27-10.22 (m, 1H), 8.21 (s, 1H), 7.77 (s, 1H), 7.63-7.45 (m, 1H), 5.22-5.09 (m, 1H), 5.02-4.85 (m, 2H), 4.76-4.71 (m, 1H), 4.17-4.06 (m, 5H), 4.03-3.97 (m, 1H), 3.94-3.88 (m, 2H), 3.85-3.80 (m, 2H), 3.54 (s, 3H), 3.10 (S, 2H), 2.96-2.88 (m, 3H), 2.35-2.20 (m, 1H), 2.17-1.96 (m, 5H);

MS m/z (ESI): 564.2 [M+H]$^+$.

Example 97

(R)—N-(5-Cyano-4-((2-methoxyethyl)amino)pyridin-2-yl)-6-((1-ethyl-N-methylpyrrolidin-2-carboxamido)methyl)-7-formyl-3,4-dihydro-1,8-naphthyridin-1(2H)-carboxamide

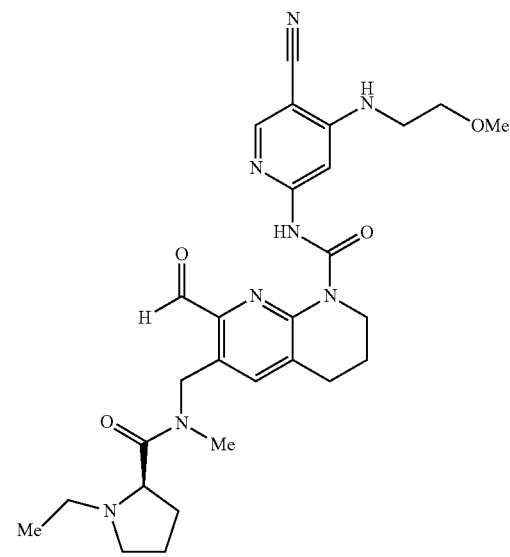 [SMILES: CCN1CCC[C@@H]1C(=O)N(C)Cc1cc2c(nc1C=O)N(C(=O)Nc1cc(NCCOC)c(C#N)cn1)CCC2]

(R)—N-(5-Cyano-4-((2-methoxyethyl)amino)pyridin-2-yl)-6-((1-ethyl-N-methylpyrrolidin-2-carboxamido)methyl)-7-formyl-3,4-dihydro-1,8-naphthyridin-1(2H)-carboxamide was prepared in accordance with the method of Example 1.

$^1$H NMR (400 MHz, CDCl$_3$): δ 13.50 (m, 1H), 10.25 (m, 1H), 8.17 (s, 1H), 7.56 (m, 2H), 5.31 (m, 1H), 5.07 (m, 2H), 4.08 (m, 2H), 3.64 (m, 3H), 3.49 (m, 3H), 3.41 (s, 3H), 2.94 (m, 7H), 2.46 (m, 1H), 2.03 (m, 6H), 1.28 (m, 3H);

MS m/z (ESI): 549.3 [M+H]$^+$.

Example 98

N-(5-Cyano-4-((2-methoxyethyl)amino)pyridin-2-yl)-7-formyl-6-((N-methyltetrahydro-2H-pyran-4-carboxamido)methyl)-3,4-dihydro-1,8-naphthyridin-1(2H)-carboxamide

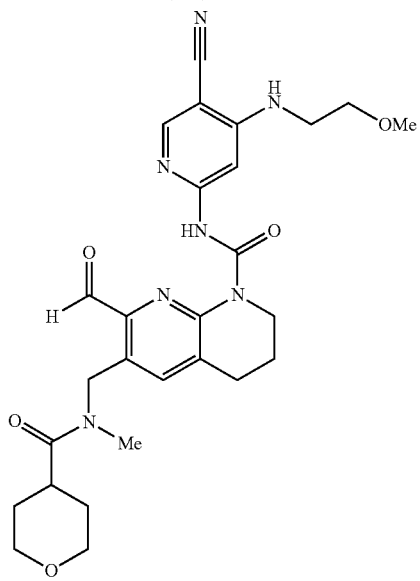 [SMILES: COCCNc1cc(NC(=O)N2CCCc3cc(CN(C)C(=O)C4CCOCC4)c(C=O)nc32)ncc1C#N]

N-(5-Cyano-4-((2-methoxyethyl)amino)pyridin-2-yl)-7-formyl-6-((N-methyltetrahydro-2H-pyran-4-carboxamido)methyl)-3,4-dihydro-1,8-naphthyridin-1(2H)-carboxamide was prepared in accordance with the method of Example 1.

$^1$H NMR (400 MHz, CDCl$_3$): δ 13.64 (m, 1H), 10.30 (s, 1H), 8.20 (s, 1H), 7.54 (m, 2H), 5.50 (m, 1H), 5.04 (m, 2H), 4.05 (m, 4H), 3.65 (m, 2H), 3.50 (m, 7H), 3.00 (m, 3H), 2.90 (m, 3H), 2.03 (m, 4H), 1.65 (m, 2H);

MS m/z (ESI): 536.2 [M+H]$^+$.

Example 99

(S)—N-(5-Cyano-4-((tetrahydrofuran-3-yl)amino)pyridin-2-yl)-7-formyl-6-((N-methyltetrahydro-2H-pyran-4-carboxamido)methyl)-3,4-dihydro-1,8-naphthyridin-1(2H)-carboxamide

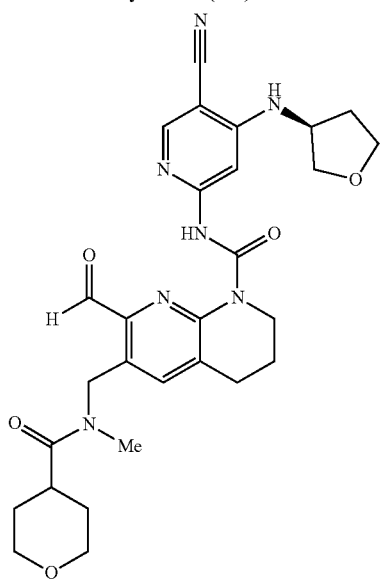

(S)—N-(5-Cyano-4-((tetrahydrofuran-3-yl)amino)pyridin-2-yl)-7-formyl-6-((N-methyltetrahydro-2H-pyran-4-carboxamido)methyl)-3,4-dihydro-1,8-naphthyridin-1(2H)-carboxamide was prepared in accordance with the method of Example 1.

$^1$H NMR (400 MHz, CDCl$_3$): δ 13.68 (m, 1H), 10.27 (m, 1H), 8.21 (m, 1H), 7.53 (m, 2H), 5.15 (m, 1H), 5.03 (m, 2H), 4.30 (m, 1H), 4.00 (m, 8H), 3.48 (m, 2H), 3.08 (m, 3H), 2.90 (m, 3H), 2.03 (m, 8H);

MS m/z (ESI): 548.2 [M+H]$^+$.

Example 100

N-(5-Cyano-4-(((R)-1-methoxypropan-2-yl)amino)pyridin-2-yl)-7-formyl-6-(((S)—N-methyltetrahydrofuran-3-carboxamido)methyl)-3,4-dihydro-1,8-naphthyridin-1(2H)-carboxamide

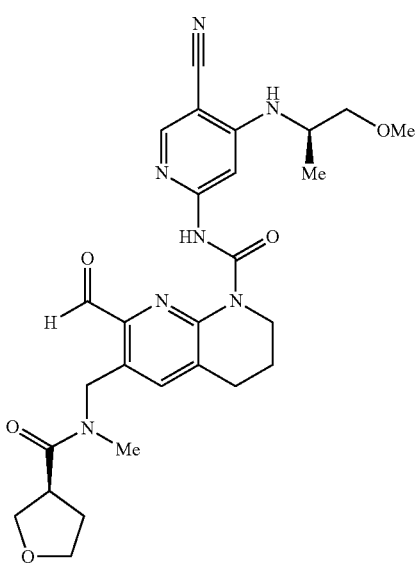 [SMILES: COC[C@@H](C)Nc1cc(NC(=O)N2CCCc3cc(CN(C)C(=O)[C@H]4CCOC4)c(C=O)nc32)ncc1C#N]

N-(5-Cyano-4-(((R)-1-methoxypropan-2-yl)amino)pyridin-2-yl)-7-formyl-6-(((S)—N-methyltetrahydrofuran-3-carboxamido)methyl)-3,4-dihydro-1,8-naphthyridin-1(2H)-carboxamide was prepared in accordance with the method of Example 1.

MS m/z (ESI): 536.2 [M+H]$^+$.

Example 101

N-(5-Cyano-4-(((R)-1-methoxypropan-2-yl)amino)pyridin-2-yl)-7-formyl-6-(((R)—N-methyltetrahydrofuran-3-carboxamido)methyl)-3,4-dihydro-1,8-naphthyridin-1(2H)-carboxamide

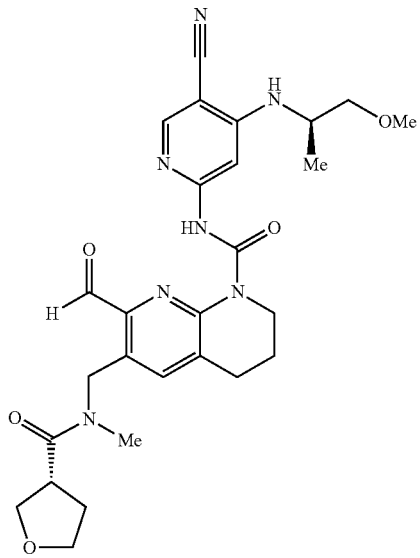 [SMILES: COC[C@@H](C)Nc1cc(NC(=O)N2CCCc3cc(CN(C)C(=O)[C@@H]4CCOC4)c(C=O)nc32)ncc1C#N]

N-(5-Cyano-4-(((R)-1-methoxypropan-2-yl)amino)pyridin-2-yl)-7-formyl-6-(((R)—N-methyltetrahydrofuran-3-carboxamido)methyl)-3,4-dihydro-1,8-naphthyridin-1(2H)-carboxamide was prepared in accordance with the method of Example 1.

MS m/z (ESI): 536.2 [M+H]$^+$.

Example 102

N-(5-Cyano-4-(((S)-tetrahydrofuran-3-yl)amino)pyridin-2-yl)-7-formyl-6-(((S)—N-methyltetrahydrofuran-3-carboxamido)methyl)-3,4-dihydro-1,8-naphthyridin-1(2H)-carboxamide

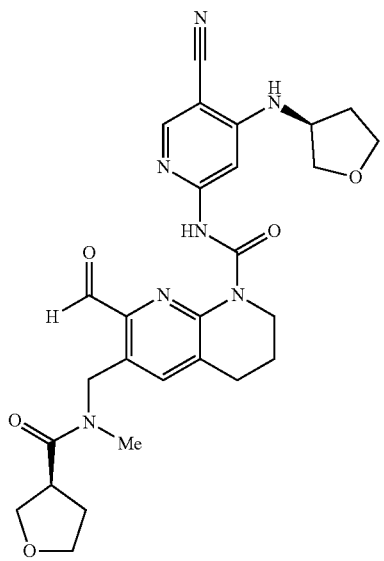 [SMILES: CN(Cc1cc2c(nc1C=O)N(C(=O)Nc1cc(N[C@H]3CCOC3)c(C#N)cn1)CCC2)C(=O)[C@H]1CCOC1]

N-(5-Cyano-4-(((S)-tetrahydrofuran-3-yl)amino)pyridin-2-yl)-7-formyl-6-(((S)—N-methyltetrahydrofuran-3-carboxamido)methyl)-3,4-dihydro-1,8-naphthyridin-1(2H)-carboxamide was prepared in accordance with the method of Example 1.

MS m/z (ESI): 534.2 [M+H]$^+$.

Example 103

N-(5-Cyano-4-(((R)-tetrahydrofuran-3-yl)amino)pyridin-2-yl)-7-formyl-6-(((S)—N-methyltetrahydrofuran-3-carboxamido)methyl)-3,4-dihydro-1,8-naphthyridin-1 (2H)-carboxamide

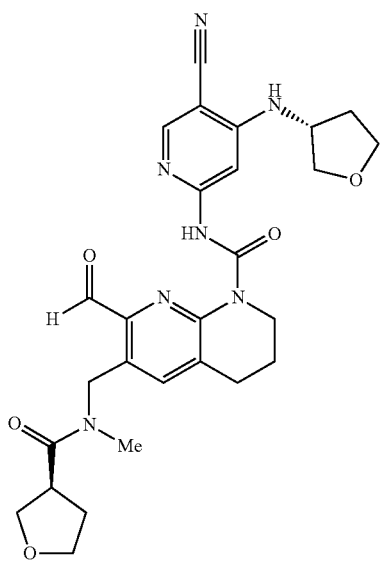 [SMILES: CN(Cc1cc2c(nc1C=O)N(C(=O)Nc1cc(N[C@@H]3CCOC3)c(C#N)cn1)CCC2)C(=O)[C@H]1CCOC1]

N-(5-Cyano-4-(((R)-tetrahydrofuran-3-yl)amino)pyridin-2-yl)-7-formyl-6-(((S)—N-methyltetrahydrofuran-3-carboxamido)methyl)-3,4-dihydro-1,8-naphthyridin-1(2H)-carboxamide was prepared in accordance with the method of Example 1.

MS m/z (ESI): 534.2 [M+H]$^+$.

Example 104

N-(5-Cyano-4-(((S)-tetrahydrofuran-3-yl)amino)pyridin-2-yl)-7-formyl-6-(((R)—N-methyltetrahydrofuran-3-carboxamido)methyl)-3,4-dihydro-1,8-naphthyridin-1 (2H)-carboxamide

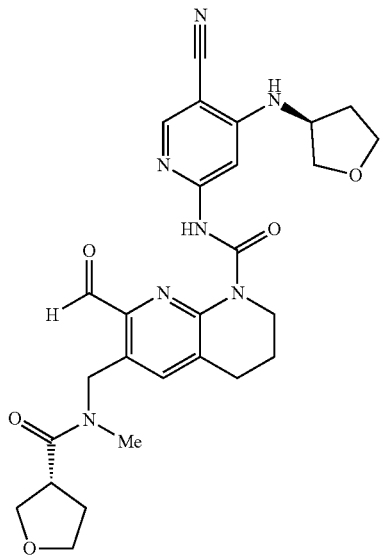 [SMILES: CN(Cc1cc2c(nc1C=O)N(C(=O)Nc1cc(N[C@H]3CCOC3)c(C#N)cn1)CCC2)C(=O)[C@@H]1CCOC1]

N-(5-Cyano-4-(((S)-tetrahydrofuran-3-yl)amino)pyridin-2-yl)-7-formyl-6-(((R)—N-methyltetrahydrofuran-3-carboxamido)methyl)-3,4-dihydro-1,8-naphthyridin-1(2H)-carboxamide was prepared in accordance with the method of Example 1.

MS m/z (ESI): 534.2 [M+H]$^+$.

Example 105

N-(5-Cyano-4-(((R)-tetrahydrofuran-3-yl)amino)pyridin-2-yl)-7-formyl-6-(((R)—N-methyltetrahydrofuran-3-carboxamido)methyl)-3,4-dihydro-1,8-naphthyridin-1 (2H)-carboxamide

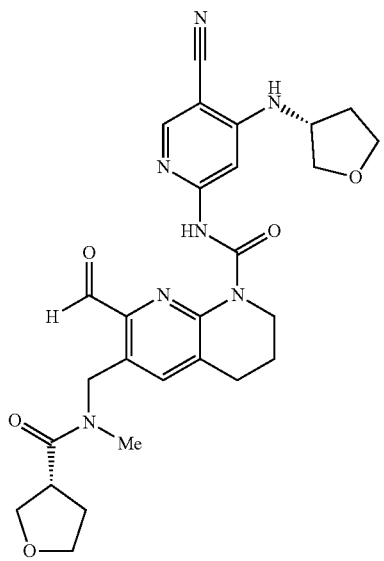 [SMILES: CN(Cc1cc2c(nc1C=O)N(C(=O)Nc1cc(N[C@@H]3CCOC3)c(C#N)cn1)CCC2)C(=O)[C@@H]1CCOC1]

N-(5-Cyano-4-(((R)-tetrahydrofuran-3-yl)amino)pyridin-2-yl)-7-formyl-6-(((R)—N-methyltetrahydrofuran-3-carboxamido)methyl)-3,4-dihydro-1,8-naphthyridin-1(2H)-carboxamide was prepared in accordance with the method of Example 1.

MS m/z (ESI): 534.2 [M+H]$^+$.

Example 106

(S)—N-(5-Cyano-4-(3-methoxypyrrolidin-1-yl)pyridin-2-yl)-7-formyl-6-((2-methoxy-N-methylacetamido)methyl)-3,4-dihydro-1,8-naphthyridin-1(2H)-carboxamide

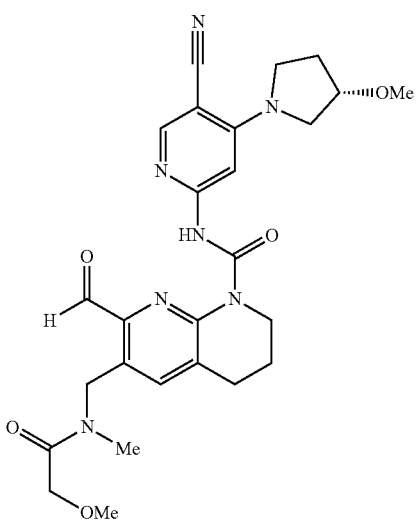 [SMILES: COCC(=O)N(C)Cc1cc2c(nc1C=O)N(C(=O)Nc1cc(N3CC[C@H](OC)C3)c(C#N)cn1)CCC2]

(S)—N-(5-Cyano-4-(3-methoxypyrrolidin-1-yl)pyridin-2-yl)-7-formyl-6-((2-methoxy-N-methylacetamido)methyl)-3,4-dihydro-1,8-naphthyridin-1(2H)-carboxamide was prepared in accordance with the method of Example 1.

$^1$H NMR (400 MHz, CDCl$_3$) δ13.54-13.40 (m, 1H), 10.26-10.22 (m, 1H), 8.20 (s, 1H), 7.63-7.40 (m, 2H), 5.08-4.96 (m, 2H), 4.18 (s, 1H), 4.11-4.05 (m, 4H), 3.84-3.77 (m, 4H), 3.49 (S, 2H), 3.39-3.35 (m, 4H), 3.01-2.96 (m, 3H), 2.95-2.87 (m, 2H), 2.26-2.19 (m, 1H), 2.08-1.99 (m, 3H);

MS m/z (ESI): 522.2 [M+H]$^+$.

Example 107

(R)—N-(5-Cyano-4-(3-methoxypyrrolidin-1-yl)pyridin-2-yl)-7-formyl-6-((2-methoxy-N-methylacetamido)methyl)-3,4-dihydro-1,8-naphthyridin-1(2H)-carboxamide

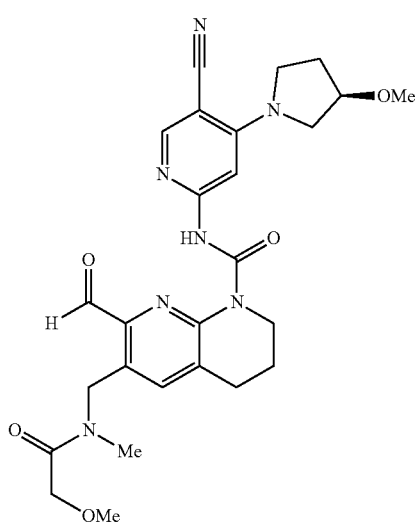 [SMILES: COCC(=O)N(C)Cc1cc2c(nc1C=O)N(C(=O)Nc1cc(N3CC[C@@H](OC)C3)c(C#N)cn1)CCC2]

(R)—N-(5-Cyano-4-(3-methoxypyrrolidin-1-yl)pyridin-2-yl)-7-formyl-6-((2-methoxy-N-methylacetamido)methyl)-3,4-dihydro-1,8-naphthyridin-1(2H)-carboxamide was prepared in accordance with the method of Example 1.

$^1$H NMR (400 MHz, CDCl$_3$) δ 13.54-13.40 (m, 1H), 10.26-10.22 (m, 1H), 8.20 (s, 1H), 7.63-7.40 (m, 2H), 5.08-4.96 (m, 2H), 4.18 (s, 1H), 4.11-4.05 (m, 4H), 3.84-3.77 (m, 4H), 3.49 (S, 2H), 3.39-3.35 (m, 4H), 3.01-2.96 (m, 3H), 2.95-2.87 (m, 2H), 2.25-2.19 (m, 1H), 2.08-1.99 (m, 3H);

MS m/z (ESI): 522.2 [M+H]$^+$.

Example 108

N-(5-Cyano-4-(((trans)-4-methoxytetrahydrofuran-3-yl)amino)pyridin-2-yl)-7-formyl-6-((2-methoxy-N-methylacetamido)methyl)-3,4-dihydro-1,8-naphthyridin-1 (2H)-carboxamide

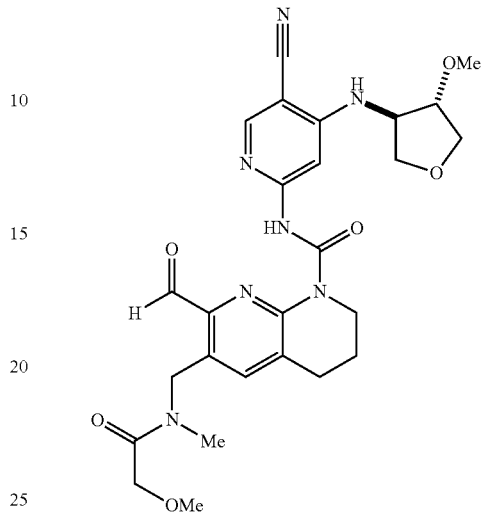

N-(5-Cyano-4-(((trans)-4-methoxytetrahydrofuran-3-yl)amino)pyridin-2-yl)-7-formyl-6-((2-methoxy-N-methylacetamido)methyl)-3,4-dihydro-1,8-naphthyridin-1(2H)-carboxamide was prepared in accordance with the method of Example 1.

$^1$H NMR (400 MHz, CDCl$_3$) δ 13.70-13.56 (m, 1H), 10.26-10.22 (m, 1H), 8.21 (s, 1H), 7.77 (s, 1H), 7.63-7.41 (m, 1H), 5.07 (d, J=2.6 Hz, 1H), 5.03-4.96 (m, 2H), 4.19-4.07 (m, 7H), 3.92-3.89 (m, 1H), 3.86-3.81 (m, 2H), 3.55-3.53 (m, 3H), 3.49 (S, 2H), 3.36 (s, 1H), 3.02-2.97 (m, 3H), 2.95-2.89 (m, 2H), 2.08-2.00 (m, 2H);

MS m/z (ESI): 538.2 [M+H]$^+$.

Example 109

(R)—N-(5-Cyano-4-((2-methoxyethyl)amino)pyridin-2-yl)-7-formyl-6-((N-((tetrahydrofuran-2-yl)methyl)acetamido)methyl)-3,4-dihydro-1,8-naphthyridin-1(2H)-carboxamide

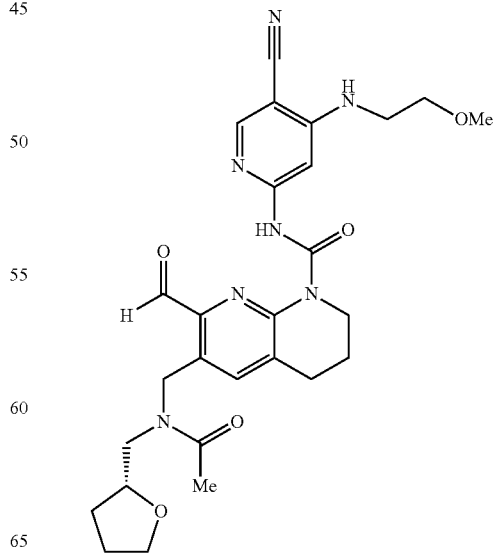

Step 1: Preparation of (R)-1-(2-(dimethoxymethyl)-5,6,7,8-tetrahydro-1,8-naphthyridin-3-yl)-N-((tetrahydro furan-2-yl)methyl)methylamine

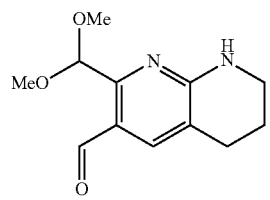 

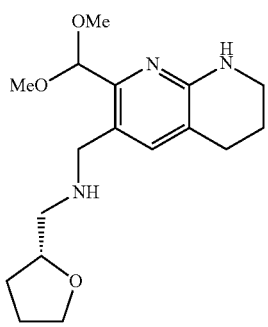

2-(Dimethoxymethyl)-5,6,7,8-tetrahydro-1,8-naphthyridin-3-carbaldehyde (1.0 g, 4.2 mmol) and (R)-(tetrahydrofuran-2-yl)methylamine (0.6 g, 5.9 mmol) were dissolved in methanol (35 mL) in a 100 mL one-neck flask. Sodium cyanoborohydride (0.68 g, 10.8 mmol) was added, and then the reaction solution was stirred overnight at room temperature. The reaction was monitored by LC-MS. After the raw material was completely converted, the reaction was stopped. After the reaction solution was concentrated under reduced pressure, the resulting residue was subjected to column chromatography to obtain (R)-1-(2-(dimethoxymethyl)-5,6,7,8-tetrahydro-1,8-naphthyridin-3-yl)-N-((tetrahydro furan-2-yl)methyl)methylamine (0.75 g, 55%).

MS m/z (ESI): 322.0[M+H]⁺.

Step 2: Preparation of (R)—N-((2-(dimethoxymethyl)-5,6,7,8-tetrahydro-1,8-naphthyridin-3-yl)methyl)-N-((tetrahydrofuran-2-yl)methyl)acetamide

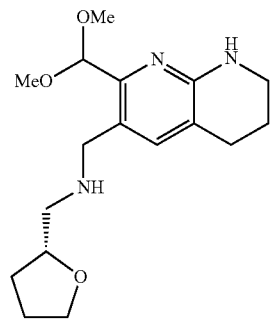 

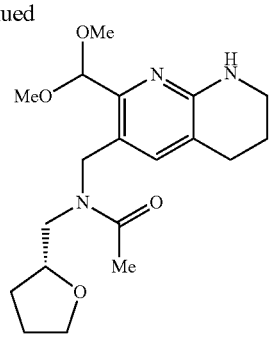

(R)—N-((2-(dimethoxymethyl)-5,6,7,8-tetrahydro-1,8-naphthyridin-3-yl)methyl)-N-((tetrahydrofuran-2-yl)methyl)acetamide (150 mg, 0.47 mmol) was dissolved in dichloromethane (15 mL) in a 100 mL one-neck flask. Acetic anhydride (57 mg, 0.56 mmol) and DIPEA (0.3 mL) were added, and then the reaction solution was stirred overnight at room temperature. The reaction was stopped, and water (50 mL) was added to quench the reaction. The reaction solution was extracted with ethyl acetate (50 mL×2). The organic phases were combined, washed with saturated sodium chloride solution (50 mL), dried over anhydrous sodium sulfate, filtered, and concentrated. The resulting residue was subjected to column chromatography to obtain (R)—N-((2-(dimethoxymethyl)-5,6,7,8-tetrahydro-1,8-naphthyridin-3-yl)methyl)-N-((tetrahydrofuran-2-yl)methyl)acetamide (90 mg, 53%).

MS m/z (ESI): 364.2 [M+H]⁺.

Step 3: (R)—N-(5-cyano-4-((2-methoxyethyl)amino)pyridin-2-yl)-7-formyl-6-((N-((tetrahydrofuran-2-yl)methylacetamino)methyl-3,4-dihydro-1,8-naphthyridin-1(2H)-carboxamide

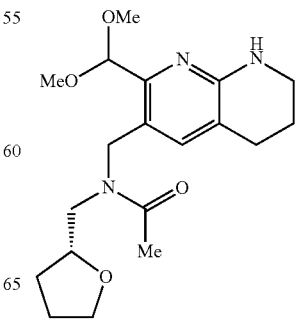

183

-continued

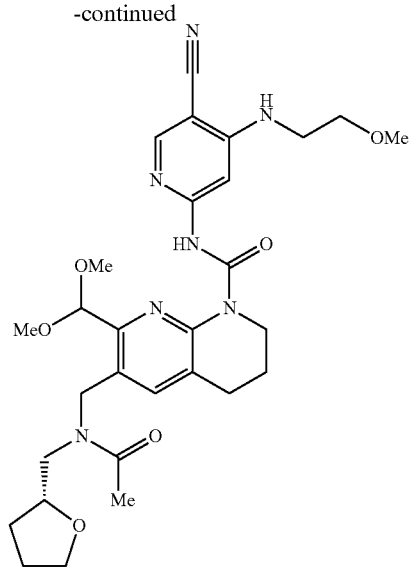

6-Amino-4-((2-methoxyethyl)amino)nicotinonitrile (90 mg, 0.47 mmol) was dissolved in anhydrous DMF (1 mL) in a 100 mL one-neck flask. The reaction solution was cooled to 0° C. in an ice bath, and then a solution of di(1H-1,2,4-triazol-1-yl)methanone (80 mg, 0.48 mol) in DMF (1 mL) was added dropwise into the aforementioned solution. After 10 minutes, the addition was completed. The reaction solution was stirred for 45 minutes at 0° C., and then stirred for 90 minutes at room temperature. A solution of (R)—N-((2-(dimethoxymethyl)-5,6,7,8-tetrahydro-1,8-naphthyridin-3-yl)methyl)-N-((tetrahydrofuran-2-yl)methyl)acetamide (70 mg, 0.19 mmol) in DMF (1.5 mL) was added to the aforementioned solution, and stirred overnight at room temperature. The reaction was stopped, and water (40 mL) was added to quench the reaction. The reaction solution was extracted with ethyl acetate (40 mL×2). The organic phases were combined, washed with saturated sodium chloride solution (50 mL), dried over anhydrous sodium sulfate, filtered, and concentrated. The resulting residue was subjected to preparative thin-layer chromatography (TLC) to obtain (R)—N-(5-cyano-4-((2-methoxyethyl)amino)pyridin-2-yl)-7-formyl-6-((N-((tetrahydro furan-2-yl)methyl) acetamino)methyl-3,4-dihydro-1,8-naphthyridin-1(2H)-carboxamide (32 mg, 31%).

MS m/z (ESI): 582.2 [M+H]⁺.

184

Step 4: Preparation of (R)—N-(5-cyano-4-((2-methoxyethyl)amino)pyridin-2-yl)-7-formyl-6-((N-((tetrahydro furan-2-yl)methyl)acetamido)methyl)-3,4-dihydro-1,8-naphthyridin-1(2H)-carboxamide

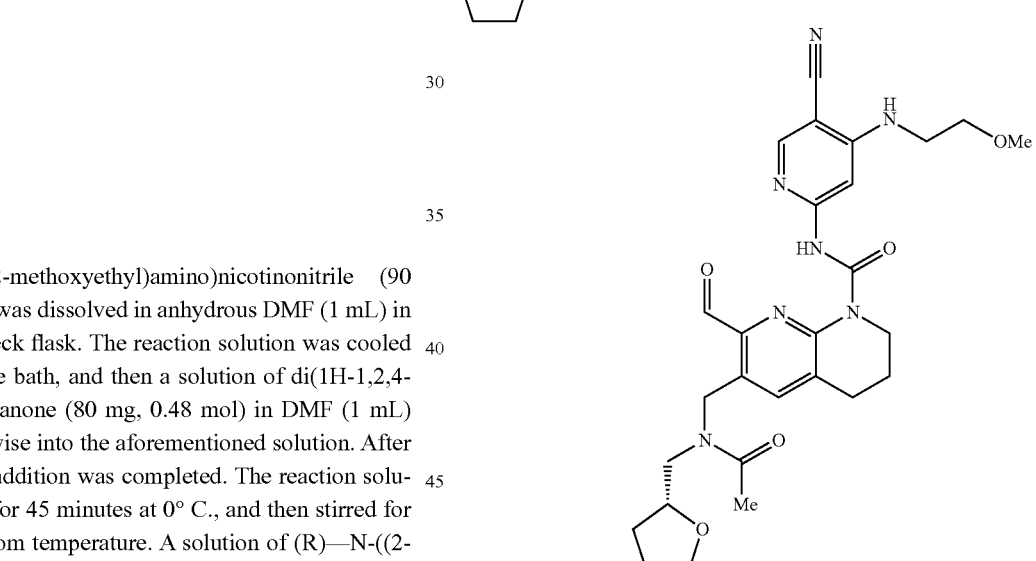

(R)—N-(5-Cyano-4-((2-methoxyethyl)amino)pyridin-2-yl)-7-formyl-6-((N-((tetra hydrofuran-2-yl)methyl)acet-amino)methyl-3,4-dihydro-1,8-naphthyridin-1(2H)-carbox-amide (36.0 mg, 0.06 mmol) was dissolved in tetrahydrofuran (5 mL) in a 100 mL one-neck flask, 4 mol/L of hydrochloric acid (1.5 mL) was added, and then the reaction solution was stirred for 4 hours at room temperature. After the reaction was stopped, saturated sodium bicarbonate solution (30 mL) was added. The reaction solution was extracted with ethyl acetate (30 mL×2), and then the organic phases were combined, washed with saturated sodium chloride (30 mL), dried over anhydrous sodium sulfate, filtered, and concentrated. The resulting residue was subjected to preparative thin-layer chromatography (TLC) to obtain (R)—N-(5-cyano-4-((2-methoxyethyl)amino)pyridin-2-yl)-7-formyl-6-((N-((tetrahydro furan-2-yl)methyl) acetamino)methyl)-3,4-dihydro-1,8-naphthyridin-1(2H)-carboxamide (26 mg, 78%).

¹H NMR (400 MHz, CDCl₃) δ 13.55(d, J=34.0 Hz, 1H), 10.25 (d, J=34.0 Hz, 1H), 8.18 (d, J=2.8 Hz, 1H), 7.58 (t, 2H), 5.33 (s, 1H), 5.17-5.00 (m, 2H), 4.14-4.04 (m, 3H), 3.88-3.62 (m, 4H), 3.51-3.43 (m, 3H), 3.41 (s, 3H), 3.25 (m, 1H), 3.93 (m, 2H), 2.25(S, 2H), 2.05 (m, 4H), 1.97 (m, 2H), 1.47 (m, 1H);

MS m/z (ESI): 536.2 [M+H]⁺.

Example 110

(R)—N-(5-Cyano-4-((2-methoxyethyl)amino)pyridin-2-yl)-7-formyl-6-((N-((tetrahydrofuran-2-yl)methyl)formylamino)methyl)-3,4-dihydro-1,8-naphthyridin-1(2H)-carboxamide

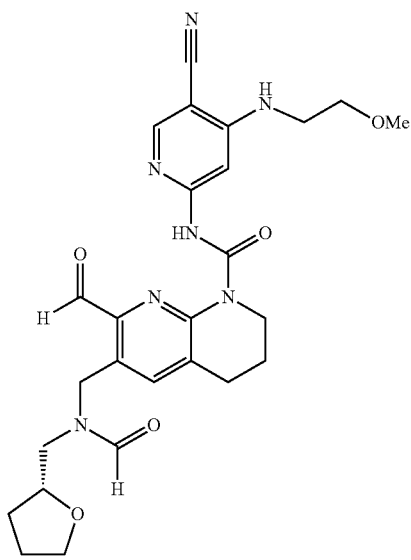 [SMILES: COCCNc1cc(NC(=O)N2CCCc3cc(CN(C=O)C[C@H]4CCCO4)c(C=O)nc32)ncc1C#N]

(R)—N-(5-Cyano-4-((2-methoxyethyl)amino)pyridin-2-yl)-7-formyl-6-((N-((tetra hydrofuran-2-yl)methyl)formylamino)methyl)-3,4-dihydro-1,8-naphthyridin-1(2H)-carboxamide was prepared in accordance with the method of Example 109.

¹H NMR (400 MHz, CDCl₃) δ 13.61-13.52 (m, 1H), 10.24 (s, 1H), 8.28 (s, 1H), 8.18 (s, 1H), 7.66-7.59 (m, 2H), 5.32 (s, 1H), 5.14-5.00 (m, 2H), 4.11-3.62 (m, 7H), 3.51-3.47 (m, 2H), 3.41 (s, 3H), 3.28-3.23 (m, 2H), 2.96-2.83 (m, 2H), 2.06-1.95 (m, 5H), 1.57-1.41 (m, 1H);

MS m/z (ESI): 522.2[M+H]⁺.

Example 111

(S)—N-(5-Cyano-4-((2-methoxyethyl)amino)pyridin-2-yl)-7-formyl-6-((N-((tetrahydrofuran-2-yl)methyl)acetamido)methyl)-3,4-dihydro-1,8-naphthyridin-1(2H)-carboxamide

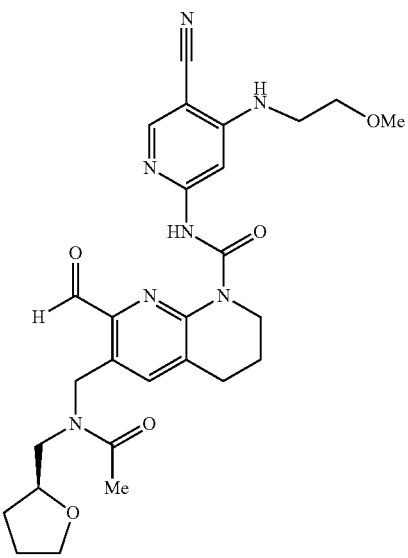 [SMILES: COCCNc1cc(NC(=O)N2CCCc3cc(CN(C[C@@H]4CCCO4)C(C)=O)c(C=O)nc32)ncc1C#N]

(S)—N-(5-Cyano-4-((2-methoxyethyl)amino)pyridin-2-yl)-7-formyl-6-((N-((tetrahydrofuran-2-yl)methyl)acetamido)methyl)-3,4-dihydro-1,8-naphthyridin-1(2H)-carboxamide was prepared in accordance with the method of Example 109.

¹H NMR (400 MHz, CDCl₃) δ 13.65-13.5 (m, 1H), 10.25 (d, J=34.0 Hz, 1H), 8.18 (d, J=2.8 Hz, 1H), 7.65-7.46 (m, 2H), 5.33 (s, 1H), 5.17-5.00 (m, 2H), 4.14-4.04 (m, 3H), 3.88-3.62 (m, 4H), 3.51-3.43 (m, 3H), 3.41 (s, 3H), 3.29-3.25 (m, 1H), 2.95-2.89 (m, 2H), 2.25(S, 2H), 2.07-1.99 (m, 4H), 1.95-1.85 (m, 2H), 1.53-1.43 (m, 1H);

MS m/z (ESI): 536.2 [M+H]⁺.

Example 112

(S)—N-(5-Cyano-4-((2-methoxyethyl)amino)pyridin-2-yl)-7-formyl-6-((N-((tetrahydrofuran-2-yl)methyl)formylamino)methyl)-3,4-dihydro-1,8-naphthyridin-1(2H)-carboxamide

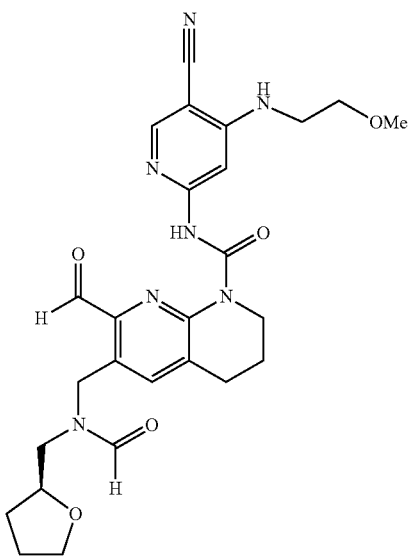 [SMILES: COCCNc1cc(NC(=O)N2CCCc3cc(CN(C=O)C[C@@H]4CCCO4)c(C=O)nc32)ncc1C#N]

(S)—N-(5-Cyano-4-((2-methoxyethyl)amino)pyridin-2-yl)-7-formyl-6-((N-((tetrahydrofuran-2-yl)methyl)formylamino)methyl)-3,4-dihydro-1,8-naphthyridin-1(2H)-carboxamide was prepared in accordance with the method of Example 109.

$^1$H NMR (400 MHz, CDCl$_3$) δ 13.60-13.52 (m, 1H), 10.24 (s, 1H), 8.28 (s, 1H), 8.18 (s, 1H), 7.66-7.50 (m, 2H), 5.32 (s, 1H), 5.14-5.00 (m, 2H), 4.11-3.62 (m, 7H), 3.51-3.47 (m, 2H), 3.41 (s, 3H), 3.30-3.25 (m, 2H), 2.96-2.89 (m, 2H), 2.06-1.95 (m, 5H), 1.53-1.43 (m, 1H);
MS m/z (ESI): 522.2[M+H]$^+$.

Example 113

(R)—N-(5-Cyano-4-((2-methoxyethyl)amino)pyridin-2-yl)-7-formyl-6-((N-(tetrahydrofuran-3-yl)acetamido)methyl)-3,4-dihydro-1,8-naphthyridin-1(2H)-carboxamide

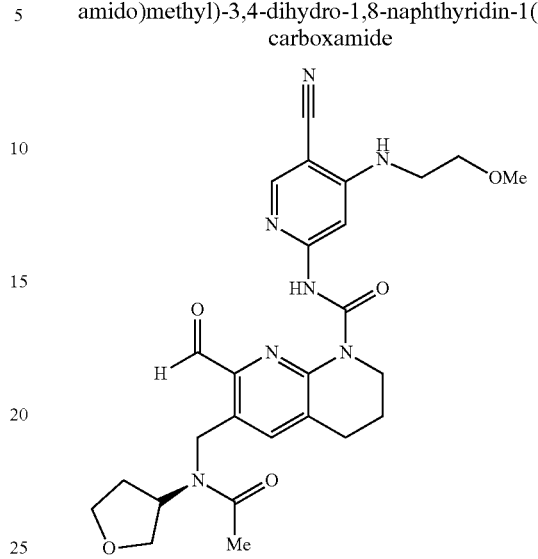

(R)—N-(5-Cyano-4-((2-methoxyethyl)amino)pyridin-2-yl)-7-formyl-6-((N-(tetrahydrofuran-3-yl)acetamido)methyl)-3,4-dihydro-1,8-naphthyridin-1(2H)-carboxamide was prepared in accordance with the method of Example 109.

$^1$H NMR (400 MHz, DMSO-d$_6$): 313.57-13.45 (m, 1H), 10.28 (s, 1H), 8.22 (s, 1H), 7.57 (s, 1H), 7.46 (s, 1H), 6.84 (s, 1H), 5.32 (m, 2H), 4.95 (m, 2H), 4.09 (m, 2H), 3.95 (m, 1H), 3.60-3.78 (m, 4H), 3.57 (m, 2H), 3.07 (s, 3H), 2.93 (m, 2H), 2.35 (s, 3H), 2.04 (m, 2H), 1.70 (m, 2H);
MS m/z (ESI): 522.2 [M+H]$^+$.

Example 114

(S)—N-(5-Cyano-4-((2-methoxyethyl)amino)pyridin-2-yl)-7-formyl-6-((N-(tetrahydrofuran-3-yl)formylamino)methyl)-3,4-dihydro-1,8-naphthyridin-1(2H)-carboxamide

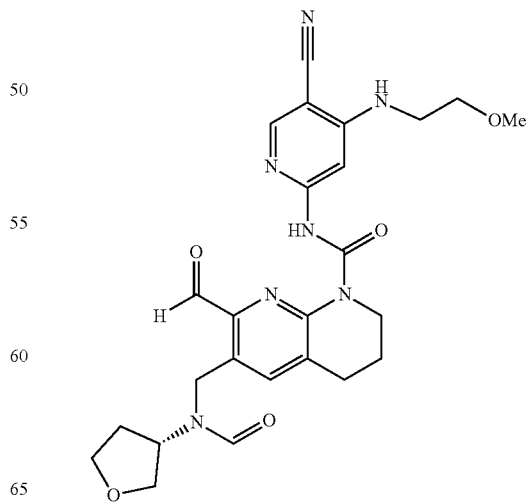

(S)—N-(5-Cyano-4-((2-methoxyethyl)amino)pyridin-2-yl)-7-formyl-6-((N-(tetrahydrofuran-3-yl)formylamino)methyl)-3,4-dihydro-1,8-naphthyridin-1(2H)-carboxamide was prepared in accordance with the method of Example 109.

$^1$H NMR (400 MHz, DMSO-d$_6$): 313.57-13.46 (m, 1H), 10.27 (s, 1H), 8.43 (s, 1H), 8.19 (s, 1H), 7.60 (s, 1H), 7.52 (s, 1H), 5.40 (s, 1H), 5.05 (S, 2H), 4.33-4.28 (m, 2H), 4.11-4.06 (m, 2H), 4.02-3.92 (m, 1H), 3.60-3.75 (m, 6H), 3.52-3.49 (m, 2H), 3.42 (s, 3H), 2.96-2.89 (m, 2H), 2.08-2.01 (m, 2H);

MS m/z (ESI): 508.2 [M+H]$^+$.

Biological Test and Evaluation

1. Enzymologic Experiment of FGFR4

In this experiment, the inhibitory effect of the compounds on FGFR4 kinase activity was tested by a fluorescence resonance energy transfer (TR-FRET) method, and the half maximal inhibitory concentration (IC$_{50}$) of the compounds on the FGFR4 kinase activity was determined.

1) 1~5 μL of FGFR4 enzyme solution were added to a 384-well plate, and the final concentration of the enzyme was 0.1~5 nM.

2) 1~5 μL of diluted solution in gradient of the compound were added.

3) 1~5 μL of a substrate mixture containing substrate polypeptide with a final concentration of 5~50 nM and ATP with a final concentration of 10~200 μM were added.

4) The mixture was incubated for 0.5-3 hours at room temperature.

5) 10 μL of EDTA and a test solution comprising labeled antibody were added, and the plate was incubated for 1 hour at room temperature.

6) The fluorescence signal values of each plate were determined by a microplate reader at 665 nm.

7) The inhibition rates were calculated according to the fluorescence signal values.

8) The IC$_{50}$ of the compound was obtained by curve fitting according to the inhibition rates at different concentrations, and the enzymatic activity of the specific example compounds is shown in Table 1.

2. Enzymologic Experiment of FGFR1

In this experiment, the inhibitory effect of the compounds on FGFR1 kinase activity was tested by a fluorescence resonance energy transfer (TR-FRET) method, and the half maximal inhibitory concentration (IC$_{50}$) of the compounds on the FGFR1 kinase activity was determined.

1) 1~5 μL of FGFR1 enzymatic solution was added to a 384-well plate, and the final concentration of the enzyme was 0.1~5 nM.

2) 1~5 μL of diluted solution in gradient of the compound was added.

3) 1~5 μL of a substrate mixture containing substrate polypeptide with a final concentration of 5~50 nM and ATP with a final concentration of 10~200 μM was added.

4) The mixture was incubated for 0.5-3 hours at room temperature.

5) 10 μL of EDTA and a test solution comprising labeled antibody were added, and the plate was incubated for 1 hour at room temperature.

6) The fluorescence signal values of each plate were determined by a microplate reader at 665 nm.

7) The inhibition rates were calculated according to the fluorescence signal values.

The IC$_{50}$ of the compound was obtained by curve fitting according to the inhibition rates at different concentrations, and the enzymatic activity of the specific example compounds is shown in Table 1.

TABLE 1

| Compound No. | FGFR4 IC$_{50}$ (nM) | FGFR1 IC$_{50}$ (nM) |
|---|---|---|
| Example 1 | 0.90 | >10000 |
| Example 2 | 0.72 | >10000 |
| Example 3 | 2.40 | >10000 |
| Example 4 | 4.54 | >10000 |
| Example 5 | 1.45 | >10000 |
| Example 6 | 0.74 | >10000 |
| Example 7 | 1.62 | >10000 |
| Example 9 | 0.74 | >10000 |
| Example 10 | 1.88 | >10000 |
| Example 15 | 2.53 | >10000 |
| Example 16 | 1.98 | >10000 |
| Example 18 | 4.2 | >10000 |
| Example 44 | 1.94 | >10000 |
| Example 45 | 0.92 | >10000 |
| Example 46 | 0.92 | >10000 |
| Example 50 | 1.20 | >10000 |
| Example 53 | 7.17 | >10000 |
| Example 54 | 2.46 | >10000 |
| Example 83 | 1.32 | >10000 |
| Example 84 | 1.01 | >10000 |
| Example 85 | 1.01 | >10000 |
| Example 86 | 1.34 | >10000 |
| Example 87 | 1.10 | >10000 |
| Example 89 | 1.00 | >10000 |
| Example 90 | 4.99 | >10000 |
| Example 91 | 1.16 | >10000 |
| Example 92 | 9.01 | >10000 |
| Example 93 | 2.09 | >10000 |
| Example 94 | 1.67 | >10000 |
| Example 95 | 1.75 | >10000 |
| Example 96 | 1.52 | >10000 |
| Example 97 | 1.47 | >10000 |
| Example 98 | 0.98 | >10000 |
| Example 99 | 1.95 | >10000 |
| Example 106 | 2.79 | >10000 |
| Example 107 | 1.49 | >10000 |
| Example 108 | 1.07 | >10000 |
| Example 109 | 2.62 | >10000 |
| Example 110 | 4.31 | >10000 |
| Example 111 | 3.71 | >10000 |
| Example 112 | 9.00 | >10000 |
| Example 114 | 2.99 | >10000 |

It can be seen from the enzymatic activity data of the specific example compounds that the series of compounds of the present invention had very strong inhibitory effect on FGFR4 kinase activity, but almost no inhibitory effect on FGFR1 kinase activity. Therefore, the series of compounds of the present invention have a very high selectivity for FGFR4 kinase activity.

3. Experiment on the Inhibition of Hep 3B Cell Proliferation

In this experiment, the inhibitory effect of the compounds on Hep 3B cell proliferation was tested by a CellTiter-Glo method, and the half maximal inhibitory concentration (IC$_{50}$) of the compounds on the activity of cell proliferation was determined.

1) A 96-well cell culture plate was seeded with 50~100 μL of Hep 3B cell suspension at a density of 1-5×10$^4$ cells/ml. The culture plate was incubated in an incubator for 16-24 hours (37° C., 5% CO$_2$).

2) Different concentrations of the test compound in a gradient dilution were added to the cells in the culture plate. The culture plate was incubated in an incubator for 72 hours (37° C., 5% CO$_2$).

3) 50-100 μL of CellTiter-Glo reagent were added to each well. Then, the culture plate was shaken or left to stand for 5~30 minutes at room temperature.

4) The chemiluminescence signal values of each plate were determined by a microplate reader.

5) The inhibition rates were calculated according to the chemiluminescence signal values.

6) The $IC_{50}$ of the compound was obtained by curve fitting according to the inhibition rates at different concentrations, and the cell activity of the specific example compounds is shown in Table 2.

4. Experiment on the Inhibition of HuH-7 Cell Proliferation

In this experiment, the inhibitory effect of the compounds on HuH-7 cell proliferation was tested by a CellTiter-Glo method, and the half maximal inhibitory concentration ($IC_{50}$) of the compounds on the activity of cell proliferation was determined.

1) A 96-well cell culture plate was seeded with 50~100 μL of HuH-7 cell suspension at a density of $1\text{-}5 \times 10^4$ cells/ml. The culture plate was incubated in an incubator for 16~24 hours (37° C., 5% $CO_2$).

2) Different concentrations of the test compound in a gradient dilution were added to the cells in the culture plate. The culture plate was incubated in an incubator for 72 hours (37° C., 5% $CO_2$).

3) 50~100 μL of CellTiter-Glo reagent were added to each well. Then, the culture plate was shaken or left to stand for 5~30 minutes at room temperature.

4) The chemiluminescence signal values of each plate were determined by a microplate reader.

5) The inhibition rates were calculated according to the chemiluminescence signal values.

6) The $IC_{50}$ of the compound was obtained by curve fitting according to the inhibition rates at different concentrations, and the cell activity of the specific Example compounds is shown in Table 2.

5. Experiment on the Inhibition of SK-HEP-1 Cell Proliferation

In this experiment, the inhibitory effect of the compounds on SK-HEP-1 cell proliferation was tested by a CellTiter-Glo method, and the half maximal inhibitory concentration ($IC_{50}$) of the compounds on the activity of cell proliferation was determined.

1) A 96-well cell culture plate was seeded with 50~100 μL of SK-HEP-1 cell suspension at a density of $1\text{-}5 \times 10^4$ cells/ml. The culture plate was incubated in an incubator for 16~24 hours (37° C., 5% $CO_2$).

2) Different concentrations of the test compound in a gradient dilution were added to the cells in the culture plate. The culture plate was incubated in an incubator for 72 hours (37° C., 5% $CO_2$).

3) 50~100 μL of CellTiter-Glo reagent were added to each well. Then, the culture plate was shaken or left to stand for 5~30 minutes at room temperature.

4) The chemiluminescence signal values of each plate were determined by a microplate reader.

5) The inhibition rates were calculated according to the chemiluminescence signal values.

The $IC_{50}$ of the compound was obtained by curve fitting according to the inhibition rates at different concentrations, and the cell activity of the specific Example compounds is shown in Table 2.

TABLE 2

| Compound No. | Hep 3B $IC_{50}$ (nM) | HuH-7 $IC_{50}$ (nM) | SK-HEP-1 $IC_{50}$ (nM) |
|---|---|---|---|
| Example 1 | 7.3 | 11.0 | >10000 |
| Example 2 | 5.3 | 5.9 | >10000 |
| Example 3 | 5.4 | 38.8 | >10000 |
| Example 5 | 9.1 | 31.7 | >10000 |
| Example 6 | 2.7 | 9.7 | >10000 |
| Example 7 | 4.7 | 10.6 | >10000 |
| Example 9 | 8.2 | 31.0 | >10000 |
| Example 15 | 3.5 | 8.0 | >10000 |
| Example 16 | 3.9 | 10.7 | >10000 |
| Example 44 | 6.0 | 6.9 | >10000 |
| Example 45 | 1.9 | 8.3 | >10000 |
| Example 46 | 2.3 | 9.0 | >10000 |
| Example 50 | 2.3 | 9.4 | >10000 |
| Example 54 | 4.4 | 11.3 | >10000 |
| Example 83 | 4.7 | 5.5 | >10000 |
| Example 84 | 2.4 | 11.0 | >10000 |
| Example 85 | 2.6 | 4.6 | >10000 |
| Example 86 | 3.0 | 13.1 | >10000 |
| Example 87 | 2.2 | 5.4 | >10000 |
| Example 89 | 1.9 | 2.3 | >10000 |
| Example 91 | 1.5 | 3.3 | >10000 |
| Example 93 | 3.7 | 5.0 | >10000 |
| Example 94 | 3.9 | 13.8 | >10000 |
| Example 95 | 2.8 | 12.9 | >10000 |
| Example 96 | 3.5 | 11.2 | >10000 |
| Example 97 | 9.8 | 43.7 | >10000 |
| Example 98 | 2.7 | 11.2 | >10000 |
| Example 99 | 5.5 | 12.0 | >10000 |
| Example 106 | 5.8 | 21.1 | >10000 |
| Example 107 | 1.6 | 7.3 | >10000 |
| Example 108 | 2.5 | 10.0 | >10000 |
| Example 109 | 6.0 | 11.1 | >10000 |
| Example 110 | 8.3 | 28.5 | >10000 |
| Example 111 | 8.3 | 21.5 | >10000 |
| Example 114 | 8.6 | 26.7 | >10000 |

It can be seen from the cell activity data of the specific example compounds that the series of compounds of the present invention had very strong inhibitory effect on the proliferation of Hep3B and HuH-7 cells with high expression of FGFT9 and FGFR4, but no inhibitory effect on the proliferation of SKI-HFP-1 cells with low expression of FGFT9 and FGFR4. Therefore, these compounds showed excellent cell activity and selectivity.

6. Pharmacokinetic (PK) Analysis in Rats

The pharmacokinetic test in rats of the preferred example compounds of the 5 present invention was performed with Sprague Dawley (SD) rats (Shanghai Jiesijie Laboratory Animal Co., LTD).

Mode of administration: a single intragastric administration.

Dosage: 5 mg/10 ml/kg.

Formulation: 0.5% CMC and 1% Tween 80, ultrasonic dissolution.

Sampling points: 0.5, 1, 2, 4, 6, 8 and 24 hours after administration.

Sample treatment:

1. 1.0 ml of intravenous blood was collected and placed in a $K_2EDTA$ test tube.

The blood was centrifuged at room temperature at the speed of 1000~3000×g for 5~20 minutes to isolate the plasma, which was then stored at −80° C. 2. 160 μL of acetonitrile were added to 40 μL of plasma sample for precipitation, and then the mixture was centrifuged at the speed of 500~2000×g for 5~20 minutes. 3. 100 μL of treated solution were taken, and the concentration of the test compound was analyzed by LC/MS/MS. The LC/MS/MS analytical instrument was AB Sciex API 4000.

Liquid Chromatography Analysis:

Condition of Liquid chromatography: Shimadzu LC-20AD pump

Chromatographic column: phenomenex Gemiu 5 um C18 50×4.6 mm

Mobile phase: Solution A is 0.1% aqueous formic acid solution, and solution B is acetonitrile Flow rate: 0.8 mL/min Elution time: 0-3.5 minutes, the eluent was as follows:

| Time/Minute | Solution A | Solution B |
|---|---|---|
| 0.01 | 80% | 20% |
| 0.5 | 80% | 20% |
| 1.2 | 10% | 90% |
| 2.6 | 10% | 90% |
| 2.7 | 80% | 20% |
| 3.8 | 80% | 20% |

Mass spectrometry analysis:

Mass spectrometer setup conditions: positive ion electrospray ionization (ESI) mode.

The main parameters were calculated with WinNonlin 6.1, and the experimental results of the pharmacokinetic test in rats are shown in Table 3 below:

TABLE 3

| | Pharmacokinetic Test (5 mg/kg) | | | | | |
|---|---|---|---|---|---|---|
| Example No. | Peak Time $t_{max}$(ng/mL) | Plasma Concentration $C_{max}$(ng/mL) | Area Under Curve $AUC_{0-t}$(ng/mL × h) | Area Under Curve $AUC_{0-\infty}$(ng/mL × h) | Half-Time $t_{1/2}$(h) | Mean Residence Time MRT(h) |
| 1 | 2 | 2073 | 6800 | 6926 | 1.1 | 3.1 |
| 2 | 2 | 2202 | 5822 | 5904 | 1.2 | 2.5 |
| 3 | 2 | 2228 | 6348 | 6656 | 1.6 | 3.3 |
| 5 | 2 | 3574 | 13038 | 13428 | 1.2 | 3.2 |
| 9 | 2 | 1700 | 4400 | 4800 | 1.3 | 3.0 |
| 10 | 2 | 1960 | 5260 | 5340 | 1.0 | 2.8 |
| 15 | 2 | 2693 | 7158 | 7968 | 1.5 | 3.0 |
| 16 | 2 | 3145 | 8756 | 8369 | 1.4 | 2.5 |
| 44 | 2 | 3010 | 9692 | 9824 | 1.0 | 2.9 |
| 45 | 2 | 3762 | 12115 | 12280 | 1.1 | 3.2 |
| 46 | 2 | 3287 | 10670 | 11327 | 1.0 | 2.9 |
| 50 | 2 | 2350 | 9215 | 9245 | 0.8 | 2.5 |
| 54 | 2 | 2869 | 7132 | 7869 | 1.0 | 2.7 |
| 83 | 2 | 2326 | 7520 | 7588 | 0.9 | 3.0 |
| 84 | 2 | 2620 | 8864 | 8954 | 0.9 | 3.1 |
| 85 | 2 | 2116 | 7280 | 7374 | 0.9 | 3.3 |
| 86 | 2 | 2764 | 6828 | 6896 | 1.0 | 2.7 |
| 87 | 2 | 3356 | 12403 | 14659 | 1.2 | 2.6 |
| 89 | 2 | 1994 | 3099 | 3130 | 1.0 | 2.5 |
| 91 | 0.5 | 2790 | 12900 | 13030 | 0.9 | 2.8 |
| 93 | 2 | 2859 | 9423 | 9483 | 0.9 | 2.5 |
| 94 | 2 | 3747 | 12996 | 12374 | 0.8 | 2.8 |
| 98 | 2 | 2689 | 6697 | 6843 | 0.9 | 3.1 |
| 107 | 4 | 1945 | 2630 | 2670 | 1.0 | 2.8 |

It can be seen from the results of the pharmacokinetic test in rats shown in the table that the Example compounds of the present invention showed good pharmacokinetic properties, and both the exposure AUC and the maximum plasma concentration $C_{max}$ performed well.

7. Procedures and Results of Pharmacodynamics Test of FGFR4

7.1 Reagents and Materials

Hep 3B2.1-7 cell line was purchased from the cell bank of Chinese Academy of Sciences. MEM cell culture medium, fetal bovine serum and trypsin were purchased from Life Technologies Company. Cell culture bottles were purchased from Corning Company. Disposable cell counting plate was purchased from Eppendorf Company, and trypan blue solution was purchased from Sigma Company. Disposable sterile syringes were purchased from Sinopharm Group. Disposable mouse gavage needles were purchased from FUCHIGAMI Company. Ophthalmic surgical scissors and ophthalmic surgical tweezers were purchased from Sinopharm Group. BALB/cA-nude mice, 5-7 weeks, female, were purchased from Sino-British SIPPR/BK Lab Animal Co., Ltd.

7.2 Cell Culture and Preparation of Cell Suspension a, A Hep 3B cell line was taken from the cell bank, and the cells were resuscitated with the MEM culture medium (MEM+10% FBS+1% Glu+1% SP). The resuscitated cells were placed in the cell culture bottles (cell type, date, the name of the culturing person and the like were marked on the bottle wall) and were incubated in a $CO_2$ incubator (the incubator temperature was 37° C., and the $CO_2$ concentration was 5%).

b, The cells were passaged after 80-90% of the bottom of the culture bottle was covered by the cells. After passage, the cells were further incubated in the $CO_2$ incubator. The process was repeated until the number of cells met the pharmacodynamics requirements in vivo.

c, The cultured cells were collected and counted by automatic cell counter.

According to the counting results, the cells were resuspended with PBS to prepare a cell suspension (density: $7 \times 10^7$/mL), which was placed in the ice box for use.

7.3 Cell Inoculation and Tumor Volume Measurement:

1. Before inoculation, the cell suspension was mixed well, 0.5 mL of cell suspension was taken with a 1 mL syringe, after removing air bubbles, and the syringe was placed on an ice bag for use.

2. The nude mice were bound with the left hand and the skin of the right back of the nude mice was disinfected with 75% alcohol. The nude mice were inoculated 30 seconds later.

3. At the time of inoculation, a 1 mL syringe was held in the right hand, and the nude mice were subcutaneously inoculated with 0.1 mL cell suspension on the right shoulder of the right back of the nude mice. The syringe was placed on the ice bag during the inoculation interval. The test nude mice were inoculated in turn.

4. Tumor was measured on Day 14 to Day 16 after inoculation depending on the tumor growth, and tumor size was calculated.

Tumor volume calculation: tumor volume (mm³)
=length (mm)×width (mm)×width (mm)/2

5. According to the size of the tumor, the mice were grouped by random grouping.

6. The tumor was measured and weighed twice a week after the test drug was administrated.

7. The data were processed with software such as Excel.

7.4 Administration:

1. Before administration, the nude mice were numbered and weighed. The needle of 1 mL syringe was replaced with No. 8 mouse gavage needle. The corresponding volume of the drug was taken with the syringe and placed for use after air bubbles were removed.

2. The nude mice were bound with the left hand, and the syringe was held with the right hand. The test nude mice were gavaged with the syringe in turn.

3. Administration frequency: twice/day

\* solvent: 0.5% CMC/1% Tween 80.

7.5 The experimental results are shown in Table 4

TABLE 4

| Grouping | Number of animals | Days of administration | Tumor inhibition rate |
|---|---|---|---|
| Blank control | 5 | 14 | — |

What is claimed is:

1. A compound selected from the group consisting of:

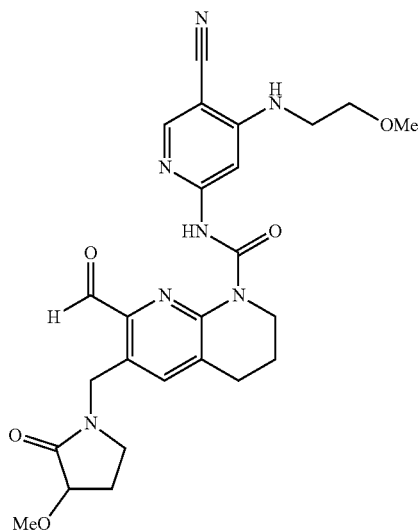

-continued

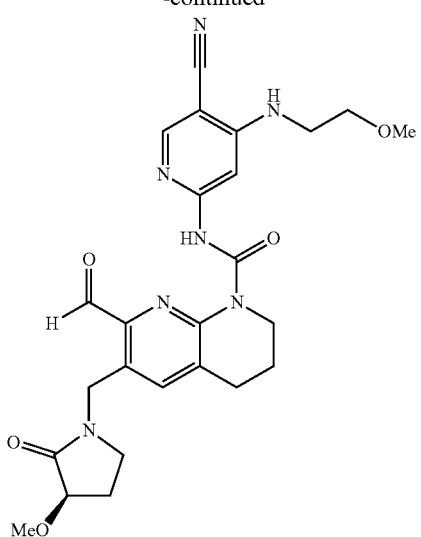

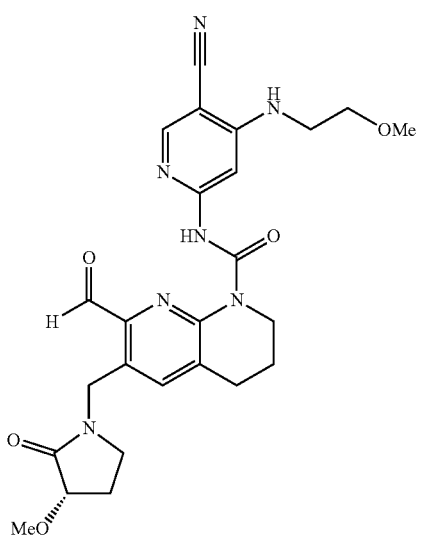

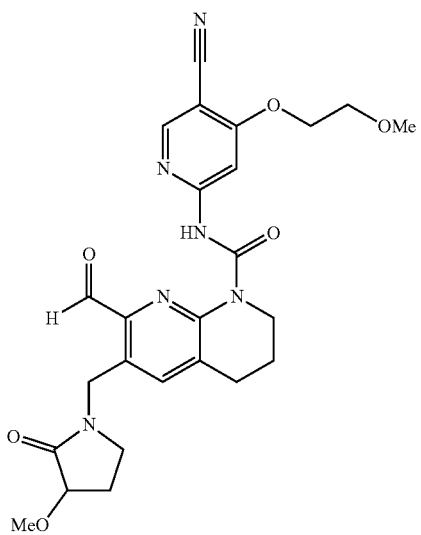

197
-continued
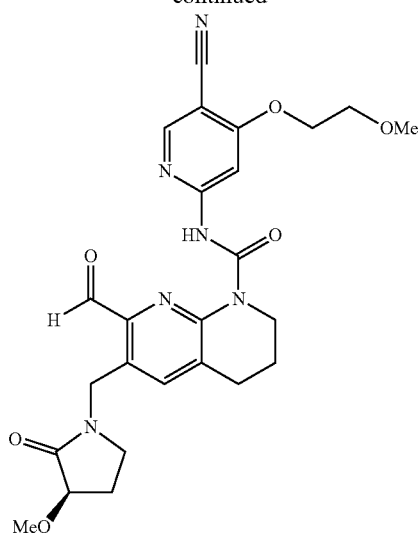
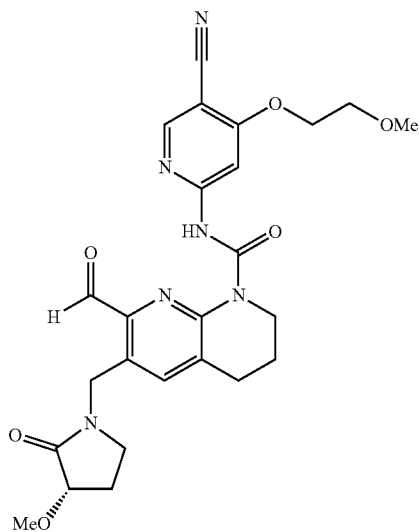
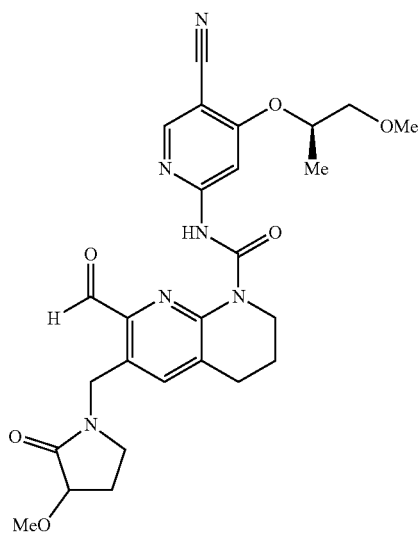
198
-continued
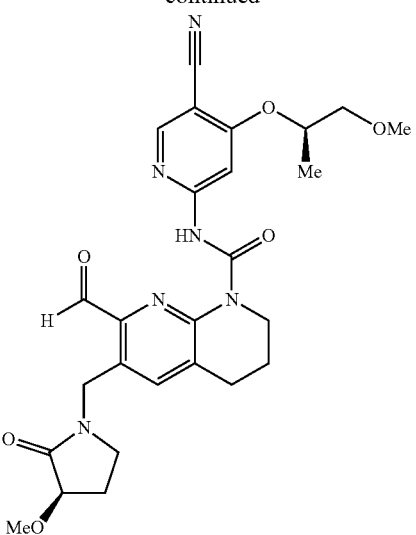
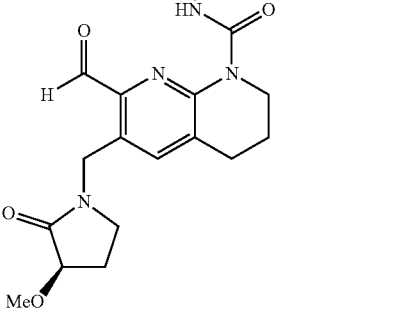
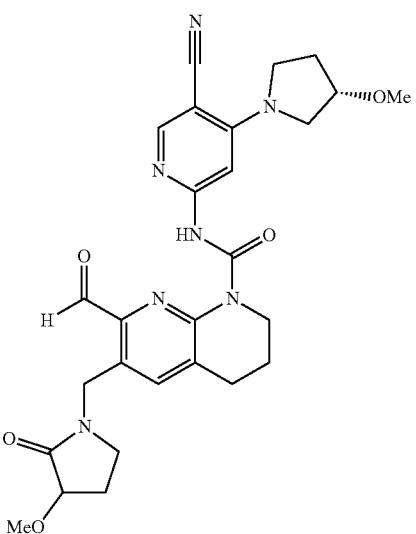

199
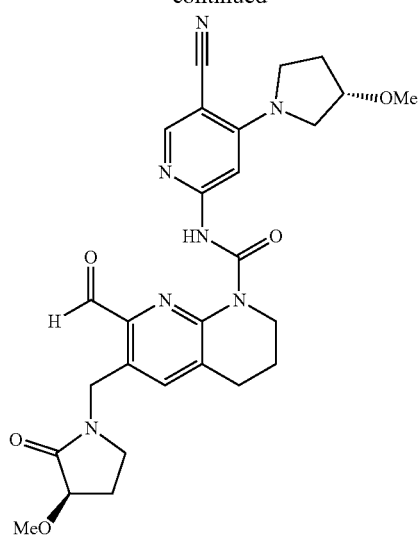
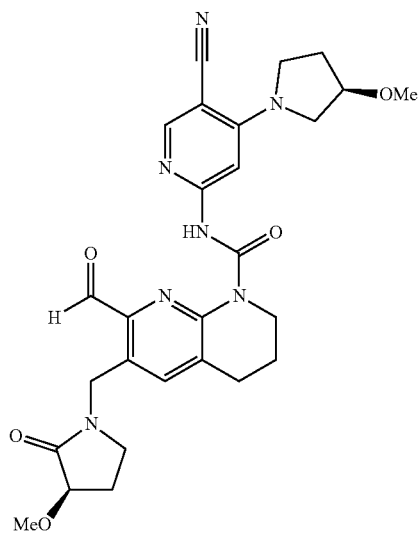
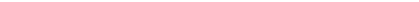
200
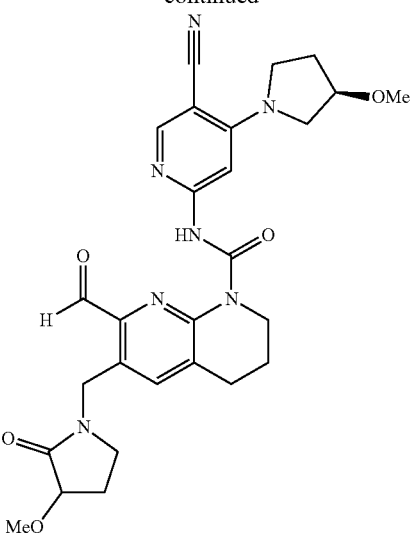
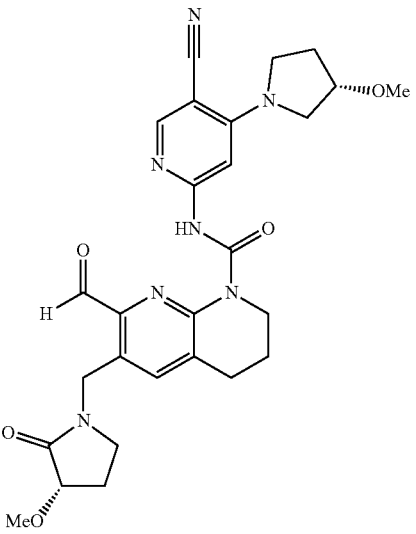
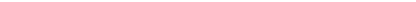

201
-continued
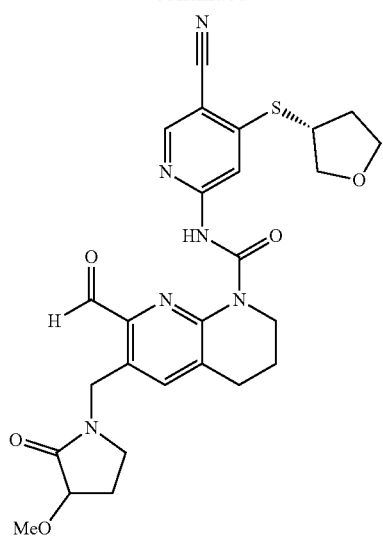
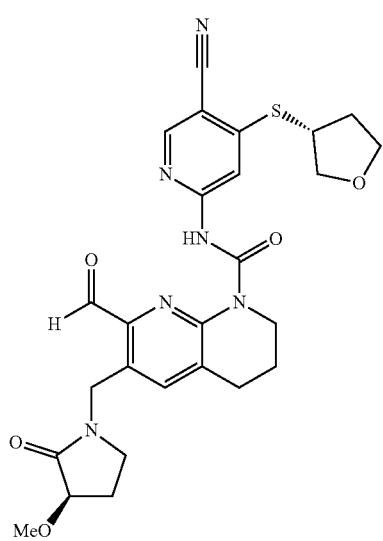
202
-continued
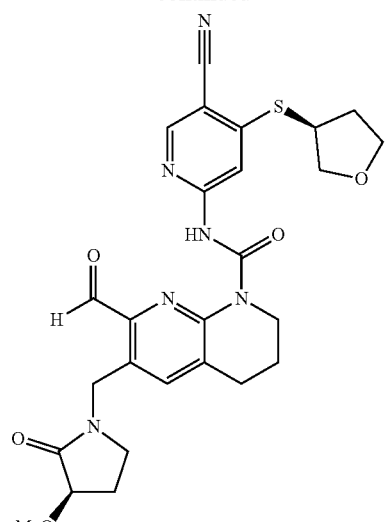

203
-continued
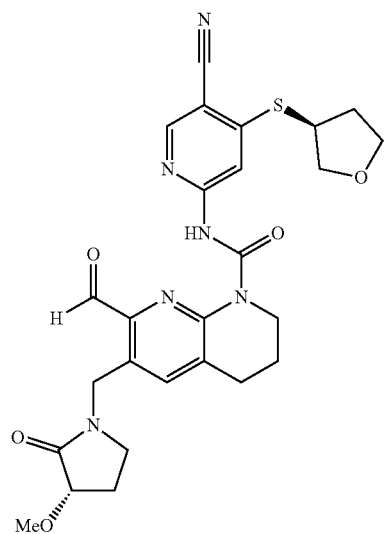
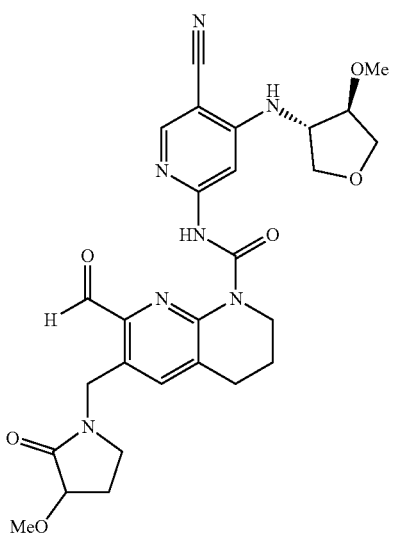
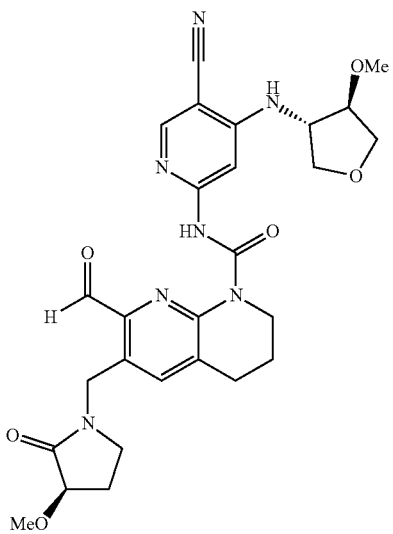
204
-continued
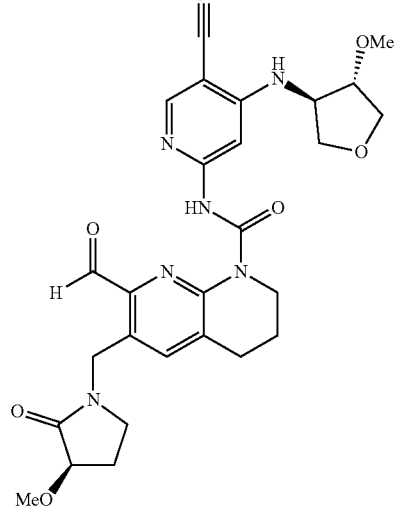
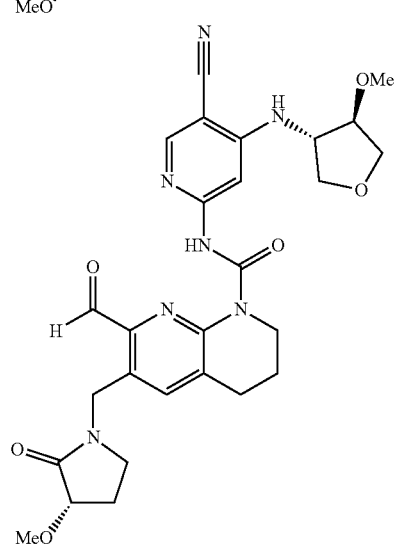
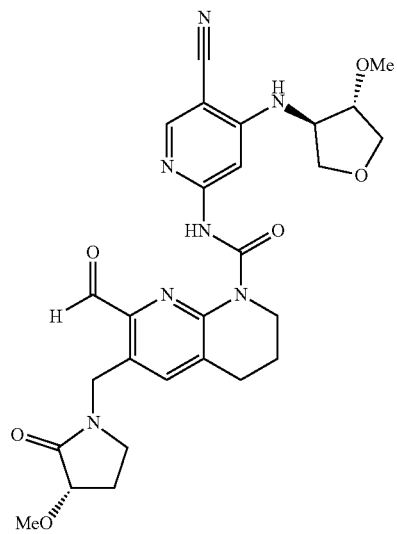

205
-continued
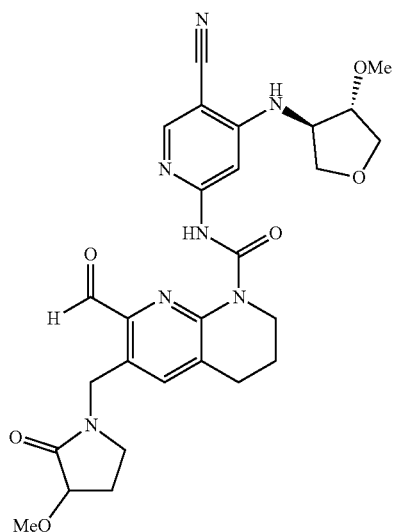
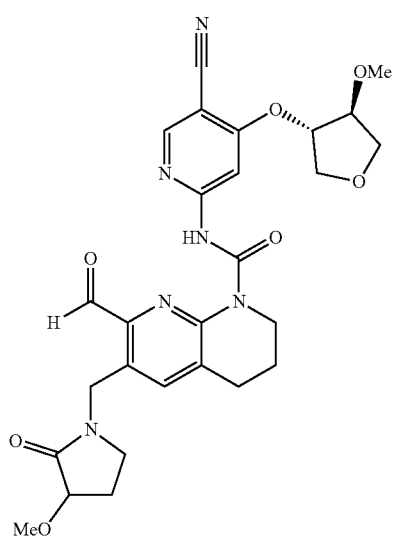
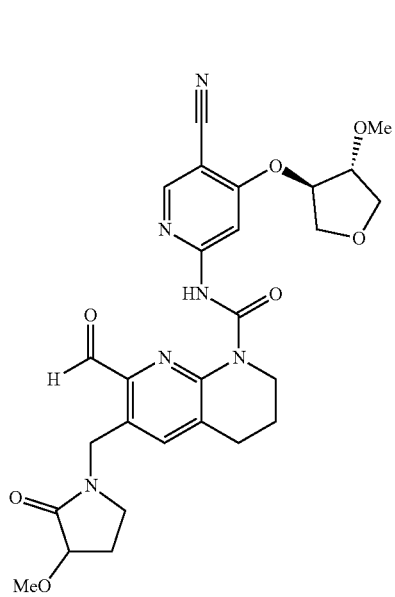
206
-continued
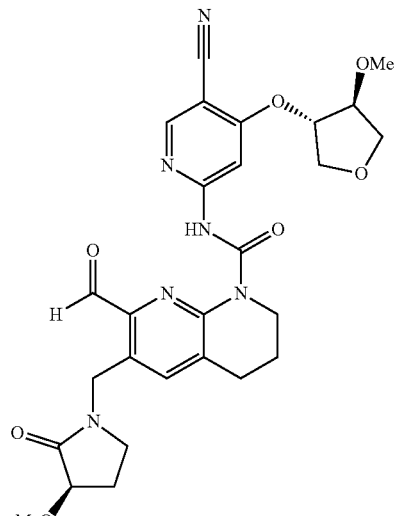
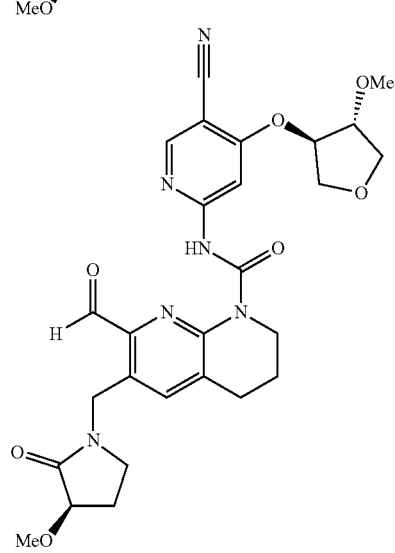
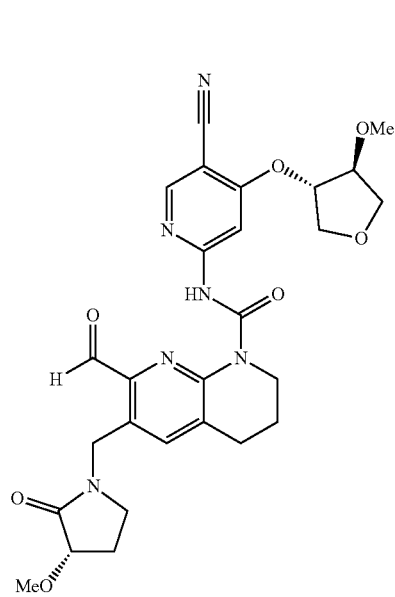

207
-continued
208
-continued
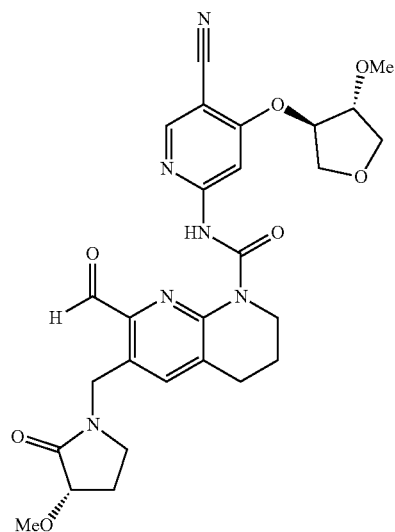
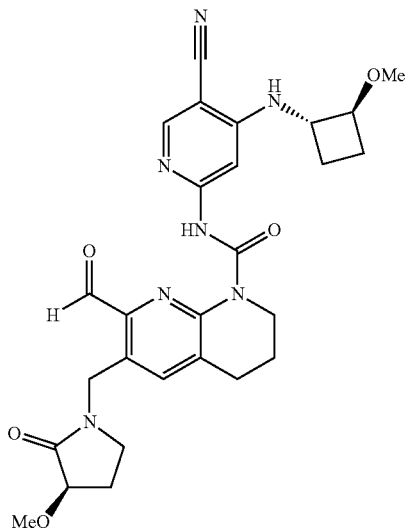
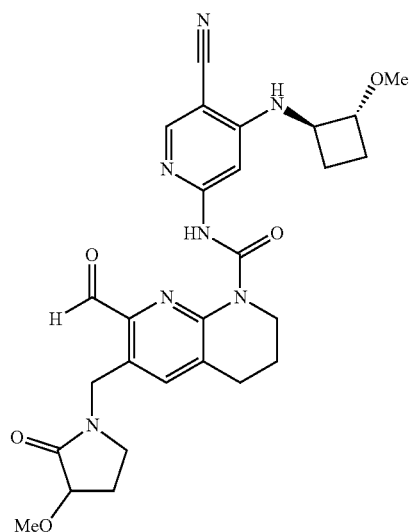

209
-continued
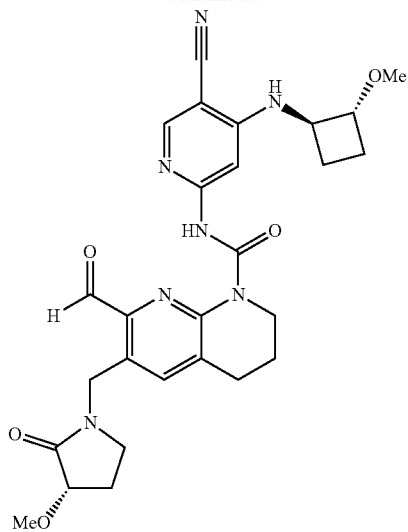
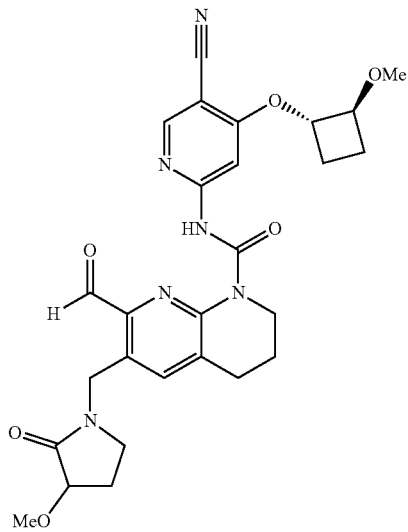
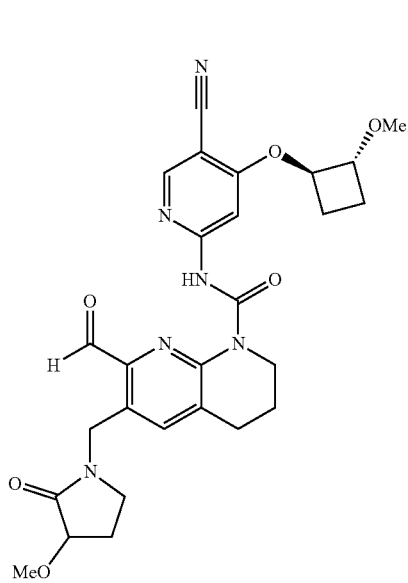
210
-continued
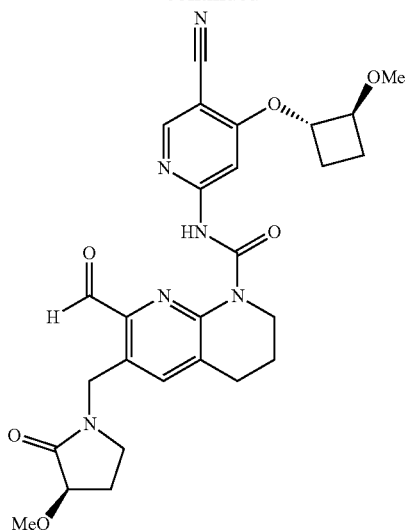
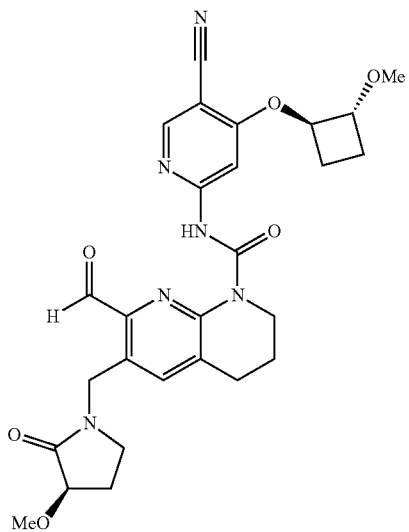
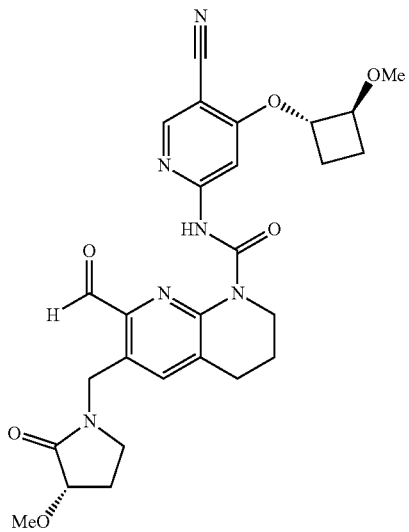

211
-continued
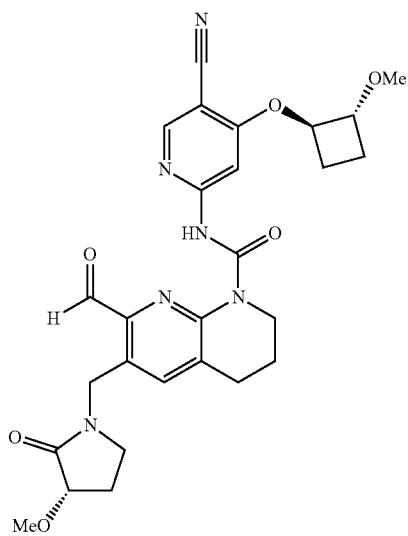
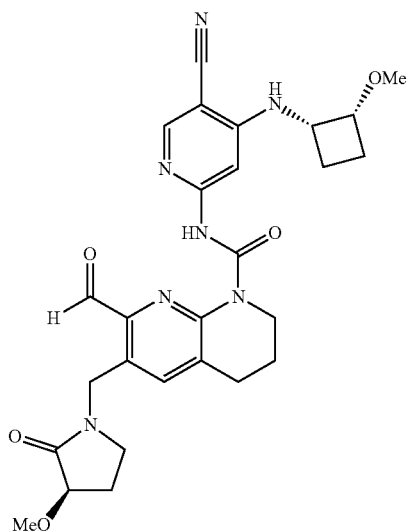
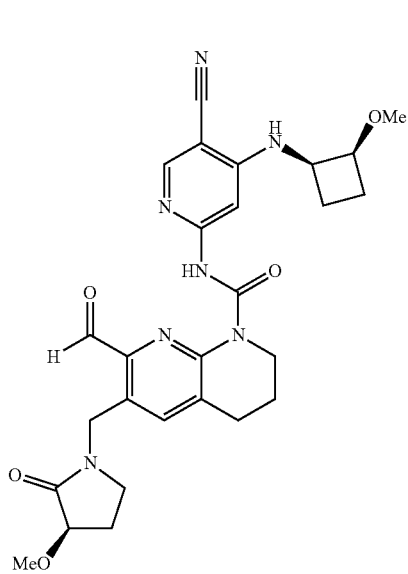
212
-continued
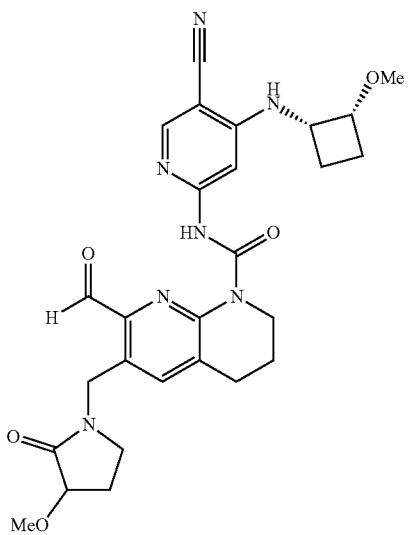
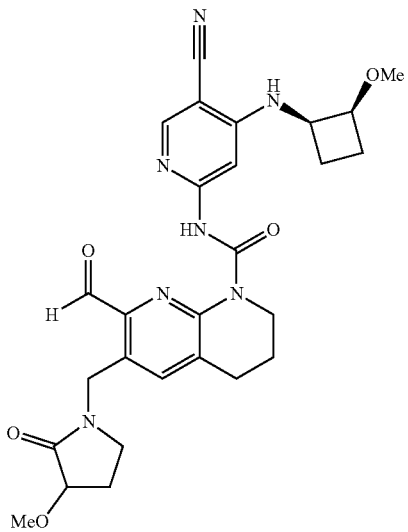
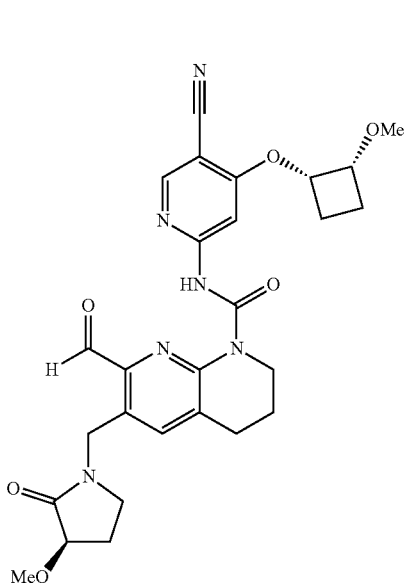

213
-continued
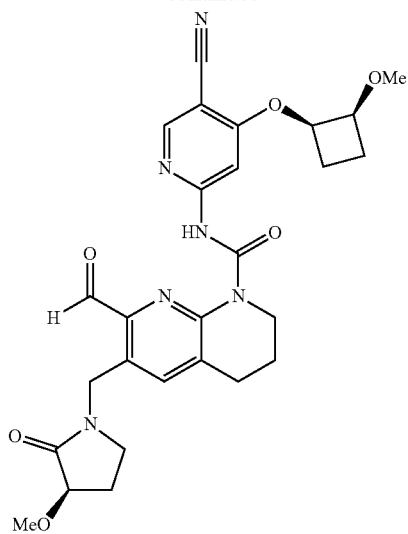
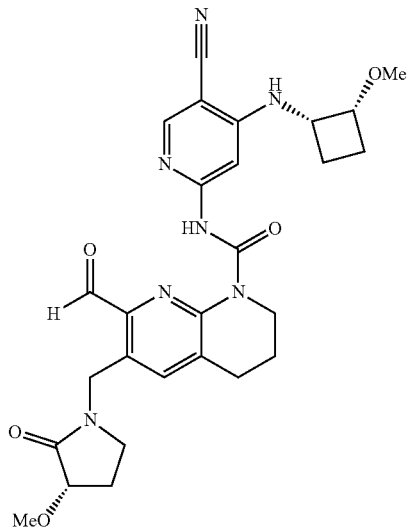
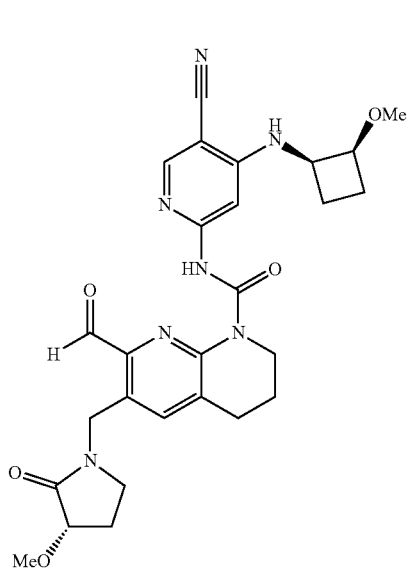
214
-continued
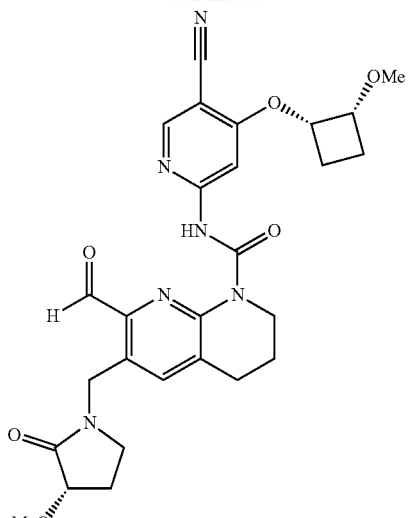
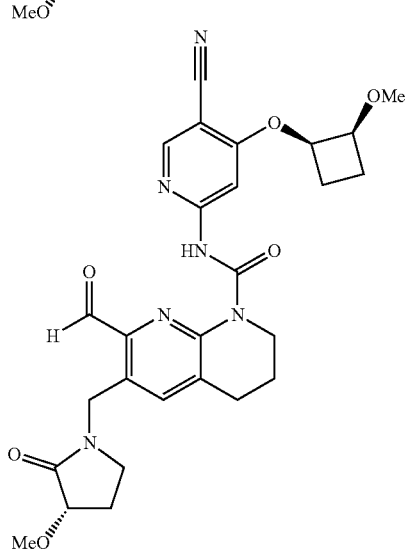
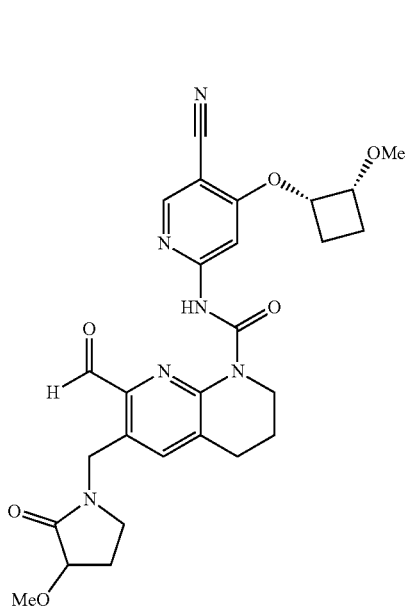

215
-continued
216
-continued
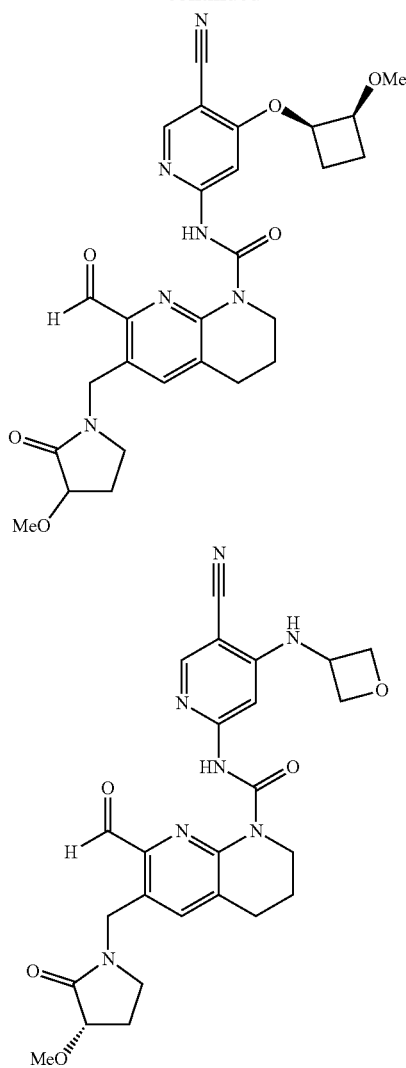
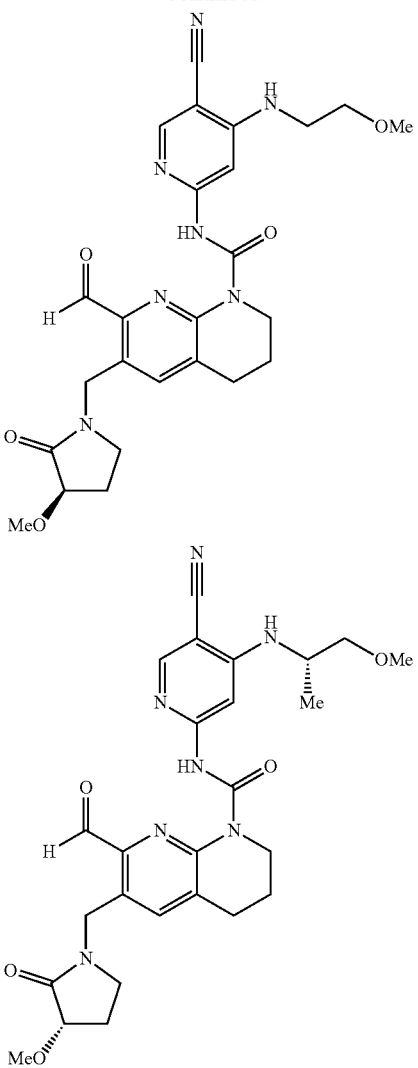
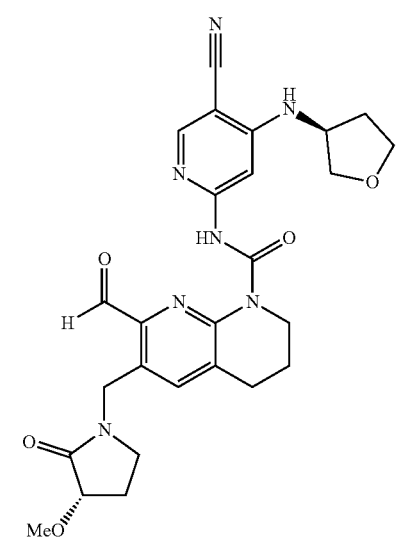

-continued
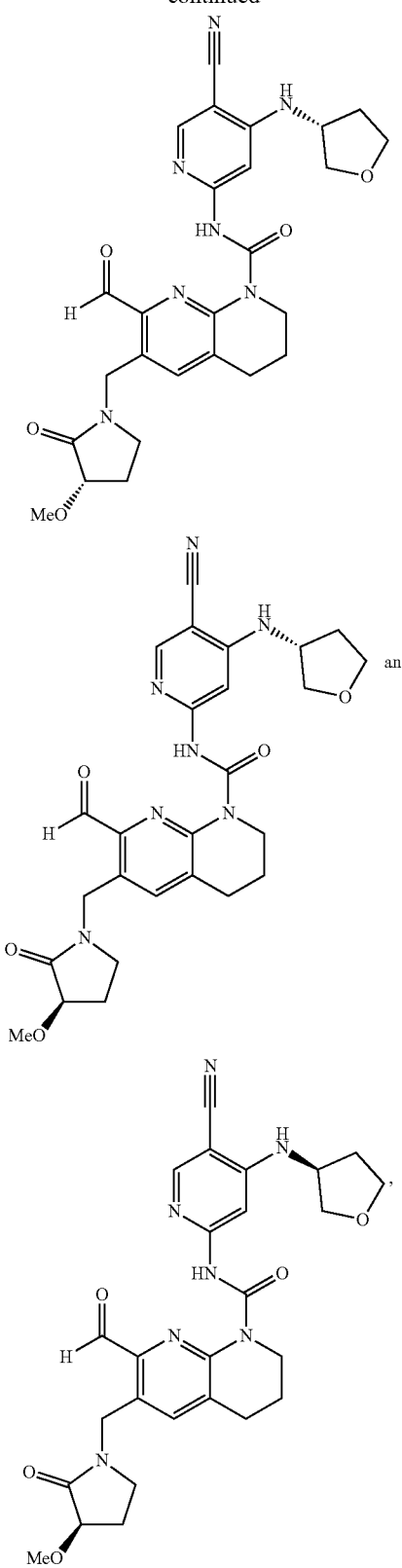
and
or a pharmaceutically acceptable salt thereof.
2. A compound selected from the group consisting of:
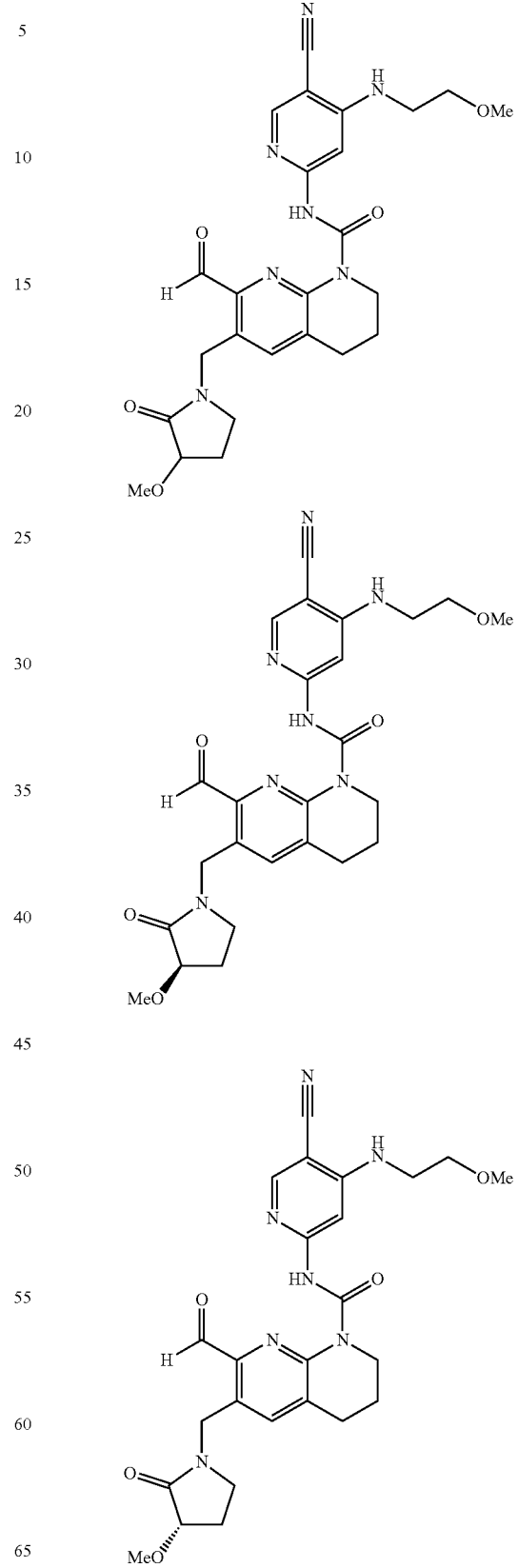

219
-continued

220
-continued

-continued

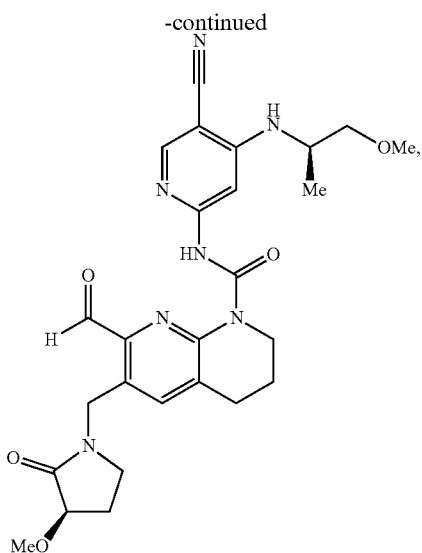

or a pharmaceutically acceptable salt thereof.

3. A pharmaceutical composition comprising a therapeutically effective amount of the compound of formula (I) or the pharmaceutically acceptable salt thereof according to claim 2, and a pharmaceutically acceptable carrier.

4. A compound of formula (III), a stereoisomer or a pharmaceutically acceptable salt thereof:

(III)

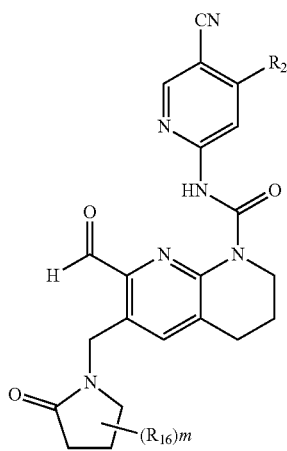

wherein:

$R_{16}$ is —$C_{0-8}$—O—$R_{10}$;

$R_2$ is selected from the group consisting of hydrogen, deuterium, halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3 to 8 membered heterocyclyl, 3 to 8 membered heterocyclyloxy, 3 to 8 membered heterocyclylthio, —$C_{0-8}$—S(O)$_r$R$_9$, —$C_{0-8}$—O—$R_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$, and —N(R$_{12}$)—C(O)OR$_{10}$, wherein the $C_{1-8}$ alkyl, $C_{2-8}$ alkenyl, $C_{2-8}$ alkynyl, $C_{3-8}$ cycloalkyl, 3 to 8 membered heterocyclyl, 3 to 8 membered heterocyclyloxy, 3 to 8 membered heterocyclylthio, —$C_{0-8}$—S(O)$_r$R$_9$, —$C_{0-8}$—O—$R_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$, and —N(R$_{12}$)—C(O)OR$_{10}$ are each optionally substituted by one or more groups selected from the group consisting of halogen, hydroxy, alkyl, halo$C_{1-8}$ alkyl, $C_{3-8}$ cycloalkyl, 3 to 8 membered heterocyclyl, 3 to 8 membered heterocyclyloxy, 3 to 8 membered heterocyclylthio, —$C_{0-8}$—S(O)$_r$R$_9$, —$C_{0-8}$—O—$R_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$;

$R_9$ is selected from the group consisting of hydrogen, deuterium, $C_{1-8}$ alkyl, $C_{1-8}$ alkoxy substituted by $C_{1-8}$ alkyl, $C_{2-8}$ alkenyl, $C_{3-8}$ cycloalkyl, substituted or unsubstituted 3 to 8 membered heterocyclyl, halo$C_{1-8}$ alkyl, phenyl, p-methylphenyl, amino, mono $C_{1-8}$ alkylamino, di $C_{1-8}$ alkylamino and $C_{1-8}$ alkanoylamino;

$R_{10}$ is $C_{1-8}$ alkyl;

$R_{11}$ is selected from the group consisting of hydrogen, deuterium, $C_{1-8}$ alkyl, $C_{1-8}$ alkoxy, $C_{3-8}$ cycloalkyl, $C_{3-8}$ cycloalkoxy, halo$C_{1-8}$ alkyl, halo$C_{1-8}$ alkoxy, hydroxy$C_{1-8}$ alkyl and hydroxy$C_{1-8}$ alkoxy;

$R_{12}$ and $R_{13}$ are each independently selected from the group consisting of hydrogen, deuterium, $C_{1-8}$ alkyl, $C_{1-8}$ alkoxy substituted by $C_{1-8}$ alkyl, $C_{1-8}$ alkyl substituted by $C_{1-8}$ alkoxy, $C_{1-8}$ alkyl substituted by $C_{3-8}$ cycloalkyl, $C_{2-8}$ alkenyl, $C_{2-8}$ alkenyl, $C_{3-8}$ cycloalkyl, substituted or unsubstituted 3 to 8 membered heterocyclyl, substituted or unsubstituted $C_{5-10}$ aryl, substituted or unsubstituted 5 to 10 membered heteroaryl and $C_{1-8}$ alkanoyl;

r is 0, 1 or 2; and m is 1.

* * * * *